United States Patent
Ren et al.

(10) Patent No.: US 10,550,122 B2
(45) Date of Patent: Feb. 4, 2020

(54) SOLID FORMS OF (S)-3-(1-(9H-PURIN-6-YLAMINO)ETHYL)-8-CHLORO-2-PHENYLISOQUINOLIN-1(2H)-ONE AND METHODS OF USE THEREOF

(71) Applicant: Infinity Pharmaceuticals, Inc., Cambridge, MA (US)

(72) Inventors: Pingda Ren, San Diego, CA (US); Michael Martin, San Marcos, CA (US); Paul Isbester, Castleton, NY (US); Benjamin S. Lane, Lynnfield, MA (US); Jason Kropp, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/799,612

(22) Filed: Oct. 31, 2017

(65) Prior Publication Data
US 2018/0273535 A1    Sep. 27, 2018

Related U.S. Application Data

(62) Division of application No. 15/016,117, filed on Feb. 4, 2016, now Pat. No. 9,840,505, which is a division of application No. 14/327,499, filed on Jul. 9, 2014, now Pat. No. 9,290,497, which is a division of application No. 13/347,423, filed on Jan. 10, 2012, now Pat. No. 8,809,349.

(60) Provisional application No. 61/578,655, filed on Dec. 21, 2011, provisional application No. 61/431,304, filed on Jan. 10, 2011.

(51) Int. Cl.
*C07D 473/34* (2006.01)
*A61K 31/52* (2006.01)
*A61P 35/00* (2006.01)
*A61P 37/00* (2006.01)
*A61P 11/06* (2006.01)

(52) U.S. Cl.
CPC ................... *C07D 473/34* (2013.01)

(58) Field of Classification Search
CPC ............... C07D 473/34; A61K 31/52
USPC ....... 514/263.22, 263.2, 263.4, 309; 544/277
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,657,744 A | 4/1972 | Ersek |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,270,537 A | 6/1981 | Romaine |
| 4,547,508 A | 10/1985 | Konz et al. |
| 4,596,556 A | 6/1986 | Morrow et al. |
| 4,656,159 A | 4/1987 | McPherson et al. |
| 4,704,381 A | 11/1987 | Schaumann et al. |
| 4,739,762 A | 4/1988 | Palmaz |
| 4,790,824 A | 12/1988 | Morrow et al. |
| 4,795,627 A | 1/1989 | Fisher et al. |
| 4,886,499 A | 12/1989 | Cirelli et al. |
| 4,940,460 A | 7/1990 | Casey et al. |
| 4,941,880 A | 7/1990 | Burns |
| 4,992,445 A | 2/1991 | Lawter et al. |
| 5,001,139 A | 3/1991 | Lawter et al. |
| 5,015,235 A | 5/1991 | Crossman |
| 5,023,252 A | 6/1991 | Hseih |
| 5,040,548 A | 8/1991 | Yock |
| 5,059,595 A | 10/1991 | Le Grazie |
| 5,061,273 A | 10/1991 | Yock |
| 5,064,413 A | 11/1991 | McKinnon et al. |
| 5,073,543 A | 12/1991 | Marshall et al. |
| 5,120,548 A | 6/1992 | McClelland et al. |
| 5,141,496 A | 8/1992 | Dalto et al. |
| 5,190,521 A | 3/1993 | Hubbard et al. |
| 5,195,984 A | 3/1993 | Schatz |
| 5,240,941 A | 8/1993 | Bruneau |
| 5,292,331 A | 3/1994 | Boneau |
| 5,294,612 A | 3/1994 | Bacon et al. |
| 5,310,731 A | 5/1994 | Olsson et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,354,556 A | 10/1994 | Sparks et al. |
| 5,364,862 A | 11/1994 | Spada et al. |
| 5,383,851 A | 1/1995 | McKinnon et al. |
| 5,409,930 A | 4/1995 | Spada et al. |
| 5,417,662 A | 5/1995 | Hjertman et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

Al-Alwan et al., "Requirement for Phosphoinositide 3-Kinase p110δ Signaling in B Cell Antigen Receptor-Mediated Antigen Presentation," *J. Immunol.* 178:2328-35 (2007).

(Continued)

*Primary Examiner* — Irina Neagu

(74) *Attorney, Agent, or Firm* — Jones Day

(57) ABSTRACT

Polymorphs of chemical compounds that modulate kinase activity, including PI3 kinase activity, and compounds, pharmaceutical compositions, and methods of treatment of diseases and conditions associated with kinase activity, including PI3 kinase activity, are described herein. Also provided herein are processes for preparing compounds, polymorphs thereof, and pharmaceutical compositions thereof.

31 Claims, 31 Drawing Sheets

(56) References Cited

U.S. PATENT DOCUMENTS

| | | |
|---|---|---|
| 5,420,419 A | 5/1995 | Wood |
| 5,428,125 A | 6/1995 | Hefner, Jr. et al. |
| 5,442,039 A | 8/1995 | Hefner, Jr. et al. |
| 5,451,233 A | 9/1995 | Yock |
| 5,466,220 A | 11/1995 | Brenneman |
| 5,480,381 A | 1/1996 | Weston |
| 5,480,883 A | 1/1996 | Spada et al. |
| 5,496,346 A | 3/1996 | Horzewski et al. |
| 5,503,627 A | 4/1996 | McKinnon et al. |
| 5,504,103 A | 4/1996 | Bonjouklian et al. |
| 5,506,347 A | 4/1996 | Erion et al. |
| 5,520,639 A | 5/1996 | Peterson et al. |
| 5,527,288 A | 6/1996 | Gross et al. |
| 5,561,134 A | 10/1996 | Spada et al. |
| 5,563,257 A | 10/1996 | Zilch et al. |
| 5,569,189 A | 10/1996 | Parsons |
| 5,591,767 A | 1/1997 | Mohr et al. |
| 5,593,997 A | 1/1997 | Dow et al. |
| 5,599,302 A | 2/1997 | Lilley et al. |
| 5,639,476 A | 6/1997 | Oshlack et al. |
| 5,639,480 A | 6/1997 | Bodmer et al. |
| 5,646,128 A | 7/1997 | Firestein et al. |
| 5,646,153 A | 7/1997 | Spada et al. |
| 5,649,912 A | 7/1997 | Peterson |
| 5,652,366 A | 7/1997 | Spada et al. |
| 5,654,307 A | 8/1997 | Bridges et al. |
| 5,656,643 A | 8/1997 | Spada et al. |
| 5,665,721 A | 9/1997 | Bhagwat et al. |
| 5,674,278 A | 10/1997 | Boneau |
| 5,674,533 A | 10/1997 | Santus et al. |
| 5,674,998 A | 10/1997 | Boyer et al. |
| 5,686,455 A | 11/1997 | Adams et al. |
| 5,704,911 A | 1/1998 | Parsons |
| 5,710,158 A | 1/1998 | Spada et al. |
| 5,714,493 A | 2/1998 | Spada et al. |
| 5,721,237 A | 2/1998 | Spada et al. |
| 5,733,566 A | 3/1998 | Lewis |
| 5,736,554 A | 4/1998 | Spada et al. |
| 5,739,108 A | 4/1998 | Mitchell |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,861,510 A | 1/1999 | Piscopio et al. |
| 5,863,949 A | 1/1999 | Robinson et al. |
| 5,879,382 A | 3/1999 | Boneau |
| 5,891,474 A | 4/1999 | Busetti et al. |
| 5,893,397 A | 4/1999 | Peterson et al. |
| 5,914,488 A | 6/1999 | Sone |
| RE36,256 E | 7/1999 | Spada et al. |
| 5,919,808 A | 7/1999 | Petrie et al. |
| 5,922,356 A | 7/1999 | Koseki et al. |
| 5,922,753 A | 7/1999 | Petrie et al. |
| 5,948,776 A | 9/1999 | Petrie et al. |
| 5,962,457 A | 10/1999 | Chenard et al. |
| 5,965,573 A | 10/1999 | Petrie et al. |
| 5,972,891 A | 10/1999 | Kamei et al. |
| 5,977,061 A | 11/1999 | Holy et al. |
| 5,980,945 A | 11/1999 | Ruiz |
| 5,981,533 A | 11/1999 | Traxler et al. |
| 5,985,589 A | 11/1999 | Chantry et al. |
| 5,990,109 A | 11/1999 | Chen et al. |
| 5,990,169 A | 11/1999 | Petrie et al. |
| 5,993,412 A | 11/1999 | Deily et al. |
| 5,993,855 A | 11/1999 | Yoshimoto et al. |
| 5,994,358 A | 11/1999 | Petrie et al. |
| 6,001,839 A | 12/1999 | Calderwood et al. |
| 6,045,830 A | 4/2000 | Igari et al. |
| 6,057,305 A | 5/2000 | Holy et al. |
| 6,057,320 A | 5/2000 | Spada et al. |
| 6,057,371 A | 5/2000 | Glennon |
| 6,084,095 A | 7/2000 | Bridges et al. |
| 6,087,324 A | 7/2000 | Igari et al. |
| 6,093,737 A | 7/2000 | Anthony et al. |
| 6,113,943 A | 9/2000 | Okada et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,197,350 B1 | 3/2001 | Yamagata et al. |
| 6,242,453 B1 | 6/2001 | Cirillo et al. |
| 6,248,363 B1 | 6/2001 | Patel et al. |
| 6,251,901 B1 | 6/2001 | Petrie et al. |
| 6,264,970 B1 | 7/2001 | Hata et al. |
| 6,265,410 B1 | 7/2001 | Bridges et al. |
| 6,267,981 B1 | 7/2001 | Okamoto et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,344,053 B1 | 2/2002 | Boneau |
| 6,350,741 B1 | 2/2002 | Golec et al. |
| 6,358,945 B1 | 3/2002 | Breitfelder et al. |
| 6,362,216 B1 | 3/2002 | Burgess et al. |
| RE37,650 E | 4/2002 | Spada et al. |
| 6,376,461 B1 | 4/2002 | Igari et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,419,961 B1 | 7/2002 | Igari et al. |
| 6,455,534 B2 | 9/2002 | Bridges et al. |
| 6,472,153 B1 | 10/2002 | Dempcy et al. |
| 6,472,562 B1 | 10/2002 | Klingler et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,589,548 B1 | 7/2003 | Oh et al. |
| 6,613,358 B2 | 9/2003 | Randolph et al. |
| 6,613,798 B1 | 9/2003 | Porter et al. |
| 6,630,495 B1 | 10/2003 | Cooke et al. |
| 6,632,789 B1 | 10/2003 | June |
| 6,645,969 B1 | 11/2003 | Spada et al. |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,664,393 B2 | 12/2003 | Klingler et al. |
| 6,667,300 B2 | 12/2003 | Sadhu et al. |
| 6,667,398 B2 | 12/2003 | Dunn et al. |
| 6,690,583 B1 | 2/2004 | Bergstedt et al. |
| 6,699,500 B2 | 3/2004 | Okada et al. |
| 6,713,484 B2 | 3/2004 | Bridges et al. |
| 6,720,344 B2 | 4/2004 | Kerwin et al. |
| 6,734,187 B2 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,825,219 B2 | 11/2004 | Cywin et al. |
| 6,849,420 B2 | 2/2005 | Vanhaesebroeck et al. |
| 6,849,637 B2 | 2/2005 | Andrianjara et al. |
| 6,849,713 B2 | 2/2005 | Zhang et al. |
| 6,852,727 B2 | 2/2005 | Goulet et al. |
| 6,858,756 B2 | 2/2005 | Rampf et al. |
| 6,906,103 B2 | 6/2005 | Zhang et al. |

(56) References Cited

U.S. PATENT DOCUMENTS

| | | |
|---|---|---|
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,005,520 B2 | 2/2006 | Dunn et al. |
| 7,026,461 B1 | 4/2006 | Shokat |
| 7,030,242 B2 | 4/2006 | Noe et al. |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,597 B1 | 8/2006 | Miwa et al. |
| 7,102,046 B2 | 9/2006 | Rampf et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,493 B2 | 4/2007 | Wrasidlo et al. |
| 7,208,601 B2 | 4/2007 | Mjalli et al. |
| 7,217,794 B2 | 5/2007 | Abdel-Meguid et al. |
| 7,223,780 B2 | 5/2007 | Nazare et al. |
| 7,230,004 B2 | 6/2007 | Adams et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,317,027 B2 | 1/2008 | Nazare et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,088 B2 | 4/2008 | Nazare et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,465,806 B2 | 12/2008 | Bauer et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,642,272 B2 | 1/2010 | Shankar et al. |
| 7,678,803 B2 | 3/2010 | Huang et al. |
| 7,700,552 B2 | 4/2010 | Waehling et al. |
| 7,700,607 B2 | 4/2010 | Hu et al. |
| 7,705,018 B2 | 4/2010 | Chen et al. |
| 7,745,485 B2 | 6/2010 | Durden |
| 7,812,164 B2 | 10/2010 | Austad et al. |
| 7,829,590 B2 | 11/2010 | Brenchley et al. |
| 7,919,046 B2 | 4/2011 | Delapierre et al. |
| 7,932,260 B2 | 4/2011 | Fowler et al. |
| 8,053,445 B2 | 11/2011 | Yamamori et al. |
| 8,053,603 B2 | 11/2011 | Shao et al. |
| 8,088,385 B2 | 1/2012 | Tapolsky et al. |
| 8,101,637 B2 | 1/2012 | Bessis et al. |
| 8,106,146 B2 | 1/2012 | Benz et al. |
| 8,124,625 B2 | 2/2012 | Yamamori et al. |
| 8,188,134 B2 | 5/2012 | Brenchley et al. |
| 8,193,182 B2 | 6/2012 | Ren et al. |
| 8,399,483 B2 | 3/2013 | Allen et al. |
| 8,557,823 B2 | 10/2013 | Tapolsky et al. |
| 8,785,456 B2 | 7/2014 | Ren et al. |
| 2001/0019829 A1 | 9/2001 | Nelson et al. |
| 2001/0027197 A1 | 10/2001 | Bridges et al. |
| 2002/0006931 A1 | 1/2002 | Beachy et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | McLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |

(56) References Cited

U.S. PATENT DOCUMENTS

| | | |
|---|---|---|
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0021493 A1 | 1/2007 | Guicherit et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0060546 A1 | 3/2007 | Ruat et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287420 A1 | 11/2008 | Castro et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0293754 A1 | 11/2008 | Austad et al. |
| 2008/0293755 A1 | 11/2008 | Castro et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312310 A1 | 12/2009 | Kawato et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |
| 2010/0009963 A1 | 1/2010 | Knight et al. |
| 2010/0022531 A1 | 1/2010 | Kincaid et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0202963 A1 | 8/2010 | Gallatin et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0286114 A1 | 11/2010 | Thomas et al. |
| 2010/0298290 A1 | 11/2010 | Anand et al. |
| 2010/0305084 A1 | 12/2010 | Castanedo et al. |
| 2010/0305096 A1 | 12/2010 | Castanedo et al. |
| 2011/0009378 A1 | 1/2011 | Lange et al. |
| 2011/0046165 A1 | 2/2011 | Ren et al. |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0190157 A1 | 8/2011 | Kipps et al. |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2011/0306622 A1 | 12/2011 | Lannutti et al. |
| 2012/0004198 A1 | 1/2012 | Liao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Yu et al. |
| 2012/0177749 A1 | 7/2012 | Tapolsky et al. |
| 2012/0183535 A1 | 7/2012 | Buggy et al. |
| 2012/0184568 A1 | 7/2012 | Ren et al. |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1 | 9/2012 | Baldwin et al. |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |

(56) References Cited

U.S. PATENT DOCUMENTS

| | | |
|---|---|---|
| 2013/0045229 A1 | 2/2013 | Iadonato et al. |
| 2013/0053362 A1 | 2/2013 | Castro et al. |
| 2013/0064812 A1 | 3/2013 | Gallatin et al. |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2013/0344061 A1 | 12/2013 | Palombella et al. |
| 2014/0024637 A1 | 1/2014 | Rice |
| 2014/0031547 A1 | 1/2014 | Sheridan et al. |
| 2014/0037622 A1 | 2/2014 | Boshoff et al. |
| 2014/0120060 A1 | 5/2014 | Palombella et al. |
| 2014/0120083 A1 | 5/2014 | Stern et al. |
| 2014/0371246 A1 | 12/2014 | Evans et al. |
| 2014/0377258 A1 | 12/2014 | Stern et al. |
| 2015/0065431 A1 | 3/2015 | Xu et al. |
| 2015/0184249 A1 | 7/2015 | Chang et al. |
| 2016/0113932 A1 | 4/2016 | Stern et al. |

FOREIGN PATENT DOCUMENTS

| | | |
|---|---|---|
| CN | 102206172 | 10/2011 |
| CN | 102731492 | 10/2012 |
| DE | 2139107 A1 | 2/1973 |
| EP | 773023 A1 | 5/1997 |
| EP | 606046 | 8/1997 |
| EP | 0818442 | 1/1998 |
| EP | 0945864 | 9/1999 |
| EP | 1004578 | 5/2000 |
| EP | 780386 | 2/2002 |
| EP | 1 262 176 A1 | 4/2002 |
| EP | 931788 | 6/2002 |
| EP | 1020445 B1 | 8/2008 |
| GB | 812366 A | 4/1959 |
| GB | 937725 A | 9/1963 |
| JP | 61-109797 A | 5/1986 |
| JP | H04211063 | 8/1992 |
| JP | 05-256693 A | 10/1993 |
| JP | 08295667 A | 11/1996 |
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| JP | 4834699 | 12/2011 |
| JP | 4846769 | 12/2011 |
| WO | WO 1983/001446 A1 | 4/1983 |
| WO | WO 1990/005719 | 5/1990 |
| WO | WO 1991/017161 A1 | 11/1991 |
| WO | WO 1992/014733 A1 | 9/1992 |
| WO | WO 1993/016091 A1 | 8/1993 |
| WO | WO 1993/016092 A1 | 8/1993 |
| WO | WO 1993/018035 A1 | 9/1993 |
| WO | WO 1993/019767 A1 | 10/1993 |
| WO | WO 1993/022443 A1 | 11/1993 |
| WO | WO 1994/013677 A1 | 6/1994 |
| WO | WO 1994/017803 A1 | 8/1994 |
| WO | WO 1994/029436 A1 | 12/1994 |
| WO | WO 1995/010628 A2 | 4/1995 |
| WO | WO 1995/012588 A1 | 5/1995 |
| WO | WO 1995/019774 | 7/1995 |
| WO | WO 1995/029673 A1 | 11/1995 |
| WO | WO 1995/032984 A1 | 12/1995 |
| WO | WO 1995/010628 A3 | 9/1996 |
| WO | WO 1996/027583 | 9/1996 |
| WO | WO 1996/033172 | 10/1996 |
| WO | WO 1996/040706 A1 | 12/1996 |
| WO | WO 1997/013537 | 4/1997 |
| WO | WO 1997/028133 A1 | 8/1997 |
| WO | WO 1997/028161 A1 | 8/1997 |
| WO | WO 1997/037705 | 10/1997 |
| WO | WO 1998/003516 | 1/1998 |
| WO | WO 1998/007697 | 2/1998 |
| WO | WO 1998/030566 | 7/1998 |
| WO | WO 1998/033768 | 8/1998 |
| WO | WO 1998/034915 | 8/1998 |
| WO | WO 1998/034918 | 8/1998 |
| WO | WO 1998/041525 A1 | 9/1998 |
| WO | WO 1998/052611 A1 | 11/1998 |
| WO | WO 1998/057952 A1 | 12/1998 |
| WO | WO 1999/007675 | 2/1999 |
| WO | WO 1999/029667 | 6/1999 |
| WO | WO 1999/034850 | 7/1999 |
| WO | WO 1999/052889 | 10/1999 |
| WO | WO 1999/052910 | 10/1999 |
| WO | WO 2000/017202 A1 | 3/2000 |
| WO | WO 2001/002369 A2 | 1/2001 |
| WO | WO 2001/016114 A2 | 3/2001 |
| WO | WO 2001/019800 | 3/2001 |
| WO | WO 2001/019829 A2 | 3/2001 |
| WO | WO 2001/021160 | 3/2001 |
| WO | WO 2001/025238 A2 | 4/2001 |
| WO | WO 2001/026664 | 4/2001 |
| WO | WO 2001/027135 | 4/2001 |
| WO | WO 2001/031063 A1 | 5/2001 |
| WO | WO 2001/038584 A2 | 5/2001 |
| WO | WO 2001/049279 | 7/2001 |
| WO | WO 2001/016114 A3 | 8/2001 |
| WO | WO 2001/055140 A1 | 8/2001 |
| WO | WO 2001/056988 A1 | 8/2001 |
| WO | WO 2001/060824 | 8/2001 |
| WO | WO 2001/019829 A3 | 9/2001 |
| WO | WO 2001/025238 A3 | 10/2001 |
| WO | WO 2001/038584 A3 | 10/2001 |
| WO | WO 2001/074344 | 10/2001 |
| WO | WO 2001/081346 A2 | 11/2001 |
| WO | WO 2002/006192 A1 | 1/2002 |
| WO | WO 2001/081346 A3 | 3/2002 |
| WO | WO 2001/002369 A3 | 4/2002 |
| WO | WO 2002/030944 A2 | 4/2002 |
| WO | WO 2002/057425 A2 | 7/2002 |
| WO | WO 2002/076986 A1 | 10/2002 |
| WO | WO 2002/080926 A1 | 10/2002 |
| WO | WO 2002/083143 A1 | 10/2002 |
| WO | WO 2002/028853 A1 | 11/2002 |
| WO | WO 2002/088025 A1 | 11/2002 |
| WO | WO 2002/090334 A1 | 11/2002 |
| WO | WO 2002/030944 A3 | 1/2003 |
| WO | WO 2003/000187 A2 | 1/2003 |
| WO | WO 2003/011219 | 2/2003 |
| WO | WO 2003/016275 A1 | 2/2003 |
| WO | WO 2003/020880 A2 | 3/2003 |
| WO | WO 2003/024969 A1 | 3/2003 |
| WO | WO 2003/028341 A2 | 4/2003 |
| WO | WO 2003/035075 A1 | 5/2003 |
| WO | WO 2003/059884 A1 | 7/2003 |
| WO | WO 2003/020880 A3 | 10/2003 |
| WO | WO 2003/082341 A1 | 10/2003 |
| WO | WO 2003/088970 | 10/2003 |
| WO | WO 2003/106426 A1 | 12/2003 |
| WO | WO 2004/006906 A2 | 1/2004 |
| WO | WO 2004/006906 A3 | 3/2004 |
| WO | WO 2004/018058 A2 | 3/2004 |
| WO | WO 2004/020599 | 3/2004 |
| WO | WO 2004/031177 A1 | 4/2004 |
| WO | WO 2004/039774 A2 | 5/2004 |
| WO | WO 2004/046128 | 6/2004 |
| WO | WO 2004/018058 A3 | 7/2004 |
| WO | WO 2004/039774 A3 | 7/2004 |
| WO | WO 2004/058717 A1 | 7/2004 |
| WO | WO 2003/000187 A3 | 8/2004 |
| WO | WO 2004/075917 A1 | 9/2004 |
| WO | WO 2004/087053 A2 | 10/2004 |
| WO | WO 2004/087679 | 10/2004 |
| WO | WO 2004/089877 | 10/2004 |
| WO | WO 2004/111014 A1 | 12/2004 |
| WO | WO 2005/002585 A1 | 1/2005 |
| WO | WO 2005/007085 A2 | 1/2005 |
| WO | WO 2005/012323 A2 | 2/2005 |
| WO | WO 2005/013800 | 2/2005 |
| WO | WO 2005/016348 A1 | 2/2005 |
| WO | WO 2005/016349 A1 | 2/2005 |
| WO | WO 2005/016528 A2 | 2/2005 |

(56) References Cited

FOREIGN PATENT DOCUMENTS

| | | |
|---|---|---|
| WO | WO 2005/021533 A1 | 3/2005 |
| WO | WO 2002/057425 A3 | 4/2005 |
| WO | WO 2005/032343 | 4/2005 |
| WO | WO 2005/033288 | 4/2005 |
| WO | WO 2005/012323 A3 | 5/2005 |
| WO | WO 2005/016528 A3 | 5/2005 |
| WO | WO 2005/042700 | 5/2005 |
| WO | WO 2005/044181 A2 | 5/2005 |
| WO | WO 2005/047289 A1 | 5/2005 |
| WO | WO 2005/061460 A1 | 7/2005 |
| WO | WO 2005/063258 A1 | 7/2005 |
| WO | WO 2005/067901 A2 | 7/2005 |
| WO | WO 2005/074603 A2 | 8/2005 |
| WO | WO 2005/007085 A3 | 9/2005 |
| WO | WO 2005/097800 A1 | 10/2005 |
| WO | WO 2005/105760 A1 | 11/2005 |
| WO | WO 2005/067901 A3 | 12/2005 |
| WO | WO 2005/112935 A1 | 12/2005 |
| WO | WO 2005/113556 A1 | 12/2005 |
| WO | WO 2005/117889 A1 | 12/2005 |
| WO | WO 2005/120511 A1 | 12/2005 |
| WO | WO 2006/015279 | 2/2006 |
| WO | WO 2005/044181 A3 | 3/2006 |
| WO | WO 2006/028958 | 3/2006 |
| WO | WO 2006/030032 A1 | 3/2006 |
| WO | WO 2006/038865 A1 | 4/2006 |
| WO | WO 2006/050351 | 5/2006 |
| WO | WO 2006/050501 A2 | 5/2006 |
| WO | WO 2006/050946 A1 | 5/2006 |
| WO | WO 2006/068760 A2 | 6/2006 |
| WO | WO 2006/078283 | 7/2006 |
| WO | WO 2004/087053 A3 | 8/2006 |
| WO | WO 2006/089106 A2 | 8/2006 |
| WO | WO 2006/108107 A1 | 10/2006 |
| WO | WO 2006/112666 A1 | 10/2006 |
| WO | WO 2005/074603 A3 | 11/2006 |
| WO | WO 2006/114064 A2 | 11/2006 |
| WO | WO 2006/114065 A2 | 11/2006 |
| WO | WO 2006/068760 A3 | 12/2006 |
| WO | WO 2006/089106 A3 | 12/2006 |
| WO | WO 2007/002293 A2 | 1/2007 |
| WO | WO 2007/006547 A1 | 1/2007 |
| WO | WO 2007/020046 A1 | 2/2007 |
| WO | WO 2007/002293 A3 | 3/2007 |
| WO | WO 2007/025090 A2 | 3/2007 |
| WO | WO 2007/029121 | 3/2007 |
| WO | WO 2006/050501 A3 | 5/2007 |
| WO | WO 2007/054623 | 5/2007 |
| WO | WO 2007/059157 | 5/2007 |
| WO | WO 2007/061737 A2 | 5/2007 |
| WO | WO 2006/114064 A3 | 6/2007 |
| WO | WO 2006/114065 A3 | 6/2007 |
| WO | WO 2007/025090 A3 | 6/2007 |
| WO | WO 2007/075554 A2 | 7/2007 |
| WO | WO 2007/079164 A2 | 7/2007 |
| WO | WO 2007/079164 A3 | 9/2007 |
| WO | WO 2007/103308 A2 | 9/2007 |
| WO | WO 2007/112005 A2 | 10/2007 |
| WO | WO 2007/114926 A2 | 10/2007 |
| WO | WO 2007/120827 | 10/2007 |
| WO | WO 2007/121453 A2 | 10/2007 |
| WO | WO 2007/121920 A2 | 11/2007 |
| WO | WO 2007/121924 A2 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/131201 | 11/2007 |
| WO | WO 2007/134828 A1 | 11/2007 |
| WO | WO 2007/135380 A2 | 11/2007 |
| WO | WO 2007/135398 A1 | 11/2007 |
| WO | WO 2007/061737 A3 | 12/2007 |
| WO | WO 2007/125315 A3 | 12/2007 |
| WO | WO 2007/121920 A3 | 1/2008 |
| WO | WO 2008/001236 A2 | 1/2008 |
| WO | WO 2008/012326 A1 | 1/2008 |
| WO | WO 2007/103308 A3 | 2/2008 |
| WO | WO 2007/112005 A3 | 2/2008 |
| WO | WO 2007/125310 A3 | 3/2008 |
| WO | WO 2008/025755 A1 | 3/2008 |
| WO | WO 2008/047821 A1 | 4/2008 |
| WO | WO 2008/063625 A2 | 5/2008 |
| WO | WO 2008/064018 A1 | 5/2008 |
| WO | WO 2008/070357 | 6/2008 |
| WO | WO 2008/070507 A2 | 6/2008 |
| WO | WO 2007/121453 A3 | 7/2008 |
| WO | WO 2008/079028 A1 | 7/2008 |
| WO | WO 2008/082487 A2 | 7/2008 |
| WO | WO 2008/094737 A2 | 8/2008 |
| WO | WO 2007/121924 A3 | 9/2008 |
| WO | WO 2008/110611 | 9/2008 |
| WO | WO 2008/112715 A2 | 9/2008 |
| WO | WO 2008/112913 | 9/2008 |
| WO | WO 2007/114926 A3 | 10/2008 |
| WO | WO 2008/117050 | 10/2008 |
| WO | WO 2008/118454 A2 | 10/2008 |
| WO | WO 2008/118455 A1 | 10/2008 |
| WO | WO 2008/118468 A1 | 10/2008 |
| WO | WO 2008/125014 A1 | 10/2008 |
| WO | WO 2008/125207 A1 | 10/2008 |
| WO | WO 2008/127226 A2 | 10/2008 |
| WO | WO 2008/131354 | 10/2008 |
| WO | WO 2007/126841 A3 | 11/2008 |
| WO | WO 2008/112715 A3 | 11/2008 |
| WO | WO 2008/118454 A3 | 11/2008 |
| WO | WO 2008/136457 A1 | 11/2008 |
| WO | WO 2008/082487 A3 | 12/2008 |
| WO | WO 2008/127226 A3 | 12/2008 |
| WO | WO 2009/000412 A1 | 12/2008 |
| WO | WO 2009/004621 A1 | 1/2009 |
| WO | WO 2009/010925 A2 | 1/2009 |
| WO | WO 2009/019531 A2 | 2/2009 |
| WO | WO 2009/023718 A2 | 2/2009 |
| WO | WO 2008/094737 A3 | 3/2009 |
| WO | WO 2009/029617 A1 | 3/2009 |
| WO | WO 2009/023718 A3 | 4/2009 |
| WO | WO 2009/044707 A1 | 4/2009 |
| WO | WO 2009/050506 A2 | 4/2009 |
| WO | WO 2009/064802 A2 | 5/2009 |
| WO | WO 2009/010925 A3 | 7/2009 |
| WO | WO 2009/064802 A3 | 7/2009 |
| WO | WO 2009/088986 A1 | 7/2009 |
| WO | WO 2009/088990 A1 | 7/2009 |
| WO | WO 2009/100406 A2 | 8/2009 |
| WO | WO 2009/103022 | 8/2009 |
| WO | WO 2009/114870 | 9/2009 |
| WO | WO 2009/117157 A1 | 9/2009 |
| WO | WO 2009/118765 | 10/2009 |
| WO | WO 2009/050506 A3 | 11/2009 |
| WO | WO 2009/100406 A3 | 11/2009 |
| WO | WO 2010/006086 A2 | 1/2010 |
| WO | WO 2010/009207 A1 | 1/2010 |
| WO | WO 2010/019210 A2 | 2/2010 |
| WO | WO 2010/036380 A1 | 4/2010 |
| WO | WO 2010/039534 A2 | 4/2010 |
| WO | WO 2010/019210 A3 | 5/2010 |
| WO | WO 2010/053998 | 5/2010 |
| WO | WO 2010/057048 A1 | 5/2010 |
| WO | WO 2010/065923 A2 | 6/2010 |
| WO | WO 2010/070032 A1 | 6/2010 |
| WO | WO 2010/039534 A3 | 8/2010 |
| WO | WO 2010/092340 A1 | 8/2010 |
| WO | WO 2010/133836 A1 | 11/2010 |
| WO | WO 2011/008302 A1 | 1/2011 |
| WO | WO 2011/041399 | 4/2011 |
| WO | WO 2011/058108 A1 | 5/2011 |
| WO | WO 2011/058109 A1 | 5/2011 |
| WO | WO 2011/058110 A1 | 5/2011 |
| WO | WO 2011/075628 A1 | 6/2011 |
| WO | WO 2011/094890 | 8/2011 |
| WO | WO 2011/111880 | 9/2011 |
| WO | WO 2011/146882 A1 | 11/2011 |
| WO | WO 2012/009452 | 1/2012 |
| WO | WO 2012/032334 A1 | 3/2012 |

(56) References Cited

FOREIGN PATENT DOCUMENTS

| WO | WO 2012/037204 | 3/2012 |
|---|---|---|
| WO | WO 2012/052540 | 4/2012 |
| WO | WO 2012/061696 A1 | 5/2012 |
| WO | WO 2012/064973 A2 | 5/2012 |
| WO | WO 2012/068096 | 5/2012 |
| WO | WO 2012/068106 | 5/2012 |
| WO | WO 2012/071519 | 5/2012 |
| WO | WO 2012/097000 A1 | 7/2012 |
| WO | WO 2012/121953 A1 | 9/2012 |
| WO | WO 2012/129562 | 9/2012 |
| WO | WO 2012/135750 | 10/2012 |
| WO | WO 2012/136549 | 10/2012 |
| WO | WO 2013/006532 | 1/2013 |
| WO | WO 2013/012915 A1 | 1/2013 |
| WO | WO 2013/013504 | 1/2013 |
| WO | WO 2013/013505 | 1/2013 |
| WO | WO 2013/025498 | 2/2013 |
| WO | WO 2013/044169 | 3/2013 |
| WO | WO 2013/059738 A2 | 4/2013 |
| WO | WO 2013/066483 | 5/2013 |
| WO | WO 2013/074583 | 5/2013 |
| WO | WO 2013/086131 | 6/2013 |
| WO | WO 2013/090725 | 6/2013 |
| WO | WO 2013/113838 | 8/2013 |
| WO | WO 2013/113841 | 8/2013 |
| WO | WO 2013/188763 | 12/2013 |
| WO | WO 2014/004470 | 1/2014 |
| WO | WO 2014/018567 A1 | 1/2014 |
| WO | WO 2014/046617 | 3/2014 |
| WO | WO 2014/071105 | 5/2014 |
| WO | WO 2014/071109 A1 | 5/2014 |
| WO | WO 2014/071125 A1 | 5/2014 |
| WO | WO 2014/072937 A1 | 5/2014 |
| WO | WO 2014/075393 | 5/2014 |
| WO | WO 2014/124458 | 8/2014 |
| WO | WO 2014/141165 | 9/2014 |
| WO | WO 2014/168975 | 10/2014 |
| WO | WO 2014/175267 | 10/2014 |
| WO | WO 2014/194254 A1 | 12/2014 |
| WO | WO 2014/203959 | 12/2014 |
| WO | WO 2015/002729 | 1/2015 |
| WO | WO 2015/010641 A1 | 1/2015 |
| WO | WO 2015/037005 | 3/2015 |
| WO | WO 2015/051252 | 4/2015 |
| WO | WO 2015/054099 | 4/2015 |
| WO | WO 2015/054355 | 4/2015 |
| WO | WO 2015/081127 | 6/2015 |
| WO | WO 2015/083008 | 6/2015 |
| WO | WO 2015/095807 | 6/2015 |
| WO | WO 2015/095819 | 6/2015 |
| WO | WO 2015/095825 | 6/2015 |
| WO | WO 2015/095829 | 6/2015 |
| WO | WO 2015/095831 | 6/2015 |
| WO | WO 2015/095834 | 6/2015 |
| WO | WO 2015/095838 | 6/2015 |
| WO | WO 2015/095840 | 6/2015 |
| WO | WO 2015/095842 | 6/2015 |
| WO | WO 2015/109286 | 7/2015 |
| WO | WO 2015/143382 | 9/2015 |
| WO | WO 2015/160975 | 10/2015 |
| WO | WO 2015/160986 | 10/2015 |
| WO | WO 2015/175966 | 11/2015 |
| WO | WO 2015/179772 | 11/2015 |
| WO | WO 2015/181053 | 12/2015 |
| WO | WO 2015/181055 | 12/2015 |
| WO | WO 2015/188119 | 12/2015 |

OTHER PUBLICATIONS

Ali et al., "Essential role for the p110δ phosphoinositide 3-kinase in the allergic response," *Nature* 431:1007-11 (2004).
Ali et al., "Isoform-Specific Functions of Phosphoinositide 3-Kinases p110δ but Not p110γ Promotes Optimal Allergic Responses In Vivo," *J. Immunol.* 180:2538-44 (2008).
Asbahr et al., "Obsessive-Compulsive and Related Symptoms in Children and Adolescents With Rheumatic Fever With and Without Chorea: A Prospective 6-Month Study," *Am. J. Psychiatry* 155:1122-1124 (1998).
Barber et al., "Class $I_B$-Phosphatidylinositol 3-Kinase (PI3K) Deficiency Ameliorates $I_A$-PI3K-Induced Systemic Lupus but Not T Cell Invasion," *J. Immunol.* 176(1):589-93 (2006).
Bartok et al., "Phosphoinositide 3-Kinase Delta (PI3K) Regulation and Function in RA," *Arthritis Rheum.* 62(Suppl 10):362 (2010).
Berge et al., "Pharmaceutical Salts," *J. Pharm. Sci.* 66(1):1-19 (1977).
Bilancio et al., "Key role of the p110δ isoform of PI3K in B-cell antigen and IL-4 receptor signaling: comparative analysis of genetic and pharmacologic interference with p110δ function in B cells," *Blood* 107(2):642-50 (2006).
Bolland et al., "Spontaneous Autoimmune Disease in FcγRIIB-Deficient Mice Results from Strain-Specific Epistasis," *Immunity* 13:277-285 (2000).
Buchwald et al., "Long-term, continuous intravenous heparin administration by an implantable infusion pump in ambulatory patients with recurrent venous thrombosis," *Surgery* 88(4):507-516 (1980).
Bundgaard, "Design of prodrugs: Bioreversible derivatives for various functional groups and chemical entities," *Design of Prodrugs*, pp. 1-92 (Elsevier, Amsterdam, 1985).
Condliffe et al., "Sequential activation of class IB and class IA PI3K is important for the primed respiratory burst of human but not murine neutrophils," *Blood* 106(4):1432-1440 (2005).
Dil et al., "Role of phosphoinositide 3-kinase p110δ in TLR4- and TLR9-mediated B cell cytokine production and differentiation," *Mol. Immunol.* 46(10):1970-1978 (2009).
Donahue et al., "Measuring Phosphorylated Akt and Other Phosphoinositide 3-kinase-Regulated Phosphoproteins in Primary Lymphocytes," *Methods Enzymol.* 434:131-54 (2007).
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," *J. Pharmacol. Exp. Ther.* 328(3):758-65 (2009).
Durand et al., "Phosphoinositide 3-Kinase p110δ Regulates Natural Antibody Production, Marginal Zone and B-1 B Cell Function, and Autoantibody Responses," *J. Immunol.* 183:5673-84 (2009).
Furman et al., "Interim results from a phase I study of CAL-101, a selective oral inhibitor of phosphatidylinositol 3-kinase p110d isoform, in patients with relapsed or refractory hematologic malignancies," *J. Clin. Oncol.* 28(15_suppl):3032 (ASH Annual Meeting 2010).
Gaestel et al., "Protein kinases as small molecule inhibitor targets in inflammation," *Curr. Med. Chem.* 14(21):2214-2234 (2007).
Garçon et al., "CD28 provides T-cell costimulation and enhances PI3K activity at the immune synapse independently of its capacity to interact with the p85/p110 heterodimer," *Blood* 111(3):1464-71 (2008).
Garvey et al., "PANDAS: The Search for Environmental Triggers of Pediatric Neuropsychiatric Disorders. Lessons from Rheumatic Fever," *J Child Neurol.* 13:413-423 (1998).
Garvey et al., "Treatment of Sydenham's Chorea With Intravenous Immunoglobulin, Plasma Exchange, or Prednisone," *J. Child Neurol.* 20:424-429 (2005).
Geng et al., "A Specific Antagonist of the p110δ Catalytic Component of Phosphatidylinositol 3'-Kinase, IC486068, Enhances Radiation-Induced Tumor Vascular Destruction," *Cancer Res.* 64(14):4893-4899 (2004).
Goodson, "Dental Applications," *Medical Applications of Controlled Release* 2:115-138 (1984).
Guo et al., "The p110δ of PI3K plays a critical role in NK cell terminal maturation and cytokine/chemokine generation," *J. Exp. Med.* 205(10):2419-2435 (2008).
Harris et al., "PI3K isoforms as drug targets in inflammatory diseases: Lessons from pharmacological and genetic strategies," *Curr. Opin. Investig. Drugs* 10(11):1151-1162 (2009).
Hirschtritt et al., "Executive and Attention Functioning Among Children in the PANDAS Subgroup," *Child Neuropsychol.* 15:179-194 (2009).

(56) References Cited

OTHER PUBLICATIONS

Hoellenriegel et al., "Spleen Tyrosine Kinase (Syk) Inhibitors Block B Cell Receptor Signaling and Survival in Chronic Lymphocytic Leukemia," *Blood* 116:3604 (ASH Annual Meeting Abstracts 2010).
Hoffman et al., "A Murine Model for Neuropsychiatric Disorders Associated with Group A β-Hemolytic Streptococcal Infection," *J. Neurosci.* 24(7):1780-1791 (2004).
Hollander et al., "B Lymphocyte Antigen 08/17 and Repetitive Behaviors in Autism," *Am. J. Psychiatry* 156:317-320 (1999).
Jarmin et al., "T cell receptor-induced phosphoinositide-3-kinase p110δ activity is required for T cell localization to antigenic tissue in mice," *J. Clin. Invest.* 118(3):1154-1164 (2008).
Ji et al., "Inactivation of PI3Kγ and PI3Kδ distorts T-cell development and causes multiple organ inflammation," *Blood* 110:2940-2947 (2007).
Kahl et al., "Clinical Safety and Activity in a Phase 1 Study of CAL-101, An Isoform-Selective Inhibitor of Phosphatidylinositol 3-Kinase P110δ, In Patients with Relapsed or Refractory Non-Hodgkin Lymphoma," *Blood* 116:1777 (ASH Annual Meeting Abstracts 2010).
Kashishian et al., "Anti-tumor activity of CAL-101, a potent selective inhibitor of the p110δ isoform of PI3K, in models of human glioblastoma," (AACR Annual Meeting Abstracts 2011).
Kim et al., "The multiple roles of phosphoinositide 3-kinase in mast cell biology," *Trends Immunol.* 29(10):493-501 (2008).
Kim et al., "The p110delta catalytic isoform of PI3K is a key player in NK-cell development and cytokine secretion," *Blood* 110:3202-3208 (2007).
Kirvan et al., "Antibody-mediated neuronal cell signaling in behavior and movement disorders," *J. Neuroimmunol.* 179:173-179 (2006).
Konrad et al., "Phosphoinositide 3-Kinases γ and δ, Linkers of Coordinate C5a Receptor-Fcγ Receptor Activation and Immune Complex-induced Inflammation," *J. Biol. Chem.* 283(48):33296-33303 (2008).
Kurlan et al., "The Pediatric Autoimmune Neuropsychiatric Disorders Associated With Streptococcal Infection (PANDAS) Etiology for Tics and Obsessive-Compulsive Symptoms: Hypothesis or Entity? Practical Considerations for the Clinician," *Pediatrics* 113(4):883-886 (2004).
Langer, "New Methods of Drug Delivery," *Science* 249:1527-1533 (1990).
Lee et al. "Phosphoinositide 3-kinase-d inhibitor reduces vascular permeability in a murine model of asthma," *J. Allergy Clin. Immunol.* 118:403-409 (2006).
Lee et al., "Inhibition of phosphoinositide 3-kinase δ attenuates allergic airway inflammation and hyperresponsiveness in murine asthma model," *FASEB J.* 20:455-465 (2006).
Leslie et al., "Neuropsychiatric Disorders Associated With Streptococcal Infection: A Case-Control Study Among Privately Insured Children," *J. Am. Acad. Child Adolesc. Psychiatry* 47(10):1166-1172 (2008).
Liu et al., "The p110δ Isoform of Phosphatidylinositol 3-Kinase Controls the Quality of Secondary Anti-Leishmania Immunity by Regulating Expansion and Effector Function of Memory T Cell Subsets," *J. Immunol.* 184:3098-3105 (2010).
Lucas et al., "Design of 1-piperazinyl-4-arylphthalazines as potent Smoothened antagonists," *Bioorg. Med. Chem. Lett.* 20:3618-3622 (2010).
Margutti et al., "Autoantibodies Associated with Psychiatric Disorders," *Curr. Neurovasc. Res.* 3(2):149-157 (2006).
Marwick et al., "Inhibition of PI3K6 Restores Glucocorticoid Function in Smoking-induced Airway Inflammation in Mice," *Am. J. Respir. Crit. Care Med.* 179:542-548 (2009).
Okkenhaug et al., "Impaired B and T Cell Antigen Receptor Signaling in p110γ PI 3-Kinase Mutant Mice," *Science* 297:1031-1034 (2002).
Okkenhaug et al., "The p110δ Isoform of Phosphoinositide 3-Kinase Controls Clonal Expansion and Differentiation of Th Cells," *J. Immunol.* 177:5122-5128 (2006).

Pan et al., "Discovery of NVP-LDE225, a Potent and Selective Smoothened Antagonist," *ACS Med. Chem. Lett.* 1:130-134 (2010).
Peterson et al., "Preliminary Findings of Antistreptococcal Antibody Titers and Basal Ganglia Volumes in Tic, Obsessive-compulsive, and Attention-Deficit/Hyperactivity Disorders," *Arch. Gen. Psychiatry* 57:364-372 (2000).
Pinho et al., "Tissue- and Stimulus-Dependent Role of Phosphatidylinositol 3-Kinase Isoforms for Neutrophil Recruitment Induced by Chemoattractants In Vivo," *J. Immunol.* 179:7891-7898 (2007).
Randis et al., "Role of PI3Kδ and PI3Kγ in inflammatory arthritis and tissue localization of neutrophils," *Eur. J. Immunol.* 38:1215-1224 (2008).
Reif et al., "Cutting Edge: Differential Roles for Phosphoinositide 3-Kinases, p110γ and p110δ, in Lymphocyte Chemotaxis and Homing," *J. Immunol.* 173:2236-2240 (2004).
Robarge et al., "GDC-0449—A potent inhibitor of the hedgehog pathway," *Bioorg. Med. Chem. Lett.* 19:5576-5581 (2009).
Rominger et al., "Evidence for Allosteric Interactions of Antagonist Binding to the Smoothened Receptor," *J. Pharmacol. Exp. Ther.* 329(3):995-1005 (2009).
Rudin et al., "Treatment of Medulloblastoma with Hedgehog Pathway Inhibitor GDC-0449," *N. Engl. J. Med.* 361(12):1173-1178 (2009).
Rudolph et al., "Cytogenetic characterization of a BCR-ABL transduced mouse cell line," *Cancer Genet. Cytogenet.* 161(1):51-56 (2005).
Sadhu et al., "Essential Role of Phosphoinositide 3-Kinase δ in Neutrophil Directional Movement," *J. Immunol.* 170:2647-2654 (2003).
Saudek et al., "A Preliminary Trial of the Programmable Implantable Medication System for Insulin Delivery," *N. Engl. J. Med.* 321(9):574-579 (1989).
Saudemont et al., "p110γ and p110δ isoforms of phosphoinositide 3-kinase differentially regulate natural killer cell migration in health and disease," *Proc. Natl. Acad. Sci.* 106(14):5795-5800 (2009).
Sefton, "Implantable Pumps," *Crit. Rev. Biomed. Eng.* 14(3):201-240 (1987).
Singh et al, "In vitro Metabolism of a Potent HIV-protease Inhibitor (141W94) Using Rat, Monkey and Human Liver S9," *Rapid Commun. Mass Spectrom.* 10:1019-1026 (1996).
Siu et al., "A first-in-human, phase I study of an oral hedgehog (HH) pathway antagonist, BMS-833923 (XL139), in subjects with advanced or metastatic solid tumors," *J. Clin. Oncol.* 28(15_suppl):2501 (ASCO Annual Meeting Abstracts 2010).
Sokol et al., "D8/17 Expression on B Lymphocytes in Anorexia Nervosa," *Am. J. Psychiatry* 159:1430-1432 (2002).
Sokol, "Infection-Triggered Anorexia Nervosa in Children: Clinical Description of Four Cases," *J. Child Adolesc. Psychopharmacol.* 10(2):133-145 (2000).
Tassi et al., "p110γ and p110δ Phosphoinositide 3-Kinase Signaling Pathways Synergize to Control Development and Functions of Murine NK Cells," *Immunity* 27:214-227 (2007).
Vanhaesebroeck et al., "Synthesis and Function of 3-phosphorylated Inositol Lipids," *Annu. Rev. Biochem.* 70:535-602 (2001).
Von Hoff et al., "Inhibition of the Hedgehog Pathway in Advanced Basal-Cell Carcinoma," *N. Engl. J. Med.* 361(12):1164-1672 (2009).
Webb et al., "Clinical Pharmacokinetics of CAL-101, a p110δ Isoform-Selective PI3K Inhibitor, Following Single- and Multiple-Dose Administration in Healthy Volunteers and Patients with Hematological Malignancies," *Blood* 116:1774 (ASH Annual Meeting Abstracts 2010).
Webb et al., "Cutting Edge: T Cell Development Requires the Combined Activities of the p110γ and p110δ Catalytic Isoforms of Phosphatidylinositol 3-Kinase," *J. Immunol.* 175:2783-2787.
Wilen et al., "Strategies in Optical Resolutions," *Tetrahedron* 33:2725-2736 (1977).
Wilen, Tables of Resolving Agents and Optical Resolutions pp. 268-298 (Univ. of Notre Dame Press, 1972).
Williams et al., "Discovery of Dual Inhibitors of the Immune Cell PI3Ks p110δ and p110γ: a Prototype for New Anti-inflammatory Drugs," *Chem. Biol.* 17:123-134 (2010).

(56) References Cited

OTHER PUBLICATIONS

Wu et al., "Shared signaling networks active in B cells isolated from genetically distinct mouse models of lupus," *J. Clin. Invest.* 117(8):2186-2196 (2007).
Yaddanapudi et al., "Passive transfer of *Streptococcus*-induced antibodies reproduces behavioral disturbances in a mouse model of pediatric autoimmune neuropsychiatric disorders associated with streptococcal infection," *Mol. Psychiatry* 15:712-726 (2010).
Yauch et al., "Smoothened Mutation Confers Resistance to a Hedgehog Pathway Inhibitor in Medulloblastoma," *Science* 326:572-574 (2009).
Zhang et al., "Genetic or pharmaceutical blockade of p110δ phosphoinositide 3-kinase enhances IgE production," *J. Allergy Clin. Immunol.* 122(4):811-819 (2008).
Abdel-Mohsen, "Synthesis, Reactions and Antimicrobial Activity of 2-Amino-4-(8-quinolino1-5-yI)-1-(p-tolyl)-pyrrole-3-carbonitrile," *Bull. Korean Chem. Soc.* 26(5):719-728 (2005).
Abe et al., "T cell receptor-mediated recognition of self-ligand induces signaling in immature thymocytes before negative selection," *J. Exp. Med.* 176(2):459-468 (1992).
Abrahamian et al., "Immunological and Clinical Profile of Adult Patients with Selective Immunoglobulin Subclass deficiency: response to intravenous immunoglobulin therapy," *Clin. Exp. Immunol.* 159(3):344-350 (2010).
Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).
Ames et al., "Heterocyclic Syntheses from o-Halogen-acids. Part II. Thienopyridinones and Thienopyranones from 3-Bromothiophen-2- and 4-Bromothiophen-3-carboxylic Acids," *J.C.S. Perkin I* 1390-1395 (1975).
Anderson et al., "Paradoxical inhibition of T-cell function in response to CTLA-4 blockade; heterogeneity within the human T-cell population," *Nat. Med.* 6(2):211-214 (2000).
Andrews et al., "Effects of the 11β-hydroxysteroid dehydrogenase inhibitor carbenoxolone on insulin sensitive in men with type 2 diabetes," *J. Clin. Endocrinol. Metab.* 88(1):285-291 (2003).
Arcaro et al., "Wortmannin is a potent phosphatidylinositol 3-kinase inhibitor: the role of phosphatidylinositol 3,4,5-triphosphate in neutrophil responses," *Biochem. J.*, 296(Pt 2):297-301 (1993).
Arnold et al., "Pyrrolo[2,3-d]pyrimidines containing an extended 5-substituent as potent and selective inhibitors of Ick I," *Bioorg. Med. Chem. Lett.* 10(19):2167-2170 (2000).
Augustine et al., "Interleukin 2- and polyomavims middle T antigen-induced modification of phosphatidylinositol 3-kinase activity in activated T lymphocytes," *Mol. Cell. Biol.* 11(9):4431-4440 (1991).
Baggiolini et al., "Inhibition of the phagocytosis-induced respiratory burst by the fungal metabolite wortmannin and some analogues," *Exp. Cell. Res.* 169(2): 408-418 (1987).
Ballell et al. "New Thiopyrazolo[3,4-d] pyrimidine derivatives as anti-mycobacterial agents," *Bioorg. Med. Chem. Lett.* 17(6):1736-1740 (2007).
Banker et al., Modern Pharmaceutics, pp. 451, 596, 3$^{rd}$ ed, Marcel Dekker, New York (1996).
Bansal et al., "The Molecular Biology of Endometrial Cancers and the Implications for Pathogenesis, Classification, and Targeted Therapies," *Cancer Control* 16(1):8-13 (2009).
Barber et al., "PI3Kgamma inhibition blocks glomerulonephritis and extends lifespan in a mouse model of systemic lupus," *Nat. Med.* 11(9):933-935 (2005). (Epub Aug. 28, 2005).
Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).
Bartholomeusz et al., "Targeting the PI3K Signaling Pathway in Cancer Therapy," *Expert Opin. Ther. Targets* 16(1):121-130 (2012).
Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.
Beeram et al., "Akt-induced endocrine therapy resistance is reversed by inhibition of mTOR signaling," *Ann Oncol.* 18(8):1323-1328 (2007).
Bell et al., "Glucokinase mutations insulin secretion, and diabetes mellitus", *Annu. Rev. Physiol.* 58:171-186 (1996).
Berndt et al., "The p110δ crystal structure uncovers mechanisms for selectivity and potency of novel PI3K inhibitors," *Nat. Chem. Biol.* 6(2):117-124 (2010).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bi et al., "Proliferative defect and embryonic lethality in mice homozygous for a deletion in the p110α subunit of phosphoinositide 3-kinase," *J. Biol. Chem.* 274:10963-10968 (1999).
Billottet et al., "A selective inhibitor of the p110δ isoform of PI 3-kinase inhibits AML cell proliferation and survival and increases the cytotoxic effects of VP16," *Oncogene* 25:6648-6659 (2006).
Billottet et al "Inhibition of Class 1 Phosphoinositide 3-Kinase Activity Impairs , Proliferation and Triggers Apoptosis in Acute Promyelocytic Leukemia without Affecting Atra-Induced Differentiation," *Cancer Res.* 69(3):1027-1036 (2009).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bochner et al., "Immunological aspects of allergic asthma," *Annu. Rev. Immunol.* 12:295-335 (1994).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Bowers et al., "A platelet biomarker for assessing phosphoinositide 3-kinase inhibition during cancer chemotherapy," *Mol. Cancer Ther.* 6(9):2600-2607 (2007).
Brzezianska et al., "A Minireview: The Role of MAPK/ERK and PI3K/Akt Pathways in Thyroid Follicular Cell-Derived Neoplasm," *Front. Biosci.* 16:422-439 (2011).
Buitenhuis et al., "The role of the PI3k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger et al., "Phosphoinositide 3'-kinase delta: turning off BCR signaling in Chronic Lymphocytic Leukemia," *Oncotarget* 2(10):737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Campora et al., "Binuclear complexes of nickel bridged by hydrocarbon ligands. Isocyanide insertion chemistry and amide formation by intramolecular coupling of acyl and imidoyl functionalities," *Organometallics* 11(1):11-13 (1992).
Campora et al., "Isocyanide insertion chemistry. Synthesis and structural characterization of bridging imidoyl complexes of nickel and amide formation by intramolecular coupling of acyl and imidoyl functionalities," *Organometallics* 12(10):4025-4031 (1993).
Camps et al., "Blockade of PI3Kγ suppresses joint inflammation and damage in mouse models of rheumatoid arthritis," *Nat. Med.* 11(9):936-943 (2005).

(56) References Cited

OTHER PUBLICATIONS

Chaisuparat et al., "Dual inhibition of PI3Kα and mTOR as an alternative treatment for Kaposi's Sarcoma," *Cancer Res.* 68:8361-8368 (2008).
Chang et al., "The Bruton tyrosine kinase inhibitor PCI-32765 ameliorates autoimmune arthritis by inhibition of multiple effector cells," *Arthritis Research & Therapy* 13:R115 (2011).
Chappelow et al., "Neovascular age-related macular degeneration: potential therapies," *Drugs* 68(8):1029-1036 (2008).
Chapuis et al., "Dual Inhibition of PI3K and mTORC1/2 Signaling by NVP-BEZ235 as a New Therapeutic Strategy for Acute Myeloid Leukemia," *Clin. Cancer Res.* 16(22):5424-5435 (2010).
Chawla et. al., "Challenges in Polymorphism of Pharmaceuticals," *Current Research & Information on Pharmaceutical Science* 5(1):9-12 (2004).
Chen et al., "Characterization of Structurally Distinct, Isoform-Selective Phosphoinositide 3'-Kinase Inhibitors in Combination with Radiation in the Treatment of Glioblastoma," *Mol. Cancer Ther.* 7(4):841-850 (2008).
Cheson et al., "Bendamustine: Rebirth of an Old Drug," *J. Clin. Oncol.* 27(9):1492-1501 (2009).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A novel synthesis of benzo[c]phenanthridine skeleton and biological evaluation of isoquinoline derivatives," *Chem. Pharm. Bull.*(Tokyo) 47(6):900-902 (1999).
Clayton et al., "A crucial role for the p110delta subunit of phosphatidylinositol 3-kinase in B cell development and activation," *J. Exp. Med.* 196:753-763 (2002).
Closse et al., "2,3-dihydrobenzofuran-2-ones: a new class of highly potent antiinflammatory agents," *J. Med. Chem.* 24:1465-1471 (1981).
Courtney et al., "The PI3K Pathway as Drug Target in Human Cancer," *J. Clin. Oncol.* 28(6):1075-1083 (2010).
Cox et al., "Human colorectal cancer cells efficiently conjugate the cyclopentenone prostaglandin, prostaglandin $J_2$, to glutathione," *Biochem. Biophys. Acta.* 1584:37-45 (2002).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
David S et al., "Decreased mitochondrial apoptotic priming underlies stroma-mediated treatment resistance in chronic lymphocytic leukemia," *Blood* 120(17):3501-3509 (2012).
Davies et al., "The Human T3 γ Chain is Phosphorylated at Serine 126 in Response to T Lymphocyte Activation," *J. Biol. Chem.* 262(23):10918-10921 (1987).
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide," *Synthetic Commun.* 27(17):2961-2969 (1997).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).

Dijksman et al., "271.1 : 2-dihydro-2-thianaphthalene derivatives. Part I. Preparation and reactions of 1 : 2-dihydro-1-keto-2-thianaphthalenes," *J. Chem. Soc.* 1213-1218 (1951).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
Donati, G., "Emerging therapies for neovascular age-related macular degeneration: state of the art," *Ophthalmologica* 221(6):366-377 (2007).
European Examination Report for EP Application No. 07873406.8 dated Sep. 14, 2011.
European Search Report for EP Application No. 05857011.0 dated Feb. 4, 2011.
European Search Report for EP Application No. 09700784.3 dated Oct. 28, 2011.
European Search Report and Search Opinion for EP Application No. 09700424.6 dated Oct. 26, 2011.
European Search Report for EP Application No. 07873406.8 dated Mar. 1, 2010.
European Search Report for EP Application No. 07754845.1 dated Sep. 20, 2011.
Examination Report for GB Application No. GB 0819947.3 dated Oct. 27, 2010.
Extended European Search Report for EP Application No. 09816603.6 dated Mar. 19, 2012.
Extended European Search Report from European Application No. 09700784.3 dated Oct. 28, 2011.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Feldman et al., "Active-Site Inhibitors of mTOR Target Rapamycin-Resistant Outputs of mTORC1 and mTORC2," *PLoS Biol.* 7(2):371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46, (1975).
Flinn et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," *J. Clin. Oncol.* 27(15s) (Suppl: Abstr 3543) (2009).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C—C bonds on solid support," *Can. J. Chem.* 78:957-962 (2000).
Funder et al., "Mineralocorticoid action: target tissue specificity is enzyme, not receptor, mediated," *Science* 242:583-585 (1998).
Fung-Leung, W. P., "Phosphoinositide 3-kinase delta (PI3Kδ) in leukocyte signaling and function," *Cell Signal* 23:603-608 (2011).
Furukawa, T., "Molecular Targeting Therapy for Pancreatic Cancer: Current Knowledge and Perspectives from Bench to Bedside," *J. Gastroenterol.* 43(12):905-911 (2008).
Garber et al., "Diversity of gene expression in adenocarcinoma of the lung," *Proc. Natl. Acad. Sci. U.S.A.* 98(24):13784-13789 (2001).
Gillespie et al., "Antagonists of the human adenosine $A_{2A}$ receptor. Part 3: Design and synthesis of pyrazolo[3,4-d]pyrimidines, pyrrolo[2,3-d]pyrimidines and 6-arylpurines," *Bioorg. Med. Chem. Lett.* 18(9):2924-2929 (2008).
Gonzalez et al., "Protection against daunorubicin cytotoxicity by expression of a cloned human carbonyl reductase cDNA in K562 leukemia cells," Cancer Res. 55(20):4646-4650 (1995).

(56) References Cited

OTHER PUBLICATIONS

Graber et al., "The protein tyrosine kinase inhibitor herbimycin A, but not genistein, specifically inhibits signal transduction by the T cell antigen receptor," *Int. Immunol.* 4(1):1201-1210 (1992).
Graupera et al., "Angiogenesis selectively requires the p110α isoform of PI3K to control endothelial cell migration," *Nature* 453(7195):662-666 (2008).
Gunther et al., "Acute pathological effects on rats of orally administered wortmannin-containing preparations and purified wortmannin from Fusarium oxysporum," *Food Chem. Toxicol.* 27(3):173-179 (1989).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Haluska et al., "The RTK/RAS/BRAF/PI3K Pathways in Melanoma: Biology, Small Molecule Inhibitors, and Potential Applications," *Semin. Oncol.* 34(6):546-554 (2007).
Hanefeld et al., "One-pot synthesis of tetrasubstituted pyrazoles proof of regiochemistiy," *J. Chem. Soc. Perkin 1* 1545-1552 (1996).
Harada et al., "Novel role of phosphatidylinositol 3-kinase in CD28-mediated costimulation," *J. Biol. Chem.* 276(12):9003-9008 (2001).
Harding et al., "CD28-mediated signalling co-stimulates murine T cells and prevents induction of anergy in T-cell clones," *Nature* 356(6370):607-609 (1992).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Hellwinkel et al., "Heterocyclensynthesen mit MF/Al2O3-basensystemen; 2-arylbenzofurane and 2,3-diarylisochinolin-1(2H)-one," *Synthesis* 1995(9):1135-1141 (1995).
Herishanu et al., "The lymph node microenvironment promotes B-cell receptor signaling, NF-κB activation, and tumor proliferation in chronic lymphocytic leukemia," *Blood* 117(2):563-574 (2011).
Herman et al., "Phosphatidylinositol 3-kinase-δ inhibitor CAL-101 shows promising preclinical activity in chronic lymphocytic leukemia by antagonizing intrinsic and extrinsic cellular survival signals," *Blood* 116(12):2078-2088 (2010).
Herman et al., "The role of phosphatidylinositol 3-kinase-δ in the immunomodulatory effects of lenalidomide in chronic lymphocytic leukemia," *Blood* 117(16):4323-4327 (2011).
Herrera et al., "The dual PI3K/mTOR inhibitor BEZ235 is effective in lung cancer cell lines," *Anticancer Res.* 31:849-854 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).

Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
Ikeda et al., "P13K/p110δ is a novel therapeutic target in multiple myeloma," *Blood* 116(9):1460-1468 (2010).
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Preliminary Report on Patentability for PCT/US2009/000042 dated Jul. 6, 2010.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939, dated Nov. 5, 2010.
International Search Report and Written Opinion for PCT/US2012/047190 dated Oct. 2, 2012.
International Search Report and Written Opinion for PCT/US2012/020831 dated May 2, 2012.
International Search Report for PCT/US2011/037412 dated Aug. 22, 2011.
International Search Report for PCT/US1995/005213 dated Aug. 21, 1995.
International Search Report for PCT/US2007/008395 (4 pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2005/042524 (7 pages) dated Oct. 2, 2006.
International Search Report for PCT/US2007/008355 dated Sep. 25, 2008.
International Search Report for PCT/US2009/060985 dated Jun. 28, 2010.
International Search Report for PCT/US2010/002020 dated Nov. 2, 2010.
Ishiyama et al., "A stoichiometric aromatic C—H borylation catalyzed by iridium(I)/2,2'-bipyridine complexes at room temperature," *Angew. Chem. Int. Ed. Engl.* 41(16):3056-3058 (2002).
Ishiyama et al., "Mild iridium-catalyzed borylation of arenes. High turnover numbers, room temperature reactions, and isolation of a potential intermediate," *J. Am. Chem. Soc.* 124(3):390-391 (2002).
Jackson et al., "PI 3-kinase p110β: a new target for antithrombotic therapy," *Nat. Med.* 11:507-514 (2005).
Jimeno et al., "Phase I Trial of PX-866, a Novel Phosphoinositide-3-Kinase (PI-3K) Inhibitor," *J. Clin. Oncol.* 27:15s (Suppl; Abstract 3542) (2009).
Johnson et al., "Accessory cell-derived signals required for T cell activation," *Immunol. Res.* 48-64 (1993).
Jou et al., "Essential, nonredundant role for the phosphoinositide 3-kinase p110delta in signaling by the B-cell receptor complex," *Mol. Cell. Biol.* 22:8580-8591 (2002).

(56) References Cited

OTHER PUBLICATIONS

June et al., "Evidence for the involvement of three distinct signals in the induction of IL-2 gene expression in human T lymphocytes," *J. Immunol.* 143(1):153-161 (1989).
June et al., "Inhibition of tyrosine phosphorylation prevents T-cell receptor mediated signal transduction," *Proc. Natl. Acad. Sci. U.S.A.* 87:7722-7726 (1990).
June et al., "Role of CD28 receptor in T-cell activation," *Immunol. Today* 11(6):211-216 (1990).
June, C.H., "Signaling transduction in T cells," *Curr. Opin. Immunol.* 3(3):287-293 (1991).
Kajita et al., "Nickel-catalyzed decarbonylative addition of phthalimides to alkynes," *J. Am. Chem. Soc.* 130(19):6058-6059 (2008).
Kallberg et al., "Short-chain dehydrogenase/reductase (SDR) relationships: a large family with eight clusters common to human, animal, and plant genomes," *Protein Sci.* 11(3):636-641 (2002).
Kallberg et al., "Short-Chain Dehydrogenases/Reductases (SDRs)—Coenzyme-Based Functional Assignments in Completed Genomes," *Eur. J. Biochem.* 269(18):4409-4417 (2002).
Kang et al., "Oncogenic transformation induced by the p110β, -γ, and -δ7 isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8): 1097-1104 (1985).
Khwaja, a., "PI3K as a Target for Therapy in Haematological Malignancies," *Curr. Top. Microbiol. Immunol.* 347:169-188 (2010).
Kim et al., "Activation and Function of the mTORC1 Pathway in Mast Cells," *J. Immunol.* 180(7):4586-4595 (2008).
Knight et al., "A Pharmacological Map of the PI3-K Family Defines a Role for p110α in Insulin Signaling," *Cell* 125(4):733-747 (2006).
Kong, D. and Yamori, T., "Advances in Development of Phosphatidylinositol 3-Kinase Inhibitors," *Curr. Med. Chem.* 16:2839-2854 (2009).
Kost et al., "Recyclization of 3-Alkyl- and 1,3-Dialkylisoquinolinium Salts to Naphthylamines," *Chemistry of Heterocyclic Compounds* 16(9): 965-970 (1981).
Kraybill et al., "Inhibitor scaffolds as new allele specific kinase substrates," *J. Am. Chem. Soc.* 124(41):12118-12128 (2002).
Kreutzberger et al. "5-Substituierte 4-Aminopyrimidine durch Aminomethinylierung von Acetonitrilen," *Liebigs Ann. Chem.* 537-544 (1977).
Kulkarni et al., "PI3Kbeta plays a critical role in neutrophil activation by immune complexes," *Sci. Signal* 2011, vol. 4, ra23.
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc. Perkin 1* 8:857-862 (1978).
Kundu et al., "Palladium-catalysed heteroannualation with terminal alkynes; a highly regio- and stereoselective synthesis of (Z)-3-aryl(alkyl)idene isoindolin-1-ones," *Tetrahedron* 56(27):4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Kwok et al., "The anti-inflammatory natural product parthenolide from the medicinal herb Feverfew directly binds to and inhibits IκB kinase," *Chem. Biol.* 8(8):759-766 (2001).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Larabi et al., "Crystal Structure and Mechanism of Activation of TANK-Binding Kinase 1," *Cell Reports* 3:734-746 (2013).
Ledbetier et al., "CD28 ligation in T-cell activation: evidence for two signal transduction pathways," *Blood* 75(7):1531-1539 (1990).
Ledbetter et al., "Crosslinking of surface antigens causes mobilization of intracellular ionized calcium in T lymphocytes," *Proc. Natl. Acad. Sci. U. S. A.* 84(5):1384-1388 (1987).

Lee et al., "All roads lead to mTOR: integrating inflammation and tumor angiogenesis," *Cell Cycle* 6(24):3011-3014 (2007).
Lee et al., "The CD28 signal transduction pathway in T cell activation", Advances in Cell Regulation of Cell Growth, vol. 2, pp. 141-160, New York: Raven Press, Ltd. (1991).
Ley et al., "The T cell receptor/CD3 complex and CD2 stimulate the tyrosine phosphorylation of indistinguishable patterns of polypeptides in the human T leukemic cell line Jurkat," *Eur. J. Immunol.* 21(9):2203-2209 (1991).
Li et al., "Roles of PLC-beta2 and -beta3 and PI3Kgamma in chemoattractant-mediated signal transduction," *Science* 287(5455):1046-1049 (2000).
Liu et al., "Costimulation of T-cell growth," *Curr. Opin. Immunol.* 4(3):265-270 (1992).
Lu et al., "CD28-induced T cell activation. Evidence for a protein-tyrosine kinase signal transduction pathway," *J. Immunol.* 149(1):24-29 (1992).
Majumder et al., "mTOR inhibition reverses Akt-dependent prostate intraepithelial neoplasia through regulation of apoptotic and HIF-1-dependent pathways," *Nat. Med.* 10(6):594-601 (2004).
Markman et al., "Status of PI3K inhibition and biomarker development in cancer therapeutics," *Ann. Oncol.* 21(4):683-691 (2010).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition as a Potential Therapeutic Strategy in Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Mayer et al., "Small molecule inhibitor of mitotic spindle bipolarity identified in a phenotype-based screen," *Science* 286(5441):971-974 (1999).
Mazzoletti and Broggini, "PI3K/AKT/mTOR inhibitors in ovarian cancer," Curr. Med. Chem. 17(36):4433-4447 (2010).
Meadows, S.A., et al., "CAL-101, a Potent Selective Inhibitor of the p110δ Isoform of Phosphatidylinositol 3-Kinase, Attenuates Pathway Signaling, Induces Apoptosis, and Overcomes Signals From the Microenvironment in Cellular Models of Hodgkin Lymphoma," Blood (ASH Annual Meeting Abstracts), 116:Abstract 3926 (2010).
Mellinghoff et al., "TORward AKTually useful mouse models," *Nat. Med.* 10(6):579-580 (2004).
Merida et al., "IL-2 binding activates a tyrosine-phosphorylated phosphatidylinositol-3-kinase," *J. Immunol.* 147(7): 2202-2207 (1991).
Miyaura et al., "Palladium-catalyzed cross-coupling reactions of organoboron compounds," *Chem. Rev.* 95(7):2457-2483 (1995).
Modi et al., "Isoquinolones; part IV—synthesis of methyl, 3-formyl & other 3-substituted N-arylisoquinolones." *Indian J Chem.* 18B:304-306 (1979).
Moon et al., "A novel microtubule destabilizing entity from orthogonal synthesis of triazine library and zebrafish embryo screening," *J. Am. Chem. Soc.* 124(39):11608-11609 (2002).
Mosmann et al., "The expanding universe of T-cell subsets: Th1, Th2 and more," *Immunology Today* 17(3):138-146 (1996).
Nakanishi et al., "Cloning and sequence analysis of a cDNA encoding tetrameric carbonyl reductase of pig lung," *Biochem. Biophys. Res. Commun.* (3):1311-1316 (1993).
Nemazanyi et al., "3-Amino-4-aryl-1(2H)-isoquinolones," *Chemistry of Heterocyclic Compounds* 27(3):307-308 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).

(56) References Cited

OTHER PUBLICATIONS

Niswender et al., "Protein engineering of protein kinase a catalytic subunits results in the acquisition of novel inhibitor sensitivity," *J. Biol. Chem.* 277(32):28916-28922 (2002).
Nobel et al., "Purification of full-length recombinant human and rat type 1 11α-hydroxysteroid dehydrogenases with retained oxidoreductase activities," *Protein Expr. Purif.* 26(3):349-356 (2002).
Norman, "Selective PI3K-delta Inhibitors, A Review of the Patent Literature," *Expert Opinion on Therapeutic Patents*, 21(11): 1773-1790 (2011).
Nunes et al., "Signalling through CD28 T-cell activation pathway involves an inositol phospholipid-specific phospholipase C activity," *Biochem. J.* 293(Pt 3):835-842 (1993).
Oda et al., "PIK3CA cooperates with other phosphatidylinositol 3'-kinase pathway mutations to effect oncogenic transformation," *Cancer Res.* 68(19):8127-8136 (2008).
Office Action dated Dec. 13, 2012 for U.S. Appl. No. 13/112,611.
Okada et al., "Essential role of phosphatidylinositol 3-kinase in insulin-induced glucose transport and antilipolysis in rat adipocytes. Studies with a selective inhibitor wortmannin," *J. Biol. Chem.* 269(5):3568-3573 (1994).
Okada et al., "Blockage of chemotactic peptide-induced stimulation of neutrophils by wortmannin as a result of selective inhibition of phosphatidylinositol 3-kinase," *J. Biol. Chem.* 269(5):3563-3567 (1994).
Oppermann et al., "Forms and functions of human SDR enzymes," *Chem. Biol. Interact.* 130-132(1-3):699-705 (2001).
O'Shea et al., "Activation of human peripheral blood T lymphocytes by pharmacological induction of protein-tyrosine phosphorylation," *Proc. Natl. Acad. Sci. U. S. A.* 89(21):10306-10310 (1992).
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one," *Chem. Pharm. Bull.* 32(6):2160-2164 (1984).
Ozol et al., "Autoxidative transformations of 2-substituted 3-alkyl-4-hydroxy-1-oxo-1, 2-dihydroisoquinolines," *Chemistry of Heterocyclic Compounds* 14(6):644-648 (1978).
Patel et al., "Immunopathological aspects of age-related macular degeneration," *Semin. Immunopathol.* 30(2):97-110 (2008).
Pérez-Blas et al., "Impaired T cell signal transduction through CD28 in a patient with idiopathic thrombocytopenia," *Clin. Exp. Immunol.* 85(3):424-428 (1991).
Persson, "Glucocorticoids for asthma—early contributions," *Pulm. Pharmacol.* 2(3):163-166 (1989).
Petrie et al., "Novel biotinylated adenylate analogue derived from pyrazolo[3,4-d]pyrimidine for labeling DNA probes," *Bioconjug. Chem.* 2(6):441-446 (1991).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Porta and Figlin, "Phosphatidylinositol-3-kinase/Akt signaling pathway and kidney cancer, and the therapeutic potential of phosphatidylinositol-3-kinase/Akt inhibitors," *J. Urol.* 182(6):2569-2577 (2009).
Prasad et al., "Phosphatidylinositol (PI) 3-kinase and PI 4-kinase binding to the CD4-p56$^{lck}$ complex: the p56$^{lck}$ domain binds to PI 3-kinase but not PI 4-kinase," *Mol. Cell. Biol.* 13(12): 7708-7717 (1993).
Prasad et al., "Src-homology 3 domain of protein kinase p59$^{fyn}$ mediates binding to phosphatidylinositol-3-kinase in T cells," *Proc. Natl. Acad. Sci. U. S. A.* 90(15): 7366-7370 (1993).
Prasad et al., "T-cell antigen CD28 interacts with the lipid kinase phosphatidylinositol 3-kinase by a cytoplasmic Tyr(P)-Met-Xaa-Met motif," *Proc. Natl. Acad. Sci. U. S. A.* 91(7): 2834-2838 (1994).
Pudlo et al., "Synthesis, antiproliferative, and antiviral activity of certain 4-substituted and 4,5 disubstituted 7[1,3-dihydroxy-2-propoxy)methyl]pyrrolo [2,3-d]pyrimidines," *J. Med. Chem.* 33(7):1984-1992 (1990).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Reif et al., "Divergent regulation of phosphatidylinositol 3-kinase P85α and P85β isoforms upon T cell activation," *J. Biol. Chem.* 268(15):10780-10788 (1993).
Report of the Expert Committee on the Diagnosis and Classification of Diabetes Mellitus, *Diabetes Care* 2( Suppl. 1):S5-S19 (1992).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Robertson, "Eicosanoids and human disease", Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Romero et al., "Cloning and expression of the bovine 1 lb-hydroxysteroid dehydrogenase type-2," *J. Steroid Biochem. Mol. Biol.* 72(5):231-237 (2000).
Rommel et al., "PI3Kδ and PI3Kγ: partners in crime in inflammation in rheumatoid arthritis and beyond?" *Nat. Rev. Immunol.* 7:191-201 (2007).
Rott et al., "Recent developments in the use of biologics in psoriasis and autoimmune disorders. The role of autoantibodies," *BMJ* 330(7493):716-720 (2005).
Rudelius et al., "Constitutive activation of Akt contributes to the pathogenesis and survival of mantle cell lymphoma," *Blood* 108(5):1668-1676 (2006).
Saif and Chu, "Biology of colorectal cancer," *Cancer J.* 16(3):196-201 (2010).
Salmena et al., "Tenets of PTEN Tumor Suppression," *Cell* 133(3):403-414 (2008).
Sarker et al., "Targeting the PI3K/AKT pathway for the treatment of prostate cancer," *Clin. Cancer Res.* 15(15):4799-4805 (2009).
Sasaki et al., "Function of PI3Kγ in Thymocyte Development, T Cell Activation, and Neutrophil Migration," *Science* 287:1040-1046 (2000).
Schwartz et al., "Quercetin inhibition of the induction and function of cytotoxic T lymphocytes," *Immunopharmacology* 4(2):125-138 (1982).
Schwartz, "A cell culture model for T lymphocyte clonal anergy," *Science* 248(4961):1349-1356 (1990).
Shapiro et al., "Phase I Dose-Escalation Study of XL147, a PI3K Inhibitor Administered Orally to Patients with Solid Tumors," *J. Clin. Oncol.* 27:146x (Suppl Abstr 3500) (2009).
Shibasaki et al., "Different properties of monomer and heterodimer forms of phosphatidylinositol 3-kinases," *Biochem. J.* 289 ( Pt 1):227-231 (1993).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118:Abstract 4964 (2011).
Singer et al., "Optimization of in situ hybridization using isotopic and non-isotopic detection methods," *Biotechniques* 4(3):230-250 (1986).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soldan et al., "Induction of daunorubicin carbonyl reducing enzymes by daunorubicin in sensitive and resistant pancreas carcinoma cells," *Biochem. Pharmacol.* 51(2):117-123 (1996).

(56) References Cited

OTHER PUBLICATIONS

Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Stanoeva et al., "Homophthalic anhydrides and their application to the synthesis of heterocyclic compounds (review)," *Chemistry of Heterocyclic Compounds* 20(12):1305-1315 (1984).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Sykes et al., "Treatment of severe autoimmune disease by stem-cell transplantation," *Nature* 35(7042):620-627 (2005).
Takeuchi et al., "Synergistic Augmentation of Rapamycin-Induced Autophagy in Malignant Glioma Cells by Phosphatidylinositol 3-Kinase/Protein Kinase B Inhibitors," *Cancer Res* 65(8):3336-3346 (2005).
Tanaka et al., "An unbiased cell morphology-based screen for new, biologically active small molecules," *PLoS Biol.* 3(5):0764-0776 (2005).
Thompson et al., "Identification of distinct populations of PI-3 kinase activity following T-cell activation," *Oncogene* 7(4):719-725 (1992).
Torbett et al., "A chemical screen in diverse breast cancer cell lines reveals genetic enhancers and suppressors of sensitivity to PI3K isoform-selective inhibition," *Biochem. J.* 415(1):97-110 (2008).
Truitt et al., "Stimulation of CD28 triggers an association between CD28 and phosphatidylinositol 3-kinase in Jurkat T cells," *J. Exp. Med.* 179(3):1071-1076 (1994).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Ugarkar et al., "Adenosine kinase inhibitors. 2. Synthesis, enzyme inhibition, and antiseizure activity of diaryltubercidin analogues," *J. Med. Chem.* 43(15):2894-2905 (2000).
Vandenberghe et al., "Antibody and B7/BB1-mediated ligation of the CD28 receptor induces tyrosine phosphorylation in human T cells," *J. Exp. Med.* 175(4):951-960 (1992).
Vanhaesebroeck et al., "PI3K: from the bench to the clinic and back," *Curr. Top. Microbiol. Immunol.* 347:1-19 (2010).
Vara et al., "PI3K/Akt Signalling Pathway and Cancer," *Cancer Treat. Rev.* 30(2):193-204 (2004).
Vasilevsky et al., "Study of the Heterocyclization of vic-Substituted Hydrazides of Acetylenylpyrazolecarboxylic Acids into N-Amino Pyrazolopyridinones," *Journal of Heterocyclic Chemistry* 39(6):1229-1233 (2002).
Vasilevsky et al., "Unexpected results in the heterocyclization of 5-acetylenylpyrazole-4-carboxylic acid hydrazides under the influence of CuCl: formation of a diazepinone and dehydrodimerization into the corresponding bis(pyrazolo [4,3-d] [1,2] diazepinone)," *Tetrahedron Lett.* 46(26):4457-4459 (2005).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl. 5:196-200 (1993).
Vlahos et al., "A specific inhibitor of phosphatidylinositol 3-kinase, 2-(4-morpholinyl)-8-phenyl-4H-1-benzopyran-4-one (LY294002)," *J. Biol. Chem.* 269(7):5241-5248 (1994).

Vogt et al., "Phosphatidylinositol 3-kinase: the oncoprotein," *Curr. Top. Microbiol. Immunol.* 347:79-104 (2010).
Vogt et al., "Phosphoinositide 3-kinase: from viral oncoprotein to drug target," *Virology* 344(1):131-138 (2006).
Wagner et al., "A First-in-Human Phase I Study to Evaluate the Pan-PI3K Inhibitor GDC-0941 Administered QD or BID in Patients with Advanced Solid Tumors," *J. Clin. Oncol.* 27:146s (Suppl, Abstr 3501) (2009).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood* (*ASH Annual Meeting Abstracts*) 118: Abstract 3490 (2011).
Ward et al "Inhibition of CD28-mediated T cell costimulation by the phosphoinositide 3-kinase inhibitor wortmannin," *Eur. J. Immunol.* 25(2):526-532 (1995).
Ward et al., "Ligation of CD28 receptor by B7 induces formation of D-3 phosphoinositides in T lymphocytes independently of T cell receptor/CD3 activation," *Eur. J. Immunol.* 23(10):2572-2577 (1993).
Ward et al., "Regulation of D-3 phosphoinositides during T cell activation via the T cell antigen receptor/CD3 complex and CD2 antigens," *Eur. J. Immunol.* 22(1):45-49 (1992).
Ward et al., "Regulation of phosphoinositide kinases in T cells. Evidence that phosphatidylinositol 3-kinase is not a substrate for T cell antigen receptor-regulated tyrosine kinases," *J. Biol. Chem.* 267(33):23862-23869 (1992).
Ward et al., "Therapeutic potential of phosphoinositide 3-kinase inhibitors," *Chem. Biol.* 10(3):207-213 (2003).
White et al., "11β-Hydroxysteroid Dehyrdogenase and the Syndrome of Apparent Mineralocorticoid Excess," *Endocr. Rev.* 18(1):135-156 (1997).
Widler et al., "7-alkyl- and 7-Cycloalkyl-5-aryl-pyrrolo[2,3-d]pyrimidines—potent inhibitors of the tyrosine kinase c-Src," *Bioorg. Med. Chem. Lett.* 11(6):849-852 (2001).
Wiesinger et al., "Antiinflammatory activity of the new mould metabolite 11-desacetoxy-wortmannin and of some of its derivatives," *Experientia* 30(2):135-136 (1974).
Wolff, Burger's Medicinal Chemistry, 5$^{th}$ ed, Part 1, pp. 975-977, John Wiley & Sons (1995).
Woscholski et al., "A comparison of demethoxyviridin and wortmannin as inhibitors of phosphatidylinositol 3-kinase," *FEBS Lett.* 342(2):109-114 (1994).
Wu et al., "Decreased immunological responses by wortmannin-containing rice culture of Fusarium oxysporum and by purified wortmannin in avian species," *Immunopharmacol. Immunotoxicol.* 14(4):913-923 (1992).
Wu et al., "Wortmannin (a mycotoxin) inhibited immune responses in chickens," *Poultry Sci.* Vo. 71, Suppl 1, pp. 13 (1992).
Yaguchi et al., "Antitumor activity of ZSTK474, a new phosphatidylinositol 3-kinase inhibitor," *J. Natl. Cancer Inst.* 98(8):545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," *J. Exp. Med.* 168(4):1457-1468 (1988).
Yano et al "Inhibition of histamine secretion by wortmannin through the blockade of , phosphatidylinositol 3-kinase in RBL-2H3 cells," *J. Biol. Chem.* 268(34):25846-25856 (1993).
Yoshida et al., "Quercetin arrests human leukemic T-cells in late G1 phase of the cell cycle," *Cancer Res.* 52(23):6676-6681 (1992).
Zhao and Vogt, "Class I PI3K in oncogenic cellular transformation," *Oncogene* 27(41):5486-5496 (2008).
American Cancer Society. Non-Hodgkin's Lymphoma. Last Revised Mar. 11, 2015, Retrieved online: <http://www.cancer.org/cancer/nonhodgkinlymphoma/detailedguide/non-hodgkin-lymphoma-types-of-non-hodgkin-lymphoma>.
Ameriks et al., "Small Molecule Inhibitors of Phosphoinositide 3-Kinase (PI3K) δ and γ", Curr Top Med Chem, 2009, vol. 9, pp. 738-753.
Barnes et al., "Glucocortiod resistance in inflammatory diseases," *The Lancet*, 373:1905-1917.
Bojarczuk et al., "B-cell receptor pathway inhibitors affect CD20 levels and impair antitumor activity of anti-CD20 monoclonal antibodies," Leukemia (2014), 1-5.

(56) References Cited

OTHER PUBLICATIONS

Bouska et al. ,"Genome-wide copy-number analyses reveal genomic abnormalities involved in transformation of follicular lymphoma", Blood, Mar. 13, 2014, vol. 123, N. 11, pp. 1681-1690.
Boyle et al., "Efficacy of the potent PI3K-δ,γ inhibitor IPI-145 in rat adjuvant arthritis,"*Arthritis & Rheumatism*, 64:S879 (2012).
Brown et al. "Phase I Trial of SAR245408 (S08), a Pan-Phosphatidylinositol 3 Kinase (PI3K) Inhibitor, in Patients with Chronic Lymphocytic Leukemia (CLL) and Lymphoma", Blood (ASH Annual Meeting Abstracts) 2011 118: Abstract 2683, Downloaded from the Internet.
Brown et al., "Idelalisib, an inhibitor of phosphatidylinositol 3-kinase p110d, for relapsed/refractory chronic lymphocytic leukemia", BLOOD, May 29, 2014, vol. 123, No. 22, pp. 3390-3397.
Caira, M., "Crystalline Polymorphism of Organic Compounds," Topics in Current Chemistry, Springer, Berlin, DE, v. 198 (Jan. 1, 1998), p. 163-208.
Calin et al., "A MicroRNA Signature Associated with Prognosis and Progression in Chronic Lymphocytic Leukemia", *N Engl J Med*, 353:1793-801 (2005).
Castor et al., "PI$_3$Kγ controls leukocyte recruitment, tissue injury, and lethality in a model of graft-versus-host disease in mice," *J. Leukoc. Biol.*, 89:955-964 (2011).
Cheson et al., "Novel Targeted Agents and the Need to Refine Clinical End Points in Chronic Lymphocytic Leukemia", Journal of Clinical Oncology, vol. 30, No. 23 Aug. 10, 2012, pp. 2820-2822.
Cheung et al., "Genome-wide profiling of follicular lymphoma by array comparative genomic hybridization reveals prognostically significant DNAcopy number imbalances", Blood, Jan. 1, 2009, ,vol. 113, No. 1, pp. 137-148.
Cheung et al., "High Resolution Analysis of Follicular Lymphoma Genomes Reveals Somatic Recurrent Sites of Copy-Neutral Loss of Heterozygosity and Copy Number Alterations that Target Single Genes", Genes, Chromosomes & Cancer 49; 669-681 (2010), DOI 10.1002/gcc.
Chiron et al., "Cell-Cycle Reprogramming for PI3K Inhibition Overrides a Relapse-Specific C481S BTK Mutation Revealed by Longitudinal Functional Genomics in Mantle Cell Lymphoma", Cancer Discovery, (Sep. 2014), vol. 4, pp. 1022-1035, Published OnlineFirst Jul. 31, 2014; DOI: 10.1158/2159-8290.CD-14-0098.
ClinicalTrials.gov, "Dose Escalation Study of CAL-101 in Select Relapsed or Refractory Hematologic Malignancies" [online] (2008) [Retrieved on Jul. 23, 2014] Retrieved from <http://clinicaltrials.gov/ct2/show/NCT00710528>.
ClinicalTrials.gov, NCT01476657 Study, "A Phase 1 Study of IPI-145 in Patients with Advanced Hematologic Malignancies", Nov. 17, 2011.
Conte et al., "Inhibition of PI3K Prevent the Proliferation and Differentiation of Human Lung Fibroblasts into Myofibroblasts: The Role of Class I P110 Isoforms," PLOS ONE (2011), 6(10):e24663, pp. 1-10.
Cui et al., "MicroRNA-155 influences B-cell receptor signaling and associates with aggressive disease in chronic lymphocytic leukemia", *Blood*, 124(4):546-554 (2014).
D'Amore et al., "Clonal Evolution in t(14;18)-Positive Follicular Lymphoma, Evidence for Multiple Common Pathways, and Frequent Parallel Clonal Evolution", Clin Cancer Res 2008;14(22) Nov. 15, 2008, pp. 7180-7187.
D'Cruz et al. "Novel Bruton's tyrosine kinase inhibitors currently in development," OncoTargets and Therapy, Mar. 5, 2013, vol. 6, pp. 161-176.
De Frias et al., "Akt inhibitors induce apoptosis in chronic lynphocytic leukemia cells", Haematologica (2009), vol. 94, pp. 1698-1707.
De Vos et al., "A Phase 1 Study of the Selective Phosphatidylinositol 3-Kinase-Delta (PI3K delta) Inhibitor, Cal-101 (GS1101), in Combination with Rituximab and/or Bendamustine in Patients with Previously Treated, Indolent Non-Hodgkin Lymphoma (iNHL)", BLOOD, ASH, US, vol. 118, No. 21, Dec. 13, 2011, p. 1160, XP008152289, ISSN: 0006-4971.

Engelman, J. "Targeting PI3K signalling in cancer: opportunities, challenges and limitations", *Nature Reviews: Cancer*, 9:550-562 (2009).
Flinn et al., "A Phase 1 Evaluation of Duvelisib (IPI-145), a PI3K-delta,gamma Inhibitor, in Patients with Relapsed/Refractory iNHL", American Society of Hematology Meeting, Dec. 6, 2014.
Flinn et al., "Clinical Safety and Activity in a Phase 1 Trial of IPI-145, a Potent Inhibitor of Phosphoinositide-3-Kinase-δ, γ, in Patients with advanced Hematologic Malignancies," Blood, vol. 120, No. 21, Nov. 16, 2012, p. 3663, XP008166549, & 54th ASH Annual Meeting (Dec. 10, 2012).
Fruman et al., "PI3Kδ Inhibitors in Cancer: Rationale and Serendipity Merge in the Clinic," Cancer Discovery, 1:562-572 (2011).
Fulci et al., "Quantitative technologies establish a novel microRNA profile of chronic lymphocytic leukemia", *Blood*, 109(11):4944-4951 (2007).
Furman et al., "CAL-101, An Isoform-Selective Inhibitor of Phosphatidylinositol 3-Kinase P110 delta, Demonstrates Clinical Activity and Pharmacodynamic Effects in patients with Relapsed or Refractory Chronic Lymphocytic Leukemia," BLOOD; 52nd Annual Meeeting of ASH, Orlando, FL, USA, vol. 116, No. 21, Nov. 1, 2010, p. 31, XP008168032, ISSN: 0006-4971.
Ghigo et al., "PI3K Inhibition in Inflammation. Toward tailored therapies for specific diseases," BioEssays 32 (2010), pp. 185-196.
Graham et al., "The TAM family: phosphatidylserinesensing receptor tyrosine kinases gone awry in cancer", *Nature Rev Cancer*, 14:769-785 (2014).
Hall et al., "The dual PI3K/mTOR inhibitor NVP-BEZ235 enhances dexamethasone induced apoptosis in models of T-cell ALL with PTEN dysfunction and hyperactivated PI3K/Akt pathway.", Cancer Research: Apr. 15, 2013; vol. 73, Issue 8, Supplement 1, doi: 10.1158/1538-7445.AM2013-2757.
Harris et al., "PI3K isoforms as drug targets in inflammatory diseases: Lessons from pharmacological and genetic strategies", Curr. Opin. in Inv. Drugs, 2009, vol. 10(11), pp. 1151-1162.
Henderson et al., "Delineation of a Minimal Region of Deletion at 6q16.3 in Follicular Lymphoma and Construction of a Bacterial Artificial Chromosome Contig Spanning a 6-Megabase Region of 6q16-q21" , Genes, Chromosomes & Cancer 40:60-65 (2004).
Herman et al., "Molecular Pathways: Targeting the Phosphoinositide 3-Kinase (PI3-Kinase) p110 delta in Chronic Lymphocytic Leukemia", Clin. Cancer Res. Aug. 2012, vol. 18, pp. 4013-4018.
Higgs et al., "Patients with systemic lupus erythematosus, myositis, rheumatoid arthritis and scleroderma share activation of a common type I interferon pathway", Ann Rheum Dis, 2011, vol. 70 pp. 2029-2036.
Hoe et al., "Drugging the p53 pathway: understanding the rout to clinical efficacy", Nature Reviews Drug Discovery, Mar. 2014, vol. 13, pp. 217-236.
Horwitz et al., "Duvelisib (IPI-145), a Phosphoinositide-3-Kinase-Delta,Gamma Inhibitor, Shows Activity in Patients with Relapsed/Refractory T-Cell Lymphoma", American Society of Hematology Meeting, Dec. 6, 2014.
Kassern, Noreen, "Top Ten Bone Diseases," LiveStrong.com, Apr. 29, 2011. <http://www.livestrong.com/article/119479-top-ten-bone-diseases/>.
Kavanagh, et al., "Patient. Mylodysplastic syndromes. 2012," [online], Retrieved on Apr. 24, 2015, <http://www.patient.co.uk/doctor/myelodysplastic-syndromes-pro>.
Kridel et al., "Pathogenesis of follicular lymphoma", J. of Clinical Investigation, vol. 122, No. 10, Oct. 2012, pp. 3424-3431.
Kukulski et al., "The P2 receptor antagonist PPADS abrogates LPS-induced neutrophil migration in the murine air pouch via inhibition of MIP-2 and KC production," *Mol. Immun.*, 47(4):833-839 (2010).
Macias-Perez and Flinn, "B-Cell Receptor Pathobiology and Tarteting in NHL," Curr. Oncol. Rep., 14:411-418 (2012).
Mansour et al., "Discovery of a Secreted Tumor Suppressor Provides a Promising Therapeutic Strategy for Follicular Lymphoma", Cancer Cell 20, Nov. 15, 2011, pp. 559-561.
MedicineNet.com, Cancer Definition, http://www.medterms.com, 2004.

(56) References Cited

OTHER PUBLICATIONS

Medline Plus, Autoimmune Diseases, NIH, 2014. <http://www.nlm.nih.gov/medlineplus/autoimmunediseases.html>.
Kiefer, "Lymphoma Prevention," Healthline. 2011, <http://www.healthline.com/health/lymphoma/prevention>.
Mraz and Kipps, "MicroRNAs and B cell receptor signaling in chronic lymphocytic leukemia", Leukemia & Lymphoma, 54(8):1836-1839 (2013).
Mraz et al., "MicroRNAs in chronic lymphocytic leukemia pathogenesis and disease subtypes", Leukemia & Lymphoma, 50(3):506-509 (2009).
Mraz et al., "miR-150 influences B-cell receptor signaling in chronic lymphocytic leukemia by regulating expression of GAB1 and FOXP1", Blood 124(1):84-95 (2014).
Musilova and Mraz, "MicroRNAs in B-cell lymphomas: how a complex biology gets more complex", Leukemia 1-14 (2015).
National Cancer Institute, "AIDS-Related Lymphoma Treatment," 2015. <http://www.cancer.gov/cancertopics/pdq/treatment/AIDS-related-lymphoma/Patient/page1>.
NCBI, Nutritional and Metabolic Diseases, NCBI Bookshelf, 1998. <http://www.ncbi.nlm.nih.gov/books/NBK22259/>.
NCBI, The Nervous System, NCBI Bookshelf, 1998. <http://www.ncbi.nlm.nih.gov/books/NBK22197/>.
Infinity Pharmaceuticals, Inc.—Press Release dated Jul. 18, 2012, "Infinity Regains Worldwide Rights to PI3K, FAAH and Early Discovery Programs," Retrieved from the Internet: URL:http://phx.corporate-.net/phoenix.zhtml?c=121941&p=irol-newsArticle_print&ID=1715695&hightlight= [retrieved on Jan. 10, 2014].
O'Connor, "Adult T-Cell Leukemia/Lymphoma (HTLV-1)", Lymphoma Research Foundation, 2008, 1-4.
Okosun et al., "Integrated genomic analysis identifies recurrent mutations and evolution patterns driving the initiation and progression of follicular lymphoma", Nature Genetics (2014) vol. 46, No. 2, pp. 176-181.
Okosun et al., Supplementary Information "Integrated genomic analysis identifies recurrent mutations and evolution patterns driving the initiation and progression of follicular lymphoma", Nature Genetics (2014), doi:10.1038/ng.2856.
Oricchio et al., "The Eph-Receptor A7 Is a Soluble Tumor Suppressor for Follicular Lymphoma", Cell 147, 554-564, Oct. 28, 2011.
Patel et al., "Early Clinical Activity and Pharmacodynamic Effects of Duvelisib, a PI3K-delta,gamma Inhibitor, in Patients with Treatment-Naïve CLL", ASCO Annua Meeting 2015, May 29-Jun. 2, Chicago, IL (poster).
Pharmacyclics Inc. Form 8-K Filing. May 16, 2013. Article retrieved from the Internet: <http://www.sec.gov/Archives/edgar/data/949699/000092189513001115/0000921895-13-001115-index.htm> on Dec. 11, 2014.
Porter et al, "The Potent Phosphoinositide-3-Kinase-(δ,γ) Inhibitor IPI-145 is Active in Preclinical Models of Arthritis and Well Tolerated in Healthy Adult Subjects," Arthritis & Rheumatism, 64:S147 (2012).
Ross et al., "ComprehensiveAnalysis of Copy Number and Allele Status Identifies Multiple Chromosome Defects Underlying Follicular Lymphoma Pathogenesis", Clin Cancer Res 2007; 13(16), pp. 4777-4785, Aug. 15, 2007.
Schwaenen et al., "Microarray-Based Genomic Profiling Reveals Novel Genomic Aberrations in Follicular Lymphoma Which Associate with Patient Survival and Gene Expression Status", Genes, Chromosomes & Cancer 48:39-54 (2009) DOI 10.1002/gcc.
Seda and Mraz, "B-cell receptor signalling and its crosstalk with other pathways in normal and malignant cells", European Journal of Haematology 94(3):193-205 (2015).
Sharman et al., "A Phase 1 Study of the Selective Phosphatidylinositol 3-Kinase-Delta (PI3K delta) Inhibitor, CAL-101 (GS-1101), in Combination with Rituximab and/or Bendamustine in Patients with Relapsed or Refractory Chronic Lymphocytic Leukemia (CLL)", BLOOD; 53rd ASH Annual Meeting, San Diego, CA, vol. 118, No. 21, Nov. 18, 2011, p. 779-780, XP008152290, ISSN: 006-4971 Retrieved from the Internet.
Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(4):471-474 (2011) (abstract only).
Stone, Richard. "Mast Cell Leukemia and Other Mast Cell Neoplasms." In: Kufe DW, Pollock RE, Weichselbaum RR, et al., editors. Holland-Frei Cancer Medicine. 6th Edition Hamilton (ON): BC Decker, 2003. URL: <http://www.ncbi.nlm.nih.gov/books/NBK13427/>.
Suralkar et al., "In-Vivo Animal Models for Evaluationof Anti-Inflammatory Activity," Pharmainfo.net/reviews, vol. 6, Issue 2, Mar. 17, 2008; downloaded Nov. 4, 2014.
Sylvester Comprehensive Cancer Center, "Definition: Leukemia, Lymphoma and Myeloma," 2015. URL: <http://sylvester.org/cancer/leukemia-lymphoma-and-myeloma/education/definition>.
Treon et al., "A Prospective Multicenter Study of the Bruton's Tyrosine Kinase Inhibitor Ibrutinib in Patients with Relapsed or Refractory Waldenstrom's Macroglobulinemia," ASH Annual Meeting, Oral Presentation 251, Dec. 9, 2013.
Venable et al., "Phosphoinositide 3-kinase gamma (PI3Kgamma) inhibitors for the treatment of inflammation and autoimmune disease", Recent Pat Inflamm Allergy Drug Discov (2010) 4:1-15.
Viardot et al., "Clinicopathologic Correlations of Genomic Gains and Losses in Follicular Lymphoma", Journal of Clinical Oncology, vol. 20, No. 23 Dec. 1, 2002: pp. 4523-4530.
Vora et al., "CDK 4/6 Inhibitors Sensitize PIK3CA Mutant Breast Cancer to PI3K Inhibitors", Cancer Cell (Jul. 2014), vol. 26, pp. 136-149.
WebMD, "Chronic Myeloproliferative Disorders Treatment (PDQ®): Treatment-Patient Information [NCI]—General Information About Chronic Myeloproliferative Disorders," 2014. <http://webmd.com/cancer/tc/chronic-myeloproliferative-disorders-treatment-patient-information-nci-pdq-general-information>.
WebMD, "HIV & AIDS Heath Center HTLV Type I and Type II," 2014. <http://www.webmd.com/hiv-aids/htlv-type-i-and-type-ii>.
WebMD, Leukemia-Prevention. Cancer Health Center. 2012. <http://www.webmd.com/cancer/tc/leukemia-prevention>.
WebMD, Lung Disease Overview. (2014). <http://www.webmd.com/lung/lung-diseases-overview>.
Wei et al., "A phosphoinositide 3-kinase-γ inhibitor, AS605240 prevents bleomycin-induced pulmonary fibrosis in rats," Biochem. Biophy. Res. Comm. 397:311-317 (2010).
Wen et al., "Current clinical development of PI3K pathway inhibitors in glioblastoma", Neuro-Oncology (2012) vol. 14, pp. 819-829.
Winkler et al., "PI3K-d and PI3K-g Inhibition by IPI-145 Abrogates Immune Responses and Suppresses Activity in Autoimmune and Inflammatory Disease Models," Chemistry & Biology (2013),://dx.doi.org/10.1016/j.chembiol.2013.09.017.
Wong et al., "Targeting the PI3K signaling pathway in Cancer," Current Opinion in Genetics & Development, vol. 20, (2010), pp. 87-90.
Woyach et al., "Resistance Mechanisms for the Bruton's Tyrosine Kinase Inhibitor Ibrutinib," N Engl J Med 2014; 370; p. 2286-2294.
Wymann et al., "Phosphoinositide 3-kinase γ: a key modulator in inflammation and allergy,"Biochem Soc. Transactions, 31(part 1):275-280 (2003).
Veliz et al., "Treatment of relapsed or refractory chronic lymphocytic leukemia", Cancer Control, 2012, vol. 19, pp. 37-53.
Zhao et al, "TNF-α promotes $LPA_1$- and LPA3-mediated recruitment of leukocytes in vivo through CXCR2 ligand chemokines," J. Lipid Res., 52(7):1307-1318 (2011).
Ashizawa, Kazuhide, Science of polymorphism and crystallization in pharmaceutical products:, Maruzen Planet Co., Sep. 20, 2002, pp. 3-16.
Liu et al., "Improved synthesis of α-BOC-aminoketones from α-BOC-amino-Weinreb amides using a pre-deprotonation protocol", Tetrahedron Letters, 43(46):8223-8226 (2002).
Nakai, Yoshinobu, et. al., ed., New galenical pharmacy, NANZANDO Co., Ltd., Apr. 25, 1984, pp. 102-103, 232-233.

(56) References Cited

OTHER PUBLICATIONS

Nishigaki, Sadao, Dispensing pharmacy (Principle and application), NANZANDO Co., Ltd, Sep. 20, 1977, pp. 142-145.
Okano, Teisuke, New general remarks of practical pharmacy, 3rd ed., Nankodo Co., Ltd, Apr. 10, 1987, p. 111.
The Chemical Society of Japan ed., Jikken kagaku kouza (zoku), 2. Bunri to seisei (Experimental chemical lecture, second series, 2. Separation and purification), MARUZEN Co., Ltd., Jan. 25, 1967, pp. 159-178, 186-187.
Yu et al., "Development of a Practical Synthesis of DPP IV Inhibitor LY2497282", Organic Process Research & Development, 12(2):218-225 (2008).
Buet et al., "Cotargeting signaling pathways driving survival and cell cycle circumvents resistance to Kit inhibitors in leukemia", Blood, 119(18):4228-4241 (2012).
Campbell, et al., "The Potent PI3K-δ,γ Inhibitor, IPI-145, Exhibits Differential Activity in Diffuse Large B-cell Lymphoma (DLBCL) Cell Lines", Dec. 7, 2013, 55th ASH Annual Meeting and Exposition, New Orleans, LA, Poster 1832.
Cao et al., "The BCL2 antagonist ABT-199 triggers apoptosis, and augments ibrutinib and idelalisib mediated cytotoxicity in CXCR4Wildtype and CXCR4WHIM mutated Watdenstmm macroglabulinaemia cells", British Journal of Haematology, 170(12):134-138 (2015).
Chang et al., "PI3-Kinase Inhibitors in Chronic Lymphocytic Leukemia", Current Hematologic Malignancy Reports, 9(1):33-43 (2014).
Chang et al., "Novel Synthesis and Reactions of 5, 7-Dialkyl-4,6-dioxo-4,5,6,7-tetrahydro-isothiazolo[3,4,-d]pyrimidine-3-carbonitriles and 6-Methyl-4-oxo-4H-1-aza-5-oxa-2-thiaindene-3-carbonitrile", Org. Lett. 5(4):507-510 (2003).
Chiron et al., "791 Induction of Early G1-Arrest by CDK4/CDK6 Inhibition Sensitizes Mantle Cell Lymphoma Cells to Selective PI3Kδ Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper52021.html.
Choudhary et al., "MCL-1 and BCL-xL-dependent resistance to the BGL-2 inhibitor ABT-199 can be overcome by preventing PI3KJ AKT/mT4R activation in lymphoid malignancies", Cell Death & Disease 2015, 6: e1593 (2015).
Equivalent Surface Area Dosage Conversion Factors (https://ncifrederick.cancer.gov/lasp/acuc/frederick/Media/Documents/ACUC42.pclf, Aug. 2007).
Flinn et al., "Preliminary Safety and Efficacy of IPI-145, a Potent Inhibitor of Phosphoinositide-3-Kinase-δ,γ, In Patients With Chronic Lymphocytic Leukemia", Blood, 122(21):677 (2013).
Goodman, A., "Encouraging Early Results With Novel Agents in CLL", The ASCO Post, Mar. 1, 2014, Reterieved from the internet: URL: http://www.ascopost.com/issues/march-1,-2014/encouraging-early-results-with-novel-agents-in-cll.aspx.
Harb et al., "Combined Pharmacologic Inhibition of Bcl-X1/Bcl-2 and mTORC1/2 Survival Signals Trigger Apoptosis in BCR-ABL1+ in Vitro Models of Blast Crisis Chronic Myelogenous Leukemia (CML-BC), and Primary CD34+/CD38− Stem and CD34+ progenitor Cells From CML-BC Patients", Blood, 53rd Ash Annual Meeting and Exposition, San Diego, CA, Dec. 10-13, 2011, Retrieved from: https://ash.confex.com/ash/2011Jwebprogram/Paper44381.html.
Infinity Pharmaceuticals, Inc., "Infinity Reports Preclinical Data at ASH Annual Meeting in Diffuse Large B-Cell Lymphoma and T-Cell Acute Lymphoblastic Leukemia Suggesting Broad Potential of IPI-145 in Blood Cancers", http://businesswire.com, Dec. 7, 2013, Downloaded from: http://www.businesswire.com/news/home/20131207005015/en/Infinity-Reports-Preclinical-Data-ASH-Annual-Meeting.
Letai et al., "Antiapoptotic BCL-2 is required for maintenance of a model leukemia", Cancer Cell, 6(3):241-249 (2004).
Linhua et al., "Efficacy and Mechanisms of Apoptosis Induction by Simultaneous Inhibition of PI3K with GDC-0941 and Blockade of Bcl-2 (ABT-737) or FLT3 (Sorafenib) In AML Cells In the Hypoxic Bone Marrow Microenvironment", Blood, 116:777 (2010).
Martin-Sanchez et al., "Simultaneous inhibition of pan-phosphatidylinositol-3-kinases and MEK as a potential therapeutic strategy in peripheral T-cell lymphomas", Haematologica, 98(1):57-64 (2013).
Mashkovskiy, Lekarstvennye sredstva, vol. 1, 2001, p. 11.
Milella et al., 566 POSTER Anti-leukemic activity of the novel MEK inhibitor PD0325901, European Journal of Cancer Supplement, 4(12):172 (2006).
Morrison, C., "First PI3k inhibitor launches info crowded hematology markets", Nature Biotechnology, 32(10):963-964 (2014).
Muranen et al "Inhibition of PI3K/mTOR Leads to Adaptive Resistance in Matrix-Attached , Cancer Cells", Cancer Cell, 21(2):227-239 (2011).
Muranen et al., "Promising Rationally Derived Combination Therapy with PI3K and CDK4/6 Inhibitors", Cancer Cell, 26(1):7-9 (2014).
Okkenhaug, K., "Two Birds with One Stone: Dual p110δ and p110γ Inhibition", Chemistry and Biology, 20(11):1309-1310 (2013).
Iersdorf et al., "An inhibitor of Bcl-2 family proteins induces regression of solid tumours", Nature, 435:677-681 (2005).
Qian et al., "Synergy between phosphatidylinositol 3-kinase/Akt pathway and Bcl-xL, in the control of apoptosis in adenocarcinoma cells of the lung", Molecular Cancer Therapeutics, 8(1):101-109 (2009).
Rahmani et al., "Dual Inhibition of Bcl-2 and Bcl-xL, Strikingly Enhances PI3K Inhibition-Induced Apoptosis in Human Myeloid Leukemia Cells through a GSK3- and Bim-Dependent Mechanism", Cancer Research, 73(4):1340-1351 (2013).
Roberts et al., "Substantial Susceptibility of Chronic Lymphocytic Leukemia to BCL2 Inhibition: Results of a Phase I Study of Navitoclax in Patients With Relapsed or Refractory Disease", Journal of Clinical Oncology, 30(5):488-496 (2012).
Schwamb et al., "B-cell receptor triggers drug sensitivity of primary CLL cells by controlling glucosylation of ceramides", Blood, 120(19):3978-3985 (2012).
Seymour et al., "Bcl-2 Inhibitor ABT-199 (GDC-0199) Monotherapy Shows Anti-Tumor Activity Including Complete Remissions in High-Risk Relapsed/Refractory (R/R) Chronic Lymphocytic Leukemia (CLL) and Small Lymphocytic Lymphoma (SLL)", Blood, 122(21):872 (2013).
Simioni et al., "Cytotoxic activity of the novel Akt inhibitor, MK-2206, in T-cell acute lymphoblastic leukemia", Leukemia, 26(11):2336-2342 (2012).
Tong et al., "Perifosine induces protective autophagy and upregulation of ATG5 in human chronic myelogenous leukemia cells in vitro", Acta Pharmacologica Sinica, 33(4):542-550 (2012).
Vachhani et al., "Ratianal combination of dual PI3K/mTOR blockade and Bcl-2/-xl inhibition in AML", Physiological Genomics, 46(13):448-456 (2014).
Wullschleger et al., "Quantitative MRI Establishes the Efficacy of PI3K Inhibitor (GDC-0941) Multi-Treatments in PTEN-deficient Mice Lymphoma", Anticancer Research, 32(2):415-420 (2012).
Zhu et al., "PI3K inhibition potentiates Bcl-2-dependent apoptosis in renal carcinoma cells", Journal of Cellular and Molecular Medicine, 17(3):377-385 (2013).
CAL-101, PubChem CID 11625818, created date Oct. 26, 2006.
Akinleye et al., "Phosphatidylinositol 3-kinase (PI3K) inhibitors as cancer therapeutics", Journal of Hematology & Oncology, Nov. 2013, vol. 6:88, pp. 1-18.
Brittain, H.G., et al. "Polymorphism in pharmaceutical solids" edited by H. G. Brittain, Marcel Dekker, D.J.W., Grant (chapter 1), p. 1-10 and J. K. Guillory (chapter 5); p. 183-226 (1999).
Byrn, S. et al. "Pharmaceutical Solids: A Strategic Approach to Regulatory Considerations"; S. Byrn et al.; Pharmaceutical research, vol. 12, No. 7, p. 945-954 (1995).
Chabner et al., "Chemotherapy and the war on cancer", Nature Reviews Cancer, 2005, Nature Publishing Group, vol. 5, pp. 65-72.
D'Cruz et al., "Protein kinase inhibitors against malignant lymphoma", Expert Opinion on Pharmacotherapy, Mar. 2013, Taylor and Francis Group, vol. 14(6), pp. 707-721.

(56) References Cited

OTHER PUBLICATIONS

Kakkola et al., "Anticancer compound ABT-263 accelerates apoptosis in virus-infected cells and imbalances cytokine production and lowers survival rates of infected mice", Cell Death & Disease (2013) 4, e742.
Leaf, "Why We're Losing the War on Cancer—and How to Win it", Fortune, Mar. 9 2004, Time Inc., pp. 1-28.
Vaillant et al., "Targeting BCL-2 with the BH3 Mimetic ABT-199 in Estrogen Receptor-Positive Breast Cancer", Cancer Cell 24, pp. 120-129, Jul. 8, 2013.
Vanhaesebroek et al., "Molecules in medicine mini-review: isoforms of PI3K in biology and disease," J. Mol. Med., 94(1):5-11 (2016). e-published Dec. 10, 2015.
Stedman's Medical Dictionary Stedman's online. Autoimmune disease; <http://stedmansonline.com/content.aspx?id=mlrA2100002481 &termtype=> (accessed Mar. 11, 2017).
Hirayama, Noriaki, Yuki Kagoubutsu Kessyo Sakusei Handbook—Genri to Nouhau (Handbook of organic compound crystal production—principle and know-how-), Maruzen Co., Ltd., Jul. 25, 2008, pp. 57-74.
Akira Ogata, Chemical experiment manual, Nankodo Co.,Ltd., Jun. 20, 1977, 36th edit., pp. 515-535.
Shadan-hojin Japan Chemistry Association, Kagaku Binran Ouyou Kagaku hen, 6th edit., Maruzen Co., Ltd., Jan. 30, 2003, pp. 178.
White et al., "Abstract 376: Combination of duvelisib with either ibrutinib or dexamethasone prevents mTOR-dependent feedback in aggressive B-cell lymphoma cell lines", Cancer Research, vol. 76, No. Suppl. 14, Apr. 2016, Proceedings of the 107th Annual Meeting of the American Association for Cancer Research; Apr 16-20, 2016; New Orleans, LA, Retrieved from the Internet: URL:http://cancerres.aacrjournals.org/content/76/14_Supplement/376 [retrieved on Sep. 13, 2017].
Bedognetti et al., "Checkpoint Inhibitors and Their Application in Breast Cancer (supplementary information)", Breast Care, vol. 11, No. 2, Apr. 26, 2016, pp. 108-115.
De Henau et al., "Abstract 554: Checkpoint blockade therapy is improved by altering the immune suppressive microenvironment with IPI-549, a potent and selective inhibitor of PI3K-gamma, in preclinical models", Cancer Research, Apr. 2016, 107th Annual Meeting of the American Association for Cancer Research; Apr. 16-20, 2016; New Orleans, LA, Retrieved from the Internet: URL:http://cancerres.aacrjournals.org/content/76/14_Supplement/554 [retrieved on Sep. 13, 2017].
U.S. Appl. No. 13/885,473, filed Jul. 18, 2012, U.S. Pat. No. 9,056,877, Heterocyclic Compounds and Uses Thereof, Patented.
U.S. Appl. No. 13/842,265, filed Mar. 15, 2013, U.S. Pat. No. 8,940,742, Heterocyclic Compounds and Uses Thereof, Patented.
U.S. Appl. No. 13/403,394, filed Feb. 23, 2012, U.S. Pat. No. 8,785,456, Certain Chemical Patented Entities, Compositions and Methods, Patented.
U.S. Appl. No. 13/289,540, filed Nov. 4, 2011, U.S. Pat. No. 8,785,454, Heterocyclic Compoungs and Uses Thereof, Patented.
U.S. Appl. No. 13/292,828, filed Nov. 10, 2011, U.S. Pat. No. 8,901,133, Heterocyclic Compounds and Uses Thereof, Patented.
U.S. Appl. No. 13/112,611, filed May 20, 2011, U.S. Pat. No. 8,604,032, Chemical Compounds, Compositions and Methods for Kinase Modulation, Patented.
U.S. Appl. No. 13/347,423, filed Jan. 10, 2012, U.S. Pat. No. 8,809,349, Processes for Preparing Isoguinolinones and Solid Forms of Isoquinolinones, Patented.
U.S. Appl. No. 14/302,340, filed Jun. 11, 2014, U.S. Pat. No. 9,315,505, Heterocyclic Compounds and Uses Thereof, Patented.
U.S. Appl. No. 15/059,962, filed Mar. 3, 2016, U.S. Pat. No. 9,822,131, Certain Chemical Entities, Compositions and Methods, Patented.
U.S. Appl. No. 15/264,417, filed Sep. 13, 2016, 2017-0088553, Solid Forms of Isoquinolinones, and Process of Making, Composition Comprising, and Methods of Using the Same, Published.

U.S. Appl. No. 14/884,612, filed Oct. 6, 2015, 2016-0022692, Treatment of Rheumatoid Arthritis and Asthma Using PI3 Kinase Inhibitors, Abandoned.
U.S. Appl. No. 15/347,489, filed Nov. 9, 2016, 2017-0281614, Certain Chemical Entities, Compositions and Methods, Published.
U.S. Appl. No. 15/621,815, filed Jun. 13, 2017, 2017-0369511, Heterocyclic Compounds and Uses Thereof, Published.
U.S. Appl. No. 15/675,185, filed Aug. 11, 2017, Unpublished, Unassigned, Heterocyclic Compounds and Uses Thereof, Pending.
U.S. Appl. No. 15/794,816, filed Oct. 26, 2017, 2018-0044346, Heterocyclic Compounds and Uses Thereof, Published.
U.S. Appl. No. 15/789,868, filed Oct. 20, 2017, Unpublished, Unassigned, Certain Chemical Entities, Compositions and Methods, Pending.
Bedognetti et al., "Checkpoint Inhibitors and Their Application in Breast Cancer (including supplementary information)", Breast Care, vol. 11, No. 2, Apr. 26, 2016, pp. 108-115.
Mittendorf et al., "PD-L1 expression in triple-negative breast cancer", Cancer Immunol. Res. 2014, 2:361-370.
U.S. Appl. No. 13/552,460, filed Jul. 18, 2012, U.S. Pat. No. 8,969,363, Heterocyclic Compounds and Uses Thereof, Patented.
U.S. Appl. No. 13/552,473, filed Jul. 18, 2012, U.S. Pat. No. 9,056,877, Heterocyclic Compounds and Uses Thereof, Patented.
U.S. Appl. No. 13/552,516, filed Jul. 18, 2012, U.S. Pat. No. 8,785,470, Heterocyclic Compounds and Uses Thereof, Patented.
U.S. Appl. No. 13/841,265, filed Mar. 15, 2013, U.S. Pat. No. 8,940,742, Heterocyclic Compounds and Uses Thereof, Patented.
U.S. Appl. No. 13/839,912, filed Mar. 15, 2013, 2014-0120060, Treatment of Rheumatoid Arthritis and Asthma Using PI3 Kinase Inhibitors, Abandoned.
U.S. Appl. No. 14/209,842, filed Mar. 13, 2014, U.S. Pat. No. 9,481,667, Salts and Solid Forms of Isoquinolinones and Composition Comprising and Methods of Using the Same, Patented.
U.S. Appl. No. 13/840,822, filed Mar. 15, 2013, 2014-0120083, Treatment of Cancers Using PI3 Kinase Isoform Modulators, Published.
U.S. Appl. No. 12/811,695, filed Nov. 11, 2010, U.S. Pat. No. 8,703,777, Substituted Bicyclic Compounds and Methods of Use Thereof, Patented.
U.S. Appl. No. 12/503,776, filed Jul. 15, 2009, U.S. Pat. No. 8,193,182, Substituted Isoquinolin-1(2H)-Ones, and Methods of Use Thereof, Patented.
U.S. Appl. No. 13/403,394, filed Feb. 23, 2012, U.S. Pat. No. 8,785,456, Certain Chemical Entities, Compositions and Methods, Patented.
U.S. Appl. No. 13/350,444, filed Jan. 13, 2012, U.S. Pat. No. 8,569,323, Substituted Isoquinolin-1(2H)-One Compounds, Compositions, and Methods Thereof, Patented.
U.S. Appl. No. 13/121,157. filed Aug. 2, 2011, U.S. Pat. No. 8,703,778, Heterocyclic Kinase Inhibitors, Patented.
U.S. Appl. No. 13/289,540, filed Nov. 4, 2011, U.S. Pat. No. 8,785,454, Heterocyclic Compounds and Uses Thereof, Patented.
U.S. Appl. No. 13/293,828, filed Nov. 10, 2011, U.S. Pat. No. 8,901,133, Heterocyclic Compounds and Uses Thereof, Patented.
U.S. Appl. No. 13/122,611, filed May 20, 2011, U.S. Pat. No. 8,604,032, Chemical Compounds, Compositions and Methods for Kinase Modulation, Patented.
U.S. Appl. No. 13/347,423, filed Jan. 10, 2012, U.S. Pat. No. 8,809,349, Processes for Preparing Isoquinolinones and Solid Forms of Isoquinolinones, Patented.
U.S. Appl. No. 13/837,195, filed Mar. 15, 2013, U.S. Pat. No. 8,828,998, Treatment of Lupus, Fibrotic Conditions, and Inflammatory Myopathies and Other Disorders Using PI3 Kinase Inhibitors, Patented.
U.S. Appl. No. 14/222,488, filed Mar. 21, 2014, 2014-0206684, Certain Chemical Entities, Compositions and Methods, Abandoned.
U.S. Appl. No. 14/085,660, filed Nov. 20, 2013, U.S. Pat. No. 9,181,221, Chemical Compounds, Compositions and Methods for Kinase Modulation, Patented.
U.S. Appl. No. 14/099,831, filed Dec. 6, 2013, U.S. Pat. No. 9,115,141, Heterocyclic Compounds and Uses Thereof, Patented.

(56) References Cited

OTHER PUBLICATIONS

U.S. Appl. No. 14/776,604, filed Sep. 14, 2015, 2016-0024051, Salts and Solid Forms of Isoquinolinones and Composition Comprising and Methods of Using the Same, Abandoned.
U.S. Appl. No. 13/971,793, filed Aug. 20, 2013, U.S. Pat. No. 9,206,182, Certain Chemical Entities, Compositions and Methods, Patented.
U.S. Appl. No. 15/026,947, filed Apr. 1, 2016, U.S. Pat. No. 9,751,888, Heterocyclic Compounds and Uses Thereof, Patented.
U.S. Appl. No. 14/506,429, filed Oct. 3, 2014, U.S. Pat. No. 9,359,365, Heterocyclic Compounds and Uses Thereof, Patented.
U.S. Appl. No. 14/222,500, filed Mar. 21, 2014, U.S. Pat. No. 9,296,742, Heterocyclic Kinase Inhibitors, Patented.
U.S. Appl. No. 14/292,475, filed May 30, 2014, 2014-0377258, Treatment of Cancers Using PI3 Kinase Isoform Modulators, Published.
U.S. Appl. No. 15/030,701, filed Apr. 20, 2016, 2016-0244452, Unassigned, Heterocyclic Compounds and Uses Thereof, Abandoned.
U.S. Appl. No. 14/297,526, filed Jun. 5, 2014, U.S. Pat. No. 9,546,180, Heterocyclic Compounds and Uses Thereof, Patented.
U.S. Appl. No. 14/296,953, filed Jun. 5, 2014, U.S. Pat. No. 9,216,982, Certain Chemical Entities, Compositions and Methods, Patented.
U.S. Appl. No. 14/302,340, filed Jun. 11, 2014, U.S. Pat. No. 9,326,505, Heterocyclic Compounds and Uses Thereof, Patented.
U.S. Appl. No. 14/327,499, filed Jul. 9, 2014, U.S. Pat. No. 9,290,497, Processes for Preparing Isoquinolinones and Solid Forms of Isoquinolinones, Patented.
U.S. Appl. No. 14/439,965, filed Apr. 30, 2015, 2015-0283142, Treatment of Cancers Using PI3 Kinase Isoform Modulators, Published.
U.S. Appl. No. 14/448,998, filed Jul. 31, 2014, U.S. Pat. No. 9,527,847, Treatment of Lupus, Fibrotic Conditions, and Inflammatory Myopathies and Other Disorders Using PI3 Kinase Inhibitors, Patented.
U.S. Appl. No. 14/512,262, filed Oct. 10, 2014, U.S. Pat. No. 9,388,183, Heterocyclic Compounds and Uses Thereof, Patented.
U.S. Appl. No. 14/573,961, filed Dec. 17, 2014, U.S. Pat. No. 9,255,108, Heterocyclic Compounds and Uses Thereof, Patented.
U.S. Appl. No. 15/059,962, filed Mar. 3, 2016, U.S. Pat. No. 9,822,131, Certain Chemical Entities, Composition and Methods, Patented.
U.S. Appl. No. 14/661,656, filed Mar. 18, 2015, U.S. Pat. No. 9,775,844, Heterocyclic Compounds and Uses Thereof, Patented.
U.S. Appl. No. 14/592,628, filed Jan. 8, 2015, U.S. Pat. No. 9,718,815, Heterocyclic Compounds and Uses Thereof, Patented.
U.S. Appl. No. 14/687,714, filed Apr. 15, 2015, 2015-0320754, Combination Therapies, Published.
U.S. Appl. No. 14/687,768, filed Apr. 15, 2015, 2015-0320755, Combination Therapies, Published.
U.S. Appl. No. 14/695,699, filed Apr. 24, 2015, U.S. Pat. No. 9,828,377, Heterocyclic Compounds and Uses Thereof, Patented.
U.S. Appl. No. 14/710,336, filed May 12, 2015, U.S. Pat. No. 9,605,003, Heterocyclic Compounds and Uses Thereof, Patented.
U.S. Appl. No. 15/051,529, filed Feb. 23, 2016, U.S. Pat. No. Re. 46,621, Processes for Preparing Isoquinolinones and Solid Forms of Isoquinolinones, Patented.
U.S. Appl. No. 14/874,328, filed Oct. 2, 2015, U.S. Pat. No. 9,708,348, Heterocyclic Compounds and Uses Thereof, Patented.
U.S. Appl. No. 15/264,417, filed Sep. 13, 2016, U.S. Pat. No. 10,160,761, Solid Forms of Isoquinolinones, and Process of Making, Composition Comprising, and Methods of Using the Same, Patented.
U.S. Appl. No. 14/869,637, filed Sep. 29, 2015, U.S. Pat. No. 9,738,644, Chemical Compounds, Compositions and Methods for Kinase Modulation, Patented.
U.S. Appl. No. 14/876,589, filed Oct. 6, 2015, 2016-0022692, Treatment of Rheumatoid Arthritis and Asthma Using PI3 Kinase Inhibitors, Abandoned.
U.S. Appl. No. 14/884,612, filed Oct. 15, 2015, U.S. Pat. No. 9,522,146, Certain Chemical Entities, Compositions and Methods, Patented.
U.S. Appl. No. 14/894,854, filed Nov. 30, 2015, 2016-0113932, Unassigned, Treatment of Cancers Using PI3 Kinase Isoform Modulators, Abandoned.
U.S. Appl. No. 14/938,647, filed Nov. 11, 2015, U.S. Pat. No. 9,655,892, Certain Chemical Entities, Compositions and Methods, Patented.
U.S. Appl. No. 14/971,954, filed Dec. 16, 2015, 2016-0207940, Heterocyclic Compounds and Uses Thereof, Abandoned.
U.S. Appl. No. 15/016,117, filed Feb. 4, 2016, U.S. Pat. No. 9,840,505, Processes for Preparing Isoquinolinones and Solid Forms of Isoquinolinones, Patented.
U.S. Appl. No. 16/085,536, filed Sep. 14, 2018, 2019-0202835, Isotopologues of Isoquinolinone and Quinazolinone Compounds and Uses Thereof As PI3K Kinase Inhibitors, Published.
U.S. Appl. No. 15/050,029, filed Feb. 22, 2016, U.S. Pat. No. 9,790,228, Heterocyclic Kinase Inhibitors, Patented.
U.S. Appl. No. 16/1312,896, filed Dec. 21, 2018, 2019-0216816, Unassigned, Combination Therapies, Published.
U.S. Appl. No. 16/308,377, filed Dec. 7, 2018, 2019-0135833, Unassigned, Heterocyclic Compounds and Uses Thereof, Published.
U.S. Appl. No. 15/179,570, filed Jun. 10, 2016, Unpublished, Unassigned, Heterocyclic Compounds and Uses Thereof, Abandoned.
U.S. Appl. No. 15/333,803, filed Oct. 25, 2016, 2017-0137407, Heterocyclic Compounds and Uses Thereof, Abandoned.
U.S. Appl. No. 15/347,489, filed Nov. 9, 2016, 2017-0281614, Certain Chemical Entities, Compositions and Methods, Abandoned.
U.S. Appl. No. 15/599,378, filed May 18, 2017, 2018-0098983, Certain Chemical Entities, Compositions and Methods, Published.
U.S. Appl. No. 15/621,815, filed Jun. 13, 2017, U.S. Pat. No. 10,253,047, Heterocyclic Compounds and Uses Thereof, Patented.
U.S. Appl. No. 15/621,764, filed Jun. 13, 2017, Unpublished, Unassigned, Chemical Compounds, Compositions and Methods for Kinase Modulation, Abandoned.
U.S. Appl. No. 15/672,964, filed Aug. 9, 2017, 2018-0055852, Heterocyclic Compounds and Uses Thereof, Published.
U.S. Appl. No. 15/675,185, filed Aug. 11, 2017, Unpublished, Unassigned, Heterocyclic Compounds and Uses Thereof, Abandoned.
U.S. Appl. No. 15/794,816, filed Oct. 26, 2017, U.S. Pat. No. 10,329,299, Heterocyclic Compounds and Uses Thereof, Patented.
U.S. Appl. No. 15/789,868, filed Oct. 20, 2017, 2018-0258103, Certain Chemical Entities, Compositions and Methods, Published.
U.S. Appl. No. 16/172,539, filed Oct. 26, 2018, Unpublished, Unassigned, Certain Chemical Entities, Compositions and Methods, Pending.
U.S. Appl. No. 16/197,195, filed Nov. 20, 2018, 2019-0185477, Solid Forms of Isoquinolinones, and Process of Making, Composition Comprising, and Methods of Using the Same, Published.
U.S. Appl. No. 16/290,545, filed Mar. 1, 2019, Unpublished, Unassigned, Heterocyclic Compounds and Uses Thereof, Pending.
U.S. Appl. No. 16/417,420, filed May 20, 2019, Unpublished, Unassigned, Heterocyclic Compounds and Uses Thereof, Pending.

Polymorph Form A

Polymorph Form B

Polymorph Form C

Polymorph Form D

Polymorph Form E

Polymorph Form F

Polymorph Form H

Polymorph Form I

Polymorph Form J

Amorphous Compound of Formula (I)

Form E

SOLID FORMS OF (S)-3-(1-(9H-PURIN-6-YLAMINO)ETHYL)-8-CHLORO-2-PHENYLISOQUINOLIN-1(2H)-ONE AND METHODS OF USE THEREOF

CLAIM OF PRIORITY

This application is a divisional application of U.S. patent application Ser. No. 15/016,117, filed Feb. 4, 2016, which is a divisional application of U.S. patent application Ser. No. 14/327,499, filed Jul. 9, 2014, now U.S. Pat. No. 9,290,497, which is a divisional application of U.S. patent application Ser. No. 13/347,423, filed Jan. 10, 2012, now U.S. Pat. No. 8,809,349, which claims the benefit of U.S. Provisional Application Ser. No. 61/431,304, filed on Jan. 10, 2011, and U.S. Provisional Application Ser. No. 61/578,655, filed on Dec. 21, 2011, all of which are incorporated herein by reference in their entireties.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3-kinases, PI4-Kinases), diacylglycerol kinases, and sphingosine kinases.

Phosphoinositide 3-kinases (PI3Ks) constitute a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate a lipid product termed $PIP_3$, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2.

The PI3K signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

Many inhibitors of PI3Ks have been generated. While such compounds are often initially evaluated for their activity when dissolved in solution, solid state characteristics such as polymorphism play an important role. Polymorphic forms of a drug substance, such as an inhibitor of PI3K, can have different chemical and physical properties, including crystallinity, melting point, chemical reactivity, solubility, dissolution rate, optical and mechanical properties, vapor pressure, and density. These properties can have a direct effect on the ability to process or manufacture a drug substance and the drug product. Moreover, polymorphism is often a factor under regulatory review of the 'sameness' of drug products from various manufacturers. For example, polymorphism has been evaluated in compounds such as warfarin sodium, famotidine, and ranitidine. Polymorphism can affect the quality, safety, and/or efficacy of a drug product, such as a kinase inhibitor. Thus, research directed towards polymorphs of PI3K inhibitors and processes for preparing polymorphs of PI3K inhibitors represents a significantly useful field of investigation in the development of active pharmaceutical ingredients (APIs).

In addition, PI3K inhibitors have been used to treat various diseases and disorders in humans (e.g., in clinical trials). For the production of a drug substance intended for use in humans, current Good Manufacturing Practices (GMP) are applicable. Procedures need to be in place that can control the levels of impurities and ensure that API products are produced which consistently meet their predetermined specifications. Thus, a significant need exists for a process to prepare PI3K inhibitors suitable for human use, particularly on a commercial scale, that is, inter alia, safe, scalable, efficient, economically viable, and/or having other desirable properties. Among other entities, disclosed herein are polymorphic forms of PI3K inhibitors which address these needs and provide exemplary advantages.

SUMMARY

In one embodiment, provided herein are polymorphic forms of a compound of Formula (I):

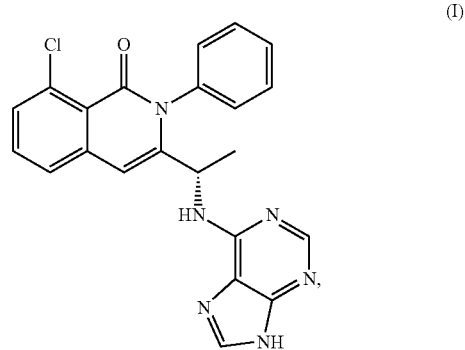 [SMILES: C[C@H](Nc1ncnc2[nH]cnc12)c1cc2cccc(Cl)c2c(=O)n1-c1ccccc1]

herein referred to as Form A, Form B, Form C, Form D, Form E, Form F, Form G, Form H, Form I, Form J, or an amorphous form of a compound of Formula (I), or a salt, solvate, or hydrate thereof; or a mixture of two or more thereof. In one embodiment, the polymorphic form of a compound of Formula (I) can be a crystalline form, a partially crystalline form, an amorphous form, or a mixture of crystalline form(s) and/or amorphous form(s).

In one embodiment, provided herein is a method of preparing a compound of Formula (I):

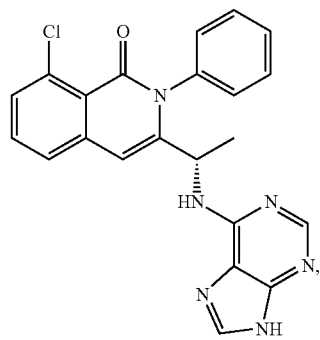

or a pharmaceutically acceptable salt, solvate, or hydrate thereof. In one embodiment, the method comprises any one, two, three, four, five, six, seven, or eight, or more of the following steps:

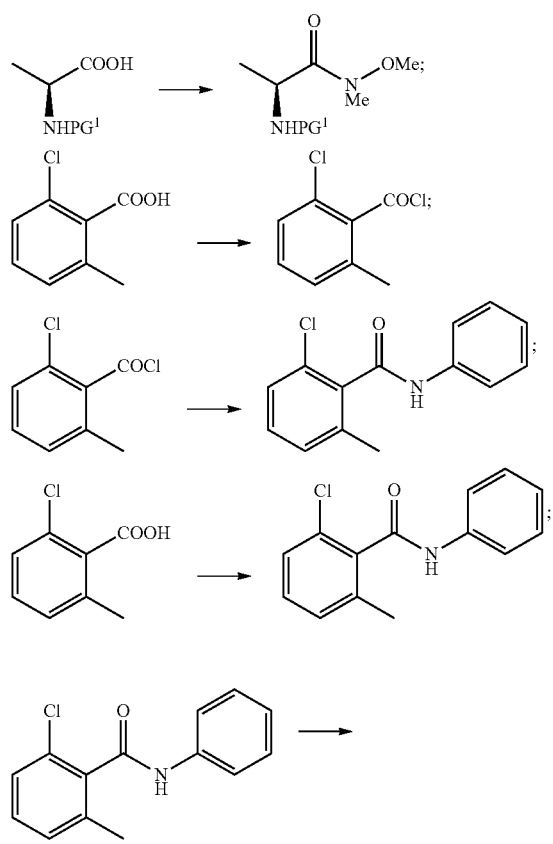

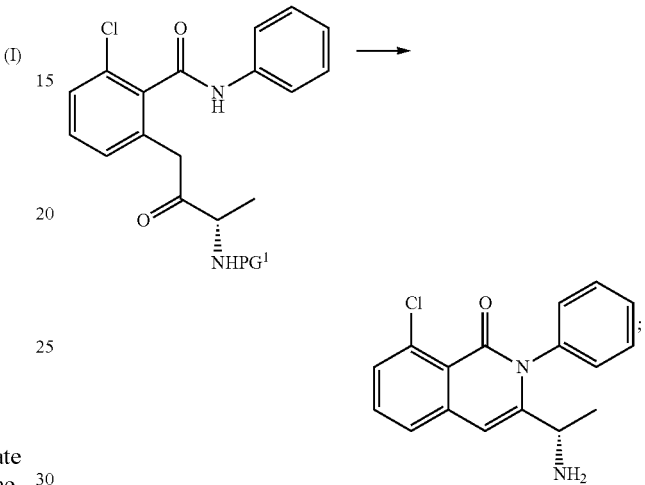

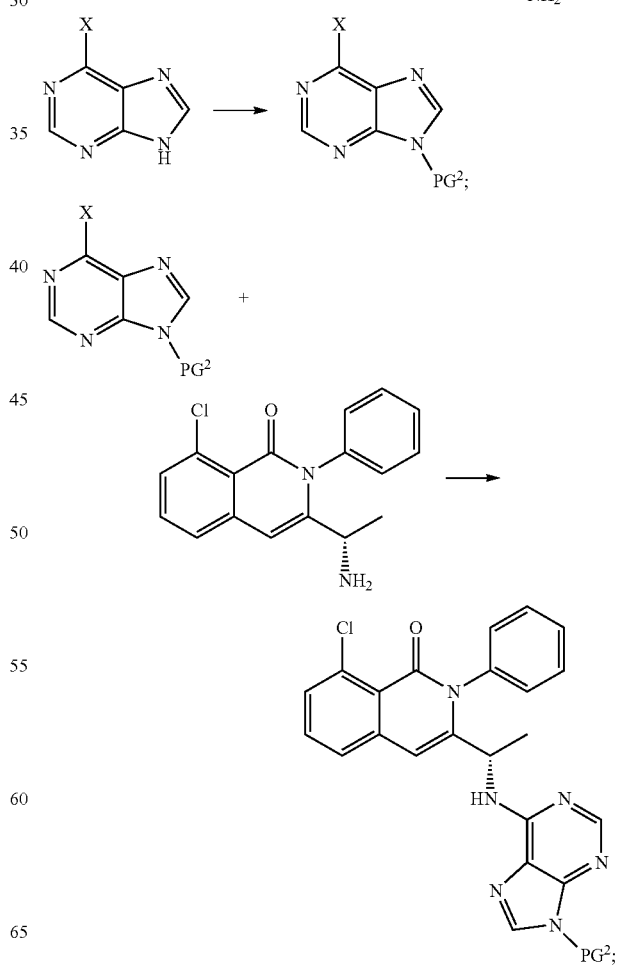

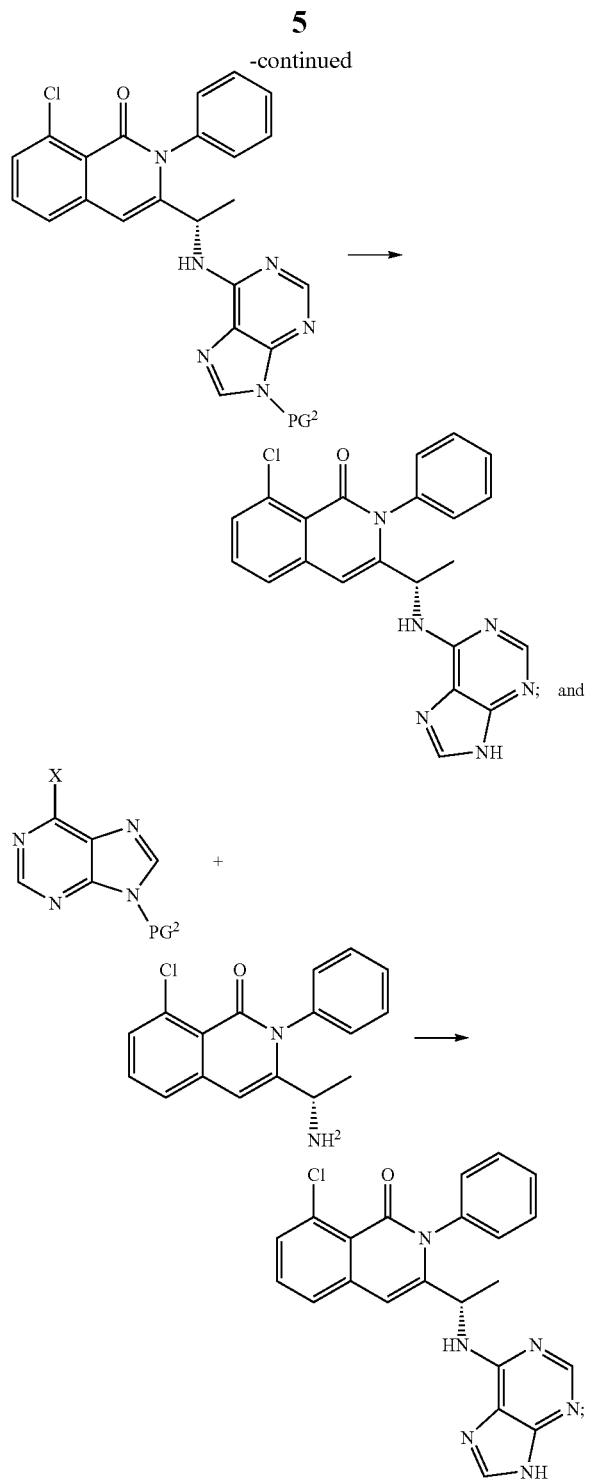

wherein:
X is selected from fluoro, chloro, bromo, iodo, —O—SO₂-4-methylphenyl, and —O—SO₂-methyl;
PG¹ is selected from benzyl, substituted benzyl, methoxycarbonyl, ethoxycarbonyl, substituted ethoxycarbonyl, 9-fluorenyloxycarbonyl, substituted 9-fluorenyloxycarbonyl, 2,2,2,-trichloroethoxycarbonyl, 2-trimethylsilylethoxycarbonyl, (2-phenyl-2-trimethylsilyl)ethoxycarbonyl, 2-phenylethoxycarbonyl, 1,1-dimethyl-2,2-dibromoethoxycarbonyl, 1,1-dimethyl-2,2,2-trichloroethoxycarbonyl, t-butoxycarbonyl, 1-adamantyloxycarbonyl, 2-adamantyloxycarbonyl, triisopropylsiloxycarbonyl, vinyloxycarbonyl, 1-isopropoxycarbonyl, 8-quinolyloxycarbonyl, 2,4-dimethylpent-3-yloxycarbonyl, benzyloxycarbonyl, and substituted benzyloxycarbonyl;

PG² is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl; and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In one embodiment, provided herein is a method of preparing a polymorph Form C of a compound of Formula (I):

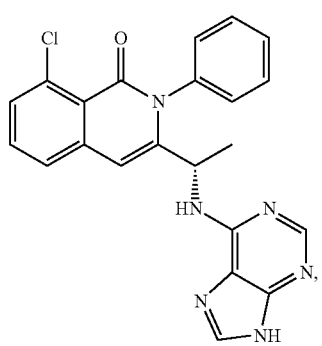

(I)

wherein the method comprises:
(i) exposing a composition comprising at least one non-Form C polymorph of a compound of Formula (I), or a salt, solvate, or hydrate thereof, to a non-anhydrous condition for a period of time sufficient to convert at least about 50% of the total amount of non-Form C polymorph(s) into Form C of a compound of Formula (I); and
(ii) recovering said polymorph Form C.

In one embodiment, a non-anhydrous condition includes water, such as, in a form of water vapor and/or liquid water. In one embodiment, a non-anhydrous condition includes a solvent system comprising a non-water solvent and liquid water. In one embodiment, the non-water solvent is a water-miscible solvent. For example, liquid water can be present in an amount of about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% by volume of the solvent system. In one embodiment, liquid water is present in an amount of between about 10% and about 50% by volume of the solvent system.

In one embodiment, a non-anhydrous condition includes a solvent system comprising water (e.g., about 90% v/v) and isopropyl alcohol (e.g., about 10% v/v). In one embodiment, a non-anhydrous condition includes a solvent system comprising water and ethanol. In one embodiment, a non-anhydrous condition includes a solvent system comprising water and a water-miscible solvent, such as, e.g., $C_1$-$C_4$ alcohol, acetone, acetonitrile, among others. In one embodiment, a water-miscible solvent is an alcohol, such as, e.g., methanol, ethanol, 1-propanol, 2-propanol, 1-butanol, 2-butanol, t-butanol, ethylene glycol, among others. In one embodiment, the ratio of water and water-miscible solvent in a solvent system provided herein is about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, or about 1:50 v/v. In one embodiment, the ratio of water and water-miscible solvent in a solvent system provided herein is from about 50:1 to about 1:1, from about 40:1 to about 1:1, from about 30:1 to about 1:1, from about 20:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 3:1, from about 2:1 to about 1:2, from about 1:1 to about 1:4, from about 1:1 to about 1:5, from about 1:1 to about 1:6, from about 1:1 to about 1:7, from about 1:1 to about 1:8, from about 1:1 to about 1:9, from about 1:1 to about 1:10, from about 1:1 to about 1:20, from about 1:1 to about 1:30, from about 1:1 to about 1:40, or from about 1:1 to about 1:50 v/v.

In one embodiment, a non-Form C polymorph is a solid form of a compound of Formula (I), or a salt, solvate, or hydrate thereof (e.g., a crystalline form, an amorphous form, or a mixture of crystalline form(s) and/or amorphous form(s)), which is not polymorph Form C of a compound of Formula (I). In one embodiment, a non-Form C polymorph is Form A, Form B, Form D, Form E, Form F, Form G, Form H, Form I, Form J, or an amorphous form of a compound of Formula (I), or a salt, solvate, or hydrate thereof, or a mixture of two or more thereof. In one embodiment, a non-Form C polymorph can comprise at least about 50% by weight polymorph Form A of a compound of Formula (I). In one embodiment, a non-Form C polymorph (e.g., Form A or Form B) can be obtained from a composition comprising Form C.

In one embodiment, provided herein is a method of preparing polymorph Form C of a compound of Formula (I):

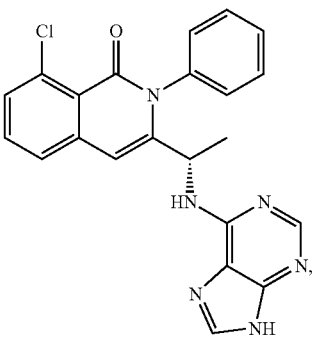

(I)

wherein the method comprises:
(i) combining a compound of Formula (Ia):

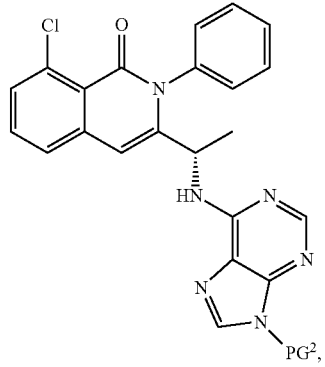

(Ia)

wherein
$PG^2$ is a protecting group selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate;

with one or more reagents to remove the protecting group $PG^2$ to form the compound of Formula (I); and
(ii) recovering polymorph Form C of the compound of Formula (I);
wherein at least one of steps (i) and (ii) occurs in a non-anhydrous condition.

In some embodiments, one or more reagents to remove the protecting group $PG^2$ includes, but is not limited to, acids such as HCl, HBr and TFA; carbonate bases, such as $Na_2CO_3$ and $K_2CO_3$; hydroxide bases, such as NaOH and KOH; lithium bases, such as methyl lithium, ethyl lithium, propyl lithium, n-butyl lithium, n-pentyl lithium, and n-hexyl lithium; oxidants such as ceric ammonium nitrate; hydrogenation conditions, such as cyclohexadiene/Pd black, and $H_2$/Pd on carbon; TBAF, and $BF_3.Et_2O$. In one embodiment, a non-anhydrous condition includes water, such as in a form of water vapor and/or liquid water. In one embodiment, a non-anhydrous condition includes a solvent system comprising a non-water solvent and liquid water, as described herein elsewhere.

In certain embodiments, a polymorph provided herein is polymorph Form C of a compound of Formula (I). In certain embodiments, provided herein is a solid form of a compound of Formula (I) comprising Form C of a compound of Formula (I). In certain embodiments, provided herein is a solid form of a compound of Formula (I) comprising Form C of a compound of Formula (I), which is substantially pure. In one embodiment, Form C can be characterized by having X-ray powder diffraction (XRPD) peaks at about 10.4, about 13.3, and about 24.3 degrees 2θ. In certain embodiments, Form C is characterized by having differential scanning calorimetry (DSC) comprising an endotherm at about 208° C. In other embodiments, Form C is characterized by having differential scanning calorimetry (DSC) comprising an endotherm at about 208° C., and exotherm at about 222° C., and an endotherm at about 280° C. In certain embodiments, Form C can be characterized by thermogravimetric analysis where the % weight loss observed is about 1.7% at about 80° C. and about 0.2% at about 190° C.

In one embodiment, provided herein is a method of preparing polymorph Form A of a compound of Formula (I):

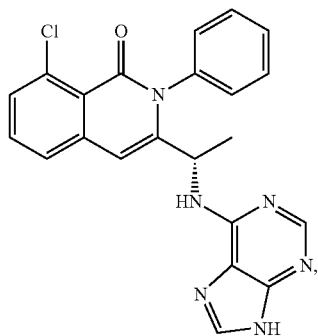

(I)

wherein the method comprises:
(i) combining a compound of Formula (Ia):

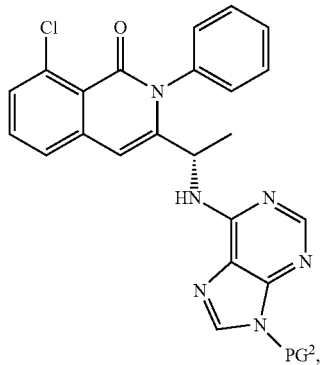

(Ia)

wherein
PG² is a protecting group selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate; with one or more reagents to remove the protecting group PG² to form a compound of Formula (I); and
(ii) recovering polymorph Form A of the compound of Formula (I).

In some embodiments, step (ii) can include recrystallization of a compound of Formula (I), or a salt, solvate, or hydrate thereof, from a mono-solvent system, or from a multi-solvent system that does not contain both ethyl acetate and hexane. In certain embodiments, the method further comprises a step of dissolving a compound of Formula (I), or a salt, solvate, or hydrate thereof, in a mono-solvent system or a multi-solvent system, removing residual solid matter to yield a liquid solution, cooling said liquid solution at a rate to effect crystallization of Form A, and recovering Form A from the liquid solution.

In some embodiments, one or more reagents to remove the protecting group PG² includes, but is not limited to, acids such as HCl, HBr and TFA; carbonate bases, such as $Na_2CO_3$ and $K_2CO_3$; hydroxide bases, such as NaOH and KOH; lithium bases, such as methyl lithium, ethyl lithium, propyl lithium, n-butyl lithium, n-pentyl lithium, and n-hexyl lithium; oxidants such as ceric ammonium nitrate; hydrogenation conditions, such as cyclohexadiene/Pd black, and $H_2$/Pd on carbon; TBAF, and $BF_3.Et_2O$.

In one embodiment, provided herein is a composition comprising a compound of Formula (I):

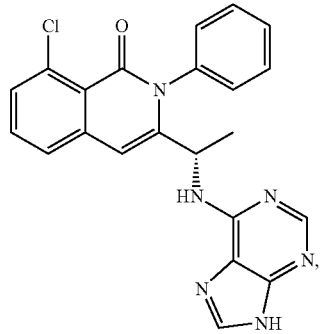

(I)

or a pharmaceutically acceptable salt, solvate, or hydrate thereof, and one or more pharmaceutically acceptable excipients.

In one embodiment, the composition comprises polymorph Form C. In one embodiment, the composition comprises a mixture of polymorph Form C and at least one non-Form C polymorph of a compound of Formula (I), or a pharmaceutically acceptable salt, solvate, or hydrate thereof. For example, in certain embodiments, the composition can comprise polymorph Form C and polymorph Form A. In other embodiments, the composition can comprise polymorph Form C and polymorph Form B. In other embodiments, the composition can comprise polymorph Form C and polymorph Form D. In other embodiments, the composition can comprise polymorph Form C and polymorph Form E. In other embodiments, the composition can comprise polymorph Form C and polymorph Form F. In other embodiments, the composition can comprise polymorph Form C and polymorph Form G. In other embodiments, the composition can comprise polymorph Form C and polymorph Form H. In other embodiments, the composition can comprise polymorph Form C and polymorph Form I. In other embodiments, the composition can comprise polymorph Form C and polymorph Form J. In other embodiments, the composition can comprise polymorph Form C and an amorphous form of a compound of Formula (I), or a pharmaceutically acceptable salt, solvate, or hydrate thereof. In one embodiment, the ratio of polymorph Form C to the total amount of non-Form C polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In one embodiment, the composition comprising Form C is a pharmaceutical composition. In one embodiment, the composition is at least about 98% by weight of a compound of Formula (I), or a pharmaceutically acceptable salt, solvate, or hydrate thereof.

In one embodiment, the composition comprises a mixture of polymorph Form A and at least one non-Form A polymorph of a compound of Formula (I), or a pharmaceutically acceptable salt, solvate, or hydrate thereof. For example, in certain embodiments, the composition can comprise polymorph Form A and polymorph Form B. In other embodiments, the composition can comprise polymorph Form A and polymorph Form C. In other embodiments, the composition can comprise polymorph Form A and polymorph Form D. In other embodiments, the composition can comprise polymorph Form A and polymorph Form E. In other embodiments, the composition can comprise polymorph Form A and polymorph Form F. In other embodiments, the composition can comprise polymorph Form A and polymorph Form G. In other embodiments, the composition can comprise polymorph Form A and polymorph Form H. In other embodiments, the composition can comprise polymorph Form A and polymorph Form I. In other embodiments, the composition can comprise polymorph Form A and polymorph Form J. In other embodiments, the composition can comprise polymorph Form A and an amorphous form of a compound of Formula (I), or a pharmaceutically acceptable salt, solvate, or hydrate thereof. In one embodiment, the ratio of polymorph Form A to the total amount of non-Form A polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In one embodiment, the ratio of polymorph Form A to the total amount of non-Form A polymorph(s) is less than about 1:1, less than about 2:1, less than about 3:1, less than about 4:1, less than about 5:1, less than about 6:1, less than about 7:1, less than about 8:1, or less than about 9:1. In one embodiment, the composition comprising Form A is a pharmaceutical composition. In one embodiment, the composition is at least about 98% by weight of a compound of Formula (I), or a pharmaceutically acceptable salt, solvate, or hydrate thereof.

In one embodiment, the composition provided herein is a solid dosage form comprising a polymorph of a compound of Formula (I), or a pharmaceutically acceptable salt, solvate, or hydrate thereof and one or more pharmaceutically acceptable excipients. In one embodiment, the composition provided herein is a single unit dosage form comprising a polymorph of a compound of Formula (I), or a pharmaceutically acceptable salt, solvate, or hydrate thereof. In one embodiment, the composition provided herein is a tablet or a capsule. In one embodiment, the composition provided herein is a capsule.

In one embodiment, the composition provided herein comprises a therapeutically effective amount of a polymorph of a compound of Formula (I), or a pharmaceutically acceptable salt, solvate, or hydrate thereof. In some embodiments, the therapeutically effective amount is about 0.5, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 600, about 700, about 800, about 900, or about 1000 mg, or more. In one embodiment, the composition provided herein comprises at least one pharmaceutically acceptable carrier or excipient. In some embodiments, the composition provided herein comprises one or more pharmaceutically acceptable carrier(s) or excipient(s), including, e.g., microcrystalline cellulose, crospovidone, and/or magnesium stearate. In one embodiment, the composition provided herein is an immediate-release dosage form. In some embodiments, the composition provided herein is a hard gelatin capsule. In some embodiments, the composition provided herein is a soft gelatin capsule. In some embodiments, the composition provided herein comprises Form C of a compound of Formula (I). In some embodiments, the composition provided herein comprises Form A of a compound of Formula (I). In some embodiments, the composition provided herein comprises an amorphous form of a compound of Formula (I). In some embodiments, the composition provided herein comprises a mixture of two or more polymorphs of a compound of Formula (I), or a pharmaceutically acceptable salt, solvate, or hydrate thereof, e.g., polymorphs A, B, C, D, E, F, G, H, I, and J as described herein.

In other embodiments, the composition provided herein is a suspension comprising carboxymethyl cellulose and water. In one embodiment, the composition provided herein can further comprise one or more excipients, such as, e.g., polysorbate, polyethyleneglycol, cyclodextrin, dextrose, n-methylpyrrolidone, pH buffers, dilute hydrochloric acid, polyoxyethylene esters of 12-hydroxystearic acid, or a mixture of two or more thereof. Other excipients that can be used in exemplary formulations include, but are not limited to, fillers such as lactose, mannitol, starch, sorbitol, sucrose, dicalcium phosphate, and microcrystalline cellulose; disintegrants such as croscarmellose sodium and sodium starch glycolate; glidants such as colloidal silicon dioxide, silicon dioxide, magnesium silicate, and talc; lubricants such as sodium stearyl fumarate and stearic acid; and surfactants such as sodium lauryl sulphate, sodium dodecyl sulphate, Tween® 80, and Lutrol®.

In one embodiment, the composition provided herein is used for the treatment of a PI3K-associated disorder (e.g., a disease or disorder described herein elsewhere or known in the art). In one embodiment, the composition provided herein is used for inhibiting PI3K kinase activity. The efficacy of the compound of Formula (I) in these methods and others as disclosed herein has been described in, for example, US 2009/0312319.

In one embodiment, provided herein is a method of treating a PI3K-associated disorder (e.g., a disorder or disease described herein elsewhere or known in the art), wherein the method comprises administering a polymorph of a compound of Formula (I), or a pharmaceutically acceptable salt, solvate, or hydrate thereof, to a subject in need thereof. In one embodiment, provided herein is a method of treating a PI3K-associated disorder, wherein the method comprises administering a polymorph of a compound of Formula (I), or a pharmaceutically acceptable salt, solvate, or hydrate thereof, to a subject in need thereof. In one embodiment, provided herein is a method of treating a PI3K-associated disorder, wherein the method comprises administering a composition provided herein, to a subject in need thereof. In one embodiment, the method comprises administering a polymorph of a compound of Formula (I), or a pharmaceutically acceptable salt, solvate, or hydrate thereof, or a composition thereof, to a subject in need thereof, orally, parenterally, or topically. In one embodiment, the method comprises co-administering one or more additional therapeutic agent(s) or treating the subject with one or more additional therapy(ies) (e.g., radiation therapy or surgery).

DETAILED DESCRIPTION

Figure 1:
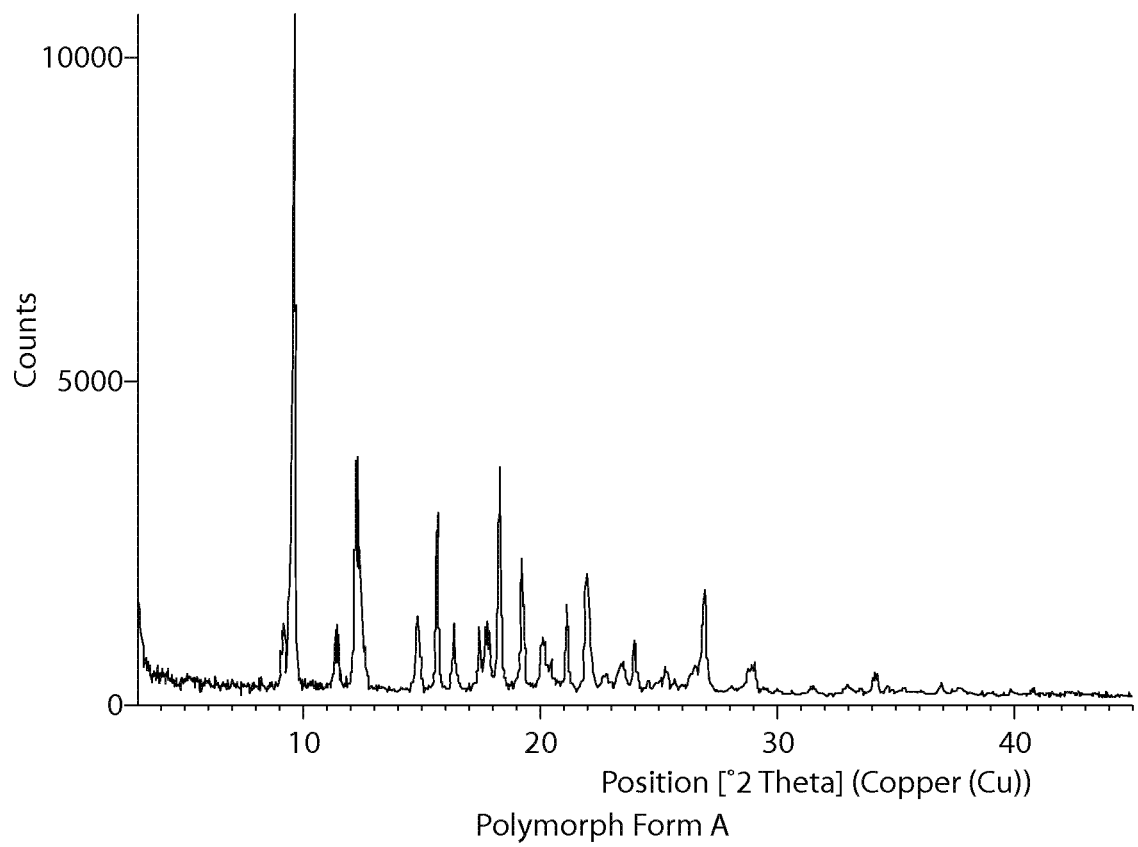
FIG. 1 shows an X-ray powder diffraction (XRPD) for Polymorph Form A.

Certain features of the disclosure are set forth with particularity in the appended claims. An understanding of various features and/or advantages of the present disclosure can be obtained by reference to the following detailed description that sets forth illustrative embodiments.

While various embodiments of the present disclosure have been shown and described herein, it will be apparent to those skilled in the art that such embodiments are provided by way of example only. Numerous variations, changes, and substitutions will now occur to those skilled in the art without departing from the present disclosure. It should be understood that various alternatives to the embodiments described herein can be employed in view of the present disclosure.

I. Definitions

Unless defined otherwise, all technical and scientific terms used herein have the same meaning as is commonly understood by one of skill in the art.

As used in the specification and claims, the singular form "a", "an" and "the" includes plural references unless the context clearly dictates otherwise.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range can vary from, for example, between 1% and 15%, between 1% and 10%, between 1% and 5%, between 0.5% and 5%, and between 0.5% and 1%, of the stated number or numerical range. As disclosed herein, every instance where a number or numerical range preceded by the term "about" also includes the embodiment of the given number(s). For example, "about 3° C." discloses the embodiment of the temperature being "3° C.". The terms "about" and "approximately" are used completely interchangeable throughout the disclosure. The term "between" includes the endpoint numbers on both limits of the range. For example, the range described by "between 3 and 5" is inclusive of the numbers "3" and "5".

As used herein, and unless otherwise specified, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present disclosure.

As used herein, and unless otherwise specified, the term "agonist" refers to a compound having the ability to initiate or enhance a biological function of a target protein, whether by enhancing or initiating the activity or expression of the target protein. Accordingly, the term "agonist" is defined in the context of the biological role of the target protein. While agonists provided herein can specifically interact with (e.g., bind to) the target, compounds that initiate or enhance a biological activity of the target protein by interacting with other members of the signal transduction pathway of which the target protein is a member are also specifically included within this definition.

As used herein, and unless otherwise specified, the terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While antagonists provided herein can specifically interact with (e.g., bind to) the target, compounds that inhibit a biological activity of the target protein by interacting with other members of the signal transduction pathway of which the target protein is a member are also specifically included within this definition. In one embodiment, a biological activity inhibited by an antagonist is associated with the development, growth, or spread of a tumor, or an undesired immune response, e.g., as manifested in autoimmune disease.

As used herein, and unless otherwise specified, an "anti-cancer agent", "anti-tumor agent" or "chemotherapeutic agent" refers to any agent useful in the treatment of a neoplastic condition. One class of anti-cancer agents comprises chemotherapeutic agents. As used herein, and unless otherwise specified, "chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

As used herein, and unless otherwise specified, the term "cell proliferation" refers to a phenomenon by which the cell number has changed as a result of division. In one embodiment, this term also encompasses cell growth by which the cell morphology has changed (e.g., increased in size) consistent with a proliferative signal.

As used herein, and unless otherwise specified, the term "co-administration," "administered in combination with," and their grammatical equivalents, encompasses administration of two or more agents to an animal either simultaneously or sequentially. In one embodiment, both agents and/or their metabolites are present in the animal at the same time. In one embodiment, co-administration includes simultaneous administration in separate compositions, administration at different times in separate compositions, or administration in a composition in which both agents are present.

As used herein, and unless otherwise specified, the term "effective amount" or "therapeutically effective amount" refers to an amount of a compound described herein that is sufficient to effect an intended application or effect, including, but not limited to, disease treatment, as defined herein. The therapeutically effective amount can vary depending upon the intended application (in vitro or in vivo), or the subject and disease condition being treated, e.g., the weight and age of the subject, the severity of the disease condition, the manner of administration, and the like, which can be determined by one of ordinary skill in the art. The term can also apply to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, and unless otherwise specified, the terms "treatment", "treating", "palliating" and "ameliorating" are used interchangeably herein, and refer to an approach for obtaining beneficial or desired results, including, but not limited to, a therapeutic benefit and/or a prophylactic benefit. In one embodiment, therapeutic benefit means eradication or amelioration of the underlying disorder being treated. In one embodiment, a therapeutic benefit is achieved with the eradication or amelioration of one or more of the physiological symptoms associated with the underlying disorder, such that an improvement is observed in the patient, notwithstanding that the patient can still be afflicted with the underlying disorder. For prophylactic benefit, the compositions can be administered to a patient at risk of developing a particular disease, or to a patient reporting one or more of the physiological symptoms of a disease, even though a diagnosis of this disease can or can not have been made.

As used herein, and unless otherwise specified, a "therapeutic effect" encompasses a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, and unless otherwise specified, "signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator can augment (agonist) or suppress (antagonist) the activity of a signaling molecule.

As used herein, and unless otherwise specified, the term "selective inhibition" or "selectively inhibit" as applied to a biologically active agent refers to the agent's ability to selectively reduce the target signaling activity as compared to off-target signaling activity, via direct or interact interaction with the target.

As used herein, and unless otherwise specified, the term "in vivo" refers to an event that takes place in a subject's body.

As used herein, and unless otherwise specified, the term "in vitro" refers to an event that takes places outside of a subject's body. For example, an in vitro assay encompasses any assay run outside of a subject assay. In vitro assays encompass cell-based assays in which cells alive or dead are employed. In one embodiment, in vitro assays also encompass a cell-free assay in which no intact cells are employed.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, and unless otherwise specified, "radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (e.g., beta emitters), conversion electron emitters (e.g., strontium-89 and samarium- 153-EDTMP), or high-energy radiation, including without limitation, x-rays, gamma rays, and neutrons.

As used herein, the term "combining" refers to bringing one or more chemical entities into association with another one or more chemical entities. Combining includes the processes of adding one or more compounds to a solid, liquid or gaseous mixture of one or more compounds (the same or other chemical entities), or a liquid solution or multiphasic liquid mixture. The act of combining includes the process or processes of one or more compounds reacting (e.g., bond formation or cleavage; salt formation, solvate formation, chelation, or other non-bond altering association) with one or more compounds (the same or other chemical entities). The act of combining can include alteration of one or more compounds, such as by isomerization (e.g., tautomerization, resolution of one isomer from another, racemization As used herein, the term "recovering" includes, but is not limited to, the action of obtaining one or more compounds by collection during and/or after a process step as disclosed herein, and the action of obtaining one or more compounds by separation of one or more compounds from one or more other chemical entities during and/or after a process step as disclosed herein. The term "collection" refers to any action (s) known in the art for this purpose, including, but not limited to, decanting a mother liquor from a solid to obtain one or more compounds, and evaporation of liquid media in a solution or other mixture to afford a solid, oil, or other residue that includes one or more compounds. The solid can be crystalline, acrystalline, partially crystalline, amorphous, containing one or more polymorphs, a powder, granular, of varying particle sizes, of uniform particle size, among other characteristics known in the art. An oil can vary in color and viscosity, and include one or more solid forms as a heterogeneous mixture, among other characteristics known in the art. The term "separation" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques. Recovering one or more compounds can involve preparation of a salt, solvate, hydrate, chelate or other complexes of the same, then collecting or separating as described above.

As used herein, a "pharmaceutically acceptable form" of a disclosed Formula (I) includes, but is not limited to, pharmaceutically acceptable salts, hydrates, solvates, chelates, non-covalent complexes, isomers, prodrugs, and isotopically labeled derivatives thereof, and mixtures thereof. Hence, the terms "chemical entity" and "chemical entities" also encompass pharmaceutically acceptable salts, hydrates, solvates, chelates, non-covalent complexes, isomers, prodrugs, and isotopically labeled derivatives, and mixtures thereof. In some embodiments, a pharmaceutically acceptable form of a disclosed Formula (I) includes a salt, a solvate, or a hydrate thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts derived from appropriate bases include alkali metal, alkaline earth metal, ammonium and $N^+(C_{1-4}alkyl)^4$- salts. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines, including naturally occurring substituted amines, cyclic amines, basic ion exchange resins, and the like, examples include, but are not limited to, isopropylamine, trimethylamine, diethylamine, triethylamine, tripropylamine, and ethanolamine. In some embodiments, the pharmaceutically acceptable base addition salt is ammonium, potassium, sodium, calcium, or magnesium salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e., two counterions) and higher salts (e.g., three or more counterions) are encompassed within the meaning of pharmaceutically acceptable salts.

In addition, if a compound of the present disclosure is obtained as an acid addition salt, the free base can be obtained by basifying a solution of the acid salt. Conversely, if a product is a free base, an acid addition salt, particularly a pharmaceutically acceptable addition salt, can be produced by dissolving the free base in a suitable organic solvent and treating the solution with an acid, in accordance with conventional procedures for preparing acid addition salts from base compounds. Those skilled in the art will recognize various synthetic methodologies that can be used to prepare non-toxic pharmaceutically acceptable addition salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. In some embodiments, the hydrate can be a channel hydrate. It will be understood that the term "compound" as used herein encompasses the compound and solvates of the compound, as well as mixtures thereof.

As used herein, and unless otherwise specified, "prodrug" is meant to indicate a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. In some embodiments, the prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active Formula (I)n vivo when such prodrug is administered to a mammalian subject. Prodrugs of an active compound, as described herein, can be prepared by modifying functional groups present in the active Formula (I)n such a way that the modifications are cleaved, either in routine manipulation or in vivo, to the parent active compound. Prodrugs include compounds wherein a hydroxy, amino or mercapto group is bonded to any group that, when the prodrug of the active Formula (I) is administered to a mammalian subject, cleaves to form a free hydroxy, free amino or free mercapto group, respectively. Examples of prodrugs include, but are not limited to, acetate, formate, and benzoate derivatives of an alcohol; or acetamide, formamide, and benzamide derivatives of an amine functional group in the active compound, and the like. Other examples of prodrugs include compounds that comprise —NO, —N$_{O2}$, —ONO, or —ON$_{O2}$ moieties. Prodrugs can typically be prepared using well-known methods, such as those described in Burger's Medicinal Chemistry and Drug Discovery, 172-178, 949-982 (Manfred E. Wolff ed., 5th ed., 1995), and Design of Prodrugs (H. Bundgaard ed., Elsevier, N.Y., 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_1$-$C_5$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the Formula (I)ncorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$) alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a Formula (I)s an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

As used herein, and unless otherwise specified, the term "stereomerically pure" means a composition or substance that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other stereoisomers (e.g., diastereoisomers or enantiomers, or syn or anti isomers, or cis or trans isomers) of the compound. A typical stereomerically pure compound comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, or greater than about 97 percent by weight of one stereoisomer of the compound and less than about 3 percent by weight of the other stereoisomers of the compound.

As used herein, and unless otherwise specified, the term "enantiomerically pure" means a stereomerically pure composition of a compound having one or more chiral center(s).

As used herein, and unless otherwise specified, the terms "enantiomeric excess" and "diastereomeric excess" are used interchangeably herein. In some embodiments, compounds with a single stereocenter can be referred to as being present in "enantiomeric excess," and those with at least two stereocenters can be referred to as being present in "diastereomeric excess." For example, the term "enantiomeric excess" is well known in the art and is defined as:

$$ee_a = \left(\frac{conc.\ of\ a - conc.\ of\ b}{conc.\ of\ a + conc.\ of\ b}\right) \times 100$$

Thus, the term "enantiomeric excess" is related to the term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than about 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the Formula (I)s made up of at least about 95%, 98%, or 99% by weight of one enantiomer.

In some embodiments, the Formula (I) is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N Y, 1962); and *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a tautomer. As used herein, the term "tautomer" is a type of isomer that includes two or more interconvertable compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. An example of keto-enol tautomerization is the interconversion of pentane-2,4-dione and 4-hydroxypent-3-en-2-one tautomers. Another example of tautomerization is phenol-keto tautomerization. Another example of phenol-keto tautomerization is the interconversion of pyridin-4-ol and pyridin-4(1H)-one tautomers.

As defined herein, the term "Formula (I)" includes (S)-3-(1-(9H-purin-6-ylamino)ethyl)-8-chloro-2-phenylisoquinolin-1(2H)-one in its imide tautomer shown below as (I-1) and in its lactim tautomer shown below as (I-2):

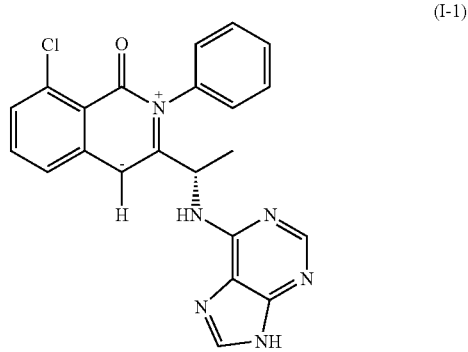

(I-1)

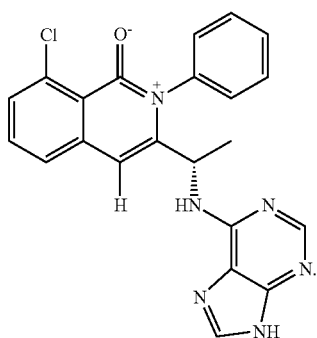

As defined herein, the term "Formula (I)" includes (S)-3-(1-(9H-purin-6-ylamino)ethyl)-8-chloro-2-phenylisoquinolin-1(2H)-one in its imide tautomer shown below as (I-1) and in its lactim tautomer shown below as (I-2):

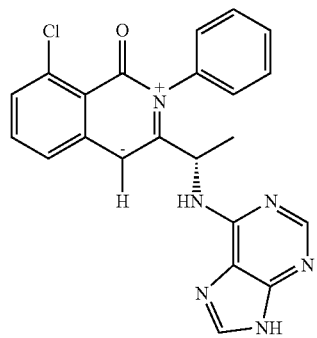

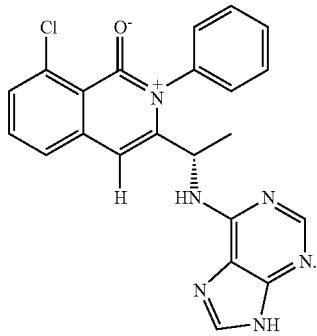

As used herein, and unless otherwise specified, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon, or the replacement of a nitrogen by $^{13}N$- or $^{15}N$-enriched nitrogen, or the replacement of an oxygen by $^{14}O$-, $^{15}O$-, $^{17}O$-, or $^{18}O$-enriched oxygen, or the replacement of a chlorine by $^{35}Cl$-, $^{36}Cl$-, or $^{37}Cl$-enriched chlorine, are within the scope of this disclosure.

In one embodiment, the compounds of the present disclosure can also contain unnatural proportions of atomic isotopes at one or more of atoms that constitute such compounds. For example, the compounds can be radiolabeled with radioactive isotopes, such as, for example, tritium ($^3H$), iodine-125 ($^{125}I$), or carbon-14 ($^{14}C$). Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of compounds of the present disclosure, whether radioactive or not, are encompassed within the scope of the present disclosure.

As used herein, and unless otherwise specified, the terms "solvent," "organic solvent," or "inert solvent" each mean a solvent inert under the conditions of the reaction being described in conjunction therewith, including, without limitation, benzene, toluene, acetonitrile, ethyl acetate, isopropyl acetate, hexane, heptanes, dioxane, tetrahydrofuran ("THF"), dimethylformamide ("DMF"), dimethylacetamide ("DMA"), chloroform, methylene chloride (dichloromethane), diethyl ether, methanol, butanol, methyl t-butyl ether ("MTBE"), 2-butanone ("MEK"), N-methylpyrrolidone ("NMP"), pyridine, and the like. Unless specified to the contrary, the solvents used in reactions described herein are inert organic solvents. Unless specified to the contrary, for each gram of a limiting reagent, one cc (or mL) of solvent constitutes a volume equivalent.

As used herein, and unless otherwise specified, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is known in the art. Except insofar as any conventional media or agent is incompatible with the active ingredient, its use in the therapeutic compositions of the present disclosure is contemplated. Supplementary active ingredients can also be incorporated into the compositions.

As used herein, and unless otherwise specified, "polymorph" can be used herein to describe a crystalline material, e.g., a crystalline form. In certain embodiments, "polymorph" as used herein are also meant to include all crystalline and amorphous forms of a compound or a salt thereof, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms, as well as mixtures thereof, unless a particular crystalline or amorphous form is referred to. Compounds of the present disclosure include crystalline and amorphous forms of those compounds, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms of the compounds or a salt thereof, as well as mixtures thereof.

As used herein, and unless otherwise specified, a particular form of a compound of Formula (I) described herein (e.g., Form A, B, C, D, E, F, G, H, I, J, or amorphous form of a compound of Formula (I), or mixtures thereof) is meant to encompass a solid form of a compound of Formula (I), or a salt, solvate, or hydrate thereof, among others.

As used herein, and unless otherwise specified, the terms "solid form" and related terms herein refer to a physical form comprising a compound provided herein or a salt or solvate or hydrate thereof, which is not in a liquid or a gaseous state. Solid forms can be crystalline, amorphous, disordered crystalline, partially crystalline, and/or partially amorphous.

As used herein, and unless otherwise specified, the term "crystalline," when used to describe a substance, component, or product, means that the substance, component, or product is substantially crystalline as determined, for example, by X-ray diffraction. See, e.g., Remington: The Science and Practice of Pharmacy, Lippincott Williams & Wilkins, 21$^{st}$ ed. (2005).

As used herein, and unless otherwise specified, the term "crystalline form," "crystal form," and related terms herein refer to the various crystalline material comprising a given substance, including single-component crystal forms and multiple-component crystal forms, and including, but not limited to, polymorphs, solvates, hydrates, co-crystals and other molecular complexes, as well as salts, solvates of salts, hydrates of salts, other molecular complexes of salts, and polymorphs thereof. In certain embodiments, a crystal form of a substance can be substantially free of amorphous forms and/or other crystal forms. In other embodiments, a crystal form of a substance can contain about 1%, about 2%, about 3%, about 4%, about 5%, about 10%, about 15%, about 20%, about 25%, about 30%, about 35%, about 40%, about 45% or about 50% of one or more amorphous form(s) and/or other crystal form(s) on a weight and/or molar basis.

Certain crystal forms of a substance can be obtained by a number of methods, such as, without limitation, melt recrystallization, melt cooling, solvent recrystallization, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, solvent-drop grinding, microwave-induced precipitation, sonication-induced precipitation, laser-induced precipitation, and/or precipitation from a supercritical fluid. As used herein, and unless otherwise specified, the term "isolating" also encompasses purifying.

Techniques for characterizing crystal forms and amorphous forms can include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies.

As used herein, and unless otherwise specified, the term "peak," when used in connection with the spectra or data presented in graphical form (e.g., XRPD, IR, Raman, and NMR spectra), refers to a peak or other special feature that one skilled in the art would recognize as not attributable to background noise. The term "significant peak" refers to peaks at least the median size (e.g., height) of other peaks in the spectrum or data, or at least 1.5, 2, or 2.5 times the background level in the spectrum or data.

As used herein, and unless otherwise specified, the term "amorphous," "amorphous form," and related terms herein mean that the substance, component or product in question is not substantially crystalline as determined by X-ray diffraction. In certain embodiments, an amorphous form of a substance can be substantially free of other amorphous forms and/or crystal forms. In certain embodiments, an amorphous form of a substance can comprise one or more disordered crystalline forms. In other embodiments, an amorphous form of a substance can contain about 1%, about 2%, about 3%, about 4%, about 5%, about 10%, about 15%, about 20%, about 25%, about 30%, about 35%, about 40%, about 45% or about 50% of one or more other amorphous forms and/or crystal forms on a weight and/or molar basis. Amorphous forms of a substance can be obtained by a number of methods, as known in the art. Such methods include, but are not limited to, heating, melt cooling, rapid melt cooling, solvent evaporation, rapid solvent evaporation, desolvation, sublimation, grinding, cryo-grinding, spray drying, and freeze drying.

As used herein and unless otherwise specified, a composition that is "substantially free" of a compound means that the composition contains less than about 20 percent by weight, less than about 10 percent by weight, less than about 5 percent by weight, less than about 3 percent by weight, or less than about 1 percent by weight of the compound.

As used herein, and unless otherwise specified, the term "substantially pure" when used to describe a polymorph, a crystal form, or a solid form of a compound or complex described herein means a solid form of the compound or complex that comprises a particular polymorph and is substantially free of other polymorphic and/or amorphous forms of the compound. A representative substantially pure polymorph comprises greater than about 80% by weight of one polymorphic form of the compound and less than about 20% by weight of other polymorphic and/or amorphous forms of the compound; greater than about 90% by weight of one polymorphic form of the compound and less than about 10% by weight of other polymorphic and/or amorphous forms of the compound; greater than about 95% by weight of one polymorphic form of the compound and less than about 5% by weight of other polymorphic and/or amorphous forms of the compound; greater than about 97% by weight of one polymorphic form of the compound and less than about 3% by weight of other polymorphic and/or amorphous forms of the compound; or greater than about 99% by weight of one polymorphic form of the compound and less than about 1% by weight of other polymorphic and/or amorphous forms of the compound.

As used herein, and unless otherwise specified, a crystal form that is "essentially free" of water and/or solvent in the crystal lattice has a quantity of water and/or solvent in the crystal lattice which is, in certain embodiments, approximately near the limit of detection, in other embodiments, approximately at the limit of detection, and in other embodiments, approximately below the limit of detection for solvent and/or water in the crystal lattice when measured using a conventional solid-state analytical technique, e.g., a technique described herein. In certain embodiments, the solid-state analytical technique used to determine the quantity of water and/or solvent in the crystal lattice is thermogravimetric analysis. In other embodiments, the solid-state analytical technique used to determine the quantity of water and/or solvent in the crystal lattice is Karl Fischer analysis. In other embodiments, a crystal form which is "essentially free" of water and/or solvent in the crystal lattice has a quantity of water and/or solvent which is less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, less than about 0.1%, less than about 0.05%, or less than about 0.01% of the total weight of the crystal form.

As used herein, a crystalline or amorphous form that is "pure," i.e., substantially free of other crystalline or amorphous forms, contains less than about 10 percent by weight of one or more other crystalline or amorphous form, less than about 5 percent by weight of one or more other crystalline or amorphous form, less than about 3 percent by weight of one or more other crystalline or amorphous form, or less than about 1 percent by weight of one or more other crystalline or amorphous form.

As used herein, and unless otherwise specified, the term "stable" refers to a compound or composition that does not readily decompose or change in chemical makeup or physical state. A stable composition or formulation provided herein does not significantly decompose under normal manufacturing or storage conditions. In some embodiments, the term "stable," when used in connection with a formulation or a dosage form, means that the active ingredient of the formulation or dosage form remains unchanged in chemical makeup or physical state for a specified amount of time and does not significantly degrade or aggregate or become otherwise modified (e.g., as determined, for example, by HPLC, FTIR, or XRPD). In some embodiments, about 70 percent or greater, about 80 percent or greater, about 90 percent or greater, about 95 percent or greater, about 98 percent or greater, or about 99 percent or greater of the compound remains unchanged after the specified period. In one embodiment, a polymorph provided herein is stable upon long-term storage (e.g., no significant change in polymorph form after about 1, 2, 3, 4, 5, 6, 7, 8, 9, 10, 11, 12, 18, 24, 30, 36, 42, 48, 54, 60, or greater than about 60 months).

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis*, 3rd ed., Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_4$ 6, $C_{4-5}$, and $C_{5-6}$ alkyl.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_6$ alkyl group. In some embodiments, alkyl groups have 1 to 10, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $-Si(R^a)_3^-$, $-OR^a$, $-SR^a$, $-OC(O)-R^a$, $-N(R^a)_2$, $-C(O)R^a$, $-C(O)OR^a$, $-OC(O)N(R^a)_2$, $-C(O)N(R^a)_2$, $-N(R^a)C(O)OR^a$, $-N(R^a)C(O)R^a$, $-N(R^a)C(O)N(R^a)_2$, $-N(R^a)C(NR^a)N(R^a)_2$, $-N(R^a)S(O)_tR^a$ (where t is 1 or 2), $-S(O)_tOR^a$ (where t is 1 or 2), $-S(O)_tN(R^a)_2$ (where t is 1 or 2), or $-O-P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include $-CF_3$, $-CF_2CF_3$, $-CF_2CF_2CF_3$, $-CCl_3$, $-CFCl_2$, $-CF_2Cl$ and the like.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Additional examples of alkenyl include heptenyl ($C_7$), octenyl ($C_8$), octatrienyl ($C_8$) and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl, including from 1 to 10 carbon atoms of a straight, branched, cyclic configuration and combinations thereof, attached to the parent molecular structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C=O)— attached to the parent molecular structure through the carbonyl carbon having from 1 to 10 carbon atoms. Thus a $C_1$-$C_6$ alkoxycarbonyl group is an alkoxy group having from 1 to 6 carbon atoms attached through its oxygen to a carbonyl linker. The $C_1$-$C_6$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_1$-$C_4$ alkoxy is an alkoxy group which encompasses both straight and branched chain alkoxy groups of from 1 to 4 carbon atoms. Unless stated otherwise in the specification, an alkoxycarbonyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_1$-$C_{10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Acyloxy" refers to a R(C=O)O— radical wherein "R" can be alkyl, alkenyl, alkynyl, heteroalkyl, heteroalkenyl, heteroalkynyl, aryl, cyclohexyl, heteroaryl or heterocycloalkyl, which are as described herein. The acyloxy group is attached to the parent molecular structure through the oxygen functionality. In some embodiments, an acyloxy group is a C$_1$-C$_4$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, i.e., a C$_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Amino" or "amine" refers to a —N(R$^b$)$_2$, —N(R$^b$)R$^b$—, or —R$^b$N(R$^b$)R$^b$— radical group, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N(R$^b$)$_2$ group has two R$^b$ other than hydrogen, they can be combined with the nitrogen atom to form a 3-, 4-, 5-, 6-, or 7-membered ring. For example, —N(R$^b$)$_2$ is meant to include, but not be limited to, 1-pyrrolidinyl and 4-morpholinyl. Unless stated otherwise in the specification, an amino group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The terms "amine" and "amino" also refer to N-oxides of the groups —N+(H)(R$^a$)O$^-$, and —N+(R$^a$)(R$^a$)O$^-$, R$^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R$^b$)$_2$ or —NR$^b$C(O)R$^b$, where R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this radical is a C$_1$-C$_4$ amido or amide radical, which includes the amide carbonyl in the total number of carbons in the radical. When a —C(O)N(R$^b$)$_2$ has two R$^b$ other than hydrogen, they can be combined with the nitrogen atom to form a 3-, 4-, 5-, 6-, or 7-membered ring. For example, N(R$^b$)$_2$ portion of a —C(O)N(R$^b$)$_2$ radical is meant to include, but not be limited to, 1-pyrrolidinyl and 4-morpholinyl. Unless stated otherwise in the specification, an amido R$^b$ group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety.

"Amidino" refers to both the —C(=NR$^b$)N(R$^b$)$_2$ and —N(R$^b$)—C(=NR$^b$)— radicals, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Aromatic" or "aryl" refers to a radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

"Azide" refers to a —N$_3$ radical.

"Carbamate" refers to any of the following radicals: —O—(C=O)—N(R$^b$)—, —O—(C=O)—N(R$^b$)$_2$, —N(R$^b$)—(C=O)—O—, and —N(R$^b$)—(C=O)—OR$^b$, wherein each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Carbonate" refers to a —O—(C=O)—O— radical.

"Carbonyl" refers to a —(C=O)— radical.

"Carboxaldehyde" refers to a —(C=O)H radical.

"Carboxyl" refers to a —(C=O)OH radical.

"Cyano" refers to a —CN radical.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$-carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Ester" refers to a radical of formula —COOR, where R is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or —O—P(=O)$(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Ether" refers to a —$R^b$—O—$R^b$— radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—$CH_2CH_2OCH_2OCH_3$), (methoxymethoxy)methanyl (—$CH_2OCH_2OCH_3$) and (methoxyethoxy)methanyl (—$CH_2OCH_2CH_2OCH_3$) and the like; amines such as —$CH_2CH_2NHCH_3$, —$CH_2CH_2N(CH_3)_2$, —$CH_2NHCH_2CH_3$, —$CH_2N(CH_2CH_3)(CH_3)$ and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or —O—P(=O)$(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heteroaryl" or, alternatively, "heteroaromatic" refers to a refers to a radical of a 5-18 membered monocyclic or polycyclic (e.g., bicyclic or tricyclic) aromatic ring system (e.g., having 6, 10 or 14 π (pi) electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. For example, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Heterocyclyl", "heterocycloalkyl" or 'heterocarbocyclyl" each refer to any 3- to 18-membered non-aromatic radical monocyclic or polycyclic moiety comprising at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or —O—P(=O)(OR)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Nitro" refers to the —NO$_2$ radical.

"Phosphate" refers to a —O—P(=O)(O$R^b$)$_2$ radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Imino" refers to the "—(C=N)—$R^b$" radical where $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Phosphonate" refers to a —O—P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Phosphinate" refers to a —P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl, ester, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), —O—P(=O)(O$R^a$)$_2$, where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

"Silyl" refers to a —Si($R^b$)$_3$ radical where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide", "thiol", "mercapto", and "mercaptan" can also each refer to the group —$R^b$SH.

"Sulfinyl" or "sulfoxide" refers to the —S(O)—$R^b$ radical, wherein for "sulfinyl", $R^b$ is H and for "sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" or "sulfone" refers to the —S(O$_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refers to the following radicals: —S(=O)$_2$—N($R^b$)$_2$, —N($R^b$)—S(=O)$_2$$R^b$, —S(=O)$_2$—N($R^b$)—, or —N($R^b$)—S(=O)$_2$-, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—N($R^b$)$_2$ can be taken together with the nitrogen to which they are attached to form a 4-, 5-, 6-, or 7-membered heterocyclyl ring. In some embodiments, the term designates a $C_1$-$C_4$ sulfonamido, wherein each $R^b$ in the sulfonamido contains 1 carbon, 2 carbons, 3 carbons, or 4 carbons total.

"Sulfoxyl" or "sulfoxide" refers to a —S(=O)$_2$OH radical.

"Sulfonate" refers to a —S(=O)$_2$—O$R^b$ radical, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Thiocarbonyl" refers to a —(C=S)— radical.

"Urea" refers to a —N($R^b$)—(C=O)—N($R^b$)$_2$ or —N($R^b$)—(C=O)—N($R^b$)— radical, where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

II. Compounds, Compositions, and Methods of Preparing

In one embodiment, provided herein are polymorphic forms of a compound of Formula (I):

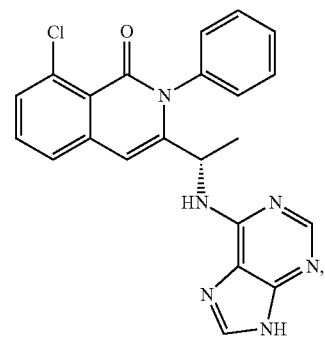

(I)

herein referred to as Form A, Form B, Form C, Form D, Form E, Form F, Form G, Form H, Form I, Form J, or an amorphous form of a compound of Formula (I), or a salt, solvate, or hydrate thereof; or a mixture of two or more thereof. In one embodiment, the polymorphic form of a compound of Formula (I) can be a crystalline form, a partially crystalline form, an amorphous form, or a mixture of crystalline form(s) and/or amorphous form(s).

In one embodiment, the polymorph provided herein is Form A, Form B, Form C, Form D, Form E, Form F, Form G, Form H, Form I, Form J, or an amorphous form of a compound of Formula (I), or a pharmaceutically acceptable salt, solvate, or hydrate thereof, or a mixture of two or more thereof. In one embodiment, the polymorph provided herein is Form B, Form C, Form D, Form E, Form F, Form G, Form H, Form I, Form J, or an amorphous form of a compound of Formula (I), or a pharmaceutically acceptable salt, solvate, or hydrate thereof. In one embodiment, the polymorph provided herein is Form A, Form B, Form C, Form D, Form E, Form F, Form G, Form H, Form I, Form J, or an amorphous form of a compound of Formula (I), or a pharmaceutically acceptable salt, solvate, or hydrate thereof, or a mixture of two or more thereof, which is substantially pure. In one embodiment, a polymorph provided herein is thermally stable. In one embodiment, a polymorph provided herein is stable upon long-term storage (e.g., no significant change in polymorph form after about 1, about 2, about 3, about 4, about 5, about 6, about 7, about 8, about 9, about 10, about 11, about 12, about 18, about 24, about 30, about 36, about 42, about 48, about 54, about 60, or greater than about 60 months). In one embodiment, after storage for a certain period of time, less than about 20%, less than about 10%, less than about 9%, less than about 8%, less than about 7%, less than about 6%, less than about 5%, less than about 4%, less than about 3%, less than about 2%, or less than about 1% w/w of a polymorph provided herein converts to other polymorph(s).

In certain embodiments, a polymorph provided herein is polymorph Form C of a compound of Formula (I). In certain embodiments, provided herein is a solid form of a compound of Formula (I) comprising Form C of a compound of Formula (I). In certain embodiments, provided herein is a solid form of a compound of Formula (I) comprising Form C of a compound of Formula (I), which is substantially pure. In one embodiment, Form C can be characterized by having X-ray powder diffraction (XRPD) peaks at about 10.4, about 13.3, and about 24.3 degrees 2θ. In certain embodiments, Form C is characterized by having differential scanning calorimetry (DSC) comprising an endotherm at about 208° C. In certain embodiments, Form C can be characterized by thermogravimetric analysis where the % weight loss observed is about 1.7% at about 80° C. and about 0.2% at about 190° C.

In one embodiment, a non-Form C polymorph is a solid form of a compound of Formula (I), or a salt, solvate, or hydrate thereof (e.g., a crystalline form, an amorphous form, or a mixture of crystalline form(s) and/or amorphous form (s)), which is not polymorph Form C of a compound of Formula (I). In one embodiment, a non-Form C polymorph is Form A, Form B, Form D, Form E, Form F, Form G, Form H, Form I, Form J, or an amorphous form of a compound of Formula (I), or a salt, solvate, or hydrate thereof, or a mixture of two or more thereof. In one embodiment, a non-Form C polymorph can comprise at least 50% by weight polymorph Form A of a compound of Formula (I). In one embodiment, a non-Form C polymorph (e.g., Form A or Form B) can be obtained from a composition comprising Form C.

In certain embodiments, a salt of a compound of Formula (I) provided herein is a salt derived from L-tartaric acid, p-toluenesulfonic acid, D-glucaronic acid, ethane-1,2-disulfonic acid (EDSA), 2-naphthalenesulfonic acid (NSA), hydrochloric acid (HCl), hydrobromic acid (HBr), citric acid, naphthalene-1,5-disulfonic acid (NDSA), DL-mandelic acid, fumaric acid, sulfuric acid, maleic acid, methanesulfonic acid (MSA), benzenesulfonic acid (BSA), ethanesulfonic acid (ESA), L-malic acid, phosphoric acid, or aminoethanesulfonic acid (taurine). In certain embodiments, a salt of a compound of Formula (I) provided herein is a mono-acid salt or a bis-acid salt. In certain embodiments, a salt of a compound of Formula (I) provided herein is an HCl salt (e.g., a mono-HCl salt or a bis-HCl salt), or a solvate or hydrate thereof. In certain embodiments, a salt, solvate, or hydrate of a compound of Formula (I) provided herein is a crystalline material, a partially crystalline material, or an amorphous material or a mixture of one or more crystalline form(s) and/or amorphous form(s).

In one embodiment, provided herein is a composition comprising a compound of Formula (I):

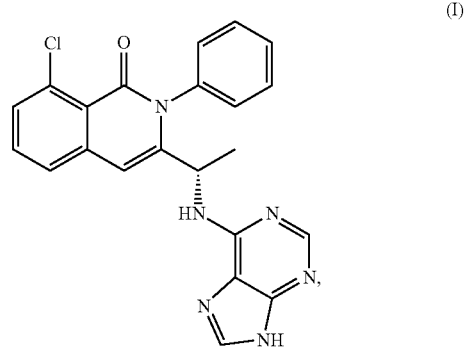 [SMILES: C[C@H](Nc1ncnc2[nH]cnc12)c1cc2cccc(Cl)c2c(=O)n1-c1ccccc1]

(I)

or a pharmaceutically acceptable salt, solvate, or hydrate thereof, and one or more pharmaceutically acceptable excipients.

In one embodiment, the composition comprises polymorph Form C. In one embodiment, the composition comprises a mixture of polymorph Form C and at least one non-Form C polymorph of a compound of Formula (I), or a pharmaceutically acceptable salt, solvate, or hydrate thereof. For example, in certain embodiments, the composition can comprise polymorph Form C and polymorph Form A. In other embodiments, the composition can comprise polymorph Form C and polymorph Form B. In other embodiments, the composition can comprise polymorph Form C and polymorph Form D. In other embodiments, the composition can comprise polymorph Form C and polymorph Form E. In other embodiments, the composition can comprise polymorph Form C and polymorph Form F. In other embodiments, the composition can comprise polymorph Form C and polymorph Form G. In other embodiments, the composition can comprise polymorph Form C and polymorph Form H. In other embodiments, the composition can comprise polymorph Form C and polymorph Form I. In other embodiments, the composition can comprise polymorph Form C and polymorph Form J. In other embodiments, the composition can comprise polymorph Form C and an amorphous form of a compound of Formula (I), or a pharmaceutically acceptable salt, solvate, or hydrate thereof. In one embodiment, the ratio of polymorph Form C to the total amount of non-Form C polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In one embodiment, the composition comprising Form C is a pharmaceutical composition. In one embodiment, the composition is at least about 98% by weight of a compound of Formula (I), or a pharmaceutically acceptable salt, solvate, or hydrate thereof.

In one embodiment, the composition comprises a mixture of polymorph Form A and at least one non-Form A polymorph of a compound of Formula (I), or a pharmaceutically acceptable salt, solvate, or hydrate thereof. For example, in certain embodiments, the composition can comprise polymorph Form A and polymorph Form B. In other embodiments, the composition can comprise polymorph Form A and polymorph Form C. In other embodiments, the composition can comprise polymorph Form A and polymorph Form D. In other embodiments, the composition can comprise polymorph Form A and polymorph Form E. In other embodiments, the composition can comprise polymorph Form A and polymorph Form F. In other embodiments, the composition can comprise polymorph Form A and polymorph Form G. In other embodiments, the composition can comprise polymorph Form A and polymorph Form H. In other embodiments, the composition can comprise polymorph Form A and polymorph Form I. In other embodiments, the composition can comprise polymorph Form A and polymorph Form J. In other embodiments, the composition can comprise polymorph Form A and an amorphous form of a compound of Formula (I), or a pharmaceutically acceptable salt, solvate, or hydrate thereof. In one embodiment, the ratio of polymorph Form A to the total amount of non-Form A polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In one embodiment, the ratio of polymorph Form A to the total amount of non-Form A polymorph(s) is less than about 1:1, less than about 2:1, less than about 3:1, less than about 4:1, less than about 5:1, less than about 6:1, less than about 7:1, less than about 8:1, or less than about 9:1. In one embodiment, the composition comprising Form A is a pharmaceutical composition. In one embodiment, the composition is at least about 98% by weight of a compound of Formula (I), or a pharmaceutically acceptable salt, solvate, or hydrate thereof.

In certain embodiments, provided herein is a composition comprising a therapeutically effective amount of a compound of Formula (I):

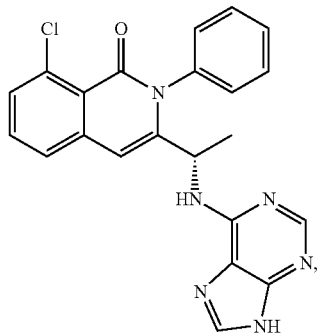

(I)

or a pharmaceutically acceptable salt, solvate, or hydrate thereof, and one or more pharmaceutically acceptable excipients.

In one embodiment, the composition comprises polymorph Form C of a compound of Formula (I). In one embodiment, the composition can further comprise one or more non-Form C polymorph(s) of a compound of Formula (I), or a pharmaceutically acceptable salt, solvate, or hydrate thereof. In certain embodiments, the ratio of polymorph Form C to the total amount of non-Form C polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In one embodiment, the composition comprises polymorph Form A of a compound of Formula (I). In one embodiment, the composition can further comprise one or more non-Form A polymorph(s) of a compound of Formula (I), or a pharmaceutically acceptable salt, solvate, or hydrate thereof. In certain embodiments, the ratio of polymorph Form A to the total amount of non-Form A polymorph(s) is greater than about 1:1, greater than about 2:1, greater than about 3:1, greater than about 4:1, greater than about 5:1, greater than about 6:1, greater than about 7:1, greater than about 8:1, or greater than about 9:1. In certain embodiments, the ratio of polymorph Form A to the total amount of non-Form A polymorph(s) is less than about 1:1, less than about 2:1, less than about 3:1, less than about 4:1, less than about 5:1, less than about 6:1, less than about 7:1, less than about 8:1, or less than about 9:1.

In one embodiment, polymorph forms provided herein are useful in the production of medicinal preparations and can be obtained by means of a crystallization process to produce crystalline and semi-crystalline forms or a solidification process to obtain the amorphous form. In certain embodiments, the crystallization is carried out by either generating a compound of Formula (I) in a reaction mixture and recovering a polymorph from the reaction mixture, or by dissolving a compound of Formula (I) in a solvent, optionally with heat, followed by crystallizing/solidifying the product by cooling and/or by the addition of an anti-solvent for a period of time. The crystallization or solidification can be followed by drying carried out under controlled conditions until a certain water content is reached in the end polymorphic form.

In one embodiment, provided herein are methods of preparing one or more polymorph(s) of a compound of the Formula (I):

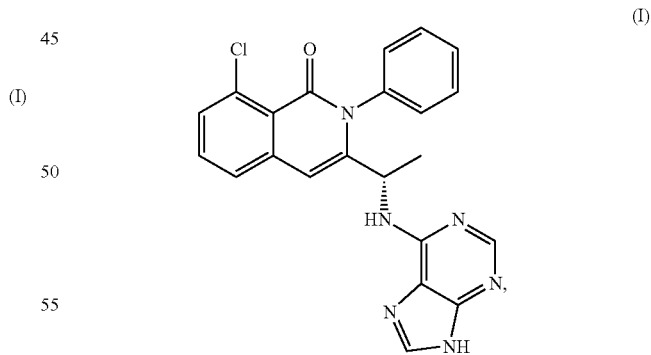

(I)

or a pharmaceutically acceptable salt, solvate, or hydrate thereof. Polymorphs prepared according to a method provided herein include Form A, Form B, Form C, Form D, Form E, Form F, Form G, Form H, Form I, Form J, or an amorphous form of a compound of Formula (I), or mixtures of two or more thereof. In one embodiment, a polymorph provided herein is a solvate or hydrate of a compound of Formula (I). In one embodiment, a polymorph provided herein is a mono-acid or bis-acid addition salt, such as, e.g., a mono-HCl salt or a bis-HCl salt of a compound of Formula (I), or a solvate or hydrate thereof.
In one embodiment, provided herein is a method of preparing a compound of Formula (I):
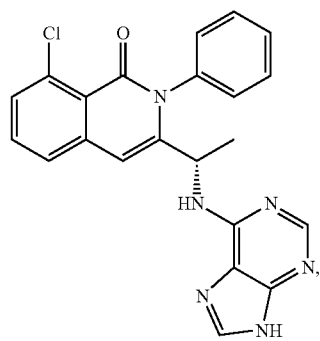
or a pharmaceutically acceptable salt, solvate, or hydrate thereof.
In one embodiment, the method comprises any one, two, three, four, five, six, seven, or eight, or more of the following steps:
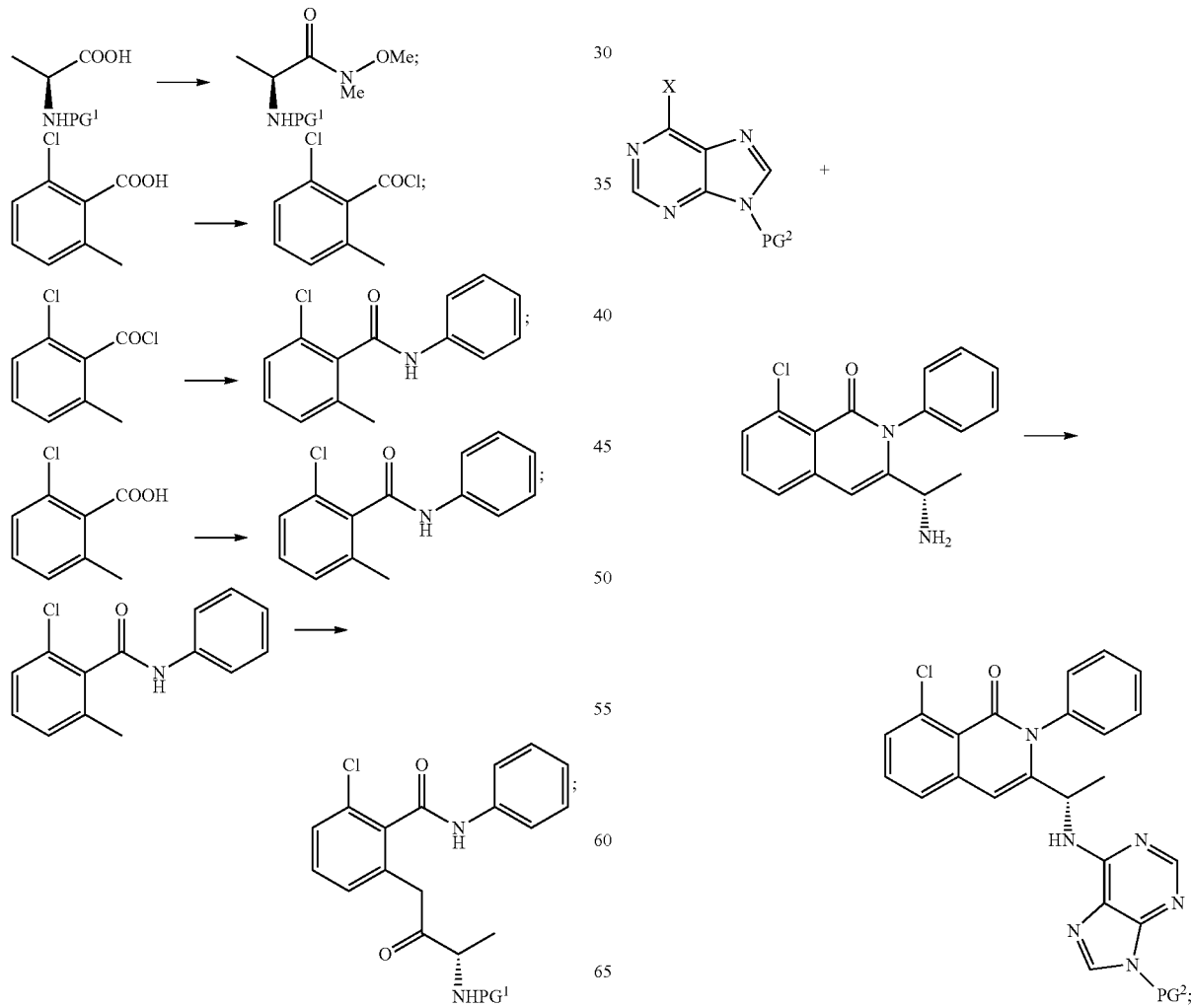
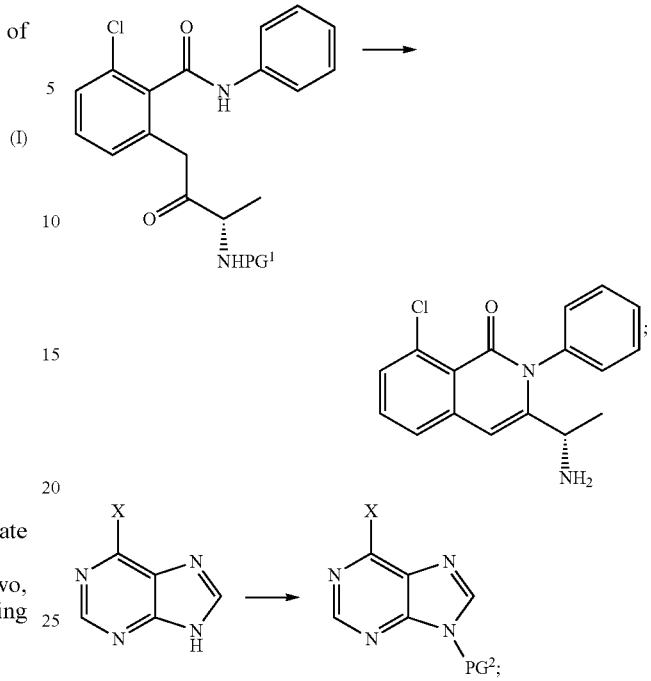

1-adamantyloxycarbonyl, 2-adamantyloxycarbonyl, triisopropylsiloxycarbonyl, vinyloxycarbonyl, 1-isopropoxycarbonyl, 8-quinolyloxycarbonyl, 2,4-dimethylpent-3-yloxycarbonyl, benzyloxycarbonyl, and substituted benzyloxycarbonyl;

PG² is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl; and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In one embodiment, provided herein is a method of preparing a compound of Formula (I), or a pharmaceutically acceptable salt, solvate, or hydrate thereof, comprising the following step:

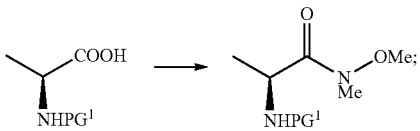

wherein

PG¹ is selected from benzyl, substituted benzyl, methoxycarbonyl, ethoxycarbonyl, substituted ethoxycarbonyl, 9-fluorenyloxycarbonyl, substituted 9-fluorenyloxycarbonyl, 2,2,2,-trichloroethoxycarbonyl, 2-trimethylsilylethoxycarbonyl, (2-phenyl-2-trimethylsilyl)ethoxycarbonyl, 2-phenylethoxycarbonyl, 1,1-dimethyl-2,2-dibromoethoxycarbonyl, 1,1-dimethyl-2,2,2-trichloroethoxycarbonyl, t-butoxycarbonyl, 1-adamantyloxycarbonyl, 2-adamantyloxycarbonyl, triisopropylsiloxycarbonyl, vinyloxycarbonyl, 1-isopropoxycarbonyl, 8-quinolyloxycarbonyl, 2,4-dimethylpent-3-yloxycarbonyl, benzyloxycarbonyl, and substituted benzyloxycarbonyl; and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In some embodiments, PG¹ is a carbamate protecting group, such as an alkoxycarbonyl or aryloxycarbonyl. In one embodiment, PG¹ is selected from t-butoxycarbonyl and benzyloxycarbonyl. In one embodiment, PG¹ is t-butoxycarbonyl.

In one embodiment, the step comprises combining the protected amino acid starting material with N,O-dimethylhydroxylamine (e.g., as a free base or in salt form such as an HCl salt) in the presence of an amide coupling reagent to afford the amide product. In some embodiments, the amide coupling reagent can include, but is not limited to, EDCI, DCC, DIC, HATU, HBTU, HCTU, TBTU, and PyBOP, optionally in the presence of HOBt, HOAt, and/or a base (e.g., an amine base such as Et$_3$N). In one embodiment, the amide coupling reagent is EDCI in the presence of HOBt.

In one embodiment, provided herein is a method of preparing a compound of Formula (I), or a pharmaceutically acceptable salt, solvate, or hydrate thereof, comprising the following step:

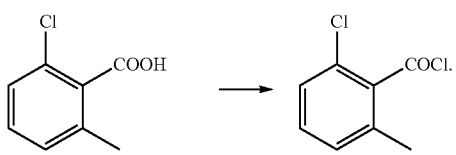

In one embodiment, the step comprises combining 2-chloro-6-methylbenzoic acid with, e.g., thionyl chloride or oxalyl chloride, optionally in the presence of a catalytic amount of DMF, to afford 2-chloro-6-methylbenzoyl chloride.

In one embodiment, provided herein is a method of preparing a compound of Formula (I), or a pharmaceutically acceptable salt, solvate, or hydrate thereof, comprising the following step:

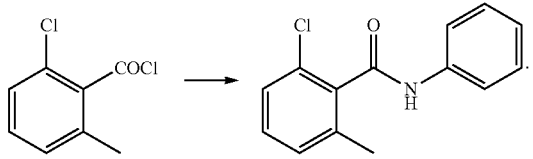 [SMILES: Cc1cccc(Cl)c1C(=O)Cl ; Cc1cccc(Cl)c1C(=O)Nc1ccccc1]

In one embodiment, the step comprises combining 2-chloro-6-methylbenzoyl chloride with aniline to afford 2-chloro-6-methyl-N-phenylbenzamide. In one embodiment, the step is optionally carried out in the presence of a base (e.g., an amine base such as Et$_3$N).

In one embodiment, provided herein is a method of preparing a compound of Formula (I), or a pharmaceutically acceptable salt, solvate, or hydrate thereof, comprising the following step:

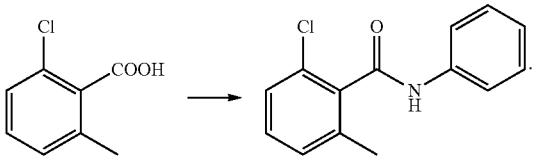 [SMILES: Cc1cccc(Cl)c1C(=O)O ; Cc1cccc(Cl)c1C(=O)Nc1ccccc1]

In one embodiment, the step comprises combining 2-chloro-6-methylbenzoic acid with aniline in the presence of an amide coupling reagent to afford 2-chloro-6-methyl-N-phenylbenzamide. In some embodiments, the amide coupling reagent can include, but is not limited to, EDCI, DCC, DIC, HATU, HBTU, HCTU, TBTU, and PyBOP, optionally in the presence of HOBt, HOAt, and/or a base (e.g., an amine base such as Et$_3$N). In certain embodiments, 2-chloro-6-methylbenzoic acid can be first converted to an acyl halide (e.g., using SOCl$_2$) or anhydride (e.g., using procedures known in the art such as, but not limited to, combining with one or more equivalents of a suitable acid, such as alkyl-COOH, and a coupling reagent), and the acyl halide or anhydride is combined with aniline to afford 2-chloro-6-methyl-N-phenylbenzamide.

In one embodiment, provided herein is a method of preparing a compound of Formula (I), or a pharmaceutically acceptable salt, solvate, or hydrate thereof, comprising the following step:

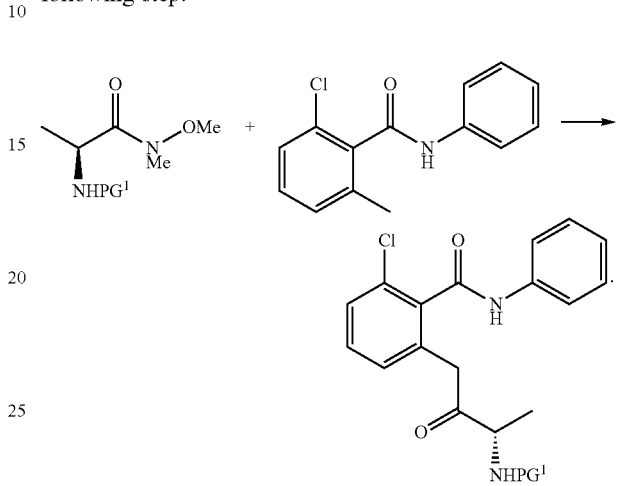

wherein
PG$^1$ is selected from benzyl, substituted benzyl, methoxycarbonyl, ethoxycarbonyl, substituted ethoxycarbonyl, 9-fluorenyloxycarbonyl, substituted 9-fluorenyloxycarbonyl, 2,2,2,-trichloroethoxycarbonyl, 2-trimethylsilylethoxycarbonyl, (2-phenyl-2-trimethylsilyl)ethoxycarbonyl, 2-phenylethoxycarbonyl, 1,1-dimethyl-2,2-dibromoethoxycarbonyl, 1,1-dimethyl-2,2,2-trichloroethoxycarbonyl, t-butoxycarbonyl, 1-adamantyloxycarbonyl, 2-adamantyloxycarbonyl, triisopropylsiloxycarbonyl, vinyloxycarbonyl, 1-isopropoxycarbonyl, 8-quinolyloxycarbonyl, 2,4-dimethylpent-3-yloxycarbonyl, benzyloxycarbonyl, and substituted benzyloxycarbonyl; and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In some embodiments, PG$^1$ is a carbamate protecting group, such as an alkoxycarbonyl or aryloxycarbonyl. In one embodiment, PG$^1$ is selected from t-butoxycarbonyl and benzyloxycarbonyl. In one embodiment, PG$^1$ is t-butoxycarbonyl.

In one embodiment, the starting material of the step, 2-chloro-6-methyl-N-phenylbenzamide, is combined with (S)-tert-butyl(1-(methoxy(methyl)amino)-1-oxopropan-2-yl)carbamate in the presence of an alkyllithium, such as n-butyllithium or n-hexyllithium, and to afford the protected amine. In another embodiment, 2-chloro-6-methyl-N-phenylbenzamide is combined with Boc-Ala-OMe, or other C$_{1-6}$ alkyl esters, under similar conditions to afford the protected amine. In another embodiment, (S)-tert-butyl(1-(methoxy(methyl)amino)-1-oxopropan-2-yl)carbamate is combined with an alkyl Grignard reagent, such as, but not limited to, isopropyl Grignard (e.g., iPrMgCl), prior to addition to a mixture comprising 2-chloro-6-methyl-N-phenylbenzamide. Other suitable Grignard reagents include, but are not limited to, organicmagnesium halides such as organomagesium chlorides and organomagnesium bromides. Non-limiting examples of Grignard reagents include methylmagnesium (chloride or bromide), substituted methylmagensium (chlorides or bromides) such as 2-naphthylenylmethylmagensium (chloride or bromide), cyclohexylmethylmagensium (chloride or bromide), and 1,3-dioxanylmethyl magnesium (chloride or bromide), ethyl magnesium (chloride or bromide), phenylmagnesium (chloride or bromide), substituted phenylmagnesium (chlorides or bromides), and others known in the art.

In one embodiment, provided herein is a method of preparing a compound of Formula (I), or a pharmaceutically acceptable salt, solvate, or hydrate thereof, comprising the following step:

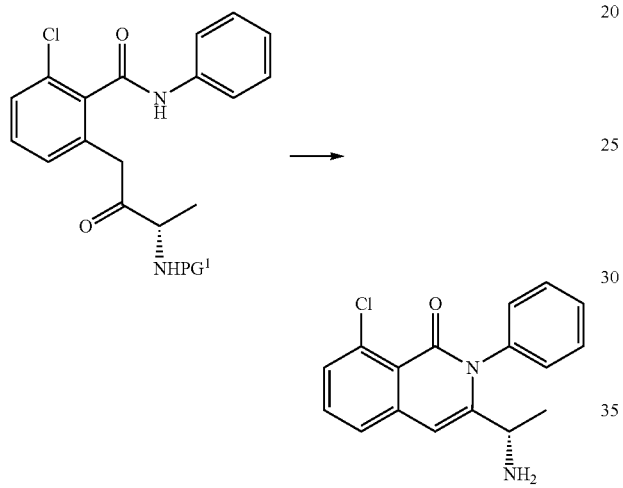

wherein
PG$^1$ is selected from benzyl, substituted benzyl, methoxycarbonyl, ethoxycarbonyl, substituted ethoxycarbonyl, 9-fluorenyloxycarbonyl, substituted 9-fluorenyloxycarbonyl, 2,2,2,-trichloroethoxycarbonyl, 2-trimethylsilylethoxycarbonyl, (2-phenyl-2-trimethylsilyl)ethoxycarbonyl, 2-phenylethoxycarbonyl, 1,1-dimethyl-2,2-dibromoethoxycarbonyl, 1,1-dimethyl-2,2,2-trichloroethoxycarbonyl, t-butoxycarbonyl, 1-adamantyloxycarbonyl, 2-adamantyloxycarbonyl, triisopropylsiloxycarbonyl, vinyloxycarbonyl, 1-isopropoxycarbonyl, 8-quinolyloxycarbonyl, 2,4-dimethylpent-3-yloxycarbonyl, benzyloxycarbonyl, and substituted benzyloxycarbonyl; and
where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In some embodiments, PG$^1$ is a carbamate protecting group, such as an alkoxycarbonyl or aryloxycarbonyl. In one embodiment, PG$^1$ is selected from t-butoxycarbonyl and benzyloxycarbonyl. In one embodiment, PG$^1$ is t-butoxycarbonyl.

In one embodiment, the protected amine is combined with an inorganic acid, such as HCl or trifluoroacetic acid, to afford the isoquinolinone. Other suitable acids include, but are not limited to, methanesulfonic acid, sulfuric acid, hydrobromic acid, nitric acid, phosphoric acid, perchloric acid, and camphorsulfonic acid.

In one embodiment, provided herein is a method of preparing a compound of Formula (I), or a pharmaceutically acceptable salt, solvate, or hydrate thereof, comprising the following step:

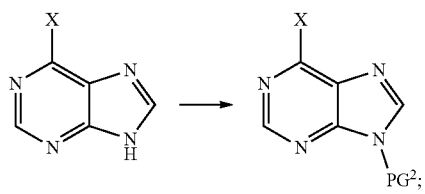

wherein
X is selected from fluoro, chloro, bromo, iodo, —O—SO$_2$-4-methylphenyl, and —O—SO$_2$-methyl;
PG$^2$ is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and
where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In one embodiment, PG$^2$ is 2-tetrahydropyranyl. In some embodiments, X is selected from fluoro, chloro, bromo, and iodo. In one embodiment, X is chloro. In certain embodiments, the step comprises combining 6-chloro-9H-purine with 3,4-dihydro-2H-pyran to afford 6-chloro-9-(tetrahydro-2H-pyran-2-yl)-9H-purine.

In one embodiment, provided herein is a method of preparing a compound of Formula (I), or a pharmaceutically acceptable salt, solvate, or hydrate thereof, comprising the following step:

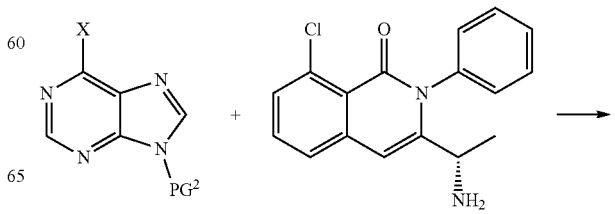

-continued

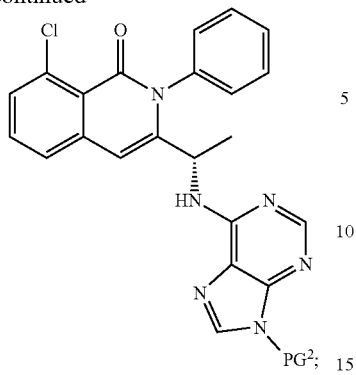

wherein
X is selected from fluoro, chloro, bromo, iodo, —O—SO$_2$-4-methylphenyl, and —O—SO$_2$-methyl;

PG$^2$ is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In one embodiment, PG$^2$ is 2-tetrahydropyranyl. In some embodiments, X is selected from fluoro, chloro, bromo, and iodo. In one embodiment, X is chloro. In one embodiment, the protected chloropurine is combined with the isoquinolinone in the presence of a base, such as an amine base (e.g., Et$_3$N), in an alcoholic solvent (e.g., MeOH, EtOH, PrOH, iPrOH).

In one embodiment, provided herein is a method of preparing a compound of Formula (I), or a pharmaceutically acceptable salt, solvate, or hydrate thereof, comprising the following step:

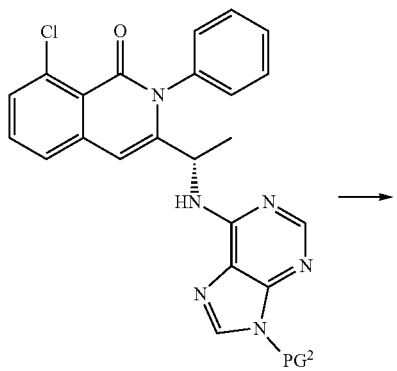

-continued

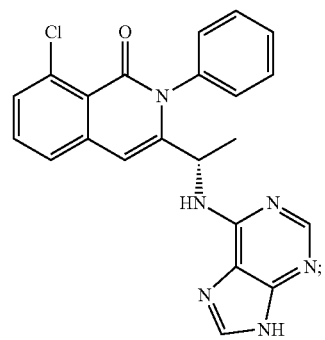

wherein
PG$^2$ is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

In one embodiment, PG$^2$ is 2-tetrahydropyranyl. In one embodiment, the protected purine is combined with an inorganic acid, such as, but not limited to, HCl, HBr, perchloric acid, sulfuric acid, nitric acid, and phosphoric acid, in an alcoholic solvent (e.g., MeOH, EtOH, PrOH, iPrOH). In one embodiment, the inorganic acid is HCl.

In one embodiment, provided herein is a method of preparing a compound of Formula (I), or a pharmaceutically acceptable salt, solvate, or hydrate thereof, comprising the following step:

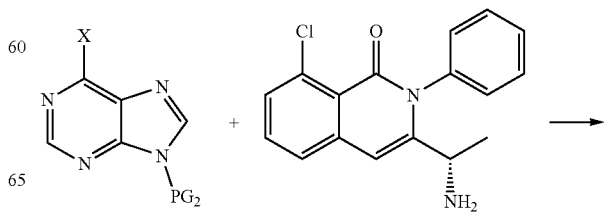

-continued

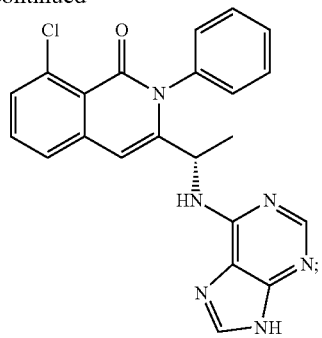

wherein

X is selected from fluoro, chloro, bromo, iodo, —O—SO$_2$-4-methylphenyl, and —O—SO$_2$-methyl.

In some embodiments, X is selected from fluoro, chloro, bromo, and iodo. In one embodiment, X is chloro. In one embodiment, the starting materials are combined with an amine base, such as Et$_3$N, in an alcoholic solvent, such as glycerol, to effect amine coupling.

In some embodiments, the intermediates for the synthesis of a compound of Formula (I), or a salt, solvate, or hydrate thereof, are made according to one or more of the following schemes.

In one embodiment, the conversion of compound 1 to compound 2 can be performed according to any method in the art. In one embodiment, compound 1 is combined with MeNHOMe (HCl) in the presence of EDCI and HOBt. In certain embodiments, a base such as triethylamine can be present.

Scheme 2

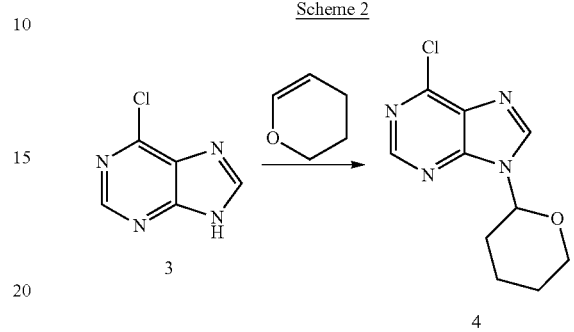

In one embodiment, the conversion of compound 3 to compound 4 occurs in the presence of para-toluenesulfonic acid. In another embodiment, installation of the THP protecting group occurs using camphorsulphonic acid in 2-methyltetrahydrofuran.

Scheme 3

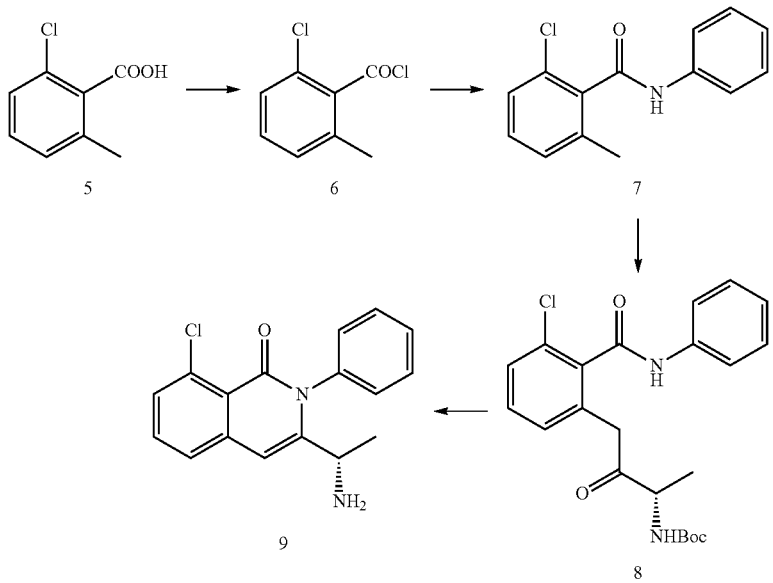

Scheme 1

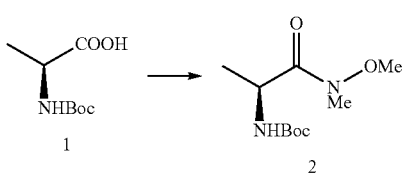

In one embodiment, the conversion of compound 5 to compound 7 can be performed according to any method in the art. In one embodiment, compound 5 is combined with thionyl chloride and DMF to yield compound 6, which is in turn combined with aniline to afford compound 7.

In one embodiment, compound 7 is converted to compound 8 by combining compound 7 with n-hexyl lithium and then adding compound 2, which has been previously combined with isopropyl Grignard (e.g., iPrMgCl). In one embodiment, compound 8 is converted to compound 9 in the presence of acid, such as hydrochloric acid, trifluoroacetic acid, or methanesulfonic acid, in a solvent, such as methanol or isopropyl alcohol. In one embodiment, the acid can be trifluoroacetic acid.

In one embodiment, a compound of Formula (I), or a salt, solvate, or hydrate thereof, is prepared by combining compound 3 and compound 9 according to the following scheme:

Scheme 4

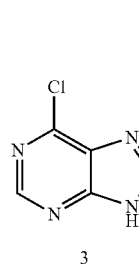

In one embodiment, the starting materials 3 and 9 are combined with an amine base, such as Et₃N, in an alcoholic solvent, such as glycerol, to effect purine coupling.

In one embodiment, the following synthetic scheme can be followed to prepare a compound of Formula (I), or a salt, solvate, or hydrate thereof:

Scheme 5:

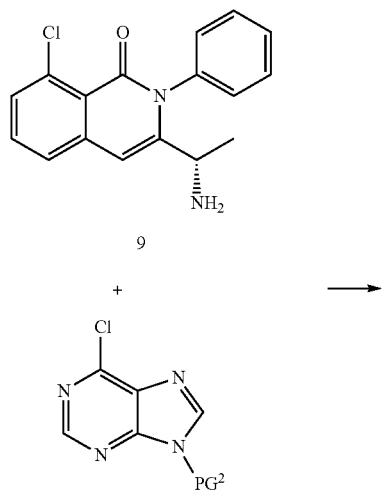

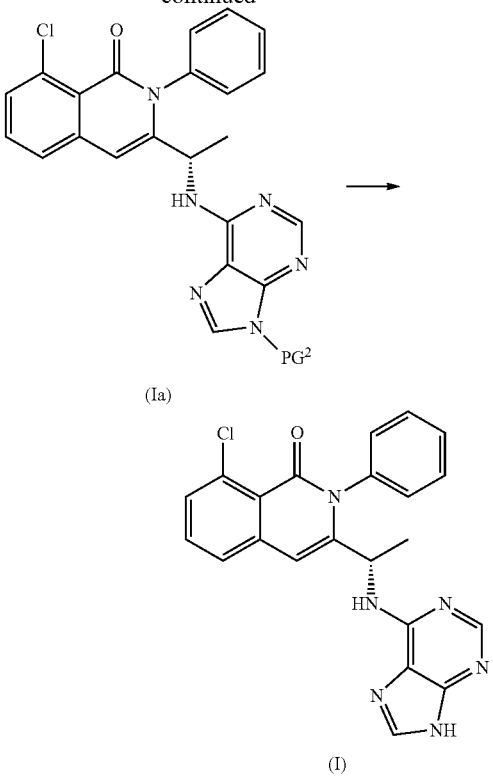

wherein
PG² is selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate.

While shown above in two steps, the above synthetic scheme can be carried out as a one-pot reaction. In one embodiment, the first step to afford compound (Ia) can be carried out in the presence of base (e.g., an amine base such as, but not limited to, Et₃N) in an alcoholic solvent (e.g., MeOH, EtOH, PrOH, iPrOH). Depending on the nature of the PG2 protecting group, the following reagents can be used to deprotect compound (Ia) to afford compound (I). One or more reagents to remove the protecting group PG² includes, but is not limited to, acids such as HCl, HBr and TFA; carbonate bases, such as Na₂CO₃ and K₂CO₃; hydroxide bases, such as NaOH and KOH; lithium bases, such as methyl lithium, ethyl lithium, propyl lithium, n-butyl lithium, n-pentyl lithium, and n-hexyl lithium; oxidants such as ceric ammonium nitrate; hydrogenation conditions, such as cyclohexadiene/Pd black, and H₂/Pd on carbon; TBAF, and BF₃.Et₂O.

In one embodiment, the following synthetic scheme is used to prepare a compound of Formula (I), or a salt, solvate, or hydrate thereof:

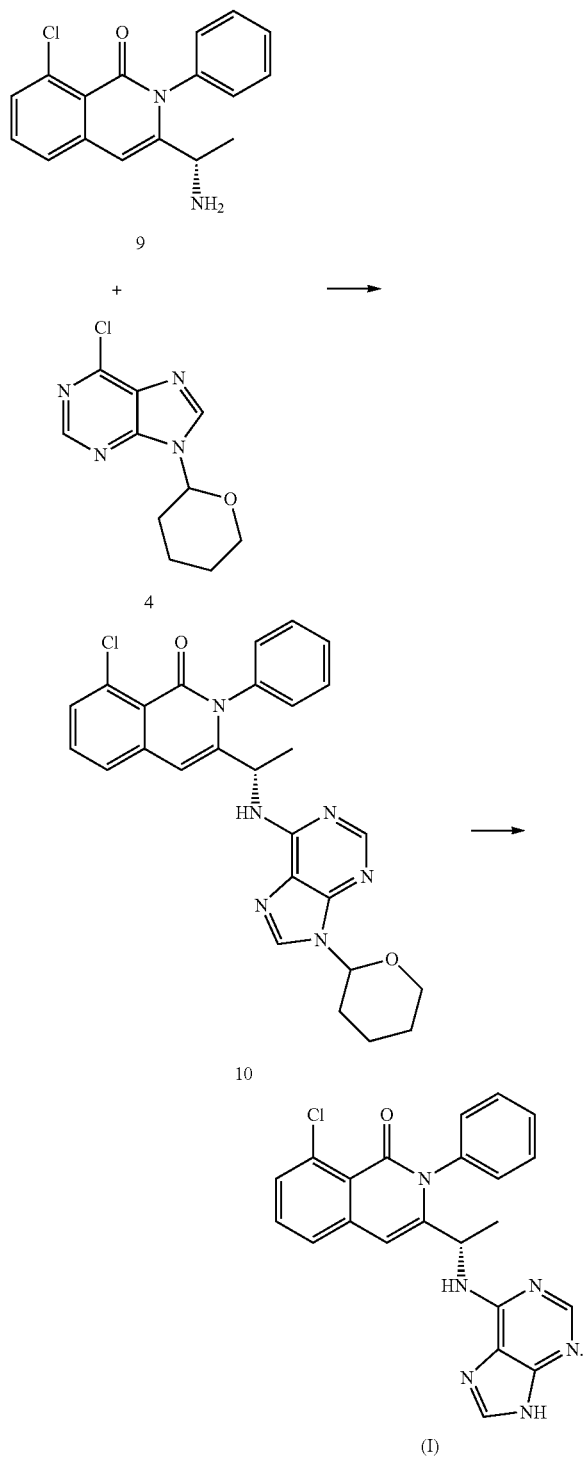

In one embodiment, the first step to afford compound 10 can be carried out in the presence of base (e.g., an amine base such as, but not limited to, Et₃N) in an alcoholic solvent (e.g., MeOH, EtOH, PrOH, iPrOH). In certain embodiments, a compound of Formula (I), or a salt, solvate, or hydrate thereof, is obtained from treatment of a protected precursor (e.g., compound 10) with hydrochloric acid in ethanol followed by treatment with dichloromethane. In certain embodiments, the product from treatment with dichloromethane is treated under aqueous conditions, such as about 90% water and about 10% 2-propanol.

In one embodiment, recovery and purification of the chemical entities and intermediates described herein can be effected by procedures, such as, but not limited to, filtration, extraction, crystallization, precipitation, silica gel column chromatography, high pressure liquid chromatography, thin-layer chromatography or thick-layer chromatography, or a combination of these procedures. Non-limiting exemplary illustrations of suitable recovery and purification procedures are provided in the examples below. However, other recovery and purification procedures known in the art can also be used.

Prior to formulation as the active pharmaceutical ingredient in a drug product, a compound of Formula (I), or a salt, solvate, or hydrate thereof, can be isolated in greater than about 90% purity, greater than about 91% purity, greater than about 92% purity, greater than about 93% purity, greater than about 94% purity, greater than about 95% purity, greater than about 96% purity, greater than about 97% purity, greater than about 98% purity, greater than about 99% purity, and purity approaching 100%.

In some embodiments, the (R)- and (S)-isomers of a compound of Formula (I), if both present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a certain enantiomer can be synthesized by asymmetric synthesis using optically active reagents, substrates, catalysts or solvents, or by converting one enantiomer to the other by asymmetric transformation. In certain embodiments, a compound of Formula (I) is present as a racemic or non-racemic mixture with its enantiomer. In one embodiment, a compound of Formula (I) is present in enantiomeric excess (ee) selected from greater than about 60%, greater than about 65%, greater than about 70%, greater than about 75%, greater than about 80%, greater than about 85%, greater than about 90%, greater than about 91%, greater than about 92%, greater than about 93%, greater than about 94%, greater than about 95%, greater than about 96%, greater than about 97%, greater than about 98%, and greater than about 99%.

In one embodiment, provided herein is a method of preparing a polymorph of a compound of Formula (I):

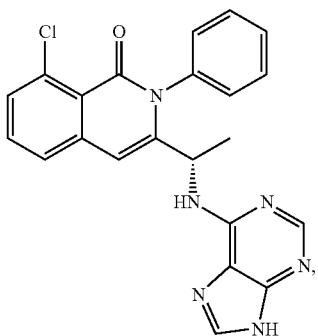

(I)

or a pharmaceutically acceptable salt, solvate, or hydrate thereof. In one embodiment, the method comprises recovering a polymorph as a first solid form after synthesis of a compound of Formula (I). In another embodiment, the method comprises recovering a polymorph as a transition from a prior solid form of a compound of Formula (I) (e.g., first recovering a solid form of a first polymorph of a compound of Formula (I), or a salt, solvate, or hydrate thereof, and converting the recovered solid form to a second polymorph under suitable conditions). Transitions from one polymorphic form to another are within the scope of the disclosure. In one embodiment, such transition processes can be used as a manufacturing method for obtaining a form for the production of medicinal preparations.

In one embodiment, provided herein is a method of preparing polymorph Form C of a compound of Formula (I):

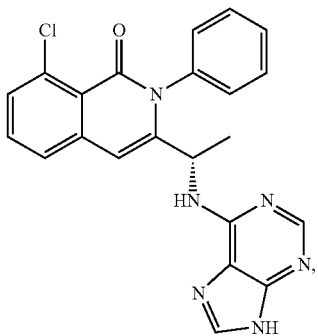

(I)

wherein the method comprises:
(i) combining a compound of Formula (Ia):

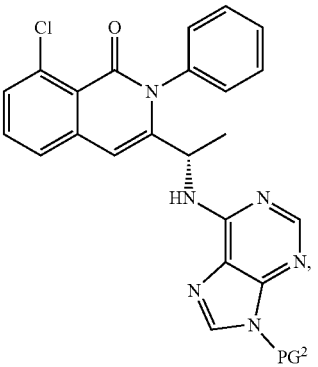

(Ia)

wherein
PG$^2$ is a protecting group selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate;

with one or more reagents to remove the protecting group PG$^2$ to form a compound of Formula (I); and
(ii) recovering polymorph Form C of the compound of Formula (I);

wherein at least one of steps (i) and (ii) occurs in a non-anhydrous condition.

In some embodiments, one or more reagents to remove the protecting group PG$^2$ includes, but is not limited to, acids such as HCl, HBr and TFA; carbonate bases, such as Na$_2$CO$_3$ and K$_2$CO$_3$; hydroxide bases, such as NaOH and KOH; lithium bases, such as methyl lithium, ethyl lithium, propyl lithium, n-butyl lithium, n-pentyl lithium, and n-hexyl lithium; oxidants such as ceric ammonium nitrate; hydrogenation conditions, such as cyclohexadiene/Pd black, and H$_2$/Pd on carbon; TBAF, and BF$_3$.Et$_2$O. In one embodiment, a non-anhydrous condition includes water, such as in a form of water vapor and/or liquid water. In one embodiment, a non-anhydrous condition includes a solvent system comprising a non-water solvent and liquid water, as described herein elsewhere.

In one embodiment, provided herein is a method of preparing a polymorph Form C of a compound of Formula (I):

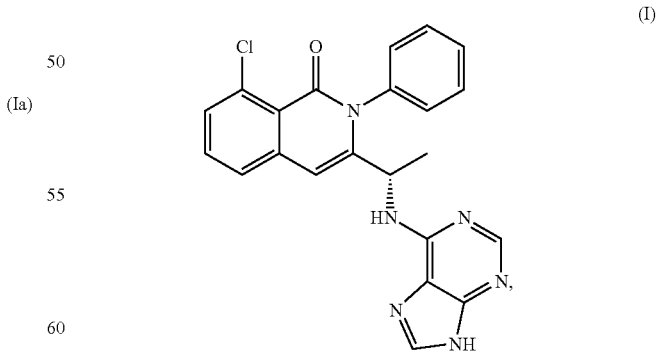

(I)

wherein the method comprises:
(i) exposing a composition comprising at least one non-Form C polymorph of a compound of Formula (I), or a salt, solvate, or hydrate thereof, to a non-anhydrous condition for a period of time sufficient to convert at least about 50% of the total amount of non-Form C polymorph(s) into Form C of a compound of Formula (I); and (ii) recovering said polymorph Form C.

In certain embodiments, the recovering step involves recrystallization of the reaction product from a mono-solvent system. In certain embodiments, the recovering step involves recrystallization of the product from a binary, tertiary, or greater solvent system, where binary, tertiary, or greater solvent systems are collectively understood as multi-solvent systems. In certain embodiments, the recovering step involves crystallization from a mono- or multi-solvent system, where the crystallization involves cooling a solution containing a compound of Formula (I). In certain embodiments, the recovering step involves crystallization from a mono- or multi-solvent system, where the crystallization involves addition of an anti-solvent either with or without a cooling step to cause precipitation of Form C. In certain embodiments, the conditions of crystallization are non-anhydrous. Where the conditions are non-anhydrous, water can be present in trace amounts, or in amounts less than about 1% by volume of solvent, or present as water vapor. In certain embodiments, water can be present as a co-solvent (or anti-solvent), for example, in an amount between about 1% and about 50%. For example, water can be present in about 5%, about 10%, about 15%, about 20%, about 25%, about 30%, about 35%, about 40%, about 45%, and about 50% by volume of solvent. In certain embodiments, water can be present in amounts equal to or greater than about 50% by volume of solvent. For example, water can be present in about 55%, about 60%, about 65%, about 70%, about 75%, about 80%, about 85%, about 90%, about 95%, and up to 100% by volume of solvent. In certain embodiments, liquid water is present in a multi-solvent system, for example, in an amount between about 10% to about 50% by volume of the solvent system. In certain embodiments, liquid water is present in a multi-solvent system, in an amount equal to or greater than about 50% by volume of the solvent system. In certain embodiments, water can be present as water vapor or ambient humidity.

In one embodiment, the non-water solvent is a water-miscible solvent. For example, liquid water can be present in an amount of about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% by volume of the solvent system. In one embodiment, liquid water is present in an amount of between about 10% and about 50% by volume of the solvent system.

In one embodiment, a non-anhydrous condition includes a solvent system comprising water (e.g., about 90% v/v) and isopropyl alcohol (e.g., about 10% v/v). In one embodiment, a non-anhydrous condition includes a solvent system comprising water and ethanol. In one embodiment, a non-anhydrous condition includes a solvent system comprising water and a water-miscible solvent, such as, e.g., $C_1$-$C_4$ alcohol, acetone, acetonitrile, among others. In one embodiment, a water-miscible solvent is an alcohol, such as, e.g., methanol, ethanol, 1-propanol, 2-propanol, 1-butanol, 2-butanol, t-butanol, ethylene glycol, among others. In one embodiment, the ratio of water and water-miscible solvent in a solvent system provided herein is about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, or about 1:50 v/v. In one embodiment, the ratio of water and water-miscible solvent in a solvent system provided herein is from about 50:1 to about 1:1, from about 40:1 to about 1:1, from about 30:1 to about 1:1, from about 20:1 to about 1:1, from about 10:1 to about 1:1, from about 9:1 to about 1:1, from about 8:1 to about 1:1, from about 7:1 to about 1:1, from about 6:1 to about 1:1, from about 5:1 to about 1:1, from about 4:1 to about 1:1, from about 3:1 to about 3:1, from about 2:1 to about 1:2, from about 1:1 to about 1:4, from about 1:1 to about 1:5, from about 1:1 to about 1:6, from about 1:1 to about 1:7, from about 1:1 to about 1:8, from about 1:1 to about 1:9, from about 1:1 to about 1:10, from about 1:1 to about 1:20, from about 1:1 to about 1:30, from about 1:1 to about 1:40, or from about 1:1 to about 1:50 v/v.

In one embodiment, provided herein is a method of preparing polymorph Form A of a compound of Formula (I):

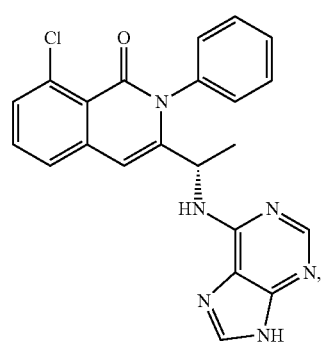

(I)

wherein the method comprises (i) combining a compound of Formula (Ia):

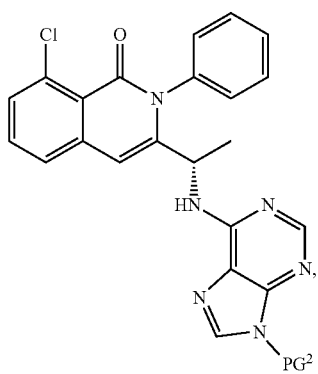

(Ia)

wherein

PG² is a protecting group selected from methylsulfonyl, substituted methylsulfonyl, benzenesulfonyl, substituted benzenesulfonyl, benzyloxycarbonyl, substituted benzyloxycarbonyl, 2,2,2,-trichloroethoxycarbonyl, 2-trimethylsilylethoxycarbonyl, t-butoxycarbonyl, 1-adamantyloxycarbonyl, 2-adamantyloxycarbonyl, alkyl, substituted alkyl, t-butyldimethylsilyl, triisopropylsilyl, allyl, benzyl, substituted benzyl, hydroxymethyl, methoxymethyl, diethoxymethyl, (2-chloroethoxy)methyl, t-butoxymethyl, t-butyldimethylsiloxymethyl, pivaloyloxymethyl, benzyloxymethyl, dimethylaminomethyl, 2-tetrahydropyranyl, substituted alkoxymethyl and substituted aryloxymethyl, and where substituents are selected from alkyl, heteroalkyl, alkenyl, alkynyl, cycloalkyl, heterocyclyl, aryl, arylalkyl, heteroaryl, heteroarylalkyl, alkoxy, cycloalkoxy, heterocyclyloxy, aryloxy, heteroaryloxy, amido, amino, acyl, acyloxy, alkoxycarbonyl, ester, ether, thio, sulfinyl, sulfonyl, sulfonamido, halo, cyano, hydroxyl, nitro, phosphate, urea, carbamate, and carbonate;

with one or more reagents to remove the protecting group PG² to form a compound of Formula (I); and (ii) recovering polymorph Form A of the compound of Formula (I).

In some embodiments, one or more reagents to remove the protecting group PG² includes, but is not limited to, acids such as HCl, HBr and TFA; carbonate bases, such as $Na_2CO_3$ and $K_2CO_3$; hydroxide bases, such as NaOH and KOH; lithium bases, such as methyl lithium, ethyl lithium, propyl lithium, n-butyl lithium, n-pentyl lithium, and n-hexyl lithium; oxidants such as ceric ammonium nitrate; hydrogenation conditions, such as cyclohexadiene/Pd black, and $H_2$/Pd on carbon; TBAF, and $BF_3.Et_2O$.

In some embodiments, step (ii) can include recrystallization of a compound of Formula (I), or a salt, solvate, or hydrate thereof, from a mono-solvent system, or from a multi-solvent system that does not contain both ethyl acetate and hexane. In certain embodiments, the method further comprises a step of dissolving a compound of Formula (I), or a salt, solvate, or hydrate thereof, in a mono-solvent system or a multi-solvent system, removing residual solid matter to yield a liquid solution, cooling said liquid solution at a rate to effect crystallization of Form A, and recovering Form A from the liquid solution.

In certain embodiments, the recovered polymorph is Form A, and the recovery step involves recrystallization of a reaction product from a mono-solvent system. In certain embodiments, the recovered polymorph is Form A, and the recovering step involves recrystallization of the product from a binary, tertiary, or greater solvent system, collectively understood as a multi-solvent system, where the multi-solvent system does not contain both ethyl acetate and hexane. In certain embodiments, the recovered polymorph is Form A, and the recovering step involves crystallization from a mono- or multi-solvent system, where the crystallization involves cooling a solution containing a compound of Formula (I). In certain embodiments, the recovered polymorph is Form A, and the recovery step involves crystallization from a mono- or multi-solvent system, where the crystallization involves addition of an anti-solvent either with or without a cooling step to enable recovery of Form A.

In one embodiment, provided herein is a method of preparing polymorph Form B of a compound of Formula (I):

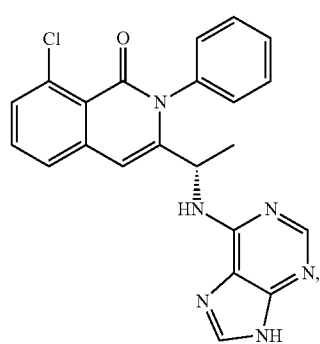

(I)

the method comprising thermal conversion from a non-Form B polymorph of a compound of Formula (I), or a salt, solvate, or hydrate thereof, to yield polymorph Form B.

In certain embodiments, a non-Form B polymorph is a solid form of a compound of Formula (I), or a salt, solvate, or hydrate thereof (e.g., a crystalline form, an amorphous form, or a mixture of crystalline form(s) and/or amorphous form(s)), which is not polymorph Form B of a compound of Formula (I). In one embodiment, a non-Form B polymorph is Form A, Form C, Form D, Form E, Form F, Form G, Form H, Form I, Form J, or an amorphous form of a compound of Formula (I), or a salt, solvate, or hydrate thereof, or a mixture of two or more thereof.

In certain embodiments, provided herein are methods of preparing a polymorph of a compound of Formula (I), or a pharmaceutically acceptable salt, solvate, or hydrate thereof, wherein the method comprises converting a first polymorph or a mixture of polymorphs of a compound of Formula (I), or a pharmaceutically acceptable salt, solvate, or hydrate thereof, into a second polymorph of a compound of Formula (I), or a pharmaceutically acceptable salt, solvate, or hydrate thereof. In certain embodiments, the methods comprise exposing a composition comprising one or more polymorphs to conditions sufficient to convert at least about 50% of the total amount of an original polymorph or a first polymorph into a second polymorph, and optionally recovering the second polymorph.

In certain embodiments, an original solid form or a first solid form of a compound of Formula (I), or a pharmaceutically acceptable salt, solvate, or hydrate thereof, contains greater than about 50% non-Form A polymorph(s) as the first polymorph, and the second polymorph is Form A.

In certain embodiments, the original solid form or a first solid form of a compound of Formula (I), or a pharmaceutically acceptable salt, solvate, or hydrate thereof, contains greater than about 50% non-Form C polymorph(s), and the second polymorph is Form C. In one embodiment, the conversion to Form C is performed in a non-anhydrous condition for a period of time sufficient to convert at least about 50% of the total amount of non-Form C polymorph(s) into Form C of a compound of Formula (I), with an optional step of recovering Form C from any non-Form C polymorph (s). Non-anhydrous conditions can include exposure of the original solid form or composition to water vapor or to liquid water. For example, non-anhydrous conditions can include exposure of the original solid form or composition to an amount of liquid water, either alone or with additional liquids or other components, to form a slurry. In certain embodiments, the original solid form or composition can be exposed to water vapor or humidity conditions for a time and at a temperature sufficient to effect conversion to Form C. In certain embodiments, the original composition comprises one or more of Form A, Form B, Form D, Form E, Form F, Form G, Form H, Form I, Form J, or an amorphous form of a compound of Formula (I), or a pharmaceutically acceptable salt, solvate, or hydrate thereof, or a mixture of two or more thereof. In certain embodiments, the original composition comprises greater than about 50% by weight polymorph Form A.

In certain embodiments, provided herein are compositions comprising a polymorph of a compound of Formula (I). In some embodiments, the polymorph of a compound of Formula (I) is a pharmaceutically acceptable salt, solvate, or hydrate. In certain embodiments, the composition comprises a mixture of a first polymorph of a compound of Formula (I), and one or more additional forms of a compound of Formula (I), e.g., an amorphous form of a compound of Formula (I), and/or one or more different polymorphs of a compound of Formula (I). In such a mixture, the first polymorph, the amorphous form, and the one or more different polymorphs can each independently be in the form of a pharmaceutically acceptable salt, solvate or hydrate thereof as disclosed herein, and no two salts, solvates or hydrates are necessarily the same as another or different than another.

In some embodiments, the composition comprises a mixture of forms of a compound of Formula (I) as disclosed herein, and has a greater amount of a first polymorph of a compound of Formula (I) relative to one or more additional forms of a compound of Formula (I) in the mixture. In certain embodiments, the first polymorph of a compound of Formula (I) is selected from Form A, Form B, Form C, Form D, Form E, Form F, Form G, Form H, Form I, and Form J. In some embodiments, the one or more additional forms of a compound of Formula (I) are selected from one or more polymorphs of a compound of Formula (I) that are not the same polymorph as the first polymorph, and an amorphous form of a compound of Formula (I). In such a mixture, the first polymorph, the amorphous form, and the one or more different polymorphs can each independently be in the form of a pharmaceutically acceptable salt, solvate or hydrate thereof as disclosed herein, and no two salts, solvates or hydrates are necessarily the same as another or different than another.

In some embodiments, the composition comprises a weight ratio of greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1, or greater than about 99:1 of a first polymorph (e.g., Form A, Form B, Form C, Form D, Form E, Form F, Form G, Form H, Form I, or Form J) relative to the one or more additional forms of a compound of Formula (I).

For example, in certain embodiments, the composition comprises Form C to non-Form C polymorph(s) at a weight ratio of greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, greater than about 60:1, greater than about 70:1, greater than about 80:1, greater than about 90:1, or greater than about 99:1. In certain embodiments, the composition comprises a first polymorph of a compound of Formula (I), e.g., Form C, and is substantially free of other forms of the compound of Formula (I). In certain embodiments, the composition comprises Form C and Form A. In certain embodiments, the composition comprises Form C and Form B. In certain embodiments, the composition comprises Form C and Form D. In certain embodiments, the composition comprises Form C and Form E. In certain embodiments, the composition comprises Form C and Form F. In certain embodiments, the composition comprises Form C and Form G. In certain embodiments, the composition comprises Form C and Form H. In certain embodiments, the composition comprises Form C and Form I. In certain embodiments, the composition comprises Form C and Form J. In certain embodiments, the composition comprises Form C and an amorphous form of a compound of Formula (I), or a pharmaceutically acceptable salt, solvate, or hydrate thereof.

In certain embodiments, provided herein is a composition comprising Form A and one or more non-Form A polymorphs of a compound of Formula (I), or one or more pharmaceutically acceptable salts, solvates, or hydrates thereof. In certain embodiments, provided herein is a composition comprising Form B and one or more non-Form B polymorphs of a compound of Formula (I), or one or more pharmaceutically acceptable salts, solvates, or hydrates thereof. In certain embodiments, provided herein is a composition comprising Form C and one or more non-Form C polymorphs of a compound of Formula (I), or one or more pharmaceutically acceptable salts, solvates, or hydrates thereof. In certain embodiments, provided herein is a composition comprising Form D and one or more non-Form D polymorphs of a compound of Formula (I), or one or more pharmaceutically acceptable salts, solvates, or hydrates thereof. In certain embodiments, provided herein is a composition comprising Form E and one or more non-Form E polymorphs of a compound of Formula (I), or one or more pharmaceutically acceptable salts, solvates, or hydrates thereof. In certain embodiments, provided herein is a composition comprising Form F and one or more non-Form F polymorphs of a compound of Formula (I), or one or more pharmaceutically acceptable salts, solvates, or hydrates thereof. In certain embodiments, provided herein is a composition comprising Form G and one or more non-Form G polymorphs of a compound of Formula (I), or one or more pharmaceutically acceptable salts, solvates, or hydrates thereof. In certain embodiments, provided herein is a composition comprising Form H and one or more non-Form H polymorphs of a compound of Formula (I), or one or more pharmaceutically acceptable salts, solvates, or hydrates thereof. In certain embodiments, provided herein is a composition comprising Form I and one or more non-Form I polymorphs of a compound of Formula (I), or one or more pharmaceutically acceptable salts, solvates, or hydrates thereof. In certain embodiments, provided herein is a composition comprising Form J and one or more non-Form J polymorphs of a compound of Formula (I), or one or more pharmaceutically acceptable salts, solvates, or hydrates thereof. In certain embodiments, provided herein is a composition comprising an amorphous form of a compound of Formula (I), or a pharmaceutically acceptable salt, solvate, or hydrate thereof. In certain embodiments, provided herein is a composition comprising an amorphous form of a compound of Formula (I) and one or more polymorphs of a compound of Formula (I) selected from Form A, B, C, D, E, F, G, H, I, and J, or one or more pharmaceutically acceptable salts, solvates, or hydrates thereof. In certain embodiments, provided herein are compositions comprising one or more of Form A, B, C, D, E, F, G, H, I, J, or amorphous form, or one or more pharmaceutically acceptable salts, solvates, or hydrates thereof.

In some embodiments, a polymorphic Form of a compound of Formula (I) can be obtained by dissolving a starting compound of Formula (I) (e.g., a different polymorphic Form, an amorphous form, or a salt, solvate, or hydrate thereof, of any of these chemical entitites) in a solvent. In some embodiments, the solvent can be a minimal amount required to dissolve the starting compound of Formula (I) at either room temperature or an elevated temperature. Optionally, the solution can be filtered. In some instances, an anti-solvent (e.g., a solvent that the starting compound is less soluble in than the first solvent) can be added to the solution. In the case of an elevated temperature solution, the solution can be cooled relatively quickly (referred to herein as "fast cooling") by, for example, holding the solution at about 4° C. overnight. Another method can include cooling the solution to ambient temperature at a rate of about 20° C./h (referred to herein as "slow cooling"), then optionally allowing the solution to equilibrate overnight at room temperature (with or without stirring). In some embodiments, the surface of a solution can be scratched with an implement known in the art, such as, but not limited to, a spatula. In other embodiments, a solution can be concentrated by methods known in the art, such as in vacuo, or by passing a stream of gas (inert gases such as argon or nitrogen; ambient air, $CO_2$, etc.), and in some instances be evaporated to a level of dryness. Solids obtained by these procedures or variants thereof can be recovered, for example, through filtration techniques or decantation of any remaining liquid. Identification of the resulting polymorph Form of a compound of Formula (I), or salt, solvate, or hydrate thereof, can be performed using any of the techniques (e.g., XRPD, DSC, TGA, etc.) described herein and known in the art.

Form A

In one embodiment, a polymorph provided herein is Form A of a compound of Formula (I).

FIG. 1 shows a representative X-ray powder diffraction (XRPD) for polymorph Form A.

In one embodiment, polymorph Form A can be characterized by any one, two, three, four, five, six, seven, eight, nine, ten, or more of significant peak(s) of FIG. 1. In one embodiment, polymorph Form A can be characterized as having at least one XRPD peak selected from 2θ=9.6° (±0.2°), 12.2° (±0.2°), and 18.3° (±0.2°). In one embodiment, polymorph Form A can be characterized as having at least one XRPD peak selected from 2θ=9.6° (±0.2°), 12.2° (±0.2°), and 18.3° (±0.2°) in combination with at least one XRPD peak selected from 2θ=15.6° (±0.2°) and 19.2° (±0.2°). In another embodiment, polymorph Form A can be characterized as having at least one XRPD peak selected from 2θ=9.6° (±0.2°), 12.2° (±0.2°), 15.6° (±0.2°), 18.3° (±0.2°), and 19.2° (±0.2°) in combination with at least one XRPD peak selected from 2θ=9.1° (±0.2°), 9.4° (±0.2°), 12.4° (±0.2°), 14.8° (±0.2°), 16.3° (±0.2°), 17.7° (±0.2°), 21.1° (±0.2°), 21.9° (+0.2°), 24.0° (±0.2°), and 26.9° (±0.2°). In one embodiment, polymorph Form A can be characterized in that it has substantially all of the peaks in its XRPD pattern as shown in FIG. 1.

Figure 12:
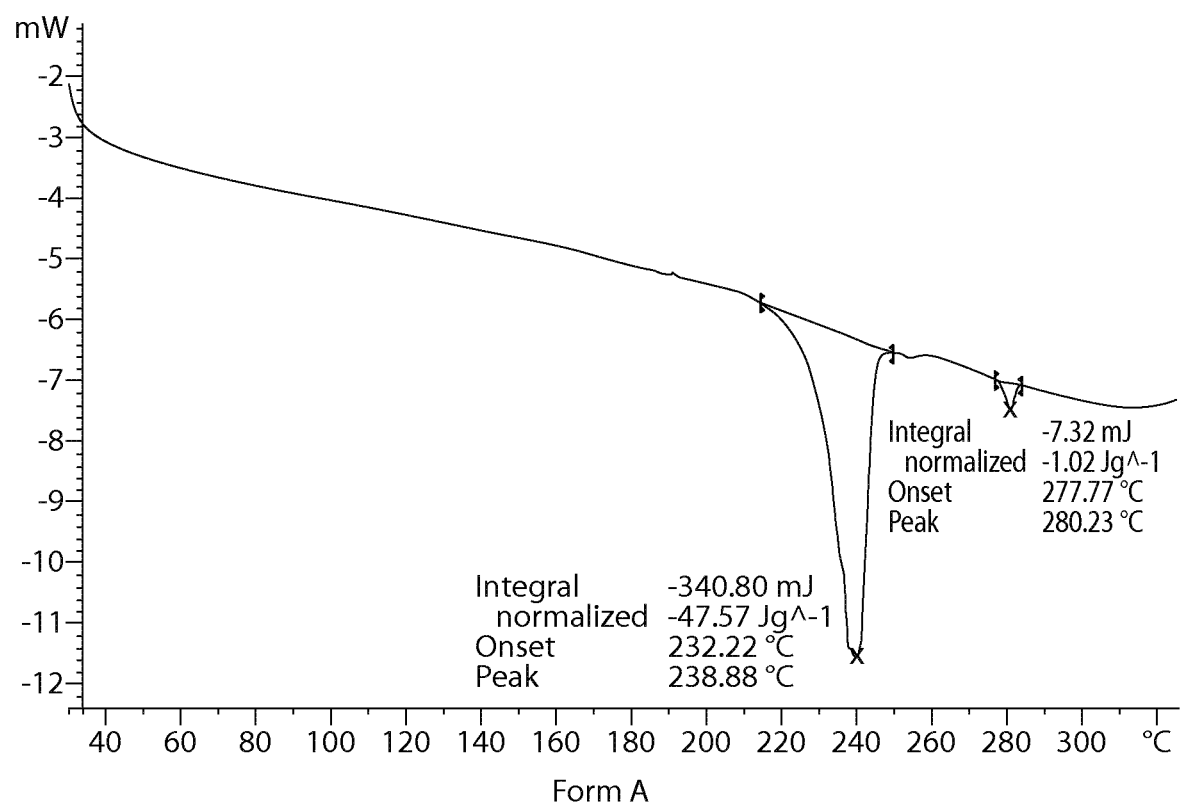
FIG. 12 shows a differential scanning calorimetry (DSC) thermogram for Polymorph Form A.
Figure 22:
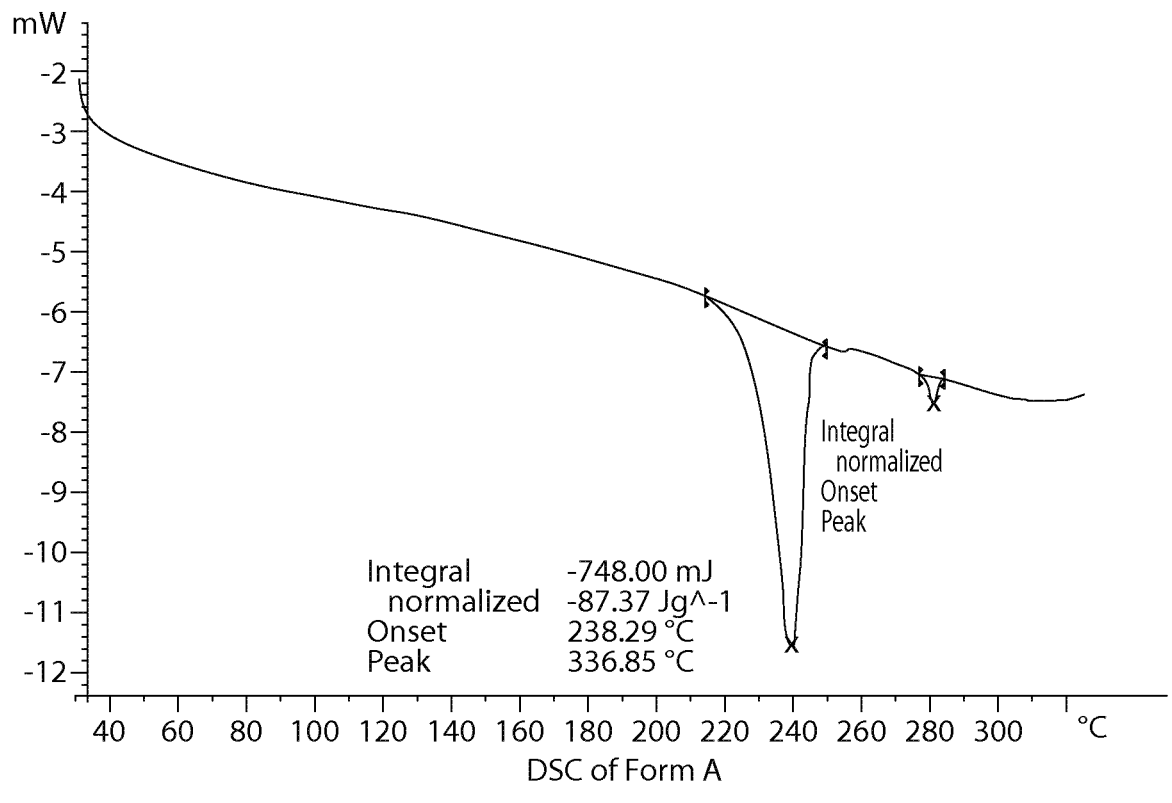
FIG. 22 shows a DSC thermogram and a thermogravimetric analysis (TGA) for Polymorph Form A.
Figure 22:
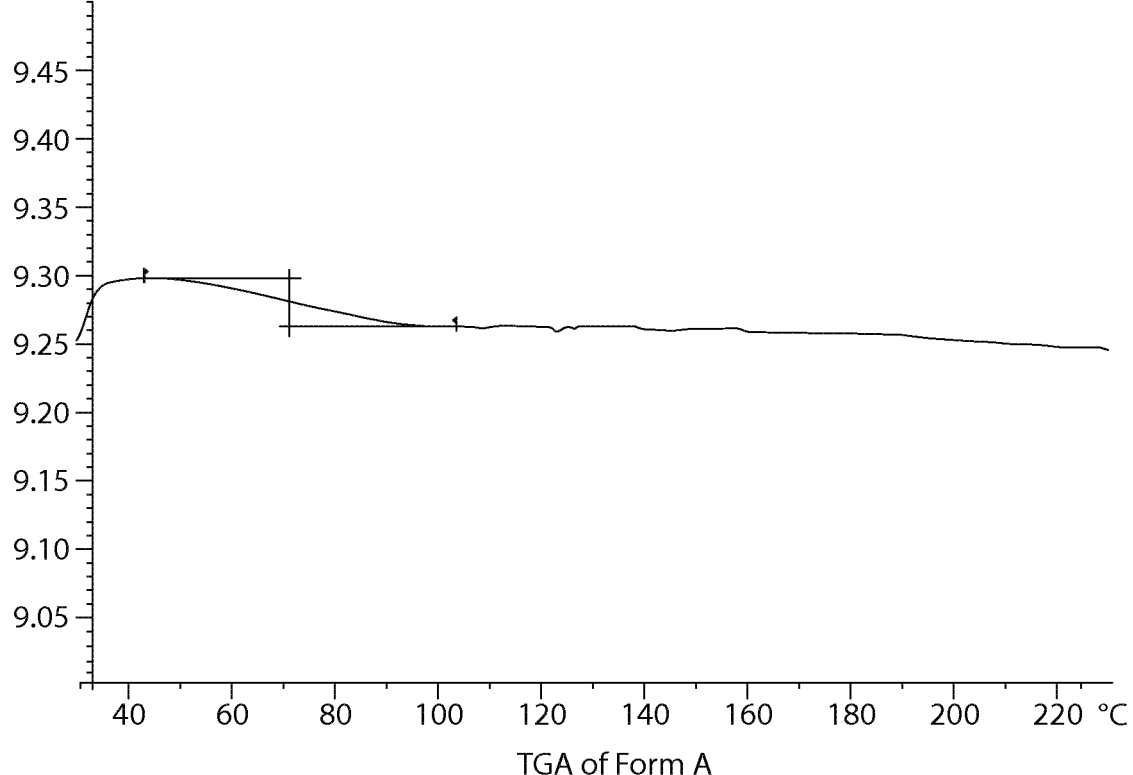

FIGS. 12 and 22 shows a differential scanning calorimetry (DSC) thermogram for polymorph Form A. In some embodiments, polymorph Form A can be characterized as having a endothermic peak at about 238° C. or about 239° C. In another embodiment, polymorph Form A can be characterized as having an endothermic peak at about 238° C. or about 239° C. and an endothermic peak at about 280° C.

FIG. 22 shows a thermogravimetric analysis (TGA) for polymorph Form A. The lack of feature in the TGA trace indicates significant weight loss was not observed upon heating.

In certain embodiments, Form A can be obtained by fast and slow cooling crystallization from single solvent systems created by dissolving Form C in the solvent, including, but not limited to, acetonitrile and n-butanol. In certain embodiments, Form A can be obtained by crystallization from binary solvent systems comprising ethyl acetate and hexanes. In other embodiments, Form A can be obtained by fast and slow cooling from binary solvent systems created by dissolving Form C in a solvent, such as, but not limited to, acetone, methylethyl ketone, DMF, dioxane, and then adding an anti-solvent, such as, without limitation, dichloromethane. In one embodiment, Form A can also be obtained from slurries in dichloromethane, acetonitrile, ethanol, and/ or isopropyl alcohol. In one embodiment, Form A can be obtained from a slurry of Form C, Form D, and/or Form E in acetonitrile.

In one embodiment, Form A is obtained by re-slurrying one or more non-Form A polymorph(s) in an anhydrous solvent. In one embodiment, non-Form A polymorphs include, without limitation, Form B, Form C, Form D, Form E, Form F, Form G, Form H, Form I, Form J, an amorphous form, and mixtures thereof. For example, in one embodiment, Form A can be obtained by re-slurrying one or more non-Form A polymorph(s) (such as, without limitation, Form C or an amorphous form) in, e.g., chloroform, dichloromethane, isopropyl alcohol, ethanol, or mixtures thereof. In another embodiment, Form A can be obtained by re-slurrying a mixture of Form A, Form B, and Form C in acetonitrile. In one embodiment, Form A can be obtained by re-slurrying a mixture of Form A, Form C, Form D, and Form E in isopropanol. In one embodiment, Form A can be obtained by crystallization from a multi-solvent system. In one embodiment, Form A can be an anhydrate.

Form B

In one embodiment, a polymorph provided herein is Form B of a compound of Formula (I).

Figure 2:
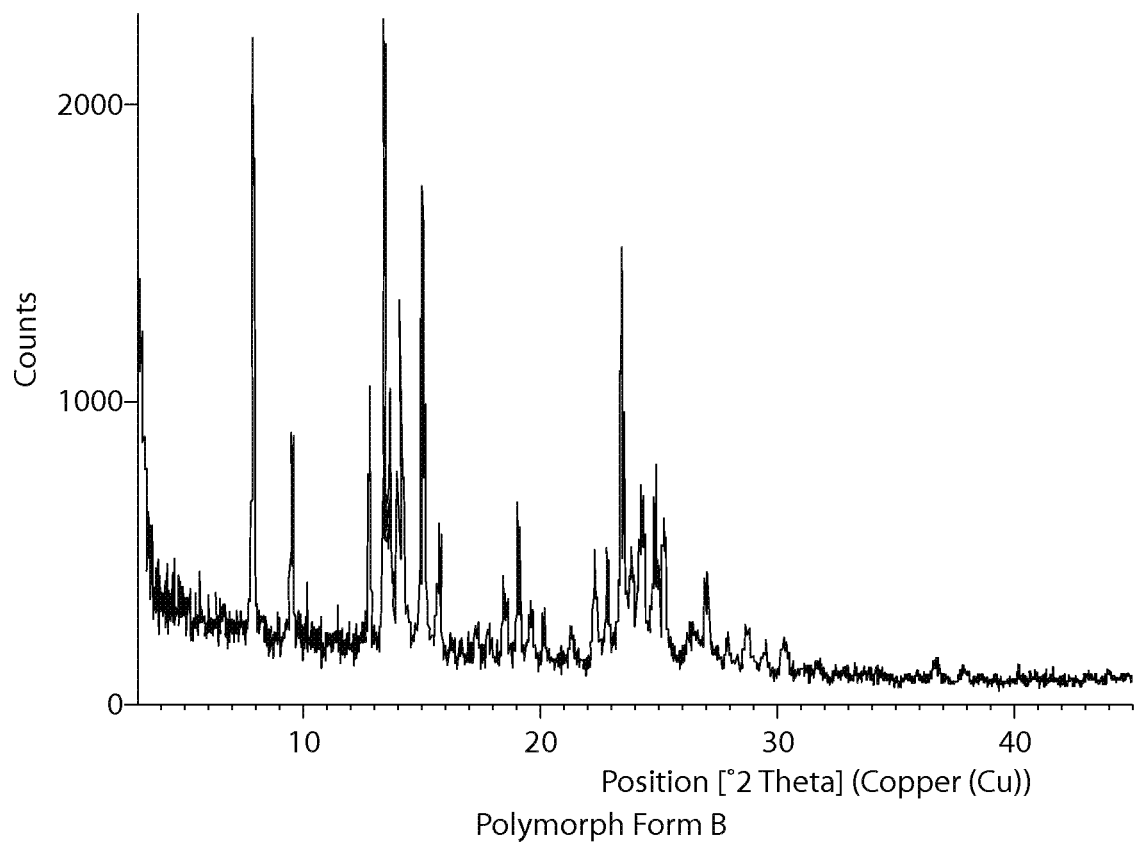
FIG. 2 shows an XRPD for Polymorph Form B.

FIG. 2 shows a representative XRPD for polymorph Form B.

In one embodiment, polymorph Form B can be characterized by any one, two, three, four, five, six, seven, eight, nine, ten, or more of significant peak(s) of FIG. 2. In one embodiment, polymorph Form B can be characterized as having at least one XRPD peak selected from 2θ=7.9° (±0.2°), 13.4° (±0.2°), and 23.4°(±0.2°). In one embodiment, polymorph Form B can be characterized as having at least one XRPD peak selected from 2θ=7.9° (±0.2°), 13.4° (±0.2°), and 23.4° (±0.2°) in combination with at least one XRPD peak selected from 2θ=14.0° (±0.2°) and 15.0° (±0.2°). In another embodiment, polymorph Form B can be characterized as having at least one XRPD peak selected from 2θ=7.9° (±0.2°), 13.4° (±0.2°), 14.0° (±0.2°), 15.0° (±0.2°), and 23.4° (±0.2°) in combination with at least one XRPD peak selected from 2θ=9.5° (±0.2°), 12.7° (±0.2°), 13.6° (±0.2°), 14.2° (±0.2°), 15.7° (±0.2°), 19.0° (±0.2°), 22.3° (±0.2°), 24.2° (±0.2°), 24.8° (±0.2°), and 26.9° (±0.2°). In one embodiment, polymorph Form B can be characterized in that it has substantially all of the peaks in its XRPD pattern as shown in FIG. 2.

Figure 13:
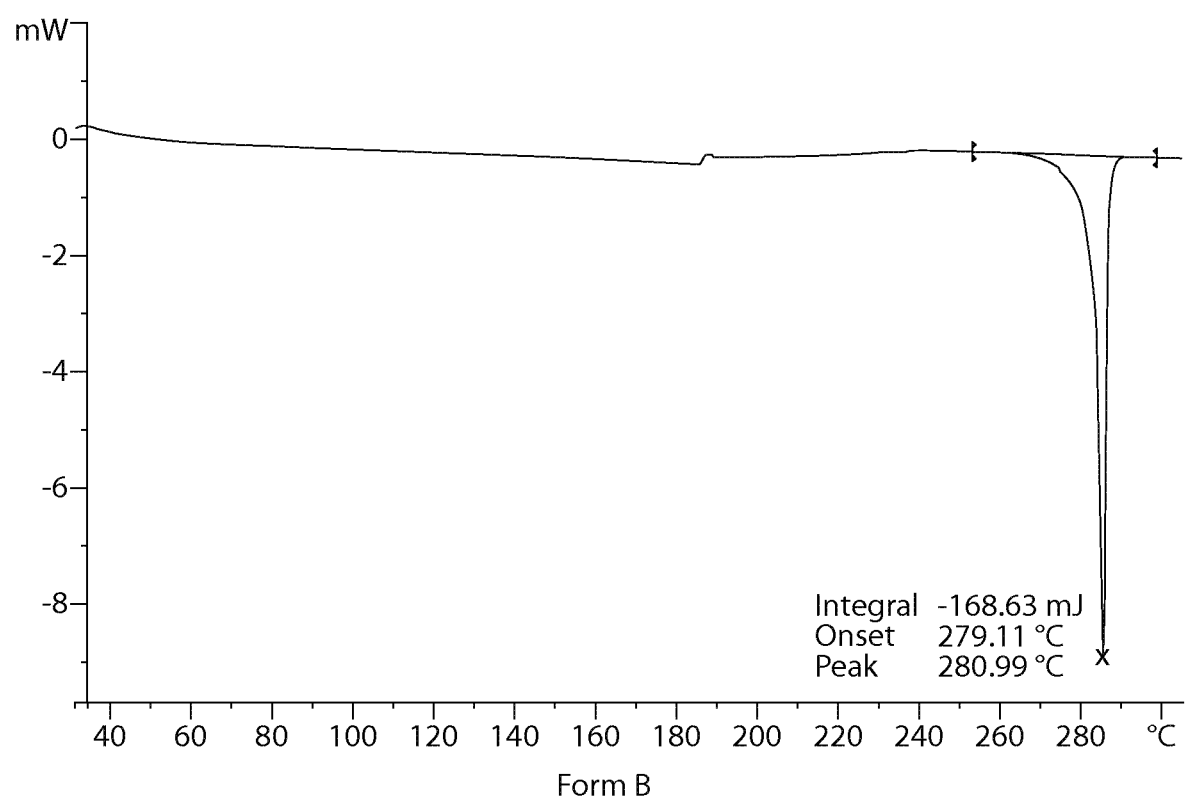
FIG. 13 shows a DSC for Polymorph Form B.

FIG. 13 shows a differential scanning calorimetry (DSC) thermogram for polymorph Form B. In some embodiments, polymorph Form B can be characterized by having a endothermic peak at about 280° C. to about 283° C. In one embodiment, the DSC endothermic peak is about 281° C. In one embodiment, the DSC endothermic peak is about 282° C. In one embodiment, the DSC endothermic peak is about 283° C.

In certain embodiments, Form B can be produced from Form A upon an isothermal hold at about 250° C. followed by cooling to room temperature. In one embodiment, Form B can be produced from Form C upon a similar thermal conversion procedure. In certain embodiments, Form B is produced by thermal conversion from a non-Form B polymorph, such as, without limitation, Form A, Form C, Form D, Form E, Form F, Form G, Form H, Form I, Form J, an amorphous form, and mixtures thereof. In one embodiment, Form B can be an anhydrate.

Form C

In one embodiment, a polymorph provided herein is Form C of a compound of Formula (I).

Figure 3:
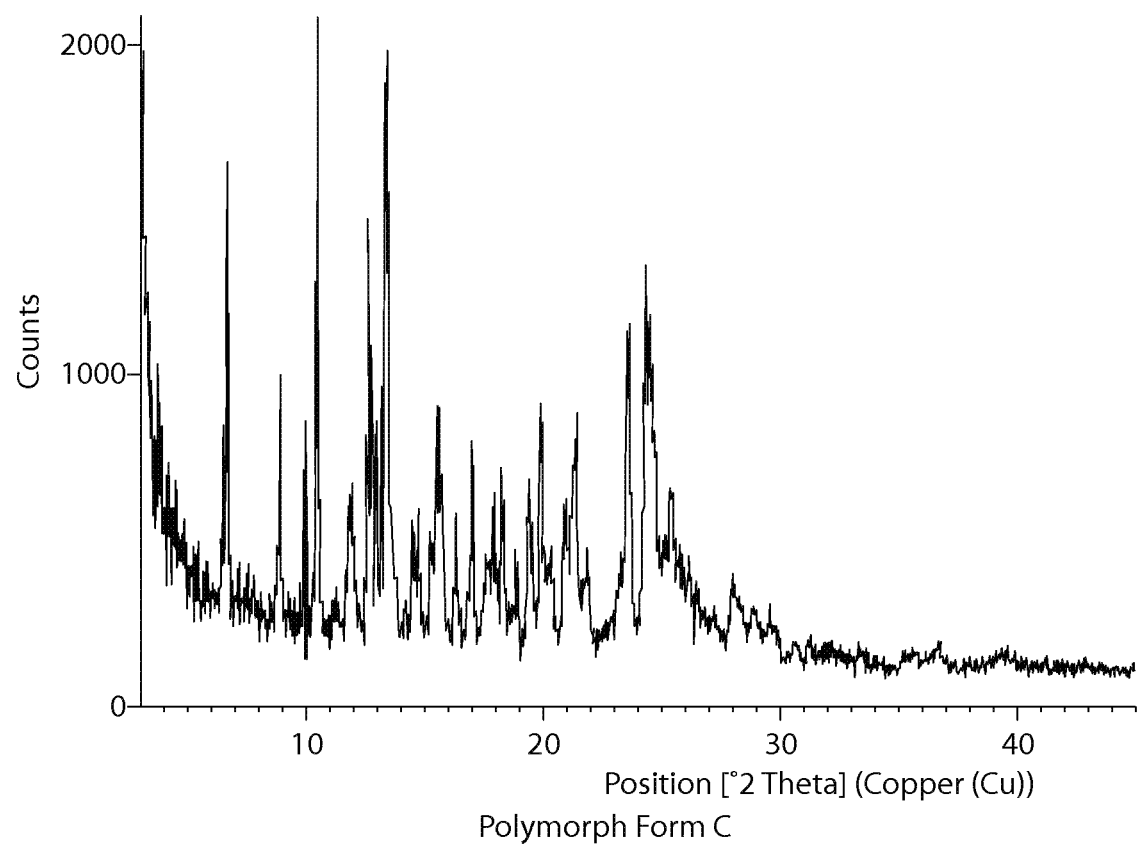
FIG. 3 shows an XRPD for Polymorph Form C.

FIG. 3 shows a representative XRPD for polymorph Form C.

In one embodiment, polymorph Form C can be characterized by any one, two, three, four, five, six, seven, eight, nine, ten, or more of significant peak(s) of FIG. 3. In one embodiment, Form C can be characterized by having at least one XRPD peak selected from 2θ=10.5° (±0.2°), 13.7° (±0.2°), and 24.5° (±0.2°). In another embodiment, Form C can be characterized by having at least one XRPD peak selected from 2θ=10.4° (±0.2°), 13.3° (±0.2°), and 24.3° (±0.2°). In one embodiment, polymorph Form C can be characterized as having at least one XRPD peak selected from 2θ=10.4° (±0.2°), 13.3° (±0.2°), and 24.3° (±0.2°) in combination with at least one XRPD peak selected from 2θ=6.6° (±0.2°) and 12.5° (±0.2°). In another embodiment, polymorph Form C can be characterized as having at least one XRPD peak selected from 2θ=6.6° (±0.2°), 10.4° (±0.2°), 12.5° (±0.2°), 13.3° (±0.2°), and 24.3° (±0.2°) in combination with at least one XRPD peak selected from 2θ=8.8° (±0.2°), 9.9° (±0.2°), 13.4° (±0.2°), 15.5° (±0.2°), 16.9° (+0.2°), 19.8° (±0.2°), 21.3° (±0.2°), 23.6° (±0.2°), 25.3° (±0.2°), and 27.9° (±0.2°). In one embodiment, polymorph Form C can be characterized in that it has substantially all of the peaks in its XRPD pattern as shown in FIG. 3.

Figure 14:
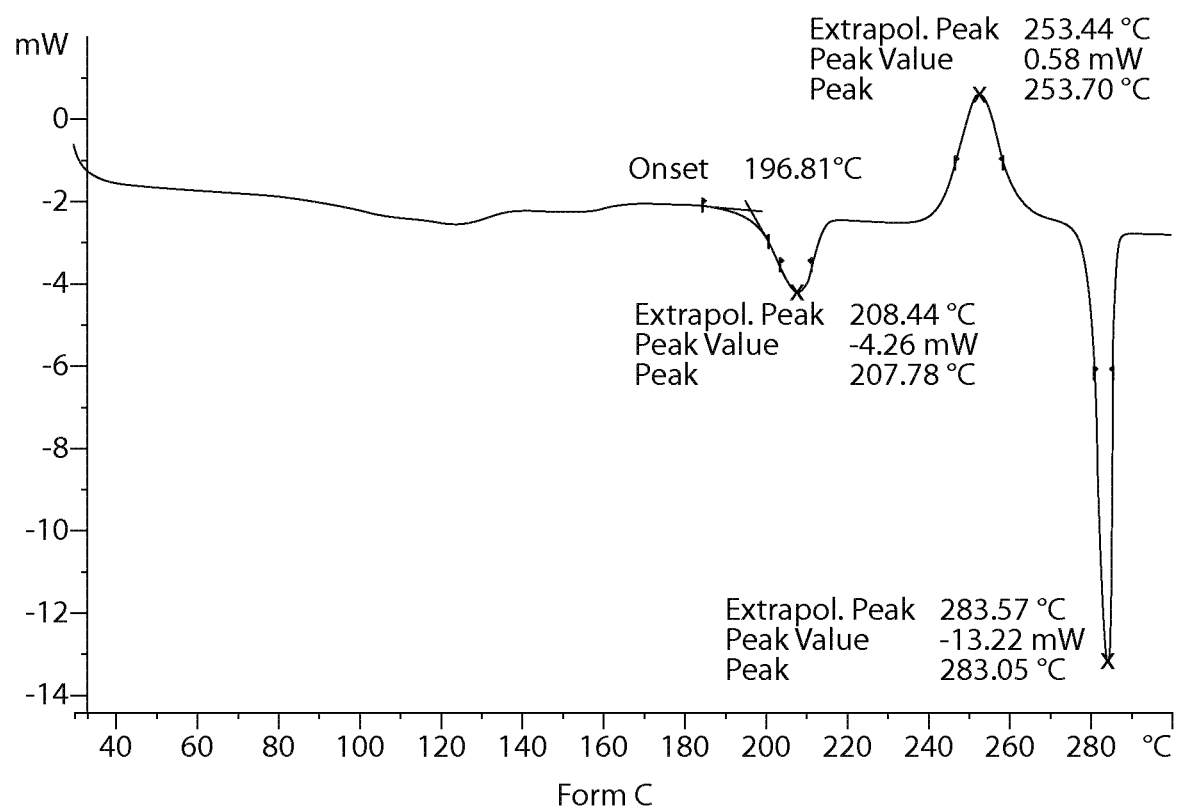
FIG. 14 shows a DSC for Polymorph Form C.
Figure 23:
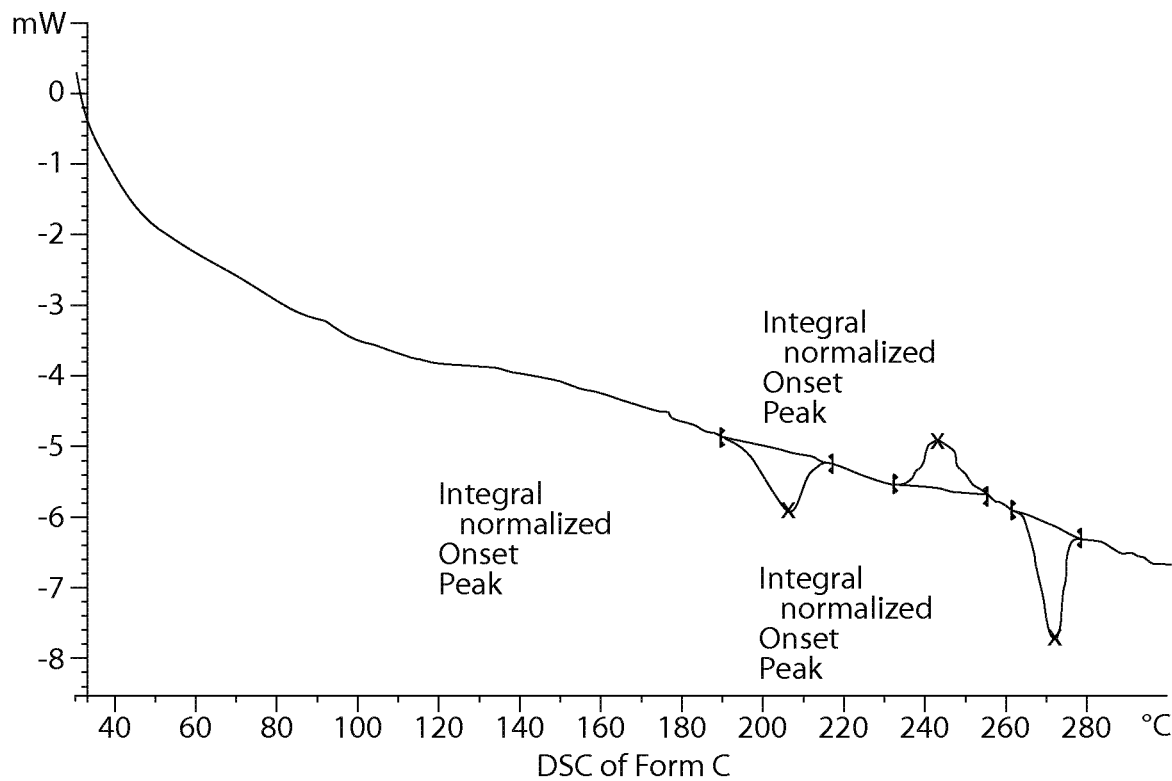
FIG. 23 shows two DSC thermograms for Polymorph Form C.
Figure 23:
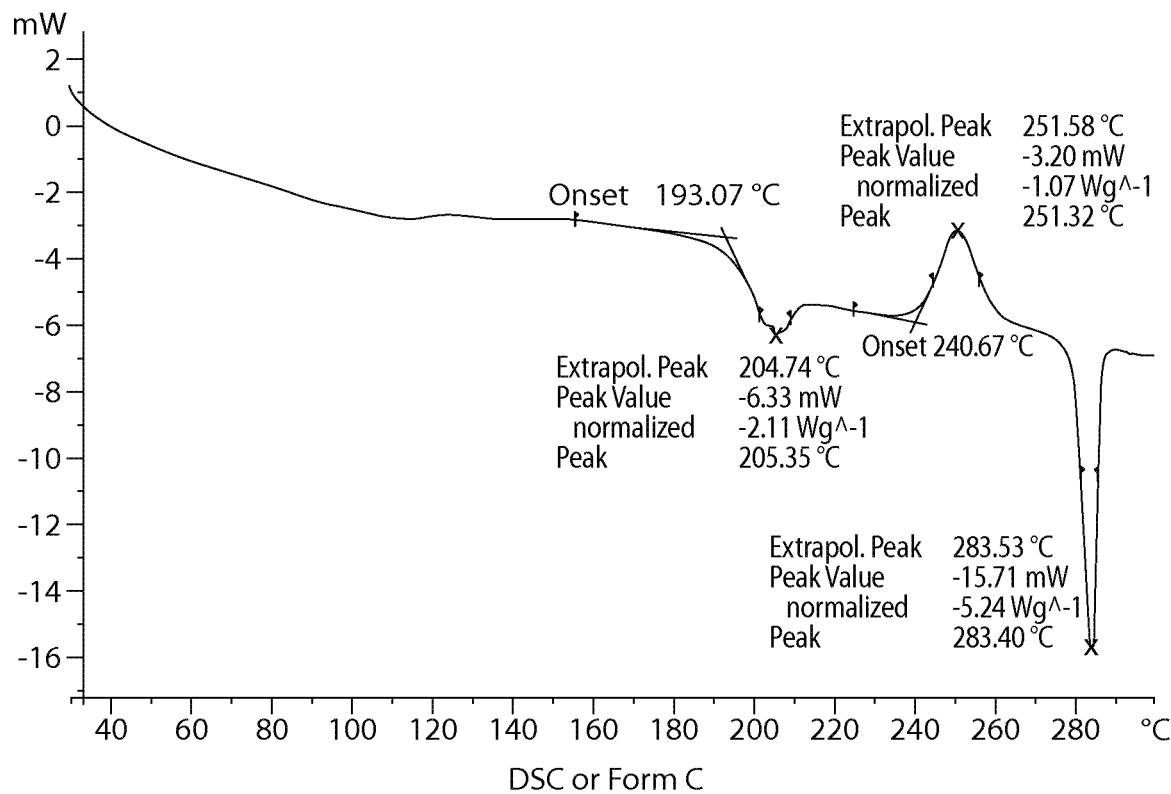

FIGS. 14 and 23 show exemplary differential scanning calorimetry (DSC) thermograms for polymorph Form C. In some embodiments, polymorph Form C can be characterized as having an endothermic peak at about 203° C. In some embodiments, polymorph Form C can be characterized as having an endothermic peak at about 206° C. or about 208° C. In another embodiment, polymorph Form C can be characterized as having an endothermic peak in the range of about 203° C. to about 208° C., and at least one peak selected from an exothermic peak in the range of about 251° C. to about 254° C., and an endothermic peak in the range of about 281° C. to about 283° C. In one embodiment, polymorph Form C can be characterized as having an endothermic peak at about 208° C., an exothermic peak at about 254° C., and an endothermic peak at about 283° C. The peak position variability is within expected observance using this thermographic analysis as described further below in the examples section. For instance, peak position can be affected by sample preparation, rate of temperature increase, and instrument utilized, among other factors known in the art.

In some embodiments, polymorph Form C can be characterized by a thermogravimetric analysis (TGA). In one embodiment, a weight loss of about 1.7% wt can be observed at about 80° C. and a weight loss of about 0.2% wt can be observed at about 190° C.

In certain embodiments, Form C is obtained in a mixture with non-Form C polymorphs, such as, without limitation, Form A, Form B, Form D, Form E, Form F, Form G, Form H, Form I, Form J, an amorphous form, and mixtures thereof. For example, in certain embodiments, Form C is present as a composition further comprising one or more non-Form C polymorphs. The amount of non-Form C polymorphs in the composition can vary. For example, in certain embodiments, the weight ratio of polymorph Form C to the total amount of one or more non-Form C polymorph(s) is greater than about 7:1, greater than about 8:1, greater than about 9:1, greater than about 9.5:1, or greater than about 99:1. Similarly, when formulated in pharmaceutical compositions, various amounts of non-C polymorph form can be present. In certain embodiments, the weight ratio of polymorph Form C to the total amount of one or more non-C polymorphs in a pharmaceutical composition is greater than about 7:1, greater than about 8:1, greater than about 9:1, greater than about 9.5:1, or greater than about 99:1.

In certain embodiments, Form C is obtained from direct workup of the synthetic step producing the compound of Formula (I), and non-C Forms are not obtained, or are obtained as a minority component. In certain embodiments, the final workup of the reaction mixture includes water to remove any soluble salts formed during the reaction. In certain embodiments, a seed crystal can be added to avoid or reduce oiling out of the compound of Formula (I). Seed crystals of any form can be used. In one embodiment, the seed crystal is of polymorph Form C. In certain embodiments, one or more non-C Forms are obtained with or without recovery and/or purification, followed by subsequent conversion of the one or more non-C Forms to Form C.

In certain embodiments, Form C is produced by placing Form A in water to form a slurry for about 18-24 hours, or until a certain amount of conversion of Form A to Form C has occurred. In certain embodiments, Form C is produced by placing Form A in water or a water-containing solvent system. Upon exposure to water or a water-containing solvent system, the combination can form a slurry. The combination of Form A and water or water-containing solvent system can be stirred, optionally with heating, until conversion of Form C has occurred. In certain embodiments, Form A is exposed to water and other solvents are excluded. In some embodiments, Form C can be obtained by slurrying Form D and/or Form E in water. In some embodiments, Form C can be obtained by slurrying a mixture of Form A, Form C, Form D, and Form E in water. In one embodiment, Form C can be obtained by slurrying a mixture of Form B and Form C in water.

In certain embodiments, the solvent system is a $C_1$-$C_6$ alcohol with water. In certain embodiments, the solvent system is a water-miscible alcohol with water. In certain embodiments, the solvent system is a non-alcohol water-miscible solvent with water. In certain embodiments, Form C is produced by fast or slow cooling from binary solvent systems, including, without limitation, ethanol, isopropyl alcohol, tetrahydrofuran, acetone, dioxane, NMP, DME, and DMF as primary solvent, and an anti-solvent, such as, without limitation, water. In certain embodiments, the solvent system is ethanol or 2-propanol with water. In some embodiments, Form C can be obtained by slurrying a mixture of Form A, Form B and Form C in ethanol and water.

Where a solvent in addition to water is used, the ratio of solvent to water can vary from about 100/1 to about 1/100. For example, the ratio of solvent to water can be selected from about 100/1, about 90/1, about 80/1, about 70/1, about 60/1, about 50/1, about 40/1, about 30/1, about 20/1, about 10/1, about 9/1, about 8/1, about 7/1, about 6/1, about 5/1, about 4/1, about 3/1, about 2/1, about 1.5/1, about 1/1, about 1/1.5, about 1/2, about 1/3, about 1/4, about 1/5, about 1/6, about 1/7, about 1/8, about 1/9, about 1/10, about 1/20, about 1/30, about 1/40, about 1/50, about 1/60, about 1/70, about 1/80, about 1/90, and about 1/100. In certain embodiments, the ratio of ethanol or isopropyl alcohol to water can be about 7/4, about 9/7, about 7/10, or the like. The total amount of solvent or solvent system can be selected from about 0.1 volumes (e.g., liters/kg), about 0.5 volumes, about 1 volume, about 2 volumes, about 3 volumes, 4 about volumes, about 5 volumes, about 6 volumes, about 7 volumes, about 8 volumes, about 9 volumes, about 10 volumes, about 11 volumes, about 12 volumes, about 13 volumes, about 14 volumes, about 15 volumes, about 16 volumes, about 17 volumes, about 18 volumes, about 19 volumes, about 20 volumes, about 30 volumes, about 40 volumes, about 50 volumes, or more. In certain embodiments, the solvent system is ethanol/water. In certain embodiments, the solvent system is isopropyl alcohol/water.

In some embodiments, a method of preparing Form C includes preparing a slurry of Form C in dichloromethane to effect a polymorph change to Form A. After recovery of the solids by filtration, the polymorph Form A can be added to water to form a slurry. After stirring for a period of time, (e.g., about 3-12 hours), the slurry can be filtered and polymorph Form C can be recovered.

In certain embodiments, Form C is obtained by recrystallization of a non-C Form, including complete dissolution of the non-C Form followed by filtration to remove any insoluble particles, and subsequent crystallization to yield Form C. In certain embodiments, complete dissolution and filtration is not performed, in which case a slurry is formed which converts to Form C without complete dissolution of one or more non-C Forms. In one embodiment, Form C can be obtained by crystallization from a multi-solvent system. In some embodiments, Form C exhibits better flow properties than that of Form A. In certain embodiments, Form C is a channel hydrate.

Form D

In one embodiment, a polymorph provided herein is Form D of a compound of Formula (I).

Figure 4:
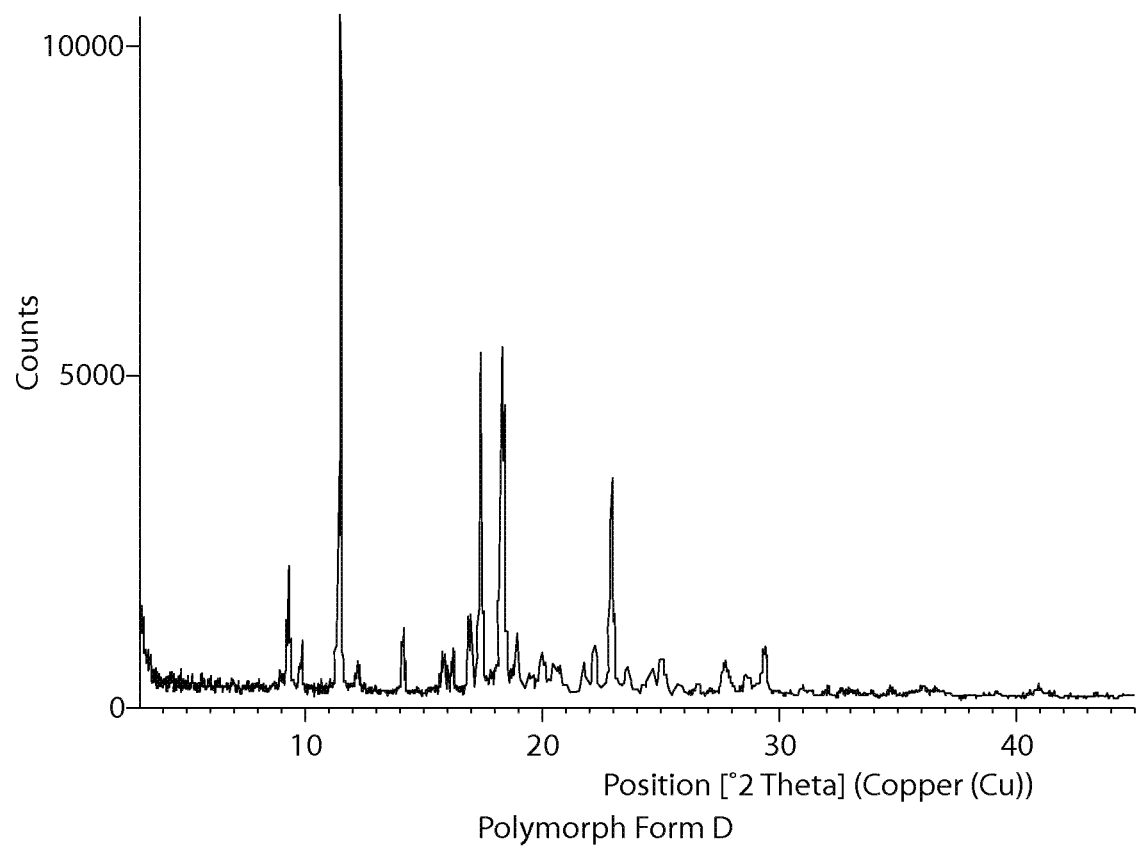
FIG. 4 shows an XRPD for Polymorph Form D.

FIG. 4 shows a representative XRPD for polymorph Form D.

In one embodiment, polymorph Form D can be characterized by any one, two, three, four, five, six, seven, eight, nine, ten, or more of significant peak(s) of FIG. 4. In one embodiment, polymorph Form D can be characterized as having at least one XRPD peak selected from $2\theta=11.4°$ ($\pm 0.2°$), 17.4° ($\pm 0.2°$), and 22.9° ($\pm 0.2°$). In one embodiment, polymorph Form D can be characterized as having at least one XRPD peak selected from $2\theta=11.4°$ ($\pm 0.2°$), 17.4° ($\pm 0.2°$), and 22.9° ($\pm 0.2°$) in combination with at least one XRPD peak selected from $2\theta=9.2°$ ($\pm 0.2°$) and 18.3° ($\pm 0.2°$). In another embodiment, polymorph Form D can be characterized as having at least one XRPD peak selected from $2\theta=9.2°$ ($\pm 0.2°$), 11.4° ($\pm 0.2°$), 17.4° ($\pm 0.2°$), 18.3° ($\pm 0.2°$), and 22.9° ($\pm 0.2°$) in combination with at least one XRPD peak selected from $2\theta=9.8°$ ($\pm 0.2°$), 12.2° ($\pm 0.2°$), 15.8° ($\pm 0.2°$), 16.2° ($\pm 0.2°$), 16.8° ($\pm 0.2°$), 18.9° ($\pm 0.2°$), 19.9° ($\pm 0.2°$), 20.0° ($\pm 0.2°$), 24.9° ($\pm 0.2°$), and 29.3° ($\pm 0.2°$). In one embodiment, polymorph Form D can be characterized in that it has substantially all of the peaks in its XRPD pattern as shown in FIG. 4.

Figure 15:
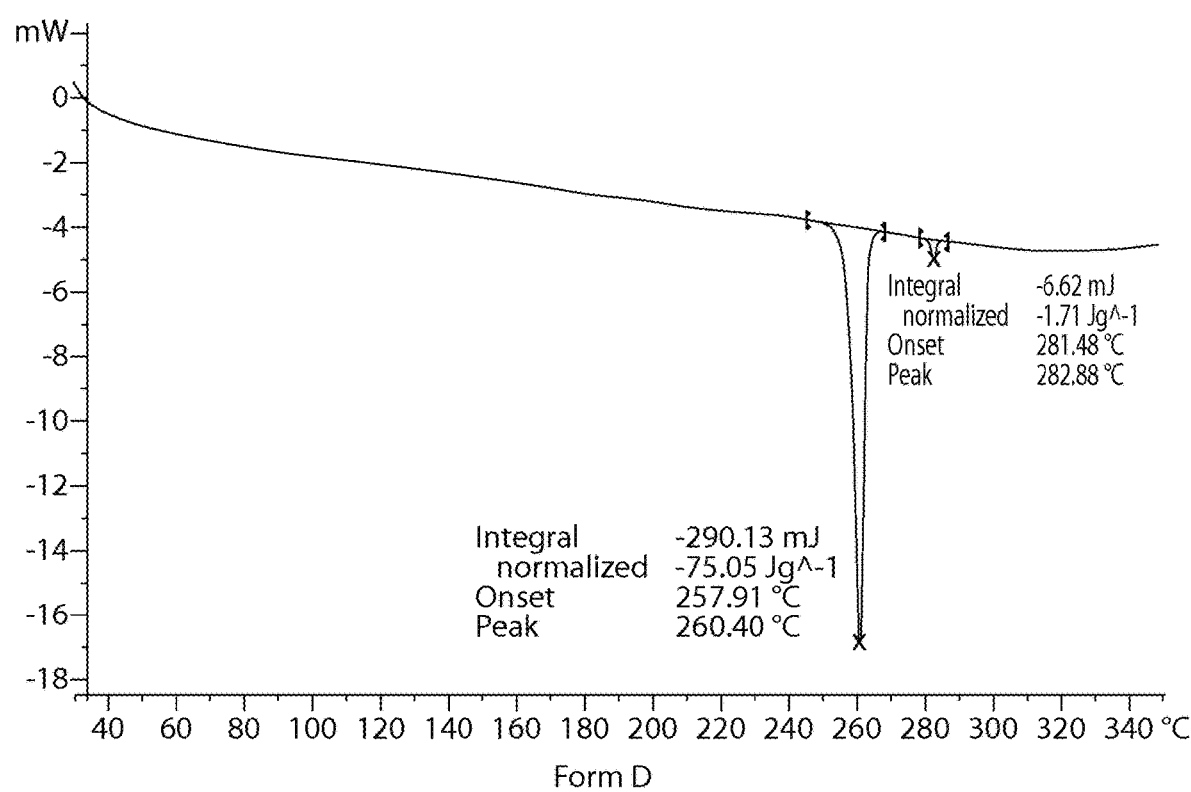
FIG. 15 shows a DSC for Polymorph Form D.

FIG. 15 shows a differential scanning calorimetry (DSC) thermogram for polymorph Form D. In some embodiments, polymorph Form D can be characterized as having an endothermic peak at about 260° C. In another embodiment, polymorph Form D can be characterized as having an endothermic peak at about 260° C. and an endothermic peak at about 283° C.

In some embodiments, polymorph Form D can be characterized by thermogravimetric analysis (TGA). In one embodiment, a weight loss of about 0.2% wt can be observed at about 150° C.

In certain embodiments, Form D can be obtained by fast cooling crystallization from a single solvent system, including, but not limited to, tetrahydrofuran, methyl ethyl ketone, dioxane, or dimethylformamide. In certain embodiments, Form D can be obtained by slow cooling crystallization from a single solvent system, including, but not limited to, tetrahydrofuran, methyl ethyl ketone, or dioxane. In one embodiment, Form D can be obtained by slurrying Form C and/or Form E in methyl ethyl ketone. In one embodiment, Form D can be obtained by slurrying a mixture of Form A, Form B and Form C in methyl ethyl ketone. In another embodiment, Form D can be obtained by slurrying a mixture of Form B and Form D in methyl ethyl ketone.

In certain embodiments, Form D can be obtained by fast cooling crystallization from a binary solvent system with, for example, tetrahydrofuran, dioxane, or DMF as the primary solvent and an anti-solvent, such as, without limitation, MTBE. In certain embodiments, Form D can be obtained by fast cooling crystallization from a binary solvent system with, for example, tetrahydrofuran, isopropanol, or DMF as the primary solvent and an anti-solvent, such as, without limitation, toluene. In one embodiment, Form D can be obtained by fast cooling crystallization from a binary solvent system with, for example, tetrahydrofuran as the primary solvent and dichloromethane as the anti-solvent. In certain embodiments, Form D can be obtained by slow cooling crystallization from a binary solvent system with, for example, methyl ethyl ketone or DMF as the primary solvent and MTBE as the anti-solvent. In certain embodiments, Form D can be obtained by slow cooling crystallization from a binary solvent system with, for example, tetrahydrofuran or DME as the primary solvent and dichloromethane as the anti-solvent. In certain embodiments, Form D can be obtained by slow cooling crystallization from a binary solvent system with, for example, isopropanol, NNP, or DME as the primary solvent and toluene as the anti-solvent.

In one embodiment, Form D can be obtained by crystallization from a multi-solvent system. In certain embodiments, Form D can be formed by slurry in methyl ethyl ketone of a non-Form D polymorph, such as, without limitation, Forms A, B, C, or E. In one embodiment, Form D can be an anhydrate.

Form E

In one embodiment, a polymorph provided herein is Form E of a compound of Formula (I).

Figure 5:
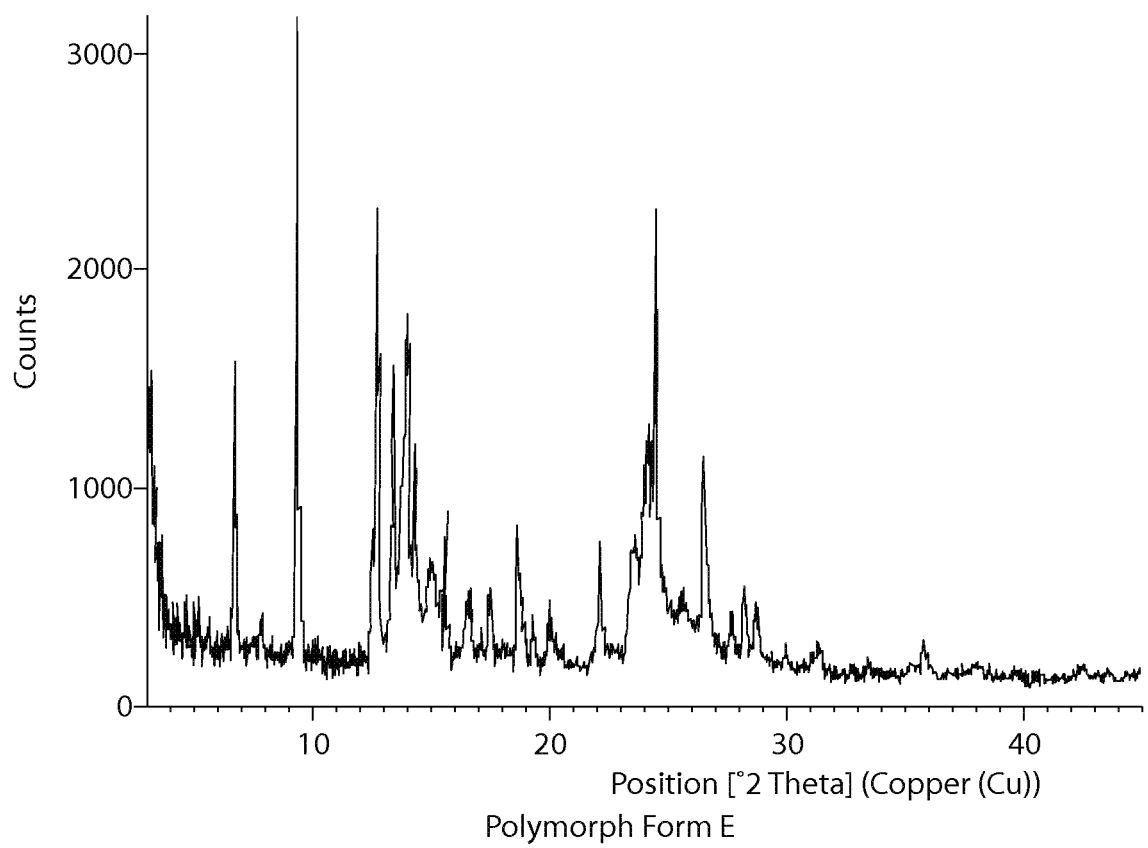
FIG. 5 shows an XRPD for Polymorph Form E.

FIG. 5 shows a representative XRPD for polymorph Form E.

In one embodiment, polymorph Form E can be characterized by any one, two, three, four, five, six, seven, eight, nine, ten, or more of significant peak(s) of FIG. 5. In one embodiment, polymorph Form E can be characterized as having at least one XRPD peak selected from $2\theta=6.7°$ ($\pm 0.2°$), 9.3° ($\pm 0.2°$), and 24.4° ($\pm 0.2°$). In one embodiment, polymorph Form E can be characterized as having at least one XRPD peak selected from $2\theta=6.7°$ ($\pm 0.2°$), 9.3° ($\pm 0.2°$), and 24.4° ($\pm 0.2°$) in combination with at least one XRPD peak selected from $2\theta=12.7°$ ($\pm 0.2°$) and 13.9° ($\pm 0.2°$). In another embodiment, polymorph Form E can be characterized as having at least one XRPD peak selected from $2\theta=6.7°$ ($\pm 0.2°$), 9.3° ($\pm 0.2°$), 12.7° ($\pm 0.2°$), 13.9° ($\pm 0.2°$), and 24.4° ($\pm 0.2°$) in combination with at least one XRPD peak selected from $2\theta=12.4°$ ($\pm 0.2°$), 13.3° ($\pm 0.2°$), 14.3° ($\pm 0.2°$), 15.5° ($\pm 0.2°$), 17.4° ($\pm 0.2°$), 18.5° ($\pm 0.2°$), 22.0° ($\pm 0.2°$), 23.9° ($\pm 0.2°$), 24.1° ($\pm 0.2°$), and 26.4° ($\pm 0.2°$). In one embodiment, polymorph Form E can be characterized in that it has substantially all of the peaks in its XRPD pattern as shown in FIG. 5.

Figure 16:
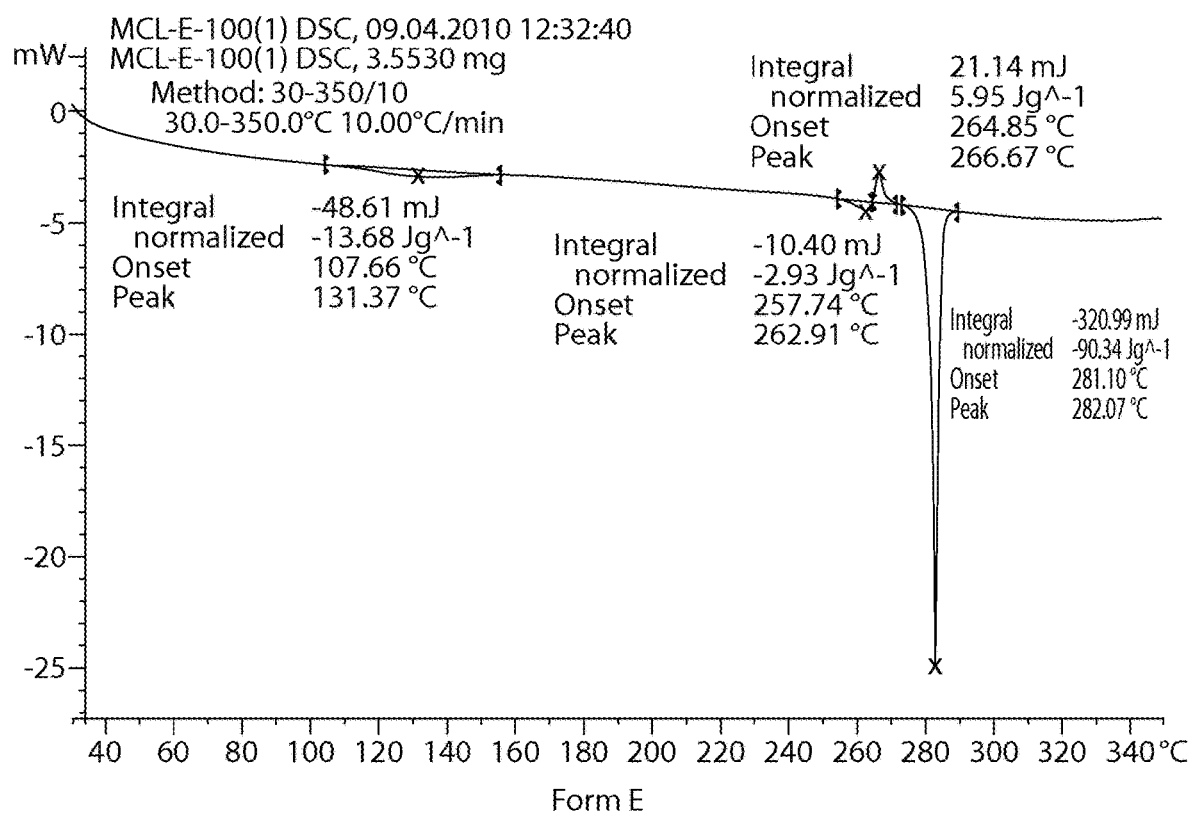
FIG. 16 shows a DSC for Polymorph Form E.

FIG. 16 shows a differential scanning calorimetry (DSC) thermogram for polymorph Form E. In some embodiments, polymorph Form E can be characterized as having an endothermic peak at about 131° C., an endothermic peak at about 263° C., an exothermic peak at about 267° C., and an endothermic peak at about 282° C.

In some embodiments, polymorph Form E can be characterized by thermogravimetric analysis (TGA). In one embodiment, a weight loss of about 0.7% wt can be observed at about 80° C. and a weight loss of about 1.3% wt can be observed at about 130° C.

In certain embodiments, Form E can be obtained from Form A by slow cooling crystallization from a single solvent system with, for example, methanol. In certain embodiments, Form E can be obtained by either fast or slow cooling crystallization from a binary solvent system with, for example, methanol as the primary solvent and water as the anti-solvent. In one embodiment, Form E can be obtained by crystallization from a multi-solvent system. In one embodiment, Form E can be an anhydrate.

Form F

In one embodiment, a polymorph provided herein is Form F of a compound of Formula (I).

Figure 6:
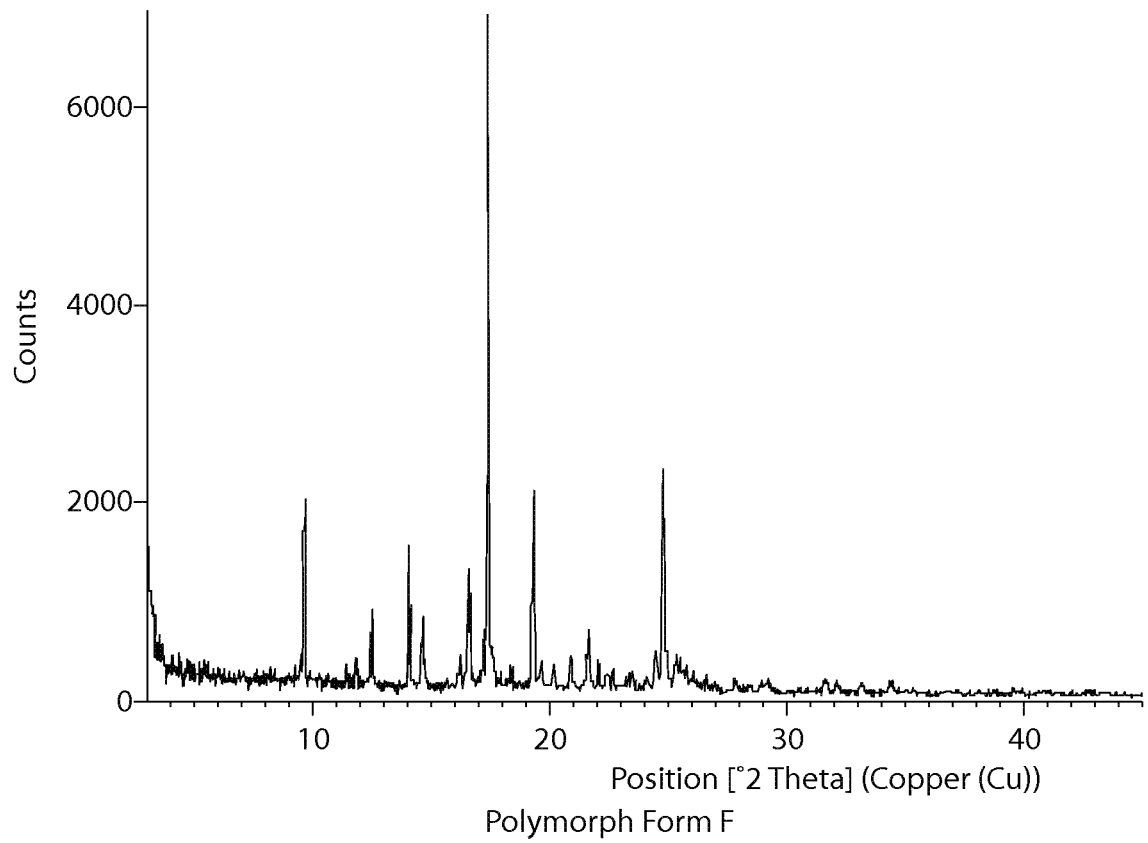
FIG. 6 shows an XRPD for Polymorph Form F.

FIG. 6 shows a representative XRPD for polymorph Form F.

In one embodiment, polymorph Form F can be characterized by any one, two, three, four, five, six, seven, eight, nine, ten, or more of significant peak(s) of FIG. 6. In one embodiment, polymorph Form F can be characterized as having at least one XRPD peak selected from 2θ=9.6° (±0.2°), 17.3° (±0.2°), and 24.6° (±0.2°). In one embodiment, polymorph Form F can be characterized as having at least one XRPD peak selected from 2θ=9.6° (±0.2°), 17.3° (±0.2°), and 24.6° (±0.2°) in combination with at least one XRPD peak selected from 2θ=14.0° (±0.2°) and 19.2° (±0.2°). In another embodiment, polymorph Form F can be characterized as having at least one XRPD peak selected from 2θ=9.6° (±0.2°), 14.0° (±0.2°), 17.3° (±0.2°), 19.2° (±0.2°), and 24.6° (±0.2°) in combination with at least one XRPD peak selected from 2θ=12.4° (±0.2°), 16.1° (±0.2°), 16.6° (±0.2°), 17.1° (±0.2°), 20.8° (±0.2°), 21.5° (±0.2°), 22.0° (±0.2°), 24.3° (±0.2°), 25.2° (±0.2°), and 25.4° (±0.2°). In one embodiment, polymorph Form F can be characterized in that it has substantially all of the peaks in its XRPD pattern as shown in FIG. 6.

Figure 17:
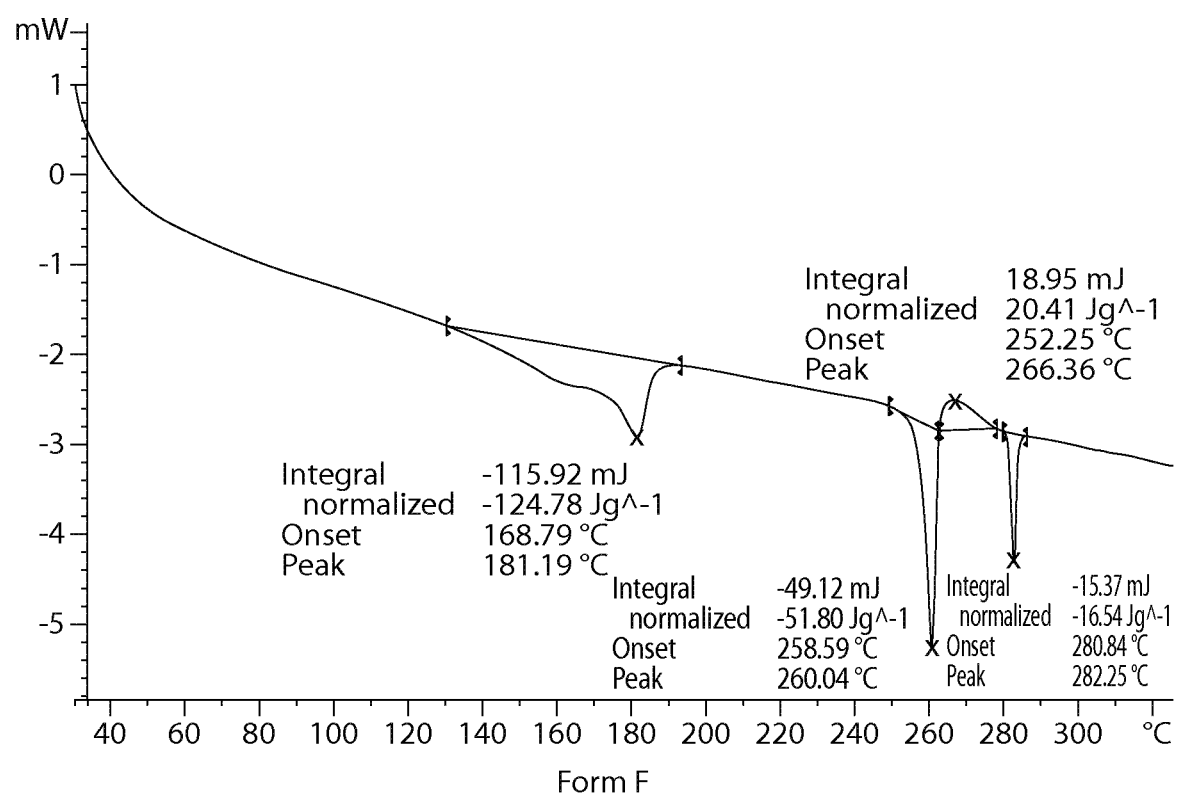
FIG. 17 shows a DSC for Polymorph Form F.
Figure 24:
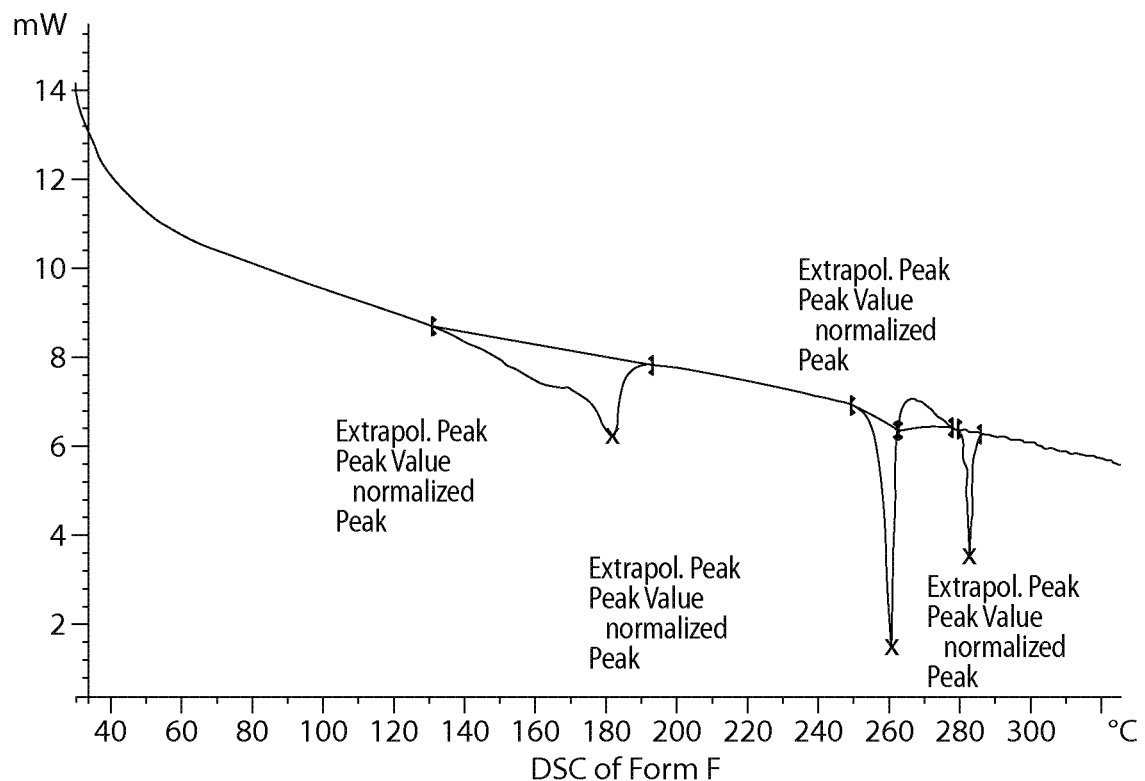
FIG. 24 shows a DSC and a TGA for Polymorph Form F.
Figure 24:
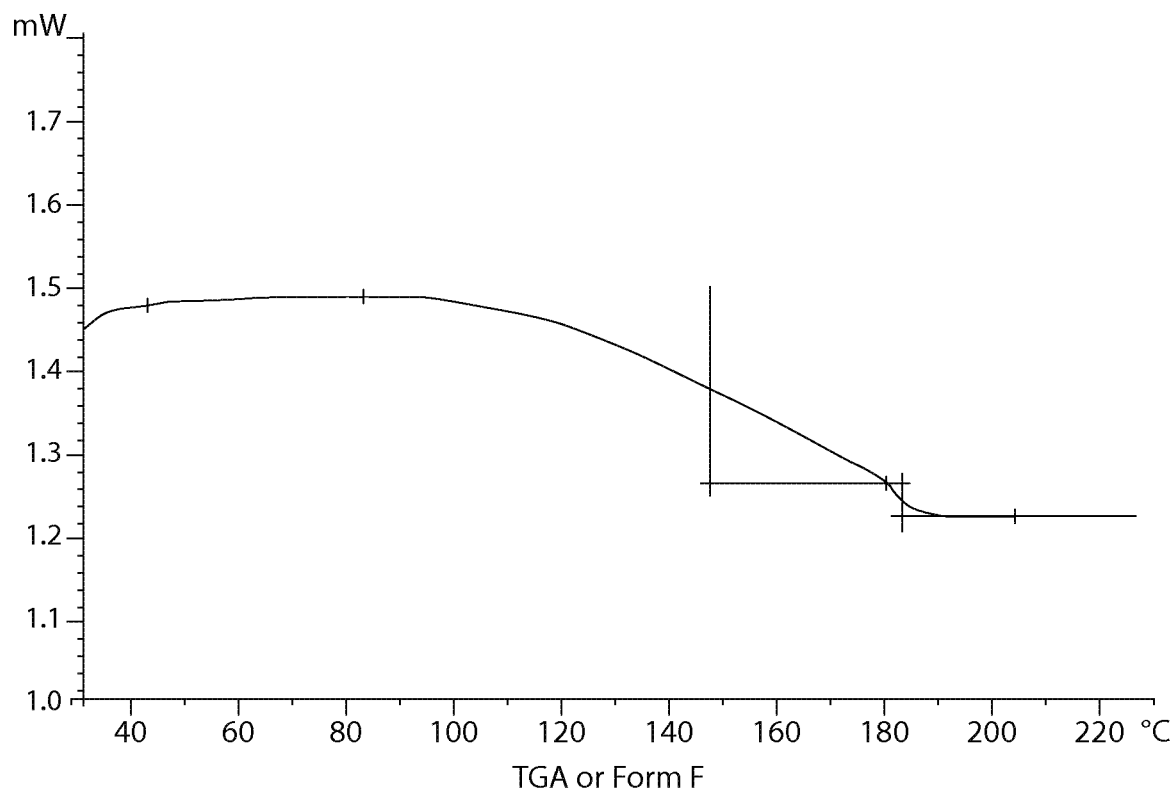

FIGS. 17 and 24 show exemplary differential scanning calorimetry (DSC) endotherm analyses for Form F. In some embodiments, polymorph Form F can be characterized as having an endothermic peak at about 181° C., an endothermic peak at about 160° C., an exothermic peak at about 266° C., and an endothermic peak at about 282° C.

FIG. 24 shows a thermogravimetric analysis (TGA) for polymorph Form F. In some embodiments, polymorph Form F can be characterized by TGA. In one embodiment, a weight loss of about 15.8% wt can be observed at about 150° C., and a weight loss of about 2.8% wt can be observed at about 180° C.

In certain embodiments, Form F can be obtained by fast cooling crystallization from a binary solvent system with, for example, NMP as the primary solvent and MBTE as the anti-solvent. In certain embodiments, Form F can be obtained by slow cooling crystallization from a binary solvent system with, for example, NMP as the primary solvent and MBTE as the anti-solvent. In some embodiments, Form F is an NMP solvate. In certain embodiments, MTBE can be present as an anti-solvent. In one embodiment, Form F can be obtained by crystallization from a multi-solvent system.

Form G

In one embodiment, a polymorph provided herein is Form G of a compound of Formula (I).

Figure 7:
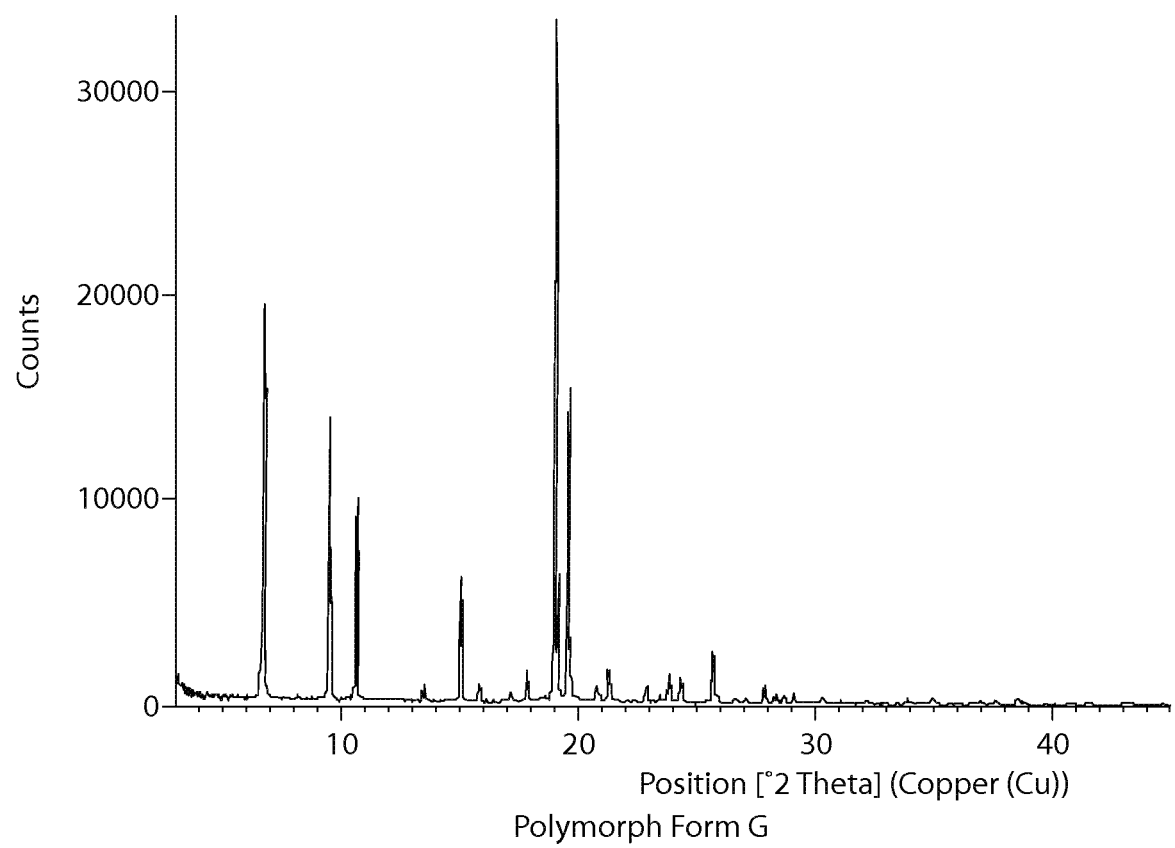
FIG. 7 shows an XRPD for Polymorph Form G.

FIG. 7 shows a representative XRPD for polymorph Form G.

In one embodiment, polymorph Form G can be characterized by any one, two, three, four, five, six, seven, eight, nine, ten, or more of significant peak(s) of FIG. 7. In one embodiment, polymorph Form G can be characterized as having at least one XRPD peak selected from 2θ=6.7° (±0.2°), 9.5° (±0.2°), and 19.0° (±0.2°). In one embodiment, polymorph Form G can be characterized as having at least one XRPD peak selected from 2θ=6.7° (±0.2°), 9.5° (±0.2°), and 19.0° (±0.2°) in combination with at least one XRPD peak selected from 2θ=10.6° (±0.2°) and 19.6° (±0.2°). In another embodiment, polymorph Form G can be characterized as having at least one XRPD peak selected from 2θ=6.7° (±0.2°), 9.5° (±0.2°), 10.6° (±0.2°), 19.0° (±0.2°), and 19.6° (±0.2°) in combination with at least one XRPD peak selected from 2θ=13.4° (±0.2°), 15.0° (±0.2°), 15.8° (±0.2°), 17.8° (±0.2°), 20.7° (±0.2°), 21.2° (±0.2°), 22.8° (±0.2°), 23.8° (±0.2°), 24.3° (±0.2°), and 25.6° (±0.2°). In one embodiment, polymorph Form G can be characterized in that it has substantially all of the peaks in its XRPD pattern as shown in FIG. 7.

Figure 18:
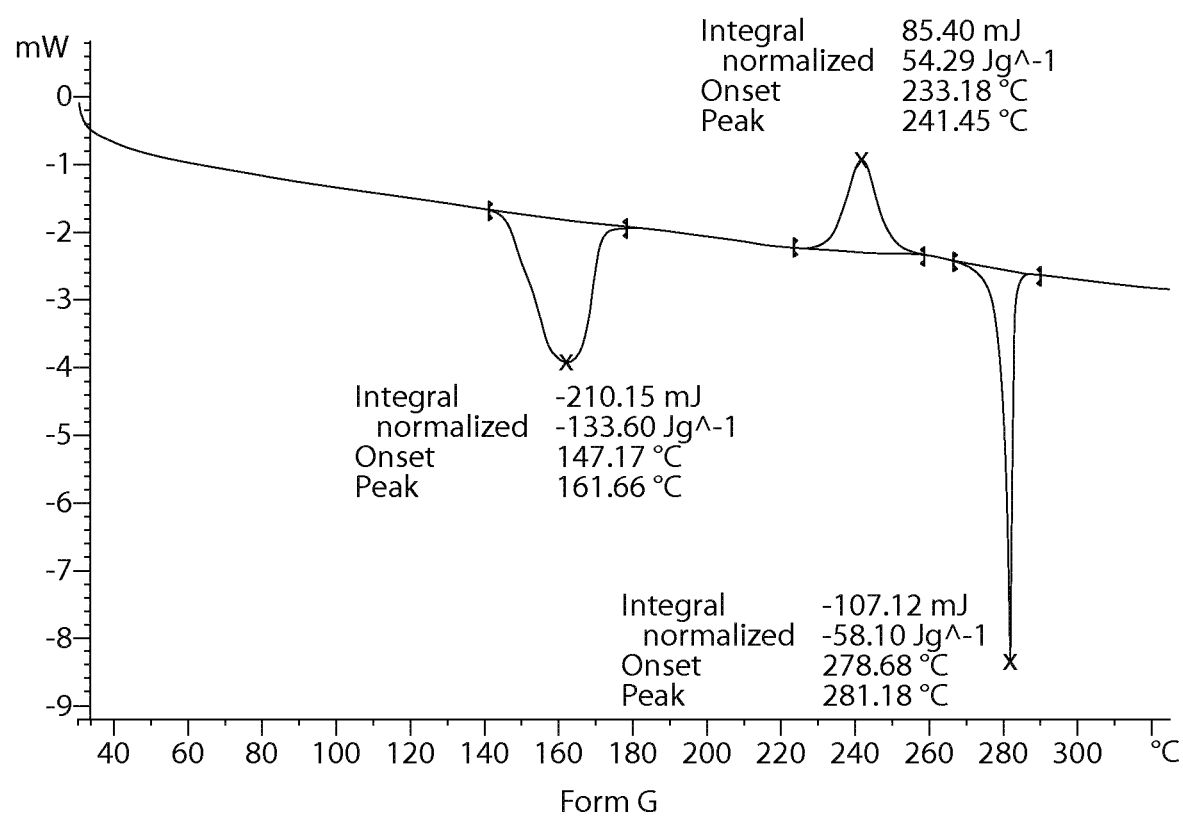
FIG. 18 shows a DSC for Polymorph Form G.

FIG. 18 shows a differential scanning calorimetry (DSC) thermogram for polymorph Form G. In some embodiments, polymorph Form G can be characterized as having an endothermic peak at about 162° C. In another embodiment, polymorph Form G can be characterized as having an endothermic peak at about 162° C., an exothermic peak at about 241° C., and an endothermic peak at about 281° C.

In some embodiments, polymorph Form G can be characterized by thermogravimetric analysis (TGA). In one embodiment, a weight loss of about 18.5% wt can be observed at about 160° C.

In certain embodiments, Form G can be obtained by fast cooling crystallization from a binary solvent system with, for example, ethanol, isopropyl alcohol, or methanol as the primary solvent. In certain embodiments, MTBE can be present as an anti-solvent. In one embodiment, Form G is an MTBE solvate. In one embodiment, Form G can be obtained by crystallization from a multi-solvent system.

Form H

In one embodiment, a polymorph provided herein is Form H of a compound of Formula (I).

Figure 8:
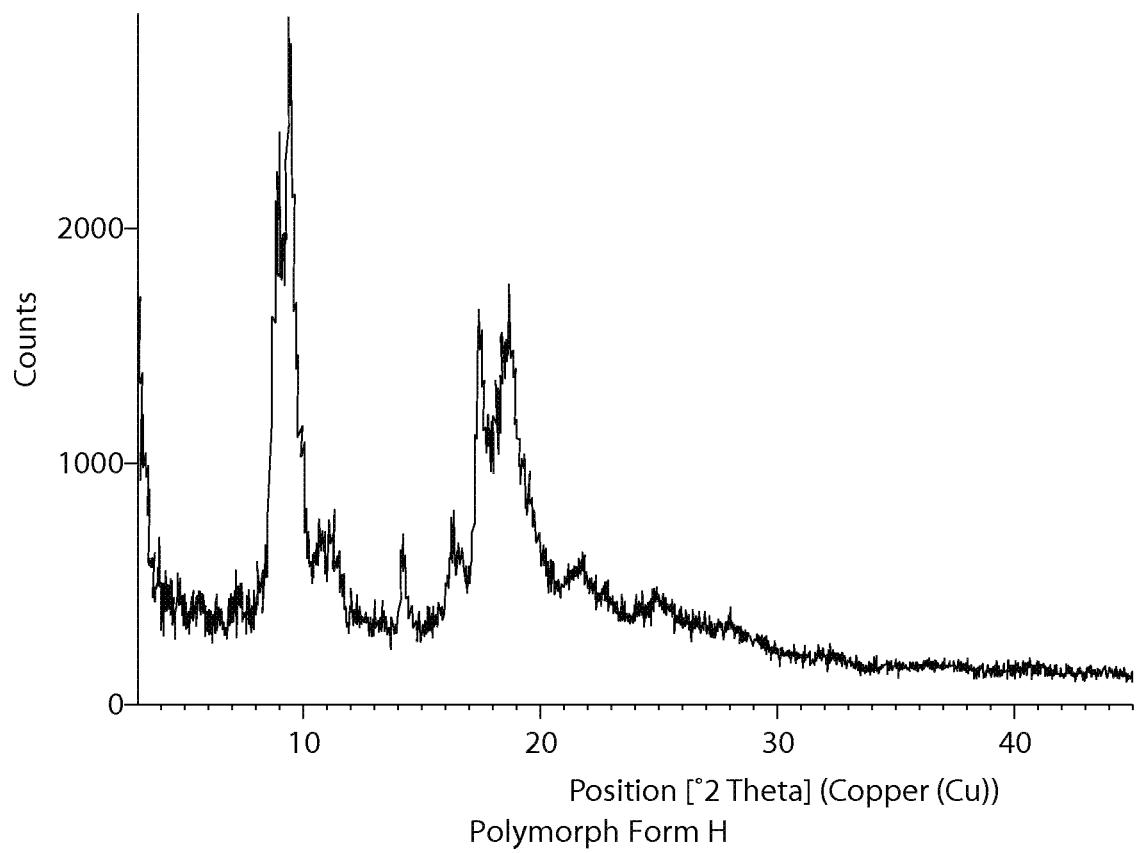
FIG. 8 shows an XRPD for Polymorph Form H.

FIG. 8 shows a representative XRPD for polymorph Form H.

In one embodiment, polymorph Form H can be characterized by any one, two, three, four, five, six, seven, eight, nine, ten, or more of significant peak(s) of FIG. 8. In one embodiment, polymorph Form H can be characterized as having at least one XRPD peak selected from 2θ=8.9° (±0.2°), 9.2° (±0.2°), and 14.1° (±0.2°). In one embodiment, polymorph Form H can be characterized as having at least one XRPD peak selected from 2θ=8.9° (±0.2°), 9.2° (±0.2°), and 14.1° (±0.2°) in combination with at least one XRPD peak selected from 2θ=17.3° (±0.2°) and 18.5° (±0.2°). In another embodiment, polymorph Form H can be characterized as having at least one XRPD peak selected from 2θ=8.9° (±0.2°), 9.2° (±0.2°), 14.1° (±0.2°), 17.3° (±0.2°), and 18.5° (±0.2°) in combination with at least one XRPD peak selected from 2θ=7.1° (±0.2°), 10.6° (±0.2°), 11.3° (±0.2°), 11.6° (±0.2°), 16.2° (±0.2°), 18.3° (±0.2°), 18.8° (±0.2°), 20.3° (±0.2°), 21.7° (±0.2°), and 24.7° (±0.2°). In one embodiment, polymorph Form H can be characterized in that it has substantially all of the peaks in its XRPD pattern as shown in FIG. 8.

Figure 19:
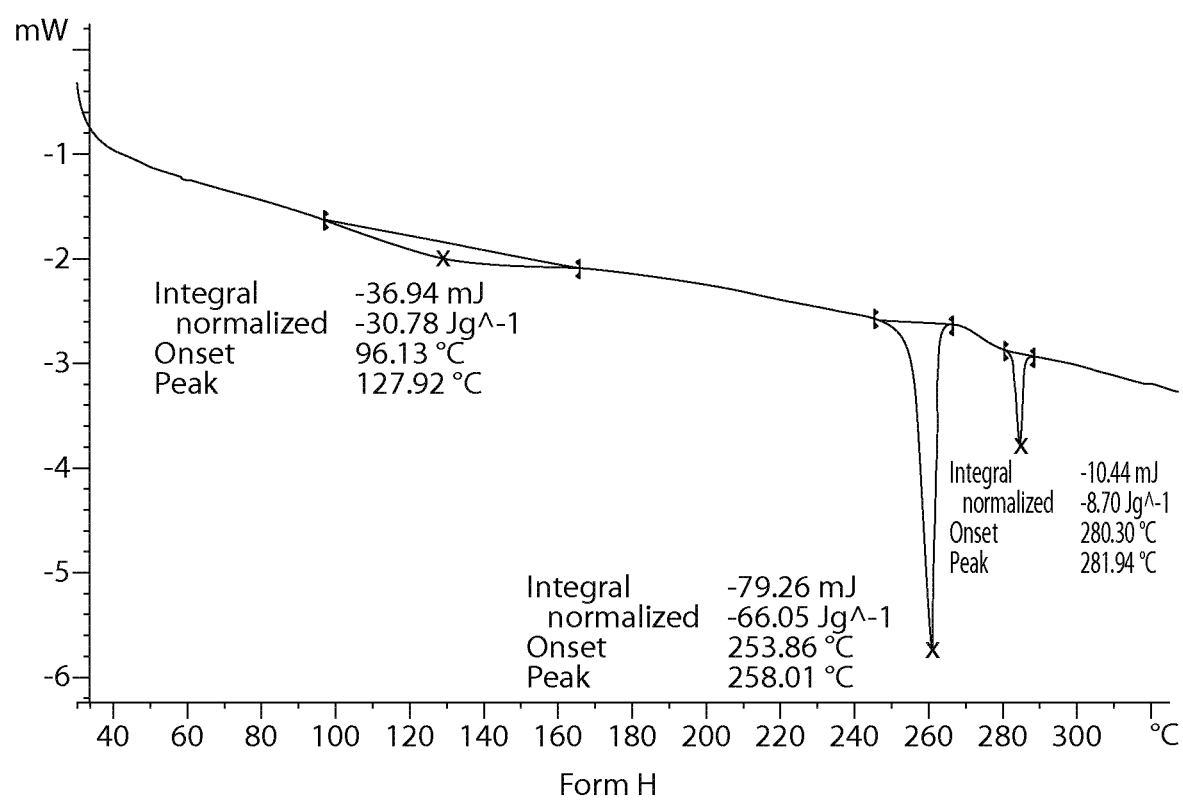
FIG. 19 shows a DSC for Polymorph Form H.

FIG. 19 shows a differential scanning calorimetry (DSC) thermogram for polymorph Form H. In some embodiments, polymorph Form H can be characterized as having an endothermic peak at about 128° C. and an endothermic peak at about 258° C. In another embodiment, polymorph Form H can be characterized as having an endothermic peak at about 128° C., an endothermic peak at about 258° C., and an endothermic peak at about 282° C.

In some embodiments, polymorph Form H can be characterized by thermogravimetric analysis (TGA). In one embodiment, a weight loss of about 7.5% wt can be observed at about 130° C.

In certain embodiments, Form H can be obtained by slow cooling crystallization from a binary solvent system with, for example, dioxane as the primary solvent, and an anti-solvent, such as, without limitation, MTBE. In one embodiment, Form H is an MTBE solvate. In one embodiment, Form H can be obtained by crystallization from a multi-solvent system.

Form I

In one embodiment, a polymorph provided herein is Form I of a compound of Formula (I).

Figure 9:
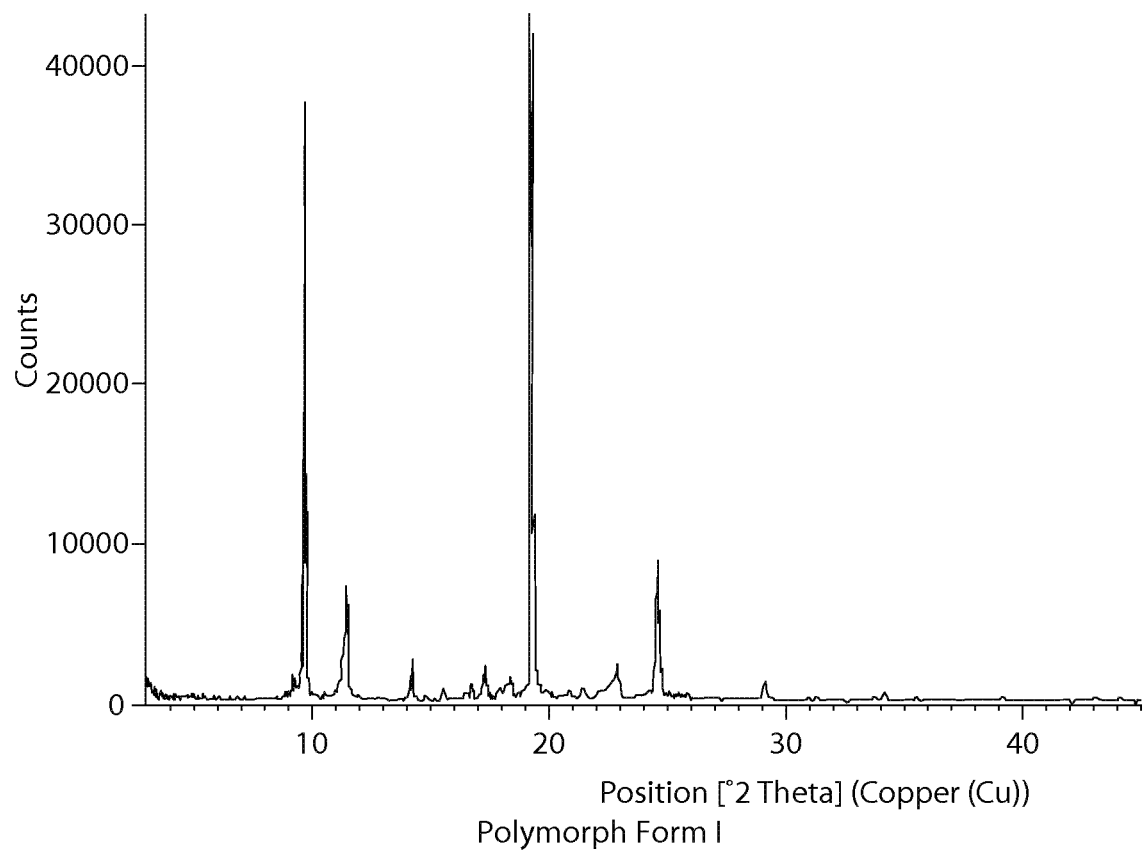
FIG. 9 shows an XRPD for Polymorph Form I.

FIG. 9 shows a representative XRPD for polymorph Form I.

In one embodiment, polymorph Form I can be characterized by any one, two, three, four, five, six, seven, eight, nine, ten, or more of significant peak(s) of FIG. 9. In one embodiment, polymorph Form I can be characterized as having at least one XRPD peak selected from 2θ=9.7° (±0.2°), 19.3° (±0.2°), and 24.5° (±0.2°). In one embodiment, polymorph Form I can be characterized as having at least one XRPD peak selected from 2θ=9.7° (±0.2°), 19.3° (±0.2°), and 24.5° (±0.2°) in combination with at least one XRPD peak selected from 2θ=11.4° (±0.2°) and 14.2° (±0.2°). In another embodiment, polymorph Form I can be characterized as having at least one XRPD peak selected from 2θ=9.7° (±0.2°), 11.4° (±0.2°), 14.2° (±0.2°), 19.3° (±0.2°), and 24.5° (±0.2°) in combination with at least one XRPD peak selected from 2θ=9.2° (±0.2°), 14.7° (±0.2°), 15.5° (±0.2°), 16.7° (±0.2°), 17.3° (±0.2°), 18.4° (±0.2°), 21.4° (±0.2°), 22.9° (±0.2°), 29.1° (±0.2°), and 34.1° (±0.2°). In one embodiment, polymorph Form I can be characterized in that it has substantially all of the peaks in its XRPD pattern as shown in FIG. 9.

Figure 20:
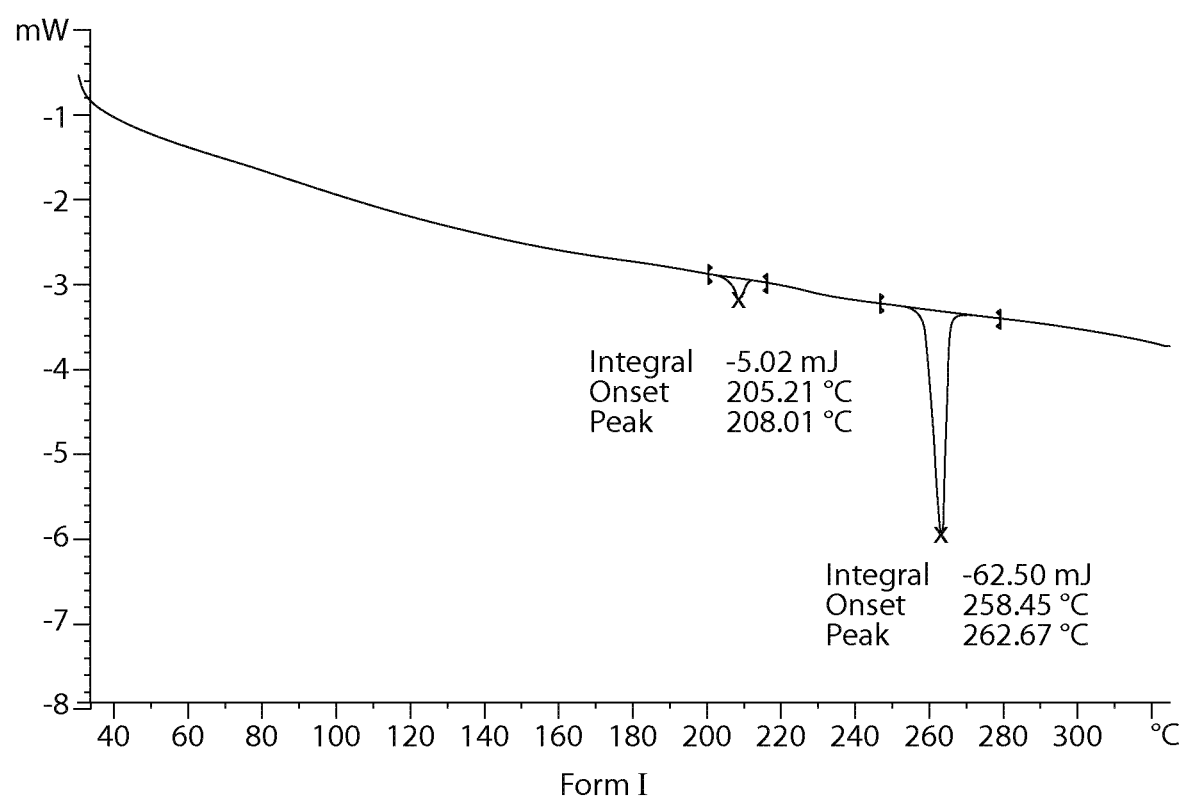
FIG. 20 shows a DSC for Polymorph Form I.

FIG. 20 shows a differential scanning calorimetry (DSC) thermogram for polymorph Form I. In some embodiments, polymorph Form I can be characterized as having an endothermic peak at about 208° C. and an endothermic peak at about 263° C.

In some embodiments, polymorph Form I can be characterized by thermogravimetric analysis (TGA). In one embodiment, a weight loss of about 10.5% wt can be observed at about 130° C. and a weight loss of about 0.8% wt can be observed at about 200° C.

In certain embodiments, Form I can be obtained by slow cooling crystallization from a binary solvent system, including, without limitation, acetone, MEK, or dioxane as the primary solvent, and an anti-solvent, such as, without limitation, toluene. In one embodiment, Form I is a hemi-toluene solvate. In one embodiment, Form I can be obtained by crystallization from a multi-solvent system.

Form J

In one embodiment, a polymorph provided herein is Form J of a compound of Formula (I).

Figure 10:
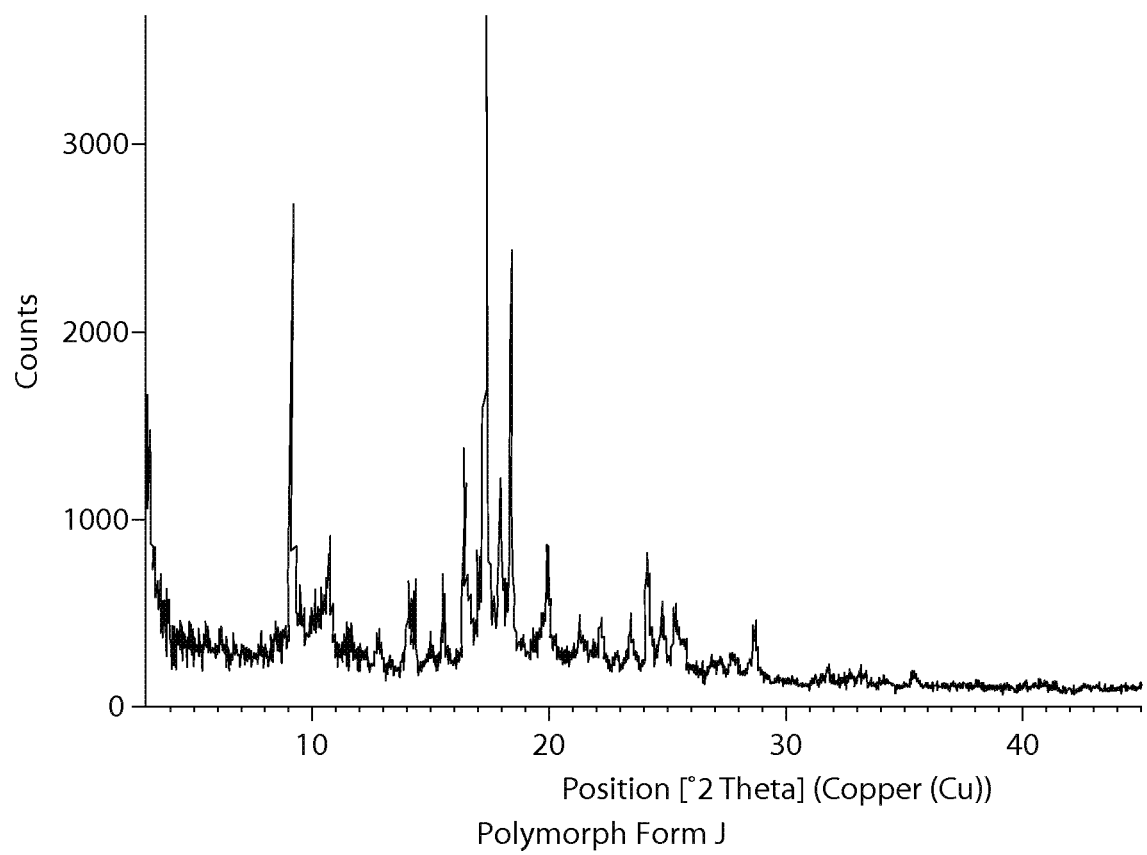
FIG. 10 shows an XRPD for Polymorph Form J.

FIG. 10 shows a representative XRPD for Polymorph Form J.

In one embodiment, polymorph Form J can be characterized by any one, two, three, four, five, six, seven, eight, nine, ten, or more of significant peak(s) of FIG. 10. In one embodiment, polymorph Form J can be characterized as having at least one XRPD peak selected from 2θ=9.1° (±0.2°), 17.3° (±0.2°), and 18.3° (±0.2°). In one embodiment, polymorph Form J can be characterized as having at least one XRPD peak selected from 2θ=9.1° (±0.2°), 17.3° (±0.2°), and 18.3° (±0.2°) in combination with at least one XRPD peak selected from 2θ=16.4° (±0.2°) and 17.9° (±0.2°). In another embodiment, polymorph Form J can be characterized as having at least one XRPD peak selected from 2θ=9.1° (±0.2°), 16.4° (±0.2°), 17.3° (±0.2°), 17.9° (±0.2°), and 18.3° (±0.2°) in combination with at least one XRPD peak selected from 2θ=9.4° (±0.2°), 10.1° (±0.2°), 10.7° (±0.2°), 14.0° (±0.2°), 14.3° (±0.2°), 15.5° (±0.2°), 16.9° (±0.2°), 19.9° (±0.2°), 24.0° (±0.2°), and 24.7° (±0.2°). In one embodiment, polymorph Form J can be characterized in that it has substantially all of the peaks in its XRPD pattern as shown in FIG. 10.

Figure 21:
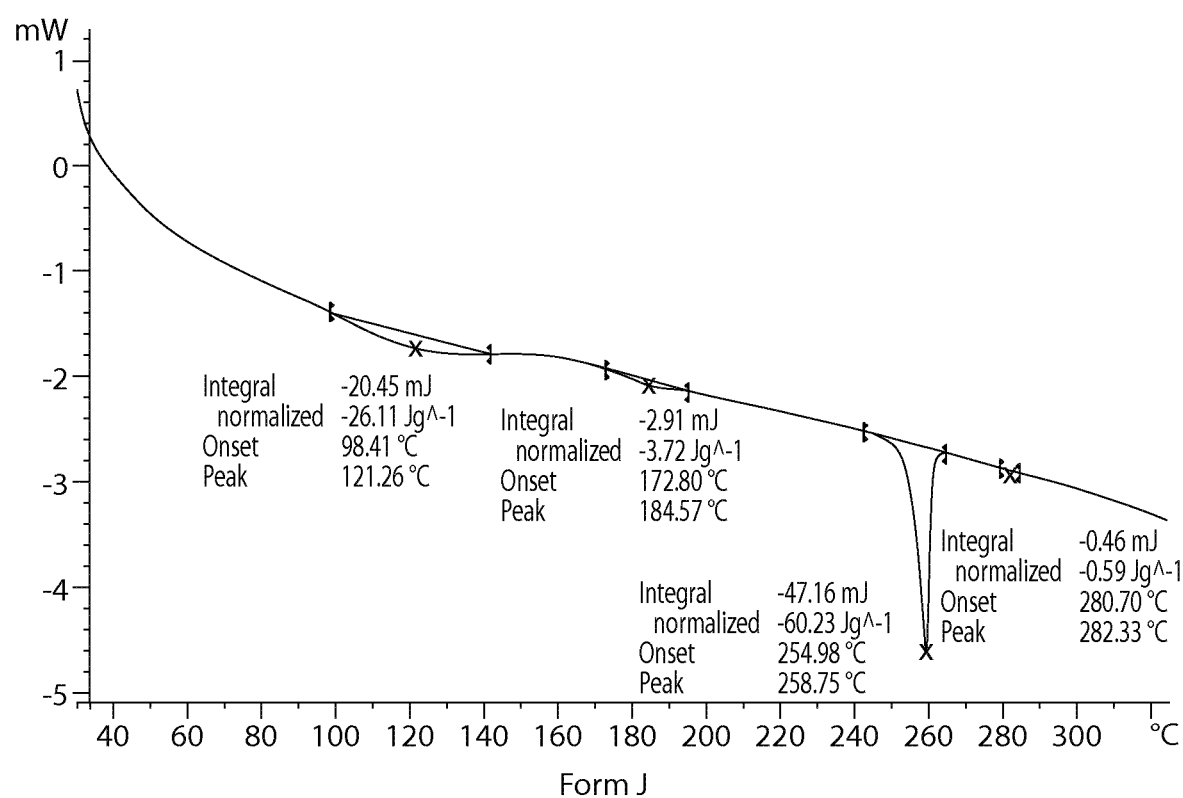
FIG. 21 shows a DSC for Polymorph Form J.

FIG. 21 shows a differential scanning calorimetry (DSC) thermogram for polymorph Form J. In some embodiments, polymorph Form J can be characterized as having an endothermic peak at about 259° C. In another embodiment, polymorph Form J can be characterized as having an endothermic peak at about 121° C., an endothermic peak at about 185° C., an endothermic peak at about 259° C. and an endothermic peak at about 282° C.

In some embodiments, polymorph Form J can be characterized by thermogravimetric analysis (TGA). In one embodiment, a weight loss of about 10.8% wt can be observed at about 100° C.

In certain embodiments, Form J can be obtained by slow cooling crystallization from a binary solvent system, including, without limitation, DMF as the primary solvent, and an anti-solvent, such as, without limitation, toluene. In one embodiment, Form J is a hemi-toluene solvate. In one embodiment, Form J can be obtained by crystallization from a multi-solvent system.

Amorphous Forms

In one embodiment, an amorphous form of a compound of Formula (I) is provided herein.

Figure 11:
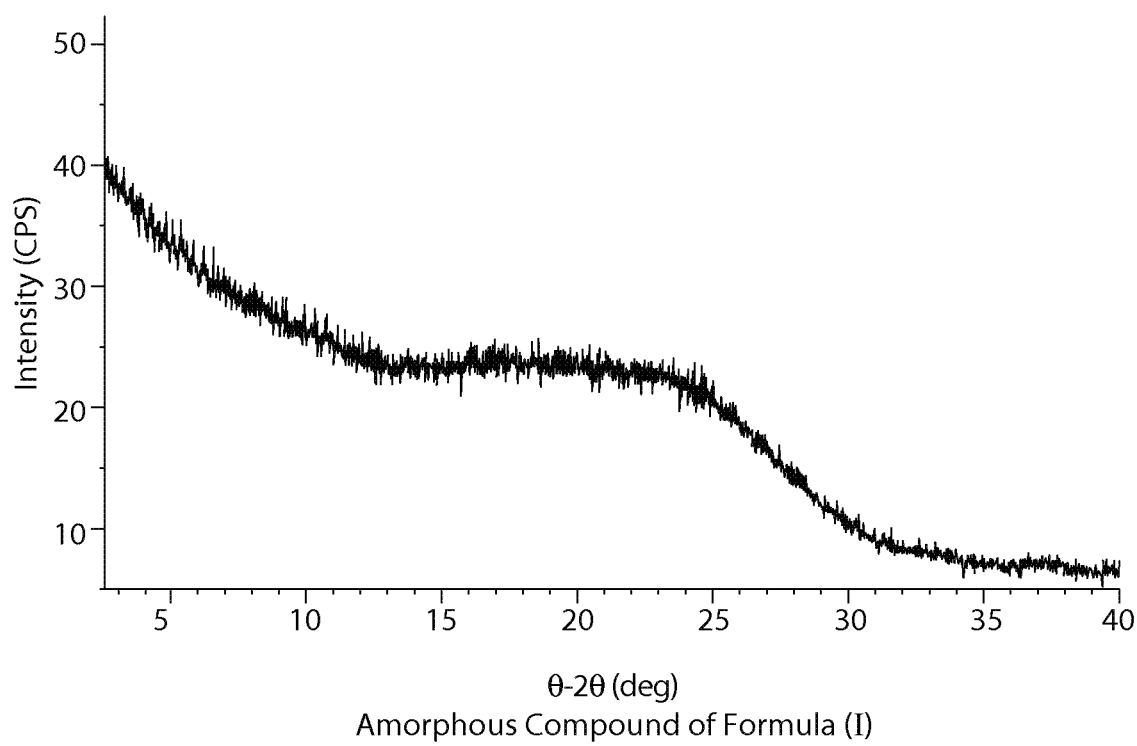
FIG. 11 shows an XRPD for amorphous compound of Formula (I).

FIG. 11 shows a representative XRPD for an amorphous form. The lack of diffraction peaks indicates the lack of crystallinity in the amorphous form.

In one embodiment, an amorphous form of a compound of Formula (I), or a pharmaceutically acceptable salt, solvate, or hydrate thereof, can be made by dissolution of a crystalline form followed by removal of solvent under conditions in which stable crystals are not formed. For example, solidification can occur by rapid removal of solvent, by rapid addition of an anti-solvent (causing the amorphous form to precipitate out of solution), or by physical interruption of the crystallization process. Grinding processes can also be used. In other embodiments, an amorphous form of a compound of Formula (I), or a pharmaceutically acceptable salt, solvate, or hydrate thereof, can be made using a process or procedure described herein elsewhere.

In certain embodiments, an amorphous form can be obtained by fast cooling from a single solvent system, such as, e.g., ethanol, isopropyl alcohol, t-amyl alcohol, n-butanol, methanol, acetone, ethyl acetate, or acetic acid. In certain embodiments, an amorphous form can be obtained by slow cooling from a single solvent system, such as, e.g., ethanol, isopropyl alcohol, t-amyl alcohol, or ethyl acetate.

In certain embodiments, an amorphous form can be obtained by fast cooling from a binary solvent system, for example, with acetone or DME as the primary solvent. In certain embodiments, an amorphous form can be obtained by slow cooling from a binary solvent system, for example, with ethanol, isopropyl alcohol, THF, acetone, or methanol as the primary solvent. In some embodiments, an amorphous form can be obtained by dissolution of a compound of Formula (I) in t-butanol and water at elevated temperature, followed by cooling procedures to afford an amorphous solid form.

In some embodiments, the amorphous compound of Formula (I) is a salt, solvate, or hydrate thereof. In some embodiments, the amorphous compound of Formula (I) is a pharmaceutically acceptable salt, solvate, or hydrate thereof. In one embodiment, the amorphous compound of Formula (I) can contain an amount of one or more partially crystalline or crystalline compounds of Formula (I). Non-limiting examples include amorphous compounds of Formula (I) containing less than about 10% of one or more partially crystalline or crystalline compounds of Formula (I), less than about 9% of one or more partially crystalline or crystalline compounds of Formula (I), less than about 8% of one or more partially crystalline or crystalline compounds of Formula (I), less than about 7% of one or more partially crystalline or crystalline compounds of Formula (I), less than about 6% of one or more partially crystalline or crystalline compounds of Formula (I), less than about 5% of one or more partially crystalline or crystalline compounds of Formula (I), less than about 4% of one or more partially crystalline or crystalline compounds of Formula (I), less than about 3% of one or more partially crystalline or crystalline compounds of Formula (I), less than about 2% of one or more partially crystalline or crystalline compounds of Formula (I), less than about 1% of one or more partially crystalline or crystalline compounds of Formula (I), less than about 0.5% of one or more partially crystalline or crystalline compounds of Formula (I), less than about 0.1% of one or more partially crystalline or crystalline compounds of Formula (I), and less than about 0.01% of one or more partially crystalline or crystalline compounds of Formula (I). In some embodiments, the amorphous compound of Formula (I), or a salt, solvate, or hydrate thereof, contains one or more partially crystalline compounds, or a salt, solvate, or hydrate thereof. In some embodiments, the amorphous compound of Formula (I), or a salt, solvate, or hydrate thereof, contains one or more crystalline compounds of Formula (I), or a salt, solvate, or hydrate thereof.

Salt Forms

In certain embodiments, a compound of Formula (I) provided herein is a pharmaceutically acceptable salt, or a solvate or hydrate thereof. In one embodiment, pharmaceutically acceptable acid addition salts of a compound provided herein can be formed with inorganic acids and organic acids. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. In other embodiments, if applicable, pharmaceutically acceptable base addition salts of a compound provided herein can be formed with inorganic and organic bases. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines including naturally occurring substituted amines, cyclic amines, basic ion exchange resins, and the like. Exemplary bases include, but are not limited to, isopropylamine, trimethylamine, diethylamine, triethylamine, tripropylamine, and ethanolamine. In some embodiments, a pharmaceutically acceptable base addition salt is ammonium, potassium, sodium, calcium, or magnesium salt. In one embodiment, bis salts (i.e., two counterions) and higher salts (e.g., three or more counterions) are encompassed within the meaning of pharmaceutically acceptable salts.

In certain embodiments, salts of a compound of Formula (I) can be formed with, e.g., L-tartaric acid, p-toluenesulfonic acid, D-glucaronic acid, ethane-1,2-disulfonic acid (EDSA), 2-naphthalenesulfonic acid (NSA), hydrochloric acid (HCl) (mono and bis), hydrobromic acid (HBr), citric acid, naphthalene-1,5-disulfonic acid (NDSA), DL-mandelic acid, fumaric acid, sulfuric acid, maleic acid, methanesulfonic acid (MSA), benzenesulfonic acid (BSA), ethanesulfonic acid (ESA), L-malic acid, phosphoric acid, and aminoethanesulfonic acid (taurine).

III. Compositions

Provided herein are compositions, including pharmaceutical compositions, comprising one or more polymorphs or amorphous forms of the compound of Formula (I), or their pharmaceutically acceptable forms (e.g., pharmaceutically acceptable salts, hydrates, solvates, chelates, non-covalent complexes, isomers, prodrugs, and isotopically labeled derivatives) thereof as provided herein. In some embodiments, provided herein are pharmaceutical compositions comprising polymorph Form C, or its pharmaceutically acceptable salts, solvates and hydrates thereof, and one or more pharmaceutically acceptable excipients. In some embodiments, provided herein are pharmaceutical compositions comprising polymorph Form C and polymorph Form A, or their pharmaceutically acceptable salts, solvates and hydrates thereof, and one or more pharmaceutically acceptable excipients, wherein the ratio of polymorph Form C to polymorph Form A is greater than about 9:1. In some embodiments, provided herein are pharmaceutical compositions comprising one or more of polymorph Forms A, B, C, D, E, F, G, H, I, and J, or amorphous compound of Formula (I), or their pharmaceutically acceptable salts, solvates and hydrates thereof, or mixtures thereof, and one or more pharmaceutically acceptable excipients. In other embodiments, provided herein are pharmaceutical compositions comprising polymorph Form C and at least one non-Form C polymorph selected from Form A, Form B, Form D, Form E, Form F, Form G, Form H, Form I, Form J, or an amorphous form of a compound of Formula (I), or a salt, solvate, or hydrate thereof, and one or more pharmaceutically acceptable excipients.

In certain embodiments, the ratio of a polymorph, such as Form C, to all other polymorphs in a composition provided herein can be greater than about 5:1, about 6:1, about 7:1, about 8:1, about 9:1, or more.

In certain embodiments, the pharmaceutical compositions provided herein are typically formulated to provide a therapeutically effective amount of a compound provided herein (e.g., a particular polymorph provided herein) as the active ingredient, or pharmaceutically acceptable salts, hydrates, solvates, chelates, esters, non-covalent complexes, isomers, prodrugs, and isotopically labeled derivatives thereof. In some embodiments, the pharmaceutical compositions contain one or more pharmaceutically acceptable salts, solvates, hydrates, and/or coordination complexes thereof, and one or more pharmaceutically acceptable excipients, such as carriers (including inert solid diluents and fillers), diluents (including sterile aqueous solution and various organic solvents), permeation enhancers, solubilizers, and/or adjuvants.

In certain embodiments, the pharmaceutical compositions provided herein can be administered alone or in combination with one or more other agents, which are also typically administered in a form of a pharmaceutical composition. In some embodiments, a polymorph provided herein and other agent(s) can be mixed into a preparation or both components can be formulated into separate preparations to use them in combination separately or at the same time.

In one embodiment, administration of polymorphs or pharmaceutical compositions provided herein can be effected by any method that enables delivery of polymorphs or pharmaceutical compositions to the site of action. These methods include, e.g., oral routes, intraduodenal routes, parenteral injection (including intravenous, intraarterial, subcutaneous, intramuscular, intravascular, intraperitoneal or infusion), topical routes (e.g., transdermal application), rectal administration, via local delivery by catheter or stent or through inhalation. In one embodiment, polymorphs can also be administered intraadiposally or intrathecally.

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. In some embodiments, compositions disclosed herein include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of polymorph(s) provided herein in a composition provided herein is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v.

In some embodiments, the concentration of one or more of polymorph(s) provided herein in a composition provided herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v.

In some embodiments, the concentration of one or more of polymorph(s) provided herein in a composition provided herein is in a range from approximately 0.0001% to approximately 50%, from approximately 0.001% to approximately 40%, from approximately 0.01% to approximately 30%, from approximately 0.02% to approximately 29%, from approximately 0.03% to approximately 28%, from approximately 0.04% to approximately 27%, from approximately 0.05% to approximately 26%, from approximately 0.06% to approximately 25%, from approximately 0.07% to approximately 24%, from approximately 0.08% to approximately 23%, from approximately 0.09% to approximately 22%, from approximately 0.1% to approximately 21%, from approximately 0.2% to approximately 20%, from approximately 0.3% to approximately 19%, from approximately 0.4% to approximately 18%, from approximately 0.5% to approximately 17%, from approximately 0.6% to approximately 16%, from approximately 0.7% to approximately 15%, from approximately 0.8% to approximately 14%, from approximately 0.9% to approximately 12%, from approximately 1% to approximately 10% w/w, w/v, or v/v.

In some embodiments, the concentration of one or more of polymorph(s) provided herein in a composition provided herein is in a range from approximately 0.001% to approximately 10%, from approximately 0.01% to approximately 5%, from approximately 0.02% to approximately 4.5%, from approximately 0.03% to approximately 4%, from approximately 0.04% to approximately 3.5%, from approximately 0.05% to approximately 3%, from approximately 0.06% to approximately 2.5%, from approximately 0.07% to approximately 2%, from approximately 0.08% to approximately 1.5%, from approximately 0.09% to approximately 1%, from approximately 0.1% to approximately 0.9% w/w, w/v or v/v.

In some embodiments, the amount of one or more of polymorph(s) provided herein in a composition provided herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of one or more of polymorph(s) provided herein in a composition provided herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, about 10 g, or more.

In some embodiments, the amount of one or more of polymorph(s) provided herein in a composition provided herein is in a range of about 0.0001 to about 10 g, about 0.0005 to about 9 g, about 0.001 to about 8 g, about 0.005 to about 7 g, about 0.01 to about 6 g about, 0.05 to about 5 g, about 0.1 to about 4 g, about 0.5 to about 4 g, or about 1 to about 3 g.

In one embodiment, the polymorphs provided herein are effective over a wide dosage range. For example, in the treatment of adult humans, dosages from about 0.01 to about 1000 mg, from about 0.5 to about 100 mg, from about 1 to about 50 mg, and from about 5 to about 40 mg per day are examples of dosages that can be used. An exemplary dosage is about 10 to about 30 mg per day. The exact dosage will depend upon the route of administration, the form in which a polymorph is administered, the subject to be treated, the body weight of the subject to be treated, and the preference and experience of the attending physician.

Described below are non-limiting exemplary pharmaceutical compositions and methods for preparing the same.

Pharmaceutical Compositions for Oral Administration:

In some embodiments, provided herein is a pharmaceutical composition for oral administration, wherein the composition comprises a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof, and a pharmaceutically acceptable excipient (e.g., an excipient suitable for oral administration).

In one embodiment, the composition provided herein is a solid dosage form comprising a polymorph of a compound of Formula (I), or a pharmaceutically acceptable salt, solvate, or hydrate thereof, and one or more pharmaceutically acceptable excipients. In one embodiment, the composition provided herein is a single unit dosage form comprising a polymorph of a compound of Formula (I), or a pharmaceutically acceptable salt, solvate, or hydrate thereof. In one embodiment, the composition provided herein is a tablet or a capsule. In one embodiment, the composition provided herein comprises a therapeutically effective amount of a polymorph of a compound of Formula (I), or a pharmaceutically acceptable salt, solvate, or hydrate thereof.

In one embodiment, the composition provided herein comprises a therapeutically effective amount of a polymorph of a compound of Formula (I), or a pharmaceutically acceptable salt, solvate, or hydrate thereof. In some embodiments, the therapeutically effective amount is about 0.5, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 600, about 700, about 800, about 900, or about 1000 mg, or more. In one embodiment, the composition provided herein comprises at least one pharmaceutically acceptable carrier or excipient. In some embodiments, the composition provided herein comprises one or more pharmaceutically acceptable carrier(s) or excipient(s), including, e.g., microcrystalline cellulose, crospovidone, and/or magnesium stearate. In one embodiment, the composition provided herein is an immediate-release dosage form. In some embodiments, the composition provided herein is a hard gelatin capsule. In some embodiments, the composition provided herein is a soft gelatin capsule. In some embodiments, the composition provided herein comprises Form C of a compound of Formula (I). In some embodiments, the composition provided herein comprises Form A of a compound of Formula (I). In some embodiments, the composition provided herein comprises an amorphous form of a compound of Formula (I). In some embodiments, the composition provided herein comprises a mixture of two or more polymorphs of a compound of Formula (I), or a pharmaceutically acceptable salt, solvate, or hydrate thereof, e.g., polymorphs described herein.

In other embodiments, the composition provided herein includes one or more compounds of Formula (I) and is a suspension comprising carboxymethyl cellulose and water. In one embodiment, the composition provided herein can further comprise one or more excipients, such as, e.g., polysorbate, polyethyleneglycol, cyclodextrin, dextrose, n-methylpyrrolidone, pH buffers, dilute hydrochloric acid, polyoxyethylene esters of 12-hydroxystearic acid, or a mixture of two or more thereof. In one embodiment, the process for preparing the suspension includes, but is not limited to, combining a pre-determined amount of a compound of Formula (I) in powder form with a vehicle, such as commercially available medium viscosity USP carboxymethylcellulose sodium (CMC) in Sterile Water for Injection (SWFI).

In some embodiments, provided herein is a solid pharmaceutical composition suitable for oral administration, comprising: (i) an effective amount of a compound provided herein or a pharmaceutically acceptable form (e.g., pharmaceutically acceptable salts, hydrates, solvates, chelates, non-covalent complexes, isomers, prodrugs, and isotopically labeled derivatives) thereof; optionally (ii) an effective amount of a second agent; and (iii) one or more pharmaceutical excipients suitable for oral administration. In some embodiments, the composition further contains: (iv) an effective amount of a third agent.

In some embodiments, provided herein is a liquid pharmaceutical composition suitable for oral administration. In some embodiments, provided herein is a capsule dosage form suitable for oral administration.

In certain embodiments, pharmaceutical compositions provided herein suitable for oral administration can be presented as discrete dosage forms, such as capsules, pills, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. In general, for solid forms, the compositions are prepared by uniformly and intimately admixing the active ingredient with liquid carriers or finely divided solid carriers or both, and then, if necessary, shaping the product into a certain presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid or semi-solid diluent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredients can be in micro-encapsulated form and can optionally contain one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms can comprise, as is normal practice, additional substances other than inert diluents, e.g., tableting lubricants and other tableting aids such a magnesium stearate and microcrystalline cellulose. In the case of capsules, tablets and pills, the dosage forms can comprise buffering agents. They can optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Also provided herein are anhydrous pharmaceutical compositions and dosage forms comprising an active ingredient, since water can facilitate the degradation of some compounds. For example, water can be added (e.g., 5%) in the pharmaceutical arts as a means of simulating long-term storage in order to determine characteristics such as shelf-life or the stability of formulations over time. Anhydrous pharmaceutical compositions and dosage forms provided herein can be prepared using anhydrous or low moisture containing ingredients and low moisture or low humidity conditions. Pharmaceutical compositions and dosage forms provided herein which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous compositions can be packaged using materials known to prevent exposure to water such that they can be included in suitable formulary kits.

Examples of suitable packaging include, but are not limited to, hermetically sealed foils, plastic or the like, unit dose containers, blister packs, and strip packs.

In certain embodiments, an active ingredient can be combined in an intimate admixture with a pharmaceutical carrier according to conventional pharmaceutical compounding techniques. The carrier can take a wide variety of forms depending on the form of preparation intended for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments, without employing the use of lactose. For example, suitable carriers include powders, capsules, and tablets, with solid oral preparations. In some embodiments, tablets can be coated by standard aqueous or nonaqueous techniques.

In one embodiment, the active ingredient can optionally be mixed with one or more inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can comprise buffering agents.

In certain embodiments, binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures of two or more thereof. In some embodiments, exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and mixtures of two or more thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures of two or more thereof.

In certain embodiments, disintegrants can be used in the compositions provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the polymorphs disclosed herein. The amount of disintegrant used can vary based upon the type of formulation and mode of administration. In certain embodiments, about 0.5 to about 15 weight percent of disintegrant, or about 1 to about 5 weight percent of disintegrant, can be used in a pharmaceutical composition provided herein. Disintegrants that can be used to form pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures of two or more thereof.

In certain embodiments, lubricants which can be used to form pharmaceutical compositions and dosage forms provided herein include, but are not limited to, calcium stearate, magnesium stearate, mineral oil, light mineral oil, glycerin, glyceryl behanate, sorbitol, mannitol, polyethylene glycol, other glycols, stearic acid, sodium lauryl sulfate, sodium benzoate, sodium acetate, sodium chloride, leucine, magnesium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, malt, and mixtures of two or more thereof. Additional lubricants include, for example, a syloid silica gel, a coagulated aerosol of synthetic silica, or mixtures of two or more thereof. In certain embodiments, a lubricant can optionally be added, in an amount of less than about 1 weight percent of the pharmaceutical composition.

In some embodiments, a pharmaceutical composition or dosage form provided herein comprises colloid particle(s). In some cases, colloid particles include at least one cationic agent and at least one non-ionic surfactant, such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound, or a mixture of two or more thereof. In some cases, the cationic agent is a biguanidine salt, such as chlorhexidine, polyaminopropyl biguanidine, phenformin, alkylbiguanidine, or a mixture of two or more thereof. In some cases, the quaternary ammonium Formula (I)s a benzalkonium halide, lauralkonium halide, cetrimide, hexadecyltrimethylammonium halide, tetradecyltrimethyl-ammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide, or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide, or a mixture of two or more thereof. In some cases, colloid particles comprise an oil phase. In some cases, the oil phase is mineral oil, light mineral oil, medium chain triglycerides (MCT), coconut oil, hydrogenated oils comprising hydrogenated cottonseed oil, hydrogenated palm oil, hydrogenate castor oil, hydrogenated soybean oil, polyoxyethylene hydrogenated castor oil derivatives comprising poluoxyl-40 hydrogenated castor oil, polyoxyl-60 hydrogenated castor oil, or polyoxyl-100 hydrogenated castor oil.

In one embodiment, when aqueous suspensions and/or elixirs are intended for oral administration, the active ingredient therein can be combined with various sweetening or flavoring agents, coloring matter or dyes and, in some embodiments, emulsifying and/or suspending agents, together with such diluents as water, ethanol, propylene glycol, glycerin, and various combinations thereof.

In certain embodiments, tablets can be uncoated or coated by known techniques to delay disintegration and absorption in the gastrointestinal tract and thereby provide a sustained action over a longer period. For example, a time delay material, such as glyceryl monostearate or glyceryl distearate, can be employed. Formulations for oral use can also be presented as hard gelatin capsules, wherein the active ingredient is mixed with an inert solid diluent, for example, calcium carbonate, calcium phosphate, or kaolin; or as soft gelatin capsules, wherein the active ingredient is mixed with water or an oil medium, for example, peanut oil, liquid paraffin, or olive oil.

In certain embodiments, surfactants which can be used to form pharmaceutical compositions and dosage forms provided herein include, but are not limited to, hydrophilic surfactants, lipophilic surfactants, and mixtures of two or more thereof. For example, a mixture of hydrophilic surfactants can be employed, a mixture of lipophilic surfactants can be employed, or a mixture of at least one hydrophilic surfactant and at least one lipophilic surfactant can be employed.

In certain embodiments, a suitable hydrophilic surfactant can generally have an HLB value of at least 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical, and cosmetic emulsions.

In certain embodiments, hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof, camitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures of two or more thereof.

Within the aforementioned group, ionic surfactants include, by way of example: lecithins, lysolecithin, phospholipids, lysophospholipids and derivatives thereof, camitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures of two or more thereof.

In certain embodiments, ionic surfactants can be ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl camitines, palmitoyl carnitines, myristoyl carnitines, salts thereof, and mixtures of two or more thereof.

In certain embodiments, hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, hydrogenated vegetable oils, and mixtures of two or more thereof. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween® 40, Tween® 60, sucrose monostearate, sucrose monolaurate, sucrose monopalmitate, PEG 10-100 nonyl phenol series, PEG 15-100 octyl phenol series, and poloxamers, and mixtures of two or more thereof.

In certain embodiments, suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures of two or more thereof. Within this group, lipophilic surfactants include glycerol fatty acid esters, propylene glycol fatty acid esters, and mixtures of two more thereof, or include hydrophobic transesterification products of a polyol with at least one member of the group consisting of vegetable oils, hydrogenated vegetable oils, and triglycerides.

In one embodiment, the pharmaceutical composition can include a solubilizer to ensure good solubilization and/or dissolution of a compound provided herein and/or to minimize precipitation of a compound provided herein. This can be useful for compositions for non-oral use, e.g., compositions for injection. A solubilizer can also be added to increase the solubility of a hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropyl alcohol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, water, and mixtures of two or more thereof. In certain embodiments, a solubilizer comprising polyglycol mono- and di-esters of 12-hydroxystearic acid and about 30% free polyethylene glycol (available as Solutol® HS 15) is used as a solubilizer in a composition provided herein.

In certain embodiments, mixtures of solubilizers can be used. Examples include, but not limited to, mixtures of two or more of triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, or dimethyl isosorbide. In certain embodiments, solubilizers include sorbitol, glycerol, triacetin, ethyl alcohol, PEG-400, glycofurol, and propylene glycol.

In certain embodiments, the amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of about 10%, about 25%, about 50%, about 100%, or up to about 200% by weight, based on the combined weight of the drug, and other excipients. In some embodiments, very small amounts of solubilizer can also be used, such as about 5%, about 2%, about 1%, or even less. In certain embodiments, the solubilizer can be present in an amount of about 1% to about 100%, or about 5% to about 25% by weight.

In one embodiment, a composition provided herein can further include one or more pharmaceutically acceptable additives and/or excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures of two or more thereof. In another embodiment, a composition provided herein can further include one or more pharmaceutically acceptable additives and/or excipients, such as, but not limited to, inert diluents, dispersing and/or granulating agents, surface active agents and/or emulsifiers, disintegrating agents, binding agents, preservatives, buffering agents, lubricating agents, and/or oils. For example, excipients such as cocoa butter and suppository waxes, coloring agents, coating agents, sweetening, flavoring, and perfuming agents can be present in the composition.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween® 20], polyoxyethylene sorbitan [Tween® 60], polyoxyethylene sorbitan monooleate [Tween® 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip, methylparaben, Germall® 115, Germaben® II, Neolone™, Kathon™, and Euxyl®. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum®), sodium lauryl sulfate, quaternary ammonium compounds, etc., and combinations thereof.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In another embodiment, an acid or a base can be incorporated into a composition provided herein to facilitate processing, to enhance stability, or for other reasons. Examples of pharmaceutically acceptable bases include, but are not limited to, amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS), and the like. In certain embodiments, pharmaceutically acceptable bases are salts of a pharmaceutically acceptable acid. Examples of pharmaceutically acceptable acids include, but are not limited to, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like; and salts of polyprotic acids, such as sodium phosphate, disodium hydrogen phosphate, and sodium dihydrogen phosphate. When the base is a salt, the cation can be any convenient and pharmaceutically acceptable cation, such as ammonium, alkali metals, alkaline earth metals, and the like. Example can include, but not limited to, sodium, potassium, lithium, magnesium, calcium and ammonium.

In one embodiment, suitable acids are pharmaceutically acceptable organic or inorganic acids. Examples of suitable inorganic acids include, but are not limited to, hydrochloric acid, hydrobromic acid, hydriodic acid, sulfuric acid, nitric acid, boric acid, phosphoric acid, and the like. Examples of suitable organic acids include, but are not limited to, acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like.

Pharmaceutical Compositions for Parenteral Administration:

In some embodiments, provided herein are pharmaceutical compositions for parenteral administration containing a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof, and a pharmaceutical excipient suitable for parenteral administration. In some embodiments, provided herein are pharmaceutical compositions for parenteral administration containing: (i) an effective amount of a disclosed compound or a pharmaceutically acceptable form (e.g., pharmaceutically acceptable salts, hydrates, solvates, chelates, non-covalent complexes, isomers, prodrugs, and isotopically labeled derivatives) thereof, optionally (ii) an effective amount of one or more second agents; and (iii) one or more pharmaceutical excipients suitable for parenteral administration. In some embodiments, the pharmaceutical composition further contains: (iv) an effective amount of a third agent.

In certain embodiments, the forms in which a composition provided herein can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, the compounds disclosed herein can be mixed with solubilizing agents such as Cremophor®, alcohols, oils, modified oils, glycols, polysorbates, cyclodextrins, polymers, and combinations thereof.

In certain embodiments, aqueous solutions in saline are used for injection. In certain embodiments, ethanol, glycerol, propylene glycol, liquid polyethylene glycol, or the like (and suitable mixtures thereof), cyclodextrin derivatives, or vegetable oils can be employed. The sterile injectable preparation can be a sterile injectable solution, suspension or emulsion in a nontoxic parenterally acceptable diluent or solvent, for example, as a solution in 1,3-butanediol. Among the exemplary vehicles and solvents that can be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The proper fluidity can be maintained, for example, by the use of a coating, such as lecithin, for the maintenance of a certain particle size in the case of dispersion or by the use of surfactants. In certain embodiments, the prevention of the action of microorganisms can be brought about by various antibacterial and antifungal agents, for example, parabens, chlorobutanol, phenol, sorbic acid, thimerosal, and the like.

In certain embodiments, sterile injectable solutions are prepared by incorporating a compound provided herein in a certain amount in an appropriate solvent with various other ingredients as enumerated herein, followed by filtration sterilization. In certain embodiments, dispersions are prepared by incorporating various sterilized active ingredients into a sterile vehicle which contains a basic dispersion medium and various other ingredients as enumerated herein. In the case of sterile powders for the preparation of sterile injectable solutions, suitable methods of preparation include, but are not limited to, vacuum-drying and freeze-drying techniques, which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

Pharmaceutical Compositions for Topical Administration:

In some embodiments, provided herein is a pharmaceutical composition for topical (e.g., transdermal) delivery comprising a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof and a pharmaceutical excipient suitable for topical (e.g., transdermal) delivery. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

In certain embodiments, compositions provided herein can be formulated into preparations in solid, semi-solid, or liquid forms suitable for local and/or topical administration, such as, e.g., gels, water soluble jellies, creams, lotions, suspensions, foams, powders, slurries, ointments, solutions, oils, pastes, suppositories, sprays, emulsions, saline solutions, and dimethylsulfoxide (DMSO)-based solutions. In one embodiment, carriers with higher densities are capable of providing an area with a prolonged exposure to an active ingredient. By contrast, a solution formulation can provide more immediate exposure of an active ingredient to the chosen area.

In some embodiments, the pharmaceutical compositions can also comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

In another embodiment, a pharmaceutical composition or dosage form for use in a method provided herein employs transdermal delivery devices ("patches"). Such transdermal patches can be used to provide continuous or discontinuous infusion of a compound provided herein in controlled amounts, either with or without another agent.

The construction and use of transdermal patches for the delivery of pharmaceutical agents is known in the art. See, e.g., U.S. Pat. Nos. 5,023,252, 4,992,445 and 5,001,139, incorporated herein by reference. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) compound of formula (I), although the concentration of the compound of formula (I) can be as high as the solubility limit of the compound of formula (I) in the solvent. In some embodiments, topically-administrable formulations can, for example, comprise from about 1% to about 9% (w/w) compound of formula (I), such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) compound of formula (I). Formulations for topical administration can further comprise one or more of the additional pharmaceutically acceptable excipients described herein.

Pharmaceutical Compositions for Inhalation Administration:

In some embodiments, provided herein are pharmaceutical compositions for inhalation administration containing a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof, and a pharmaceutical excipient suitable for topical administration. In some embodiments, provided herein are pharmaceutical compositions for inhalation administration containing: (i) an effective amount of a disclosed compound or a pharmaceutically acceptable form (e.g., pharmaceutically acceptable salts, hydrates, solvates, chelates, non-covalent complexes, isomers, prodrugs, and isotopically labeled derivatives) thereof, optionally (ii) an effective amount of one or more second agents; and (iii) one or more pharmaceutical excipients suitable for inhalation administration. In some embodiments, the pharmaceutical composition further contains: (iv) an effective amount of a third agent.

In some embodiments, provided herein are compositions for inhalation or insufflation, which can include solutions and suspensions in pharmaceutically acceptable, aqueous or organic solvents, or mixtures thereof, and suitable powders. The liquid or solid compositions can contain suitable pharmaceutically acceptable excipients as described herein. In some embodiments, the compositions are administered by the oral or nasal respiratory route for local and/or systemic effect. In certain embodiments, compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. In certain embodiments, solution, suspension, or powder compositions can be administered, e.g., orally or nasally, from devices that deliver the formulation in an appropriate manner.

Pharmaceutical Composition for Ocular Administration:

In some embodiments, provided herein is a pharmaceutical composition for treating ophthalmic disorders. In one embodiment, the composition is formulated for ocular administration and it contains an effective amount of a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof provided herein and a pharmaceutical excipient suitable for ocular administration. In certain embodiments, pharmaceutical compositions provided herein suitable for ocular administration can be presented as discrete dosage forms, such as drops or sprays each containing a predetermined amount of an active ingredient in a solution, or a suspension in an aqueous or non-aqueous liquid, an oil-in-water emulsion, or a water-in-oil liquid emulsion. Other administration foms include eye drops, intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium Formula (I)s a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

In some embodiments, eye drops can be prepared by dissolving an active ingredient in a sterile aqueous solution, such as, e.g., physiological saline or buffering solution; or by combining powder compositions to be dissolved before use. Other vehicles can be chosen, as is known in the art, including but not limited to: balance salt solution, saline solution, water soluble polyethers such as polyethyene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil, polysaccharides such as dextrans, glycosaminoglycans such as sodium hyaluronate; and mixtures of two or more thereof. In some embodiments, additives ordinarily used in the eye drops can be added. Such additives include isotonizing agents (e.g., sodium chloride), buffer agent (e.g., boric acid, sodium monohydrogen phosphate, sodium dihydrogen phosphate), preservatives (e.g., benzalkonium chloride, benzethonium chloride, chlorobutanol), thickeners (e.g., saccharide such as lactose, mannitol, maltose; e.g., hyaluronic acid or its salt such as sodium hyaluronate, potassium hyaluronate; e.g., mucopolysaccharide such as chondroitin sulfate; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose, or other agents known to those skilled in the art).

Other Routes of Administration:

In one embodiment, the compositions provided herein can also be delivered via an impregnated or coated device such as a stent, for example, or an artery-inserted cylindrical polymer. Such a method of administration can, for example, aid in the prevention or amelioration of restenosis following procedures such as balloon angioplasty. Without being bound by any particular theory, a compound provided herein can slow or inhibit the migration and proliferation of smooth muscle cells in the arterial wall which contribute to restenosis. A compound provided herein can be administered, for example, by local delivery from the struts of a stent, from a stent graft, from grafts, or from the cover or sheath of a stent. In some embodiments, a compound provided herein is admixed with a matrix. Such a matrix can be a polymeric matrix, and can serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene, and cellulose esters. Suitable matrices can be nondegrading or can degrade with time, releasing the compound or compounds. A compound provided herein can be applied to the surface of the stent by various methods such as dip/spin coating, spray coating, dip-coating, and/or brush-coating. A compound provided herein can be applied in a solvent and the solvent can be allowed to evaporate, thus forming a layer of compound onto the stent. Alternatively, the compound can be located in the body of the stent or graft, for example in microchannels or micropores. When implanted, the compound diffuses out of the body of the stent to contact the arterial wall. Such stents can be prepared by dipping a stent manufactured to contain such micropores or microchannels into a solution of a compound provided herein in a suitable solvent, followed by evaporation of the solvent. Excess drug on the surface of the stent can be removed via an additional brief solvent wash. In yet another embodiment, a compound provided herein can be covalently linked to a stent or graft. A covalent linker can be used which degrades in vivo, leading to the release of a compound provided herein. Any bio-labile linkage can be used for such a purpose, such as ester, amide or anhydride linkages. A compound provided herein can additionally be administered intravascularly from a balloon used during angioplasty. Extravascular administration of a compound provided herein via the pericardia or via advential application of formulations provided herein can also be performed to decrease restenosis.

A variety of stent devices which can be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; and 6,344,053.

Formulations for Controlled Release Administration:

In some embodiments, provided herein are pharmaceutical compositions for controlled release administration containing a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof, and a pharmaceutical excipient suitable for controlled release administration. In some embodiments, provided herein are pharmaceutical compositions for controlled release administration containing: (i) an effective amount of a disclosed polymorph or a pharmaceutically acceptable form (e.g., pharmaceutically acceptable salts, hydrates, solvates, chelates, non-covalent complexes, isomers, prodrugs, and isotopically labeled derivatives) thereof; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide a given release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound (e.g., a polymorph) as disclosed herein or a pharmaceutically acceptable form (e.g., pharmaceutically acceptable salts, hydrates, solvates, chelates, non-covalent complexes, isomers, prodrugs, and isotopically labeled derivatives) thereof, that promptly produces a therapeutic effect, and gradually and continually release other amounts of the compound to maintain this level of therapeutic or prophylactic effect over an extended period of time. In order to maintain this constant level of the Formula (I) in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, CRC Crit. Ref Biomed. Eng. 14:201 (1987); Buchwald et al., Surgery 88:507 (1980); Saudek et al., N. Engl. J Med. 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, 115-138 (vol. 2, 1984). Other controlled release systems are discussed in the review by Langer, Science 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

Dosage:

A compound (e.g., a polymorph) described herein or a pharmaceutically acceptable form (e.g., pharmaceutically acceptable salts, hydrates, solvates, chelates, non-covalent complexes, isomers, prodrugs, and isotopically labeled derivatives) thereof can be delivered in the form of pharmaceutically acceptable compositions which comprise a therapeutically effective amount of one or more compounds or a pharmaceutically acceptable form (e.g., pharmaceutically acceptable salts, hydrates, solvates, chelates, non-covalent complexes, isomers, prodrugs, and isotopically labeled derivatives) thereof described herein and/or one or more additional therapeutic agents such as a chemotherapeutic, formulated together with one or more pharmaceutically acceptable excipients. In some instances, the compound or a pharmaceutically acceptable form described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein or a pharmaceutically acceptable form and the additional therapeutic agent can be administered separately, but via the same route (e.g., both orally or both intravenously). In still other instances, the compound described herein or a pharmaceutically acceptable form and the additional therapeutic agent can be administered in the same pharmaceutical composition.

In one embodiment, polymorphs provided herein can be administered in dosages. It is known in the art that due to possible intersubject variability in pharmacokinetics, individualization of dosing regimen can be employed for optimal therapy. Dosing for a compound provided herein can be found by routine experimentation in light of the instant disclosure.

In one embodiment, the amount of a compound administered will be dependent on the mammal being treated, the severity of the disorder or condition, the route of administration, the rate of administration, the disposition of the compound, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, the discretion of the prescribing physician, and like factors well known in the medical arts. In one embodiment, an effective dosage is in a range of about 0.001 to about 100 mg per kg body weight per day, or about 1 to about 35 mg/kg/day, in single or divided dose(s). In one embodiment, for a 70 kg human, an effective dosage can amount to about 0.05 to 7 g/day, or about 0.05 to about 2.5 g/day. In some instances, dosage levels below the lower limit of the aforesaid range can be more than adequate, while in other cases still larger doses can be employed without causing any harmful side effect, e.g., in some embodiments, by dividing such larger doses into several small doses for administration throughout the day.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, can range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve a therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, a compound provided herein is administered in a single dose. In some embodiments, such administration is by injection, e.g., intravenous injection, in order to introduce the agent quickly. In other embodiments, such administration is by oral administration, e.g., for ease of administration and patient compliance. Other routes can also be used as appropriate. In some embodiments, a single dose of a compound provided herein can be used for treatment of an acute condition.

In some embodiments, a compound provided herein is administered in multiple doses. In one embodiment, dosing can be about once, twice, three times, four times, five times, six times, or more than six times per day. In one embodiment, dosing can be about once a month, once every two weeks, once a week, or once every other day. In another embodiment, a compound provided herein and another agent are administered together about once per day to about 6 times per day. In another embodiment, the administration of a compound provided herein and an agent continues for less than about 7 days. In yet another embodiment, the administration continues for more than about 6, 10, 14, or 28 days, two months, six months, or one year. In some embodiments, continuous dosing is achieved and maintained as long as necessary. In some embodiments, a compound provided herein is administered in cycles (e.g., a treatment period followed by a treatment-free period, and repeat the cycle for as long as necessary).

In some embodiments, the compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In one embodiment, administration of an agent provided herein can continue as long as necessary. In some embodiments, an agent provided herein is administered for more than 1, 2, 3, 4, 5, 6, 7, 14, or 28 day(s). In some embodiments, an agent provided herein is administered for less than 28, 14, 7, 6, 5, 4, 3, 2, or 1 day(s). In some embodiments, an agent provided herein is administered chronically on an ongoing basis, e.g., for the treatment of chronic disorders.

In one embodiment, an effective amount of a compound provided herein can be administered in either single or multiple doses by any of the accepted modes of administration of agents having similar utilities, including orally, parenterally, subcutaneously, intravenously, intraperitoneally, intramuscularly, intraarterially, topically, rectally, buccally, intranasally, transdermally, or as an inhalant. In one embodiment, the compound is administered orally as a single dose once a day. In other embodiments, the compound is administered orally at multiple doses, e.g., at least two, three or more doses per day.

In certain embodiments, the compound is administered, e.g., orally, as a single dose once a day of about 50 mg or less, about 40 mg or less, about 30 mg or less, about 25 mg or less, about 20 mg or less, about 15 mg or less, about 12.5 mg or less, about 10 mg or less, about 5 mg or less, about 4 mg or less, about 3 mg or less, about 2 mg or less, or about 1 mg or less (e.g., about 0.9 mg, about 0.8 mg, about 0.7 mg, about 0.6 mg, about 0.5 mg, about 0.4 mg, about 0.3 mg, about 0.2 mg, about 0.1 mg, or about 0.05 mg or less). In certain embodiments, the compound is administered, e.g., orally, as a single dose once a day ranging from about 0.05 mg to about 50 mg, about 0.1 mg to about 45 mg, about 0.2 mg to about 40 mg, about 0.5 mg to about 35 mg, about 0.7 mg to about 30 mg, about 1 mg to about 30 mg, about 2 mg to about 25 mg, about 5 mg to about 20 mg, about 7 mg to about 15 mg, about 10 mg to about 12 mg, about 5 mg to about 10 mg, about 1 mg to about 5 mg, about 0.01 mg to about 1 mg, about 0.01 mg to about 0.05 mg, or about 0.05 mg to about 1 mg.

In certain embodiments, the compound is administered, e.g., orally, at multiple doses per day (e.g., twice a day), wherein each dose is about 50 mg or less, about 40 mg or less, about 30 mg or less, about 25 mg or less, about 20 mg or less, about 15 mg or less, about 12.5 mg or less, about 10 mg or less, about 5 mg or less, about 4 mg or less, about 3 mg or less, about 2 mg or less, or about 1 mg or less (e.g., about 0.9 mg, about 0.8 mg, about 0.7 mg, about 0.6 mg, about 0.5 mg, about 0.4 mg, about 0.3 mg, about 0.2 mg, about 0.1 mg, or about 0.05 mg or less). In certain embodiments, the compound is administered, e.g., orally, at multiple doses per day (e.g., twice a day), wherein each dose ranges from about 0.05 mg to about 50 mg, about 0.1 mg to about 45 mg, about 0.2 mg to about 40 mg, about 0.5 mg to about 35 mg, about 0.7 mg to about 30 mg, about 1 mg to about 30 mg, about 2 mg to about 25 mg, about 5 mg to about 20 mg, about 7 mg to about 15 mg, about 10 mg to about 12 mg, about 5 mg to about 10 mg, about 1 mg to about 5 mg, about 0.01 mg to about 1 mg, about 0.01 mg to about 0.05 mg, or about 0.05 mg to about 1 mg.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 0.05 mg to about 50 mg, or about 1 to about 50 mg per day.

When a compound provided herein, is administered in a pharmaceutical composition that comprises one or more agents, and the agent has a shorter half-life than the compound provided herein unit dose forms of the agent and the compound provided herein can be adjusted accordingly.

In one aspect, compositions are featured, which include the compound of Formula (I) (e.g., a composition including one or more polymorphic forms of the compound of Formula (I), e.g., polymorph Form C), when dosed at a dose range of 0.05 mg once a day (QD) to 50 mg twice a day (BID) of active compound, are capable of producing an amount of compound sufficient to achieve a mean steady state area under the concentration time curve, AUC (e.g., $AUC_{0-24}$ or $AUC_{tau}$ ss), of at least about 0.5 ng*hr/mL, at least about 1 ng*hr/mL, at least about 2.5 ng*hr/mL, at least about 5 ng*hr/mL, at least about 10 ng*hr/mL, at least about 25 ng*hr/mL, at least about 50 ng*hr/mL, at least about 100 ng*hr/mL, at least about 150 ng*hr/mL, at least about 200 ng*hr/mL, at least about 250 ng*hr/mL, at least about 300 ng*hr/mL, at least about 500 ng*hr/mL, at least about 750 ng*hr/mL, at least about 850 ng*hr/mL, at least about 950 ng*hr/mL, at least about 1,000 ng*hr/mL, at least about 1,500 ng*hr/mL, at least about 2,000 ng*hr/mL, at least about 3,000 ng*hr/mL, at least about 5,000 ng*hr/mL, at least about 10,000 ng*hr/mL, at least about 12,000 ng*hr/mL, at least about 15,000 ng*hr/mL, at least about 20,000 ng*hr/mL, at least about 25,000 ng*hr/mL, at least about 30,000 ng*hr/mL, at least about 50,000 ng*hr/mL, at least about 75,000 ng*hr/mL, at least about 100,000 ng*hr/mL, at least about 200,000 ng*hr/mL, or at least about 300,000 ng*hr/mL. In certain embodiments, the AUC (e.g., $AUC_{0-24}$ or $AUC_{tau}$ ss) of the composition when dosed at a dose range of about 0.05 mg QD to about 50 mg BID of active compound, is at least about 5 ng*hr/mL, at least about 50 ng*hr/mL, at least about 100 ng*hr/mL, at least about 150 ng*hr/mL, at least about 200 ng*hr/mL, at least about 300 ng*hr/mL, at least about 400 ng*hr/mL, at least about 500 ng*hr/mL, at least about 600 ng*hr/mL, at least about 700 ng*hr/mL, at least about 800 ng*hr/mL, at least about 900 ng*hr/mL, at least about 1,000 ng*hr/mL, at least about 1,500 ng*hr/mL, at least about 2,000 ng*hr/mL, at least about 2,500 ng*hr/mL, at least about 3,000 ng*hr/mL, at least about 5,000 ng*hr/mL, at least about 10,000 ng*hr/mL, at least about 15,000 ng*hr/mL, at least about 20,000 ng*hr/mL, at least about 25,000 ng*hr/mL, or at least about 30,000 ng*hr/mL. In other embodiments, the AUC (e.g., $AUC_{0-24}$ or $AUC_{tau}$ ss) of the composition when dosed at a dose range of about 0.05 mg QD to about 50 mg BID of active compound, is in the range of about 0.5 ng*hr/mL to about 300,000 ng*hr/mL, about 1 ng*hr/mL to about 200,000 ng*h/mL, about 2.5 ng*hr/mL to about 250,000 ng*hr/mL, about 5 ng*hr/mL to about 30,000 ng*hr/mL, about 10 ng*hr/mL to about 200,000 ng*hr/mL, about 25 ng*hr/mL to about 100,000 ng*hr/mL, about 50 ng*hr/mL to about 75,000 ng*hr/mL, about 100 ng*hr/mL to about 50,000 ng*hr/mL, about 200 ng*hr/mL to about 40,000 ng*hr/mL, about 500 ng*hr/mL to about 30,000 ng*hr/mL, about 1,000 ng*hr/mL to about 25,000 ng*hr/mL, about 700 ng*hr/mL to about 15,000 ng*hr/mL, about 500 ng*hr/mL to about 10,000 ng*hr/mL, about 1,000 ng*hr/mL to about 5,000 ng*hr/mL, about 10,000 ng*hr/mL to about 50,000 ng*hr/mL, about 20,000 ng*hr/mL to about 40,000 ng*hr/mL, or about 25,000 ng*hr/mL to about 30,000 ng*hr/mL. In one embodiment, the AUC (e.g., $AUC_{0-24}$ or $AUC_{tau}$ ss) of the composition when dosed at a dose range of about 0.05 mg QD to about 50 mg BID of active compound, is in the range of about 5 ng*hr/mL to about 30,000 ng*hr/mL, about 1000 ng*hr/mL to about 15,000 ng*hr/mL, about 2500 ng*hr/mL to about 10,000 ng*hr/mL, about 100 ng*hr/mL to about 3,500 ng*hr/mL, about 145 ng*hr/mL to about 3,000 ng*hr/mL, about 250 ng*hr/mL to about 2,500 ng*hr/mL, about 300 ng*hr/mL to about 2,500 ng*hr/mL, about 500 ng*hr/mL to about 2,300 ng*hr/mL, about 800 ng*hr/mL to about 2,200 ng*hr/mL, about 140 ng*hr/mL to about 900 ng*hr/mL, about 500 ng*hr/mL to about 10,000 ng*hr/mL, about 1,000 ng*hr/mL to about 5,000 ng*hr/mL, about 10,000 ng*hr/mL to about 50,000 ng*hr/mL, about 20,000 ng*hr/mL to about 40,000 ng*hr/mL, or about 25,000 ng*hr/mL to about 30,000 ng*hr/mL.

In one embodiment, the compositions that include the compound of Formula (I), when dosed at a dose range of about 1 mg to about 30 mg administered to a human as a single oral dose once a day (QD) of active compound, are capable of producing an amount of compound sufficient to achieve an AUC, e.g., $AUC_{0-24}$, of at least about 40 ng*hr/mL, at least about 50 ng*hr/mL, at least about 75 ng*hr/mL, at least about 100 ng*hr/mL, at least about 150 ng*hr/mL, at least about 200 ng*hr/mL, at least about 300 ng*hr/mL, at least about 400 ng*hr/mL, at least about 500 ng*hr/mL, at least about 600 ng*hr/mL, at least about 700 ng*hr/mL, at least about 800 ng*hr/mL, at least about 900 ng*hr/mL, at least about 1,000 ng*hr/mL, at least about 1,500 ng*hr/mL, at least about 2,000 ng*hr/mL, at least about 2,500 ng*hr/mL, at least about 3,000 ng*hr/mL, at least about 5,000 ng*hr/mL, at least about 10,000 ng*hr/mL, at least about 15,000 ng*hr/mL, at least about 20,000 ng*hr/mL, at least about 30,000 ng*hr/mL, or at least about 50,000 ng*hr/mL. In one embodiment, the AUC, e.g., $AUC_{0-24}$, of the composition when dosed at a dose range of about 1 mg to about 30 mg as a single oral dose once a day (QD) of active compound, is in the range of about 5 ng*hr/mL to about 30,000 ng*hr/mL, about 100 ng*hr/mL to about 3,500 ng*hr/mL, about 145 ng*hr/mL to about 3,300 ng*hr/mL, about 200 ng*hr/mL to about 2,500 ng*hr/mL, about 300 ng*hr/mL to about 2,100 ng*hr/mL, about 500 ng*hr/mL to about 2,000 ng*hr/m, about 500 ng*hr/mL to about 5,000 ng*hr/mL, about 1,000 ng*hr/mL to about 10,000 ng*hr/mL, about 10,000 ng*hr/mL to about 50,000 ng*hr/mL, about 20,000 ng*hr/mL to about 40,000 ng*hr/mL, or about 25,000 ng*hr/mL to about 30,000 ng*hr/mL.

In another embodiment, the compositions that include the compound of Formula (I), when dosed at a dose range of about 1 mg to about 10 mg (e.g., evaluated on day 14 following 1, 2, 5, and 10 mg of repeated dosing (e.g., dosing was QD Days 1 and 14, and twice a day (BID) dosing on Days 2-13)) of active compound, are capable of producing an amount of compound sufficient to achieve a mean steady state area under the concentration time curve ($AUC_{tau}$ ss) of at least about 100 ng*hr/mL, at least about 200 ng*hr/mL, at least about 500 ng*hr/mL, at least about 700 ng*hr/mL, at least about 1,000 ng*hr/mL, at least about 1,200 ng*hr/mL, at least about 1,500 ng*hr/mL, at least about 2,000 ng*hr/mL, at least about 2,500 ng*hr/mL, at least about 3,000 ng*hr/mL, at least about 5,000 ng*hr/mL, at least about 10,000 ng*hr/mL, at least about 15,000 ng*hr/mL, at least about 20,000 ng*hr/mL, at least about 25,000 ng*hr/mL, or at least about 30,000 ng*hr/mL. In one embodiment, the AUC, e.g., $AUC_{tau}$ ss, of the composition when dosed at a dose range of about 1 mg to about 10 mg (e.g., evaluated on day 14 following 1, 2, 5, and 10 mg of repeated dosing (e.g., dosing was QD Days 1 and 14, and twice a day (BID) dosing on Days 2-13)), of active compound, is in the range of about 5 ng*hr/mL to about 30,000 ng*hr/mL, about 100 ng*hr/mL to about 3,500 ng*hr/mL, about 150 ng*hr/mL to about 3,300 ng*hr/mL, about 200 ng*hr/mL to about 2,500 ng*hr/mL, about 300 ng*hr/mL to about 2,500 ng*hr/mL, about 500 ng*hr/mL to about 5,000 ng*hr/mL, about 1,000 ng*hr/mL to about 10,000 ng*hr/mL, about 10,000 ng*hr/mL to about 50,000 ng*hr/mL, about 20,000 ng*hr/mL to about 40,000 ng*hr/mL, or about 25,000 ng*hr/mL to about 30,000 ng*hr/mL. As used herein, an "$AUC_{0-24}$" refers to an area under the mean steady state plasma concentration-time curve up to 24 hours post-dose. "$AUC_{tau}$ ss" refers to an $AUC_{0-24}$ for QD dosing, and $AUC_{0-12}$ for BID dosing. AUC corresponds to the area under the plasma concentration-time over an interval. The AUC values are provided throughout in nanogram hour per milliliter, abbreviated herein as ng hr/mL or ng*h/mL. AUC values can be determined using conventional methods known in the art, see, e.g., Goodman and Gilman's The Pharmacological Basis of Therapeutics, 10th ed.; Hardman, J. G., Limbird, L. E., Eds.; McGraw-Hill: New York, 2001.

In another aspect, compositions are disclosed, which include the compound of Formula (I) (e.g., a composition including one or more polymorphic forms of the compound of Formula (I), e.g., polymorph Form C), when dosed at a dose range of 0.05 mg once a day (QD) to 50 mg twice a day (BID) of active compound, are capable of producing an observed maximum plasma concentration (Cmax) of at least about 0.05 ng/mL, at least about 0.1 ng/mL, at least about 0.5 ng/mL, at least about 1 ng/mL, at least about 10 ng/mL, at least about 50 ng/mL, at least about 100 ng/mL, at least about 150 ng/mL, at least about 200 ng/mL, at least about 300 ng/mL, at least about 400 ng/mL, at least about 500 ng/mL, at least about 900 ng/mL, at least about 1,000 ng/mL, at least about 2,000 ng/mL, at least about 3,000 ng/mL, at least about 4,000 ng/mL, at least about 5,000 ng/mL, at least about 10,000 ng/mL, at least about 20,000 ng/mL, at least about 30,000 ng/mL, or at least about 40,000 ng/mL. In other embodiments, the Cmax of the composition when dosed at a dose range of about 0.05 mg QD to about 50 mg BID of active compound, is at least about 20 ng/mL, at least about 40 ng/mL, at least about 50 ng/mL, at least about 80 ng/mL, at least about 100 ng/mL, at least about 200 ng/mL, at least about 500 ng/mL, at least about 750 ng/mL, at least about 1,000 ng/mL, at least about 1,500 ng/mL, at least about 5,000 ng/mL, at least about 10,000 ng/mL, at least about 15,000 ng/mL, at least about 20,000 ng/mL, at least about 30,000 ng/mL, or at least about 40,000 ng/mL. In other embodiments, the Cmax of the composition when dosed at a dose range of about 0.05 mg QD to about 50 mg BID of active compound, is in the range of about 0.5 ng/mL to about 40,000 ng/mL, about 0.1 ng/mL to about 20,000 ng/mL, about 1 ng/mL to about 20,000 ng/mL, about 0.5 ng/mL to about 4,000 ng/mL, about 0.5 ng/mL to about 10,000 ng/mL, about 1 ng/mL to about 3,000 ng/mL, about 10 ng/mL to about 2,000 ng/mL, about 40 ng/mL to about 1,500 ng/mL, about 150 ng/mL to about 1,000 ng/mL, about 200 ng/mL to about 500 ng/mL, about 300 ng/mL to about 400 ng/mL, about 500 ng/mL to 1,000 ng/mL, about 1,000 ng/mL to about 5,000 ng/mL, about 5,000 ng/mL to about 10,000 ng/mL, about 10,000 ng/mL to about 20,000 ng/mL, about 20,000 ng/mL to about 30,000 ng/mL, or about 30,000 ng/mL to about 40,000 ng/mL. In one embodiment, the Cmax of the composition when dosed at a dose range of about 0.05 mg QD to about 50 mg BID of active compound, is in the range of about 0.5 ng/mL to about 4,000 ng/mL, about 20 ng/mL to about 1,500 ng/mL, about 40 ng/mL to about 1,100 ng/mL, about 50 ng/mL to about 1,000 ng/mL, about 80 ng/mL to about 900 ng/mL, about 100 ng/mL to about 500 ng/mL, about 200 ng/mL to about 450 ng/mL, about 500 ng/mL to about 1,000 ng/mL, about 1,000 ng/mL to about 5,000 ng/mL, about 5,000 ng/mL to about 10,000 ng/mL, about 10,000 ng/mL to about 20,000 ng/mL, about 20,000 ng/mL to about 30,000 ng/mL, or about 30,000 ng/mL to about 40,000 ng/mL.

In one embodiment, the compositions that include the compound of Formula (I), when dosed at a dose range of about 1 mg to about 30 mg administered to a human as a single oral dose once a day (QD) of active compound, are capable of producing a Cmax of at least about 20 ng/mL, at least about 40 ng/mL, at least about 50 ng/mL, at least about 80 ng/mL, at least about 100 ng/mL, at least about 200 ng/mL, at least about 500 ng/mL, at least about 750 ng/mL, at least about 1,000 ng/mL, or at least about 1,500 ng/mL. In other embodiments, the Cmax of the composition when dosed at a dose range of about 1 mg to about 30 mg administered to a human as a single oral dose once a day (QD) of active compound, are capable of producing a Cmax in the range of about 20 ng/mL to about 1,500 ng/mL, about 40 ng/mL to about 1,200 ng/mL, about 50 ng/mL to about 1,000 ng/mL, about 80 ng/mL to about 1,000 ng/mL, about 100 ng/mL to about 500 ng/mL, about 200 ng/mL to about 450 ng/mL, about 500 ng/mL to about 1,000 ng/mL, about 1,000 ng/mL to about 5,000 ng/mL, about 5,000 ng/mL to about 10,000 ng/mL, about 10,000 ng/mL to about 20,000 ng/mL, about 20,000 ng/mL to about 30,000 ng/mL, or about 30,000 ng/mL to about 40,000 ng/mL.

In another embodiment, the compositions that include the compound of Formula (I), when dosed at a dose range of about 1 mg to about 10 mg (e.g., evaluated on day 14 following 1, 2, 5, and 10 mg of repeated dosing (e.g., dosing was QD Days 1 and 14, and twice a day (BID) dosing on Days 2-13)) of active compound, are capable of producing an amount of compound sufficient to achieve a Cmax of at least about 40 ng/mL, at least about 50 ng/mL, at least about 60 ng/mL, at least about 100 ng/mL, at least about 200 ng/mL, at least about 300 ng/mL, at least about 400 ng/mL, at least about 500 ng/mL, at least about 590 ng/mL, at least about 750 ng/mL, at least about 1,000 ng/mL, at least about 1,500 ng/mL, at least about 5,000 ng/mL, at least about 10,000 ng/mL, at least about 15,000 ng/mL, at least about 20,000 ng/mL, at least about 30,000 ng/mL, or at least about 40,000 ng/mL. In one embodiment, the compositions that include the compound of Formula (I) (e.g., polymorph Form C), when dosed at a dose of 1 mg (BID), 2 mg (BID), 5 mg (BID), or 10 mg (QD) as a repeat dosing (e.g., evaluated on day 14 following 1, 2, 5, and 10 mg of repeated dosing (e.g., dosing was QD Days 1 and 14, and twice a day (BID) dosing on Days 2-13)) of active compound, are capable of producing a Cmax in the range of about 50 ng/mL to about 600 ng/mL, about 60 ng/mL to about 400 ng/mL, about 100 ng/mL to about 360 ng/mL, about 140 ng/mL to about 250 ng/mL, about 250 ng/mL to about 1,000 ng/mL, about 1,000 ng/mL to about 5,000 ng/mL, about 5,000 ng/mL to about 10,000 ng/mL, about 10,000 ng/mL to about 20,000 ng/mL, about 20,000 ng/mL to about 30,000 ng/mL, or about 30,000 ng/mL to about 40,000 ng/mL.

In one embodiment, the compositions that include the compound of Formula (I), when dosed at a dose range of 1 mg to 30 mg administered to a human as a single oral dose once a day (QD) of active compound, have a half-life ($t_{1/2}$) of at least 3 hours, at least 5 hours, at least 6 hours, at least 7 hours, at least 8 hours, or at least 10 hours. In other embodiments, the compositions that include the compound of Formula (I), when dosed at a dose range of about 1 mg to about 30 mg administered to a human as a single oral dose once a day (QD) of active compound, have a half-life ($t_{1/2}$) in the range of about 3 hours to 10 hours.

The Cmax and half-life ($t_{1/2}$) values can be determined using conventional methods known in the art, see, e.g., Goodman and Gilman's The Pharmacological Basis of Therapeutics, 10th ed.; Hardman, J. G., Limbird, L. E., Eds.; McGraw-Hill: New York, 2001. In one embodiment, the half-life ($t_{1/2}$) is calculated as $0.693/k_{el}$ (terminal elimination).

Kits:

In yet another embodiment, provided herein are kits. In one embodiment, the kits include a compound or polymorphs described herein or a pharmaceutically acceptable form (e.g., pharmaceutically acceptable salts, hydrates, solvates, chelates, non-covalent complexes, isomers, prodrugs, and isotopically labeled derivatives) thereof, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the compound or composition, and/or which describe dosing, administration, side effects, drug interactions, and/or other information useful to the health care provider. Such information can be based on the results of various studies, for example, studies using experimental animals involving in vivo models or studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

Pharmaceutical packs and/or kits provided can comprise a provided composition and a container (e.g., a vial, ampoule, bottle, syringe, and/or dispenser package, or other suitable container). In some embodiments, provided kits can optionally further include a second container comprising a suitable aqueous carrier for dilution or suspension of the provided composition for preparation of administration to a subject. In some embodiments, contents of provided formulation container and solvent container combine to form at least one unit dosage form.

In one embodiment, a single container can comprise one or more compartments for containing a provided composition, and/or appropriate aqueous carrier for suspension or dilution. In some embodiments, a single container can be appropriate for modification such that the container can receive a physical modification so as to allow combination of compartments and/or components of individual compartments. For example, a foil or plastic bag can comprise two or more compartments separated by a perforated seal which can be broken so as to allow combination of contents of two individual compartments once the signal to break the seal is generated. A pharmaceutical pack or kit can thus comprise such multi-compartment containers including a provided composition and appropriate solvent and/or appropriate aqueous carrier for suspension.

In some embodiments, the kits can further contain another agent. In some embodiments, the compound provided herein or a pharmaceutically acceptable form (e.g., pharmaceutically acceptable salts, hydrates, solvates, chelates, non-covalent complexes, isomers, prodrugs, and isotopically labeled derivatives) thereof and a second agent are provided as separate compositions in separate containers within the kit. In some embodiments, the compound provided herein or a pharmaceutically acceptable form (e.g., pharmaceutically acceptable salts, hydrates, solvates, chelates, non-covalent complexes, isomers, prodrugs, and isotopically labeled derivatives) thereof and a second agent are provided as a single composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

In one embodiment, the polymorphs described herein or a pharmaceutically acceptable form (e.g., pharmaceutically acceptable salts, hydrates, solvates, chelates, non-covalent complexes, isomers, prodrugs, and isotopically labeled derivatives) thereof can be used in combination with the agents disclosed herein or other suitable agents, depending on the condition being treated. Hence, in some embodiments, the polymorphs provided herein or a pharmaceutically acceptable form (e.g., pharmaceutically acceptable salts, hydrates, solvates, chelates, non-covalent complexes, isomers, prodrugs, and isotopically labeled derivatives) thereof can be co-administered with other agents as described herein. When used in combination therapy, the polymorphs described herein or a pharmaceutically acceptable form (e.g., pharmaceutically acceptable salts, hydrates, solvates, chelates, non-covalent complexes, isomers, prodrugs, and isotopically labeled derivatives) thereof can be administered with a second agent simultaneously or separately. This administration in combination can include simultaneous administration of the two agents in the same dosage form, simultaneous administration in separate dosage forms, and separate administration. In some embodiments, a polymorph described herein and any of the second agents described herein can be formulated together in the same dosage form and administered simultaneously. Alternatively, in some embodiments, a polymorph described herein or a pharmaceutically acceptable form (e.g., pharmaceutically acceptable salts, hydrates, solvates, chelates, non-covalent complexes, isomers, prodrugs, and isotopically labeled derivatives) thereof and any of the second agents described herein can be simultaneously administered, wherein both agents are present in separate formulations. In another alternative, a polymorph described herein or a pharmaceutically acceptable form (e.g., pharmaceutically acceptable salts, hydrates, solvates, chelates, non-covalent complexes, isomers, prodrugs, and isotopically labeled derivatives) thereof can be administered after, or before, the administration of any of the second agents described herein. In a separate administration protocol, a polymorph provided herein or a pharmaceutically acceptable form (e.g., pharmaceutically acceptable salts, hydrates, solvates, chelates, non-covalent complexes, isomers, prodrugs, and isotopically labeled derivatives) thereof and any of the second agents described herein can be administered a few minutes apart, or a few hours apart, or a few days apart.

IV. Methods of Treatment

Phosphoinositide 3-kinases (PI3Ks) are members of a conserved family of lipid kinases that regulate numerous cell functions, including proliferation, differentiation, cell survival and metabolism. Several classes of PI3Ks exist in mammalian cells, including Class IA subgroup (e.g., PI3K-$\alpha$, $\beta$, $\delta$), which are generally activated by receptor tyrosine kinases (RTKs); Class IB (e.g., PI3K-$\gamma$), which is activated by G-protein coupled receptors, among others. PI3Ks exert their biological activities via a "PI3K-mediated signaling pathway" that includes several components that directly and/or indirectly transduce a signal triggered by a PI3K, including the generation of secondary messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem.* 70:535-602). For example, PI3K-$\delta$ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal.* 23(4):603-8). Unlike PI3K-$\delta$, PI3K-$\gamma$ is not a Class 1A PI3K, and is not associated with a regulatory subunit of the P85 family, but rather with a regulatory subunit in the p101 family. PI3K-$\gamma$ is associated with G-protein coupled receptors (GPCRs), and is responsible for the very rapid induction of PIP3, and can be also activated by RAS.

In some embodiments, provided herein are methods of modulating a PI3K kinase activity (e.g., selectively modulating) by contacting the kinase with an effective amount of a compound, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein. Modulation can be inhibiting or activating kinase activity. In some embodiments, provided herein are methods of inhibiting kinase activity by contacting the kinase with an effective amount of a compound as disclosed herein in solution. In some embodiments, provided herein are methods of inhibiting the kinase activity by contacting a cell, tissue, or organ that expresses the kinase of interest. In some embodiments, provided herein are methods of inhibiting kinase activity in a subject by administering into the subject an effective amount of a compound as disclosed herein.

In some embodiments, provided herein are methods of inhibiting kinase activity in a solution by contacting said solution with an amount of a compound provided herein sufficient to inhibit the activity of the kinase in said solution. In some embodiments, provided herein are methods of inhibiting kinase activity in a cell by contacting said cell with an amount of a compound provided herein sufficient to inhibit the activity of the kinase in said cell. In some embodiments, provided herein are methods of inhibiting kinase activity in a tissue by contacting said tissue with an amount of a compound provided herein sufficient to inhibit the activity of the kinase in said tissue. In some embodiments, provided herein are methods of inhibiting kinase activity in an organism by contacting said organism with an amount of a compound provided herein sufficient to inhibit the activity of the kinase in said organism. In some embodiments, provided herein are methods of inhibiting kinase activity in an animal by contacting said animal with an amount of a compound provided herein sufficient to inhibit the activity of the kinase in said animal. In some embodiments, provided herein are methods of inhibiting kinase activity in a mammal by contacting said mammal with an amount of a compound provided herein sufficient to inhibit the activity of the kinase in said mammal. In some embodiments, provided herein are methods of inhibiting kinase activity in a human by contacting said human with an amount of a compound provided herein sufficient to inhibit the activity of the kinase in said human.

In some embodiments, the % of kinase activity after contacting a kinase with a compound provided herein is less than about 1, about 5, about 10, about 20, about 30, about 40, about 50, about 60, about 70, about 80, about 90, about 95, or about 99% of the kinase activity in the absence of said contacting step. In some embodiments, the percentage of inhibiting exceeds about 25%, about 30%, about 40%, about 50%, about 60%, about 70%, about 80%, or about 90%. In some embodiments, provided herein are methods of inhibiting PI3 kinase activity in a subject (including mammals such as humans) by contacting said subject with an amount of a compound as disclosed herein sufficient to inhibit the activity of the PI3 kinase in said subject.

In some embodiments, the kinase is a lipid kinase or a protein kinase. In some embodiments, the kinase is selected from a PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

In one embodiment, also provided herein are methods of modulating PI3 kinase activity by contacting a PI3 kinase with an amount of a compound provided herein sufficient to modulate the activity of the PI3 kinase. Modulating can be inhibiting or activating PI3 kinase activity. In some embodiments, provided herein are methods of inhibiting PI3 kinase activity by contacting a PI3 kinase with an amount of a compound provided herein sufficient to inhibit the activity of the PI3 kinase. In some embodiments, provided herein are methods of inhibiting PI3 kinase activity. In some embodiments, such inhibition can take place in solution, in a cell expressing one or more PI3 kinases, in a tissue comprising a cell expressing one or more PI3 kinases, or in an organism expressing one or more PI3 kinases. In some embodiments, provided herein are methods of inhibiting PI3 kinase activity in an animal (including mammal such as humans) by contacting said animal with an amount of a compound provided herein sufficient to inhibit the activity of the PI3 kinase in said animal.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound or a pharmaceutical composition as disclosed herein. In some embodiments, provided herein is a method of treating a PI3K-δ or PI3K-γ mediated disorder in a subject, the method comprising administering a therapeutically effective amount of a compound or a pharmaceutical composition as disclosed herein. In some embodiments, provided herein is a method for inhibiting at least one of PI3K-δ or PI3K-γ, the method comprising contacting a cell expressing PI3K in vitro or in vivo with an effective amount of the compound or composition disclosed herein. PI3Ks have been associated with a wide range of conditions, including immunity, cancer and thrombosis (reviewed in Vanhaesebroeck, B. et al. (2010) *Current Topics in Microbiology and Immunology*, DOI 10.1007/82_2010_65). For example, Class I PI3Ks, particularly PI3K-γ and PI3K-δ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11): 1151-62); Rommel C. et al. (2007) *Nat Rev Immunol* 7(3): 191-201; Durand C A et al. (2009) *J Immunol.* 183(9):5673-84; Dil N, Marshall A J. (2009) *Mol Immunol.* 46(10): 1970-8; Al-Alwan M M et al. (2007) *J Immunol.* 178(4): 2328-35; Zhang T T, et al. (2008) *J Allergy Clin Immunol.* 2008; 122(4):811-819.e2; Srinivasan L, et al. (2009) *Cell* 139(3):573-86).

Numerous publications support roles of PI3K-δ, PI3K-γ, and PI3K-β in the differentiation, maintenance, and activation of immune and malignant cells, as described in more detail below.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9. Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) *J Exp Med.* 196(6):753-63; Bilancio A, et al. (2006) *Blood* 107(2):642-50; Okkenhaug K. et al. (2002) *Science* 297(5583): 1031-4; Al-Alwan M M et al. (2007) *J Immunol.* 178(4):2328-35; Zhang T T, et al. (2008) *J Allergy Clin Immunol.* 2008; 122(4):811-819.e2; Srinivasan L, et al. (2009) *Cell* 139(3):573-86)

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garçon F. et al. (2008) *Blood* 111(3):1464-71; Okkenhaug K et al. (2006). *J Immunol.* 177(8):5122-8; Soond D R, et al. (2010) *Blood* 115(11):2203-13; Reif K, (2004). *J Immunol.* 2004; 173(4):2236-40; Ji H. et al. (2007) *Blood* 110(8): 2940-7; Webb L M, et al. (2005) *J Immunol.* 175(5):2783-7; Liu D, et al. (2010) *J Immunol.* 184(6):3098-105; Haylock-Jacobs S, et al. (2011) *J Autoimmun.* 2011; 36(3-4):278-87; Jarmin S J, et al. (2008) *J Clin Invest.* 118(3):1154-64).

In neutrophils, PI3K-δ along with PI3K-γ, and PI3K-β, contribute to the responses to immune complexes, FCgRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008) *Eur J Immunol.* 38(5):1215-24; Pinho V, (2007) *J Immunol.* 179(11):7891-8; Sadhu C. et al. (2003) *J Immunol.* 170(5):2647-54; Condliffe A M et al. (2005) *Blood* 106(4): 1432-40).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCgR and C5a signaling) (Randis T M, et al. (2008) *Eur J Immunol.* 38(5):1215-24; Marwick J A et al. (2009) *Am J Respir Crit Care Med.* 179(7):542-8; Konrad S, et al. (2008) *J Biol Chem.* 283(48):33296-303).

In mast cells, stem cell factor- (SCF) and IL3-dependent proliferation, differentiation and function are PI3K-δ dependent, as is chemotaxis. The allergen/IgE crosslinking of FCgR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011): 1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) *J Exp Med.* 205(10):2419-35; Tassi I, et al. (2007) *Immunity* 27(2):214-27; Saudemont A, (2009) *Proc Natl Acad Sci USA.* 106(14):5795-800; Kim N, et al. (2007) *Blood* 110(9): 3202-8).

The roles of PI3K-δ, PI3K-γ, and PI3K-β in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma and COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3K-δ and/or -γ have been shown to have anti-inflammatory activity in several autoimmune animal models for rheumatoid arthritis (Williams, O. et al. (2010) *Chem Biol,* 17(2):123-34; WO 2009/088986; WO2009/088880; WO 2011/008302). PI3K-δ is expressed in the RA synovial tissue (especially in the synovial lining which contains fibroblast-like synoviocytes (FLS), and selective PI3K-δ inhibitors have been shown to be effective in inhibiting synoviocyte growth and survival (Bartok et al. (2010) *Arthritis Rheum* 62 Suppl 10:362). Several PI3K-δ and -γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302).

The role of PI3K-δ has also been shown in models of T-cell dependent response, including the DTH model. In the murine experimental autoimmune encephalomyelitis (EAE) model of multiple sclerosis, the PI3K-γ/δ-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class 1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011): 1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2):403-9).

PI3K-δ and PI3K-γ inhibition can be used in treating COPD. In the smoked mouse model of COPD, the PI3K-δ knockout does not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3K-δ and PI3K-γ isoforms, are also associated with cancers (reviewed, e.g., in Vogt, P K et al. (2010) *Curr Top Microbiol Immunol.* 347:79-104; Fresno Vara, J A et al. (2004) *Cancer Treat Rev.* 30(2): 193-204; Zhao, L and Vogt, P K. (2008) *Oncogene* 27(41): 5486-96). Inhibitors of PI3K, e.g., PI3K-δ and/or -γ, have been shown to have anti-cancer activity (e.g., Courtney, K D et al. (2010) *J Clin Oncol.* 28(6):1075-1083); Markman, B et al. (2010) *Ann Oncol.* 21(4):683-91; Kong, D and Yamori, T (2009) *Curr Med Chem.* 16(22):2839-54; Jimeno, A et al. (2009) *J Clin Oncol.* 27:156s (suppl; abstr 3542); Flinn, I W et al. (2009) *J Clin Oncol.* 27:156s (suppl; abstr 3543); Shapiro, G et al. (2009) *J Clin Oncol.* 27:146s (suppl; abstr 3500); Wagner, A J et al. (2009) *J Clin Oncol.* 27:146s (suppl; abstr 3501); Vogt, P K et al. (2006) *Virology* 344(1):131-8; Ward, S et al. (2003) *Chem Biol.* 10(3):207-13; WO 2011/041399; US 2010/0029693; US 2010/0305096; US 2010/0305084). In an embodiment, described herein is a method of treating cancer.

Types of cancer that can be treated with an inhibitor of PI3K (particularly, PI3K-δ and/or -γ) include, e.g., leukemia (e.g., chronic lymphocytic leukemia (CLL), acute myeloid leukemia (ALL), chronic myeloid leukemia (CML) (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma (e.g., non-Hodgkin's lymphoma or Hodgkin's lymphoma) (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) *Mol Cancer Ther.* 7:841-850); endometrial cancer (e.g., Bansal, N et al. (2009) *Cancer Control.* 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6): 2569-77); colorectal cancer (e.g., Saif, M W and Chu, E (2010) *Cancer J.* 16(3): 196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and some solid tumors, including prostate, breast and glioblastomas (Chen J. S. et al. (2008) *Mol Cancer Ther.* 7(4):841-50; Ikeda H. et al. (2010) *Blood* 116(9):1460-8).

In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3):1027-36; Meadows, S A, 52$^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16):4323-7. In an embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. 52$^{nd}$ Annual ASH Meeting and Exposition; 2010 Dec. 4-7; Orlando, Fla.; Hoellenriegel, J, et al. 52$^{nd}$ Annual ASH Meeting and Exposition; 2010 Dec. 4-7; Orlando, Fla.; Webb, H K, et al. 52$^{nd}$ Annual ASH Meeting and Exposition; 2010 Dec. 4-7; Orlando, Fla.; Meadows, et al. 52$^{nd}$ Annual ASH Meeting and Exposition; 2010 Dec. 4-7; Orlando, Fla.; Kahl, B, et al. 52$^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research 102$^{nd}$ Annual Meeting; 2011 Apr. 2-6; Orlando, Fla.). PI3K-β is the PI3K isoform that is most commonly activated in tumors where the PTEN tumor suppressor is mutated (Ward S, et al. (2003) *Chem Biol.* 10(3):207-13). In this subset of tumors, treatment with the PI3K-δ inhibitor either alone or in combination with a cytotoxic agent can be effective.

Another mechanism for PI3K-δ inhibitors to have an affect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. 52$^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenviroment, including stromal cells, immune cells, and endothelial cells and be therapeutic either on its own or in conjunction with another therapy (Meadows, S A, et al. Paper presented at: 52$^{nd}$ Annual ASH Meeting and Exposition; 2010 Dec. 4-7; Orlando, Fla.; Geng L, et al. (2004) *Cancer Res.* 64(14):4893-9).

In other embodiments, inhibition of PI3K (such as PI3K-δ and/or -γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J Child Adolesc. Psychopharmacol.* 10: 133-145; Sokol, M. S. et al. (2002) *Am. J Psychiatry* 159: 1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113:883-886; Garvey, M. A. et al. (1998) *J Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J. Neuroimmunol.* 179: 173-179). Autoantibodies recognizing central nervous system (CNS) epitopes are also found in sera of most PANDAS subjects (Yaddanapudi, K. et al. (2010) *Mol. Psychiatry* 15:712-726). Thus, several neuropsychiatric disorders have been associated with immune and autoimmune components, making them suitable for therapies that include PI3K-δ and/or -γ inhibition.

In certain embodiments, a method of treating (e.g., reducing or ameliorating one or more symptoms of) a neuropsychiatric disorder, (e.g., an autoimmune brain disorder), using a PI3K-δ and/or -γ inhibitor is described, alone or in combination therapy. For example, one or more PI3K-δ and/or -γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or -γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD-Not Otherwise Specified (PDD-NOS). Animal models for evaluating the activity of the PI3K-δ and/or -γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

Provided herein are methods of using compounds or pharmaceutical compositions provided herein to treat disease conditions, including but not limited to, diseases associated with malfunctioning of one or more type(s) of PI3 kinase. For example, a detailed description of conditions and disorders mediated by p110δ kinase activity is set forth in Sadu et al., WO 01/81346, which is incorporated herein by reference in its entirety for all purposes.

In one embodiment, the treatment methods provided herein comprise administering to a subject a therapeutically effective amount of a compound provided herein. In one embodiment, provided herein is a method of treating an inflammation disorder, including autoimmune diseases in a mammal. In one embodiment, the method comprises administering to said mammal a therapeutically effective amount of a compound provided herein, or a pharmaceutically acceptable salt, ester, prodrug, solvate, hydrate or derivative thereof. Examples of autoimmune diseases include, but are not limited to, acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, skin blistering bullous pemphigoid, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. In other embodiments, the disorders or disease conditions include bone-resorption disorders and thrombosis.

Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, cutaneous lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatitis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds can also be useful in treating inflammation associated with trauma and non-inflammatory myalgia.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In some embodiments, the method of treating inflammatory or autoimmune diseases comprises administering to a subject (e.g., a mammal) a therapeutically effective amount of a compound provided herein that selectively inhibit PI3K-δ and/or PI3K-γ as compared to all other types of PI3 kinases. Such selective inhibition of PI3K-δ and/or PI3K-γ can be advantageous for treating any of the diseases or conditions described herein. For example, without being limited by a particular theory, selective inhibition of PI3K-δ can inhibit inflammatory responses associated with inflammatory diseases, autoimmune disease, or diseases related to an undesirable immune response, including but not limited to, asthma, emphysema, allergy, dermatitis, rheumatoid arthritis, psoriasis, lupus erythematosus, or graft versus host disease. Without being limited by a particular theory, selective inhibition of PI3K-δ can further provide for a reduction in the inflammatory or undesirable immune response without a concomitant reduction in the ability to reduce a bacterial, viral, and/or fungal infection. Without being limited by a particular theory, selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one embodiment, one or more of the methods provided herein are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold, or more. In another embodiment, one or more of the methods provided herein are effective in reducing antigen specific IgG3 and/or IgGM production in vivo by about 2-fold, about 3-fold, about 4-fold, about 5-fold, about 7.5-fold, about 10-fold, about 25-fold, about 50-fold, about 100-fold, about 250-fold, about 500-fold, about 750-fold, or about 1000-fold, or more.

In one embodiment, one of more of the methods provided herein are effective in ameliorating symptoms associated with rheumatoid arthritis, including but not limited to, a reduction in the swelling of joints, a reduction in serum anti-collagen levels, and/or a reduction in joint pathology, such as bone resorption, cartilage damage, pannus, and/or inflammation. In another embodiment, the methods provided herein are effective in reducing ankle inflammation by at least about 2%, about 5%, about 10%, about 15%, about 20%, about 25%, about 30%, about 50%, or about 60%, or about 75% to about 90%. In another embodiment, the methods provided herein are effective in reducing knee inflammation by at least about 2%, about 5%, about 10%, about 15%, about 20%, about 25%, about 30%, about 50%, or about 60%, or about 75% to about 90% or more. In still another embodiment, the methods provided herein are effective in reducing serum anti-type II collagen levels by at least about 10%, about 12%, about 15%, about 20%, about 24%, about 25%, about 30%, about 35%, about 50%, about 60%, about 75%, about 80%, about 86%, about 87%, or about 90%, or more. In another embodiment, the methods provided herein are effective in reducing ankle histopathology scores by about 5%, about 10%, about 15%, about 20%, about 25%, about 30%, about 40%, about 50%, about 60%, about 75%, about 80%, or about 90%, or more. In still another embodiment, the methods provided herein are effective in reducing knee histopathology scores by about 5%, about 10%, about 15%, about 20%, about 25%, about 30%, about 40%, about 50%, about 60%, about 75%, about 80%, or about 90%, or more.

In other embodiments, provided herein are methods of using compounds or pharmaceutical compositions provided herein to treat respiratory diseases, including but not limited to, diseases affecting the lobes of lung, pleural cavity, bronchial tubes, trachea, upper respiratory tract, or the nerves and muscle for breathing. For example, methods are provided to treat obstructive pulmonary disease, including COPD. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein are used for the treatment of contact or atopic dermatitis. Contact dermatitis includes irritant dermatitis, phototoxic dermatitis, allergic dermatitis, photoallergic dermatitis, contact urticaria, systemic contact-type dermatitis, and the like. Irritant dermatitis can occur when too much of a substance is used on the skin or when the skin is sensitive to certain substance. Atopic dermatitis, sometimes called eczema, is a kind of dermatitis, an atopic skin disease.

Also provided herein is a method of treating a hyperproliferative disorder in a mammal comprising administering to said mammal a therapeutically effective amount of a compound provided herein, or a pharmaceutically acceptable salt, ester, prodrug, solvate, hydrate or derivative thereof. In some embodiments, the hyperproliferative disorder is a myeloid, a myelodysplastic syndrome (MDS), a myeloproliferative disease (MPD) or a mast cell disorder. In some embodiments, said method relates to the treatment of cancer such as acute myeloid leukemia, retinoblastoma, intraocular melanoma, or cancers of thymus, brain, lung, squamous cell, skin, eye, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, or PNS, or AIDS-related (e.g., Lymphoma and Kaposi's Sarcoma) or viral-induced cancer. In some embodiments, said method relates to the treatment of a non-cancerous hyperproliferative disorder, such as benign hyperplasia of the skin (e.g., psoriasis), restenosis, or prostate (e.g., benign prostatic hypertrophy (BPH)).

Also provided herein is a method of treating diseases related to vasculogenesis or angiogenesis in a mammal comprising administering to said mammal a therapeutically effective amount of a compound provided herein, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma, and ovarian, breast, lung, pancreatic, prostate, colon, and epidermoid cancer.

In one embodiment, patients that can be treated with compounds provided herein, or pharmaceutically acceptable salt, ester, prodrug, solvate, hydrate or derivative of said compounds, according to the methods provided herein include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors, such as adenocarcinoma in the ovary and an adenocarcinoma that has migrated from the ovary into the abdominal cavity; uterine cancer; cervical cancer, such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer, such as epitheliod carcinoma in the pancreatic duct tissue and an adenocarcinoma in a pancreatic duct; bladder cancer, such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and/or colon cancer.

In one embodiment, patients that can be treated with compounds provided herein, or pharmaceutically acceptable salt, ester, prodrug, solvate, hydrate or derivative of said compounds, according to the methods provided herein include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenström's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), chronic myelomonocytic leukemia (CMML), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic adenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenström's macroglobulinemia.

In some embodiments, provided herein are methods of treating a heme malignancy in a subject comprising administering to said subject a therapeutically effective amount of a compound provided herein, or a pharmaceutically acceptable salt, ester, prodrug, solvate, hydrate or derivative thereof. In some embodiments, the heme malignancy is a myeloid malignancy. Exemplary myeloid malignancies that can be treated using the compounds provided herein include: leukemia (e.g., acute myeloid leukemia (AML) or chronic myelocytic leukemia (CML)); myelodysplastic syndromes (MDS) (e.g., high grade MDS or low grade MDS); myeloproliferative disease (MPD) (e.g., essential thrombocytosis (ET), myelofibrosis (MF), polycythemia vera (PV), or chronic myelomonocytic leukemia (CMML)), and mast cell disorders.

In some embodiments, the heme malignancy is a lymphoid malignancy, e.g., a lymphoma. Exemplary lymphomas that can be treated using the compounds provided herein include Hodgkin's lymphoma, non-Hodgkin's lymphoma (e.g., B-cell or T-cell), leukemia (e.g., acute lymphocytic leukemia (ALL) or chronic lymphocytic leukemia (CLL)), and posttransplantational lymphoproliferative disorders (PLDs). Exemplary B-cell lymphomas include: diffuse large B-cell lymphoma (DLBCL), mantle cell lymphoma, and indolent non-Hodgkin's lymphoma (iNHL). Exemplary T-cell lymphomas include peripheral T-cell lymphoma (PTCL) and cutaneous T-cell lymphoma (CTCL). Exemplary acute lymphocytic leukemias (ALLs) include T-cell ALL and B-cell ALL. Exemplary PLDs include multiple myeloma, Waldenström's PLD, and amyloid PLD.

In other embodiments, the compounds and compositions provided herein can be used for preventing a PI3K-mediated cancer, in a subject having, or at risk of having, the PI3K-mediated cancer. In one embodiment, the compounds and compositions provided herein can be used as a chemopreventive agent, e.g., as an agent that inhibits, delays, or reverses the development of a PI3K-mediated cancer. Such a role is supported, at least in part, by an extensive body showing the effects of anti-inflammatory agents, such as COX-2 inhibitors, as chemopreventive agents to reduce or inhibit the development of a cancer, including colon cancer, among others. Since both COX-2 inhibitors and PI3K inhibitors have broad anti-inflammatory activity, PI3K inhibition is expected to have chemopreventive activity in reducing or inhibiting the development of a variety of cancers.

In certain embodiments, a method of treating or preventing a relapse and/or a recurrence of a PI3K-mediated cancer (e.g., a PI3K-β mediated cancer as described herein) in a subject is provided. The method includes administering to the subject a PI3K inhibitor, e.g., one or more PI3K inhibitors as described herein, in an amount sufficient to reduce or inhibit the tumor or cancer re-growth or relapse, in the subject. In certain embodiments, the subject is a patient who is undergoing, or has undergone, cancer therapy (e.g., treatment with other anti-cancer agents, surgery and/or radiation). The PI3K inhibitor can be administered before treatment, concurrently with treatment, post-treatment, with other cancer therapies; or during remission of the cancer. The inhibition of relapse or recurrence need not be absolute, as long as the treatment or prevention delays (e.g., by a week, month, year) the relapse and/or recurrence, or reduces or retards the re-growth (e.g., by at least about 10%, about 20%, about 30%, about 40%, about 50% or more) of the PI3K-mediated cancer (e.g., compared to a subject not treated with the PI3K inhibitor).

Thus, in one embodiment, a method of extending relapse free survival in a subject with a cancer who is undergoing, or has undergone, cancer therapy by administering a therapeutically effective amount of a PI3K inhibitor to the subject is disclosed. "Relapse free survival," as understood by those skilled in the art, is the length of time following a specific point of cancer treatment during which there is no clinically-defined relapse in the cancer. In some embodiments, the PI3K inhibitor is administered concurrently with the cancer therapy. In other embodiments, the PI3K inhibitor is administered sequentially (in any order) with the cancer therapy. In instances of concurrent administration, the PI3K inhibitor can continue to be administered after the cancer therapy has ceased. In other embodiments, the PI3K inhibitor is administered after cancer therapy has ceased (e.g., with no period of overlap with the cancer treatment). The PI3K inhibitor can be administered immediately after cancer therapy has ceased, or there can be a gap in time (e.g., up to a few hours, about a day, about a week, about a month, about six months, or a year) between the end of cancer therapy and the administration of the PI3K inhibitor. Treatment with the PI3K inhibitor can continue for as long as relapse-free survival is maintained (e.g., up to about a day, about a week, about a month, about six months, about a year, about two years, about three years, about four years, about five years, or longer).

Also provided herein is a method of treating diabetes in a mammal comprising administering to said mammal a therapeutically effective amount of a compound provided herein, or a pharmaceutically acceptable salt, ester, prodrug, solvate, hydrate or derivative thereof.

In addition, the compounds described herein can be used to treat acne. In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritus.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

In some embodiments, provided herein is a method of treating a cardiovascular disease in a subject that comprises administering to said subject a therapeutically effective amount of a compound as disclosed herein, or a pharmaceutically acceptable form (e.g., pharmaceutically acceptable salts, hydrates, solvates, chelates, non-covalent complexes, isomers, prodrugs, and isotopically labeled derivatives) thereof. Examples of cardiovascular conditions include, but are not limited to, atherosclerosis, restenosis, vascular occlusion and carotid obstructive disease.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

Further, the compounds described herein, or a pharmaceutically acceptable form (e.g., pharmaceutically acceptable salts, hydrates, solvates, chelates, non-covalent complexes, isomers, prodrugs, and isotopically labeled derivatives) thereof, can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes can be infectious (bacterial, viral or parasitic pathogens), autoimmune, or paraneoplastic.

In some embodiments, provided herein are compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, for the treatment of multiorgan failure. Also provided herein are compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, for the treatment of liver diseases (including diabetes), gall bladder disease (including gallstones), pancreatitis or kidney disease (including proliferative glomerulonephritis and diabetes-induced renal disease) or pain in a subject.

In some embodiments, provided herein are compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, for the prevention of blastocyte implantation in a subject.

In some embodiments, provided herein are compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, for the treatment of disorders involving platelet aggregation or platelet adhesion, including, but not limited to Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, are provided for treating a disease which is skeletal muscle atrophy, skeletal or muscle hypertrophy. In some embodiments, provided herein are compounds, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

In other embodiments, the compounds described herein can be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

In other embodiments, the compounds provided herein can be used for the treatment of Perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/ anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressler syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other embodiments, the compounds provided herein are used for the treatment of Autoimmune hepatitis, Jejunitis, Mesenteritis, Mucositis, Non alcoholic steatohepatitis, Non viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohns disease, Diverticulitis, Enteritis, Enterocolitis, Enterohepatitis, Eosinophilic esophagitis, Esophagitis, Gastritis, Hemorrhagic enteritis, Hepatitis, Hepatitis virus infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Brutons disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Nonne Milroy Meige syndrome, Spleen disease, Splenomegaly, Thymoma, Thymus disease, Perivasculitis, Phlebitis, Pleuropericarditis, Polyarteritis *nodosa*, Vasculitis, Takayasus arteritis, Temporal arteritis, Thromboangiitis, Thromboangiitis obliterans, Thromboendocarditis, Thrombophlebitis, or COPD.

In some embodiments, provided herein are methods of treating an inflammatory or autoimmune disease in a subject comprising administering to said subject a therapeutically effective amount of a compound provided herein, or a pharmaceutically acceptable salt, ester, prodrug, solvate, hydrate or derivative thereof. In some embodiments, the inflammatory or autoimmune disease includes asthma, rheumatoid arthritis, Crohn's disease, lupus, and multiple sclerosis.

In some embodiments, the inflammatory or autoimmune disease includes: idiopathic thrombocytopenic purpura; anemia, e.g., aplastic anemia; lupus, e.g., cutaneous lupus erythematosus; and pemphigoid, e.g., skin blistering bullous pemphigoid.

Also provided herein is a method of treating a cardiovascular disease in a mammal comprising administering to said mammal a therapeutically effective amount of a compound provided herein, or a pharmaceutically acceptable salt, ester, prodrug, solvate, hydrate, or derivative thereof. Examples of cardiovascular conditions include, but are not limited to, atherosclerosis, restenosis, vascular occlusion and carotid obstructive disease.

In another embodiment, provided herein are methods for disrupting the function of a leukocyte or disrupting a function of an osteoclast. In one embodiment, the method comprises contacting the leukocyte or the osteoclast with a function disrupting amount of a compound provided herein.

In another embodiment, provided herein are methods for treating ophthalmic disease by administering a compound provided herein or a pharmaceutical composition provided herein to the eye of a subject.

V. Combination Treatment

Also provided herein are methods for combination therapies in which an agent known to modulate other pathways, or other components of the same pathway, or even overlapping sets of target enzymes are used in combination with a compound provided herein, or a pharmaceutically acceptable salt, ester, prodrug, solvate, hydrate or derivative thereof. In one embodiment, such therapy includes, but is not limited to the combination of the subject compound with chemotherapeutic agents, therapeutic antibodies, and radiation treatment, to provide a synergistic or additive therapeutic effect.

In one embodiment, the compounds or pharmaceutical compositions provided herein can present synergistic or additive efficacy when administered in combination with agents that inhibit IgE production or activity. Such combination can reduce the undesired effect of high level of IgE associated with the use of one or more PI3Kδ inhibitors, if such effect occurs. In some embodiments, this can be particularly useful in treatment of autoimmune and inflammatory disorders (AIID) such as rheumatoid arthritis. Additionally, without being limited by a particular theory, the administration of PI3Kδ or PI3Kδ/γ inhibitors provided herein in combination with inhibitors of mTOR can also exhibit synergy through enhanced inhibition of the PI3K pathway.

In another embodiment, provided herein is a combination treatment of a disease associated with PI3Kδ comprising administering to a subject a PI3Kδ inhibitor and an agent that inhibits IgE production or activity. Other exemplary PI3Kδ inhibitors are applicable and they are described in, e.g., U.S. Pat. No. 6,800,620, incorporated by reference. In some embodiments, such combination treatment is particularly useful for treating autoimmune and inflammatory diseases (AIID), including but not limited to, rheumatoid arthritis.

Agents that inhibit IgE production are known in the art, and they include, but are not limited to, one or more of TEI-9874, 2-(4-(6-cyclohexyloxy-2-naphtyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies, such as, for example, Omalizumab and TNX-901.

For treatment of autoimmune diseases, the compounds or pharmaceutical compositions provided herein can be used in combination with commonly prescribed drugs, including but not limited to, Enbrel®, Remicade®, Humira®, Avonex®, and Rebif®. For treatment of respiratory diseases, the compounds or pharmaceutical compositions provided herein can be administered in combination with commonly prescribed drugs, including but not limited to, Xolair®, Advair®, Singulair®, and Spiriva®.

In one embodiment, the compounds provided herein can be formulated or administered in conjunction with other agents that act to relieve the symptoms of inflammatory conditions, such as encephalomyelitis, asthma, and the other diseases described herein. These agents include, but are not limited to, non-steroidal anti-inflammatory drugs (NSAIDs), e.g., acetylsalicylic acid; ibuprofen; naproxen; indomethacin; nabumetone; and tolmetin. In some embodiments, corticosteroids are used to reduce inflammation and suppress activity of the immune system. For example, one commonly prescribed drug of this type is Prednisone. Chloroquine (Aralen®) or hydroxychloroquine (Plaquenil®) can also be very useful in some individuals with lupus. They are often prescribed for skin and joint symptoms of lupus. Azathioprine (Imuran) and cyclophosphamide (CYTOXAN™) suppress inflammation and tend to suppress the immune system. Other agents, e.g., methotrexate and cyclosporin can be used to control the symptoms of lupus. Anticoagulants are employed to prevent blood from clotting rapidly. For example, they range from aspirin at very low dose which prevents platelets from sticking, to heparin/coumadin. Other compounds used in the treatment of lupus include belimumab (Benlysta®).

In another embodiment, provided herein is a pharmaceutical composition for inhibiting abnormal cell growth in a mammal, comprising an amount of a compound provided herein, or a pharmaceutically acceptable salt, ester, prodrug, solvate, hydrate or derivative thereof, in combination with an amount of an anti-cancer agent (e.g., a biotherapeutic or chemotherapeutic agent). Many chemotherapeutics are presently known in the art and can be used in combination with the compounds provided herein. Other cancer therapies, that can also be used in combination with the compounds provided herein, include, but are not limited to, surgery, surgical treatments, and radiation therapy.

In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples of anti-cancer agents include, e.g., chemotherapeutic agents, cytotoxic agents, and non-peptide small molecules such as Gleevec® (Imatinib Mesylate), Velcade® (bortezomib), CASODEX™ (bicalutamide), Iressa™ (gefitinib), and Adriamycin as well as a host of chemotherapeutic agents. Non-limiting examples of chemotherapeutic agents include, e.g., alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, CASODEX™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE®, Rhone-Poulenc Rorer, Antony, France); retinoic acid; esperamicins; and capecitabine; and pharmaceutically acceptable salts, solvates, or derivatives of any of the above. Also included as suitable chemotherapeutic cell conditioners are anti-hormonal agents that act to regulate or inhibit hormone action on tumors such as anti-estrogens including, for example, tamoxifen (Novaldex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; and difluoromethylornithine (DMFO). In some embodiments, the compounds or pharmaceutical composition provided herein can be used in combination with commonly prescribed anti-cancer drugs, such as, e.g., Herceptin®, Avastin®, Erbitux®, Rituxan®, Taxol®, Arimidex®, Taxotere®, and Velcade®.

Non-limiting examples are chemotherapeutic agents, cytotoxic agents, and non-peptide small molecules include ABVD, Avicine, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone®, Atiprimod, Azathioprine, Belotecan, Bendamustine, BIBW 2992, Biricodar, Brostallicin, Bryostatin, Buthionine sulfoximine, CBV (chemotherapy), Calyculin, Crizotinib, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar®, Tesetaxel, Triplatin tetranitrate, Tris(2-chloroethyl)amine, Troxacitabine, Uramustine, Vadimezan, Vinflunine, ZD6126, and Zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354. Additional examples of hedgehog inhibitors include, but are not limited to, GDC-0449 (also known as RG3616 or vismodegib) described in, e.g., Von Hoff D. et al., *N. Engl. J Med.* 2009; 361(12): 1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science. 1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACSMed. Chem. Lett.*, 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), *vinca* alkaloids (e.g., vincristine, vinblastine, vindesine, and vinorelbine), taxoids (e.g., paclitaxel or a paclitaxel equivalent such as nanoparticle albumin-bound paclitaxel (Abraxane), docosahexaenoic acid bound-paclitaxel (DHA-paclitaxel, Taxoprexin®), polyglutamate bound-paclitaxel (PG-paclitaxel, paclitaxel poliglumex, CT-2103, XYOTAX™), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLA- DIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade®), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., Herceptin® (trastuzumab), T-DM1, AVASTIN® (bevacizumab), ERBITUX® (cetuximab), Vectibix® (panitumumab), Rituxan® (rituximab), and Bexxar® (tositumomab)).

In some embodiments, the chemotherapeutic is selected from HSP90 inhibitors. The HSP90 inhibitor can be a geldanamycin derivative, e.g., a benzoquinone or hygroquinone ansamycin HSP90 inhbitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors disclosed herein and those PI3K inhibitors not disclosed herein). In some embodiment, the PI3K inhibitor is an inhibitor of delta and gamma isoforms of PI3K. In some embodiments, the the PI3K inhibitor is an inhibitor of alpha isoforms of PI3K. In other embodiments, the PI3K inhibitor is an inhibitor of one or more alpha, beta, delta and gamma isoforms of PI3K. Exemplary PI3K inhibitors that can be used in combination are described in, e.g., WO 09/088990, WO 09/088086, WO 2011/008302, WO 2010/036380, WO 2010/006086, WO 09/114870, WO 05/113556; US 2009/0312310, and US 2011/0046165. Additional PI3K inhibitors that can be used in combination with the pharmaceutical compositions include but are not limited to, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235). In one embodiment, the PI3K inhibitor is an isoquinolinone.

Also provided herein is a method for using the compounds as disclosed herein, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein in combination with radiation therapy in inhibiting abnormal cell growth or treating the hyperproliferative disorder in a mammal. Techniques for administering radiation therapy are known in the art, and these techniques can be used in the combination therapy described herein. In such combination therapy, the compound provided herein can be administered as described herein.

In one embodiment, radiation therapy can be administered through one of several methods, or a combination of methods, including without limitation, external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner described herein include both solids and liquids. By way of non-limiting example, the radiation source can be a radionuclide, such as I-125, I-131, Yb-169, or Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

Without being limited by any theory, the compounds provided herein can render abnormal cells more sensitive to treatment with radiation for purposes of killing and/or inhibiting the growth of such cells. Accordingly, provided herein is a method for sensitizing abnormal cells in a mammal to treatment with radiation which comprises administering to the mammal an amount of a compound provided herein, or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

In one embodiment, the compounds or pharmaceutical compositions provided herein can be used in combination with an amount of one or more substances selected from anti-angiogenesis agents, signal transduction inhibitors, antiproliferative agents, glycolysis inhibitors, or autophagy inhibitors.

In one embodiment, anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound provided herein or a pharmaceutical composition described herein. Examples of useful COX-II inhibitors include Celebrex® (alecoxib), valdecoxib, and rofecoxib. Examples of useful matrix metalloproteinase inhibitors are described in, e.g., WO 96/33172, WO 96/27583, European Patent Application No. 97304971.1, European Patent Application No. 99308617.2, WO 98/07697, WO 98/03516, WO 98/34918, WO 98/34915, WO 98/33768, WO 98/30566, European Patent Publication 606,046, European Patent Publication 931,788, WO 90/05719, WO 99/52910, WO 99/52889, WO 99/29667, PCT International Application No. PCT/IB98/01113, European Patent Application No. 99302232.1, Great Britain Patent Application No. 9912961.1, U.S. Pat. Nos. 7,030,242, 5,863,949, 5,861,510, and European Patent Publication 780,386, all of which are incorporated herein by reference in their entireties. In one embodiment, MMP-2 and MMP-9 inhibitors are those that have little or no activity inhibiting MMP-1, or are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13). Some non-limiting examples of MMP inhibitors useful in the present disclosure are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including, but not limited to ATG5 (which are implicated in autophagy), can also be used.

Also provided herein are a method of, and a pharmaceutical composition for, treating a cardiovascular disease in a mammal comprising an amount of a compound provided herein, or a pharmaceutically acceptable salt, ester, prodrug, solvate, hydrate or derivative thereof, and an amount of one or more second therapeutic agent(s) useful for the treatment of cardiovascular diseases.

Examples of second therapeutic agents for use in treating cardiovascular diseases include, but are not limited to, anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. In one embodiment, a coating can be used to effect therapeutic delivery focally within the vessel wall. In one embodiment, antibiotics can also be included in combinations or coatings provided herein. In one embodiment, by incorporation of an active agent in a swellable polymer, the active agent can be released upon swelling of the polymer.

In one embodiment, the compounds describe herein can be formulated or administered in conjunction with liquid or solid tissue barriers also known as lubricants. Examples of tissue barriers include, but are not limited to, polysaccharides, polyglycans, seprafilm, interceed, and hyaluronic acid.

In one embodiment, medicaments that can be administered in conjunction with the compounds described herein include suitable drugs that can be delivered by inhalation, for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. In one embodiment, it will be clear to a person skilled in the art that, where appropriate, the medicaments can be used in a form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include, but are not limited to, agents as described herein, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

In one embodiment, therapeutic agents can also include one or more agents for pain and inflammation, such as, e.g., histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers, and leukotriene inhibitors.

In one embodiment, additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, P3-adrenergic receptor antagonists, agents for the treatment of hypercholesterolemia, and agents for the treatment of dyslipidemia.

In one embodiment, other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease, therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. In one embodiment, other therapeutic agents include antimicrobial agents, sulfonamides, trimethoprim-sulfamethoxazole quinolones, and agents for urinary tract infections, penicillins, cephalosporins, and other, beta-Lactam antibiotics, an agent comprising an aminoglycoside, protein synthesis inhibitors, drugs used in the chemotherapy of tuberculosis, *Mycobacterium avium* complex disease, and leprosy, antifungal agents, and antiviral agents including nonretroviral agents and antiretroviral agents.

In one embodiment, examples of therapeutic antibodies that can be combined with a compound provided herein include, but are not limited to, anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

In other embodiments, therapeutic agents used for immunomodulation, such as immunomodulators, immunosuppressive agents, tolerogens, and immunostimulants, are contemplated by the methods provided herein. In further embodiments, therapeutic agents acting on the blood and the blood-forming organs, hematopoietic agents, growth factors, minerals, vitamins, anticoagulant, thrombolytic, and antiplatelet drugs are contemplated by the methods provided herein.

In one embodiment, for treating renal carcinoma, one can combine a compound as disclosed herein, or a pharmaceutically acceptable form (e.g., pharmaceutically acceptable salts, hydrates, solvates, chelates, non-covalent complexes, isomers, prodrugs, and isotopically labeled derivatives) thereof, or pharmaceutical compositions as disclosed herein, with sorafenib and/or avastin. For treating an endometrial disorder, one can combine a compound as disclosed herein with doxorubincin, taxotere (taxol), and/or cisplatin (carboplatin). For treating ovarian cancer, one can combine a compound as disclosed herein with cisplatin (carboplatin), taxotere, doxorubincin, topotecan, and/or tamoxifen. For treating breast cancer, one can combine a compound as disclosed herein with taxotere (Taxol®), gemcitabine (capecitabine), tamoxifen, letrozole, Tarceva®, lapatinib, PD0325901, Avastin®, Herceptin®, OSI-906, and/or OSI-930. For treating lung cancer, one can combine a compound as disclosed herein with taxotere (taxol), gemcitabine, cisplatin, pemetrexed, Tarceva®, PD0325901, and/or Avastin®.

In one embodiment, further therapeutic agents that can be combined with a subject compound can be found in Goodman and Gilman's "The Pharmacological Basis of Therapeutics" Eleventh Edition; or the Physician's Desk Reference, both of which are incorporated herein by reference in their entirety.

In one embodiment, the compounds described herein can be used in combination with the agents disclosed herein or other suitable agents, depending on the condition being treated. Hence, in some embodiments the compounds provided herein will be co-administered with other agents as described herein. When used in combination therapy, the compounds described herein can be administered with the second agent simultaneously or separately. This administration in combination can include simultaneous administration of the two agents in the same dosage form, simultaneous administration in separate dosage forms, and separate administration. In one embodiment, a compound described herein and any of the additional agents described herein can be formulated together in the same dosage form and administered simultaneously. Alternatively, a compound provided herein and any of the additional agents described herein can be simultaneously administered, wherein the compound and the agent(s) are present in separate formulations. In another alternative, a compound provided herein can be administered before, or after, the administration of any of the additional agents described herein. In a separate administration protocol, a compound provided herein and any of the additional agents described herein can be administered a few minutes apart, or a few hours apart, or a few days apart.

The examples and preparations provided below further illustrate and exemplify the compounds, polymorphs, and compositions provided herein and methods of preparing such compounds, polymorphs, and compositions. It is to be understood that the scope of the present disclosure is not limited in any way by the scope of the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

EXAMPLES

Chemical Examples

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours. As used herein, the term "volume" or "vol." refers to 1 liter of solvent per kilogram of limiting reagent.

Isolation and purification of the chemical entities and intermediates described herein can be effected, optionally, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are given by reference to the examples hereinbelow. However, other equivalent separation or isolation procedures can also be used.

In some embodiments, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in preparing the disclosed compounds and is not intended to limit the scope of reactions or reaction sequences that can be used in preparing the compounds provided herein.

The polymorphs made according to the methods provided herein can be characterized by any methodology known in the art. For example, the polymorphs made according to the methods provided herein can be characterized by X-ray powder diffraction (XRPD), differential scanning calorimetry (DSC), thermogravimetric analysis (TGA), dynamic vapor sorption (DVS), hot-stage microscopy, optical microscopy, Karl Fischer analysis, melting point, spectroscopy (e.g., Raman, solid state nuclear magnetic resonance (ss-NMR), liquid state nuclear magnetic resonance ($^1$H- and $^{13}$C-NMR), and FT-IR), thermal stability, grinding stability, and solubility, among others.

XRPD

Compounds and polymorphs provided herein can be characterized by X-ray powder diffraction patterns (XRPD). The relative intensities of XRPD peaks can vary depending upon the sample preparation technique, the sample mounting procedure and the particular instrument employed, among other parameters. Moreover, instrument variation and other factors can affect the 2θ peak values. Therefore, in certain embodiments, the XRPD peak assignments can vary by plus or minus about 0.2 degrees theta or more, herein referred to as "(±0.2°)".

XRPD patterns for each of Forms A-J and amorphous form of the compound of Formula (I) were collected with a PANalytical CubiX XPert PRO MPD diffractometer using an incident beam of CU radiation produced using an Optix long, fine-focus source. An elliptically graded multilayer mirror was used to focus Cu Kα X-rays through the specimen and onto the detector. Samples were placed on Si zero-return ultra-micro sample holders. Analysis was performed using a 10 mm irradiated width and the following parameters were set within the hardware/software:

X-ray tube: Cu Kα, 45 kV, 40 mA
Detector: X'Celerator
Slits: ASS Primary Slit: Fixed 1°
Divergence Slit (Prog): Automatic—5 mm irradiated length
Soller Slits: 0.02 radian
Scatter Slit (PASS): Automatic—5 mm observed length
Scanning
Scan Range: 3.0-45.0°
Scan Mode: Continuous
Step Size: 0.03°
Time per Step: 10 s
Active Length: 2.54°

DSC

Compounds and polymorphs provided herein can be characterized by a characteristic differential scanning calorimeter (DSC) thermogram. For DSC, it is known in the art that the peak temperatures observed will depend upon the rate of temperature change, the sample preparation technique, and the particular instrument employed, among other parameters. Thus, the peak values in the DSC thermograms reported herein can vary by plus or minus about 2° C., plus or minus about 3° C., plus or minus about 4° C., plus or minus about 5° C., plus or minus about 6° C., to plus or minus about 7° C., or more. For some polymorph Forms, DSC analysis was performed on more than one sample which illustrates the known variability in peak position, for example, due to the factors mentioned above. The observed peak positional differences are in keeping with expectation by those skilled in the art as indicative of different samples of a single polymorph Form of a compound of Formula (I).

Impurities in a sample can also affect the peaks observed in any given DSC thermogram. In some embodiments, one or more chemical entities that are not the polymorph of a compound of Formula (I) in a sample being analyzed by DSC can result in one or more peaks at lower temperature than peak(s) associated with the transition temperature of a given polymorph as disclosed herein.

DSC analyses were performed using a Mettler 822e differential scanning calorimeter. Samples were weighed in an aluminum pan, covered with a pierced lid, and then crimped. General analysis conditions were about 30° C. to about 300° C.-about 350° C. ramped at about 10° C./min. Several additional ramp rates were utilized as part of the investigation into the high melt Form B, including about 2° C./min, about 5° C./min, and about 20° C./min. Samples were analyzed at multiple ramp rates to measure thermal and kinetic transitions observed.

Isothermal holding experiments were also performed utilizing the DSC. Samples were ramped at about 10° C./min to temperature (about 100° C. to about 250° C.) and held for about five minutes at temperature before rapid cooling to room temperature. In these cases, samples were then analyzed by XRPD or reanalyzed by DSC analysis.

TGA

A polymorphic form provided herein can give rise to thermal behavior different from that of an amorphous material or another polymorphic form. Thermal behavior can be measured in the laboratory by thermogravimetric analysis (TGA) which can be used to distinguish some polymorphic forms from others. In one embodiment, a polymorph as disclosed herein can be characterized by thermogravimetric analysis.

TGA analyses were performed using a Mettler 851e SDTA/TGA thermal gravimetric analyzer. Samples were weighed in an alumina crucible and analyzed from about 30° C. to about 230° C. and at a ramp rate of about 10° C./min.

DVS

Compounds and polymorphs provided herein can be characterized by moisture sorption analysis. This analysis was performed using a Hiden IGAsorp Moisture Sorption instrument. Moisture sorption experiments were carried out at about 25° C. by performing an adsorption scan from about 40% to about 90% RH in steps of about 10% RH and a desorption scan from about 85% to about 0% RH in steps of about −10% RH. A second adsorption scan from about 10% to about 40% RH was performed to determine the moisture uptake from a drying state to the starting humidity. Samples were allowed to equilibrate for about four hours at each point or until an asymptotic weight was reached. After the isothermal sorption scan, samples were dried for about one hour at elevated temperature (about 60° C.) to obtain the dry weight. XRPD analysis on the material following moisture sorption was performed to determine the solid form.

Optical Microscopy

Compounds and polymorphs provided herein can be characterized by microscopy, such as optical microscopy. Optical microscopy analysis was performed using a Leica DMRB Polarized Microscope. Samples were examined with a polarized light microscope combined with a digital camera (1600×1200 resolution). Small amounts of samples were dispersed in mineral oil on a glass slide with cover slips and viewed with 100× magnification.

Karl Fischer Analysis

Compounds and polymorphs provided herein can be characterized by Karl Fischer analysis to determine water content. Karl Fischer analysis was performed using a Metrohm 756 KF Coulometer. Karl Fisher titration was performed by adding sufficient material to obtain 50 µg of water, about 10 to about 50 mg of sample, to AD coulomat.

Raman Spectroscopy

Compounds and polymorphs provided herein can be characterized by Raman spectroscopy. Raman spectroscopy analysis was performed using a Kaiser RamanRXN1 instrument with the samples in a glass well. Raman spectra were collected using a PhAT macroscope at about 785 nm irradiation frequency and about 1.2 mm spot size. Samples were analyzed using 12 to 16 accumulations with about 0.5 to about 12 second exposure time and utilized cosmic ray filtering. The data was processed by background subtraction of an empty well collected with the same conditions. A baseline correction and smoothing was performed to obtain interpretable data when necessary.

FT-IR

Compounds and polymorphs provided herein can be characterized by FT-IR spectroscopy. FT-IR spectroscopy was performed using either a Nicolet *Nexus* 470 or Avatar 370 Infrared Spectrometer and the OMNIC software. Samples were analyzed using a diamond Attenuated Total Reflection (ATR) accessory. A compound sample was applied to the diamond crystal surface and the ATR knob was turned to apply the appropriate pressure. The spectrum was then acquired and analyzed using the OMNIC software. Alternative sample preparations include solution cells, mulls, thin films, and pressed discs, such as those made of KBr, as known in the art.

NMR

Compounds and polymorphs provided herein can be characterized by nuclear magnetic resonance (NMR). NMR spectra were obtained using a 500 MHz Bruker AVANCE with 5-mm BBO probe instrument. Samples (approximately 2 to approximately 10 mg) were dissolved in DMSO-d6 with 0.05% tetramethylsilane (TMS) for internal reference. $^1$H-NMR spectra were acquired at 500 MHz using 5 mm broadband observe (1H-X) Z gradient probe. A 30 degree pulse with 20 ppm spectral width, 1.0 s repetition rate, and 32-64 transients were utilized in acquiring the spectra.

High-Performance Liquid Chromatography

Compounds and polymorphs provided herein can be analyzed by high-performance liquid chromatography using an Agilent 1100 instrument. The instrument parameters for achiral HPLC are as follows:

Column: Sunfire C18 4.6×150 mm

Column Temperature: Ambient

Auto-sampler Temperature: Ambient

Detection: UV at 250 nm

Mobile Phase A: 0.05% trifluoroacetic acid in water

Mobile Phase B: 0.05% trifluoroacetic acid in MeCN

Flow Rate: 1.0 mL/minute

Injection Volume: 10 µL

Data Collection time: 20 minutes

Re-equilibration Time: 5 minutes

Diluent & Needle Wash: MeOH

Gradient Conditions:

| Time (minutes) | % A | % B |
| --- | --- | --- |
| 0.0 | 90 | 10 |
| 3.5 | 90 | 10 |
| 10.0 | 10 | 90 |
| 15.0 | 10 | 90 |
| 18.0 | 90 | 10 |
| 20.0 | 90 | 10 |

Compounds and polymorphs provided herein can be analyzed by high-performance liquid chromatography using a chiral HPLC column to determine % ee values:

Column: Chiralpak IC, 4.6 mm×250 mm, 5 µm.

Column Temperature: Room Temperature

Sample Temperature: Room Temperature

Detection: UV at 254 nm

Mobile Phase A: 60% Hexane 40% (IPA:EtOH=2:3) with 0.2% Acetic Acid and 0.1% DEA Isocratic: 100% A Flow Rate: 1 mL/min Diluent: Methanol Injection Volume: 10 µL Analysis Time: 25 min

Example 1

Synthesis of (S)-3-(1-aminoethyl)-8-chloro-2-phenylisoquinolin-1(2H)-one

Example 1A

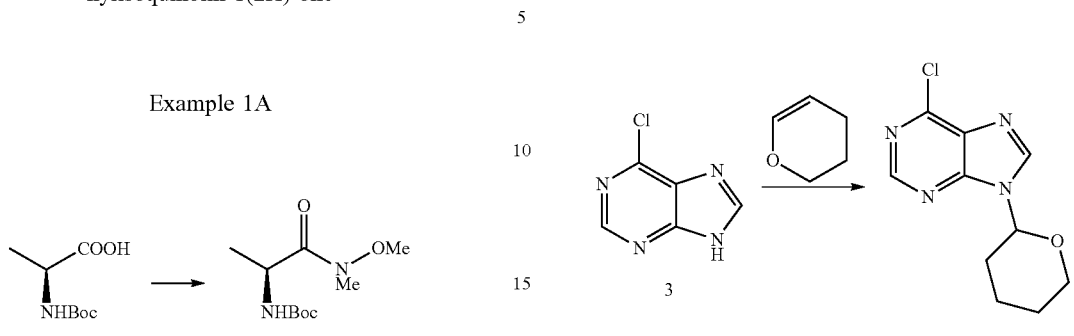

Compound 1 (6.00 kg) was treated with 1-hydroxybenzotriazole monohydrate (HOBt.H₂O), triethylamine, N,O-dimethylhydroxylamine hydrochloride, and EDCI in dimethylacetamide (DMA) at 10° C. The reaction was monitored by proton NMR and deemed complete after 2.6 hours, affording Compound 2 as a white solid in 95% yield. The R-enantiomer was not detected by proton NMR using (R)-(−)-alpha-acetylmandelic acid as a chiral-shift reagent.

Example 1B

Compound 3 (4.60 kg) was treated with p-toluenesulfonic acid monohydrate and 3,4-dihydro-2H-pyran (DHP) in ethyl acetate at 75° C. for 2.6 hours. The reaction was monitored by HPLC. Upon completion of the reaction, Compound 4 was obtained as a yellow solid in 80% yield with >99% (AUC) purity by HPLC analysis.

Example 1C

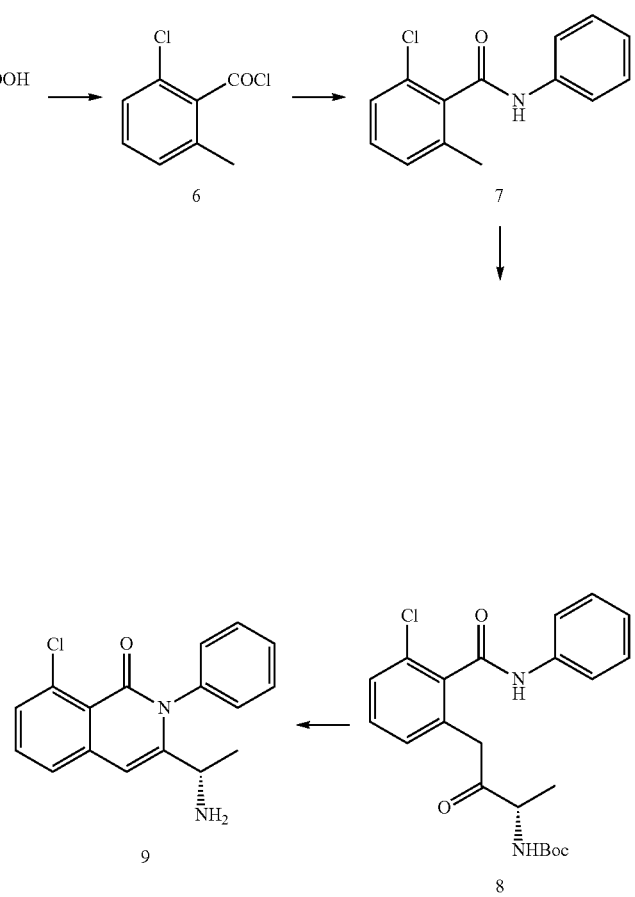

Compound 5 (3.30 kg) was treated with thionyl chloride and a catalytic amount of DMF in methylene chloride at 25° C. for five hours. The reaction was monitored by HPLC which indicated a 97.5% (AUC) conversion to compound 6. Compound 6 was treated in situ with aniline in methylene chloride at 25° C. for 15 hours. The reaction was monitored by HPLC and afforded Compound 7 as a brown solid in 81% yield with >99% (AUC) purity by HPLC analysis.

Compound 2 was treated with 2.0 M isopropyl Grignard in THF at −20° C. The resulting solution was added to Compound 7 (3.30 kg) pre-treated with 2.3 M n-hexyl lithium in tetrahydrofuran at −15° C. The reaction was monitored by HPLC until a 99% (AUC) conversion to Compound 8 was observed. Compound 8 was treated in situ with concentrated HCl in isopropyl alcohol at 70° C. for eight hours. The reaction was monitored by HPLC and afforded Compound 9 as a brown solid in 85% yield with 98% (AUC) purity and 84% (AUC) ee by HPLC analysis.

Example 1D

Compound 9 (3.40 kg) was treated with D-tartaric acid in methanol at 55° C. for 1-2 hours. The batch was filtered and treated with ammonium hydroxide in deionized (DI) water to afford enantiomerically enriched Compound 9 as a tan solid in 71% yield with >99% (AUC) purity and 91% (AUC) ee by HPLC analysis.

Example 2

Synthesis of (S)-3-(1-aminoethyl)-8-chloro-2-phenylisoquinolin-1(2H)-one

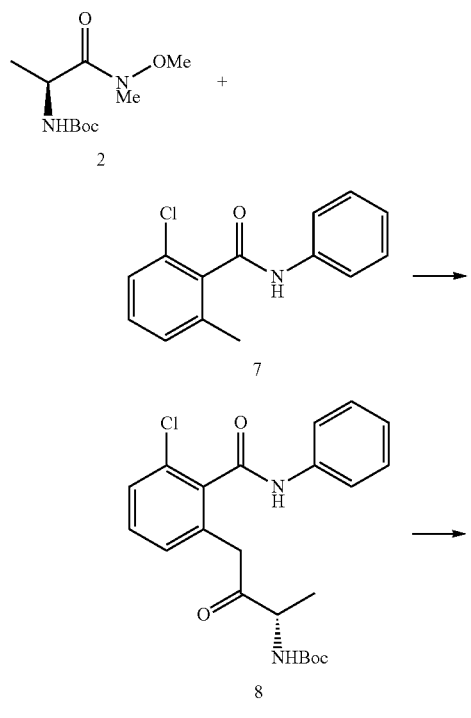

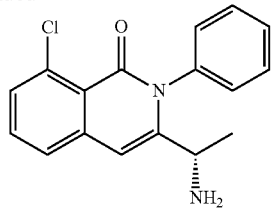

Example 2A

To Compound 7 (20.1 g) was charged 100 mL of anhydrous THF. The resulting solution was cooled to about −10° C. and 80 mL of n-hexyl lithium (2.3 M in hexanes, 2.26 equiv.) was slowly added (e.g., over about 20 min). The resulting solution was stirred at about −10° C. for about 20 min.

To Compound 2 (26.5 g; 1.39 equiv.) was charged 120 mL of anhydrous THF. The resulting mixture was cooled to about −10° C. and 60 mL of isopropyl magnesium chloride (2.0 M in THF, 1.47 equiv.) was slowly added (e.g., over about 15-20 min). The resulting mixture was then stirred at about −10° C. for about 20 min. The mixture prepared from Compound 2 was added to the solution prepared from Compound 7 while maintaining the internal temperature between about −10 and about 0° C. After the addition was complete (about 5 min), the cold bath was removed, and the resulting mixture was stirred at ambient temperature for about 1 h, then cooled.

A solution of 100 mL of anisole and 33 mL of isobutyric acid (4.37 equiv.) was prepared. The anisole solution was cooled to an internal temperature of about −3° C. The above reaction mixture was added to the anisole solution such that the internal temperature of the anisole solution was maintained at below about 5° C. The ice bath was then removed (after about 15 min, the internal temperature was about 7° C.). To the mixture, 100 mL of 10 wt % aqueous NaCl solution was rapidly added (the internal temperature increased from about 7° C. to about 15° C.). After stirring for about 30 min, the two phases were separated. The organic phase was washed with another 100 mL of 10 wt % aqueous NaCl. The organic phase was transferred to a flask using 25 mL of anisole to facilitate the transfer. The anisole solution was then concentrated to 109 g. Then, 100 mL of anisole was added.

To the approximately 200 mL of anisole solution was added 50 mL of TFA (8 equiv.) while maintaining the internal temperature below about 45-50° C. The resulting solution warmed to about 45-50° C. and stirred for about 15 hrs, then cooled to 20-25° C. To this solution was added 300 mL of MTBE dropwise and then the resulting mixture was held at 20-25° C. for 1 h. The mixture was filtered, and the wet cake washed with approximately 50 mL of MTBE. The wet cake was conditioned on the filter for about 1 h under nitrogen. The wet cake was periodically mixed and re-smoothed during conditioning. The wet cake was then washed with 200 mL of MTBE. The wet cake was further conditioned for about 2 h (the wet cake was mixed and resmoothed after about 1.5 h). The wet cake was dried in a vacuum oven at about 40° C. for about 18 h to afford Compound 9•TFA salt in about 97.3% purity (AUC), which had about 99.1% S-enantiomer (e.g., chiral purity of about 99.1%).

Compound 9•TFA salt (3 g) was suspended in 30 mL of EtOAc at about 20° C. To the EtOAc suspension was added 4.5 mL (2.2 eq.) of a 14% aqueous ammonium hydroxide solution and the internal temperature decreased to about 17° C. Water (5 mL) was added to the biphasic mixture. The biphasic mixture was stirred for 30 min. The mixing was stopped and the phases were allowed to separate. The aqueous phase was removed. To the organic phase (combined with 5 mL of EtOAc) was added 10 mL of 10% aqueous NaCl. The biphasic mixture was stirred for about 30 min. The aqueous phase was removed. The organic layer was concentrated to 9 g. To this EtOAc mixture was added 20 mL of i-PrOAc. The resulting mixture was concentrated to 14.8 g. With stirring, 10 mL of n-heptane was added dropwise. The suspension was stirred for about 30 min, then an additional 10 mL of n-heptane was added. The resulting suspension was stirred for 1 h. The suspension was filtered and the wet cake was washed with additional heptane. The wet cake was conditioned for 20 min under nitrogen, then dried in a vacuum oven at about 40° C. to afford Compound 9 free base in about 99.3% purity (AUC), which had about 99.2% S-enantiomer (e.g., chiral purity of about 99.2%).

Example 2B

A mixture of Compound 7 (100 g, 0.407 mol, 1 wt) and THF (500 mL, 5 vol) was prepared and cooled to about 3° C. n-Hexyllithium (2.3 M in hexanes, 400 mL, 0.920 mol, 2.26 equiv) was charged over about 110 minutes while maintaining the temperature below about 6° C. The resulting solution was stirred at 0±5° C. for about 30 minutes. Concurrently, a mixture of Compound 2 (126 g, 0.541 mol, 1.33 equiv) and THF (575 mL, 5.8 vol) was prepared. The resulting slurry was charged with isopropylmagnesium chloride (2.0 M in THF, 290 mL, 0.574 mol, 1.41 equiv) over about 85 minutes while maintaining the temperature below about 5° C. The resulting mixture was stirred for about 35 minutes at 0±5° C. The Compound 2 magnesium salt mixture was transferred to the Compound 7 lithium salt mixture over about 1 hour while maintaining a temperature of 0±5° C. The solution was stirred for about 6 minutes upon completion of the transfer.

The solution was added to an about −5° C. stirring solution of isobutyric acid (165 mL, 1.78 mol, 4.37 equiv) in anisole (500 mL, 5 vol) over about 20 minutes during which time the temperature did not exceed about 6° C. The resulting solution was stirred for about 40 minutes while being warmed to about 14° C. Then, a 10% sodium chloride solution (500 mL, 5 vol) was rapidly added to the reaction. The temperature rose to about 21° C. After agitating the mixture for about 6 minutes, the stirring was ceased and the lower aqueous layer was removed (about 700 mL). A second portion of 10% sodium chloride solution (500 mL, 5 vol) was added and the mixture was stirred for 5 minutes. Then, the stirring was ceased and the lower aqueous layer was removed. The volume of the organic layer was reduced by vacuum distillation to about 750 mL (7.5 vol).

Trifluoroacetic acid (250 mL, 3.26 mol, 8.0 equiv) was added and the resulting mixture was agitated at about 45° C. for about 15 hours. The mixture was cooled to about 35° C. and MTBE (1.5 L, 15 vol) was added over about 70 minutes. Upon completion of the addition, the mixture was agitated for about 45 minutes at about 25-30° C. The solids were collected by vacuum filtration and conditioned under $N_2$ for about 20 hours to afford Compound 9•TFA salt in about 97.5% purity (AUC), which had a chiral purity of about 99.3%.

Compound 9•TFA salt (100 g) was suspended EtOAc (1 L, 10 vol) and 14% aqueous ammonia (250 mL, 2.5 vol). The mixture was agitated for about 30 minutes, then the lower aqueous layer was removed. A second portion of 14% aqueous ammonia (250 mL, 2.5 vol) was added to the organic layer. The mixture was stirred for 30 minutes, then the lower aqueous layer was removed. Isopropyl acetate (300 mL, 3 vol) was added, and the mixture was distilled under vacuum to 500 mL (5 vol) while periodically adding in additional isopropyl acetate (1 L, 10 vol).

Then, after vacuum-distilling to a volume of 600 mL (6 vol), heptanes (1.5 L, 15 vol) were added over about 110 minutes while maintaining a temperature between about 20° C. and about 30° C. The resulting slurry was stirred for about 1 hour, then the solid was collected by vacuum filtration. The cake was washed with heptanes (330 mL, 3.3 vol) and conditioned for about 1 hour. The solid was dried in an about 45° C. vacuum oven for about 20 hours to afford Compound 9 free base in about 99.23% purity (AUC), which has a chiral purity of about 99.4%.

Example 3

Chiral Resolution of (S)-3-(1-aminoethyl)-8-chloro-2-phenylisoquinolin-1(2H)-one (Compound 9)

In some instances, (S)-3-(1-aminoethyl)-8-chloro-2-phenylisoquinolin-1(2H)-one (Compound 9) obtained by synthesis contained a minor amount of the corresponding (R)-isomer. Chiral resolution procedures were utilized to improve the enantiomeric purity of certain samples of (S)-3-(1-aminoethyl)-8-chloro-2-phenylisoquinolin-1(2H)-one.

In one experiment, Compound 9 (3.40 kg) was treated with D-tartaric acid in methanol at about 55° C. for about 1 to about 2 hours. The mixture was filtered and treated with ammonium hydroxide in deionized (DI) water to afford Compound 9 in greater than about 99% (AUC) purity, which had a chiral purity of about 91% (AUC).

In another procedure, MeOH (10 vol.) and Compound 9 (1 equiv.) were stirred at 55±5° C. D-Tartaric acid (0.95 equiv.) was charged. The mixture was held at 55±5° C. for about 30 min and then cooled to about 20 to about 25° C. over about 3 h. The mixture was held for about 30 min and then filtered. The filter cake was washed with MeOH (2.5 vol.) and then conditioned. The cake was returned to the reactor and water (16 vol.) was charged. The mixture was stirred at 25±5° C. $NH_4OH$ was then charged over about 1 h adjusting the pH to about 8 to about 9. The mixture was then filtered and the cake was washed with water (4 vol.) and then heptanes (4 vol.). The cake was conditioned and then vacuum dried at 45-50° C. to afford Compound 9 free base with a chiral purity of about 99.0%.

Example 4

Synthesis of (S)-3-(1-(9H-purin-6-ylamino)ethyl)-8-chloro-2-phenylisoquinolin-1(2H)-one

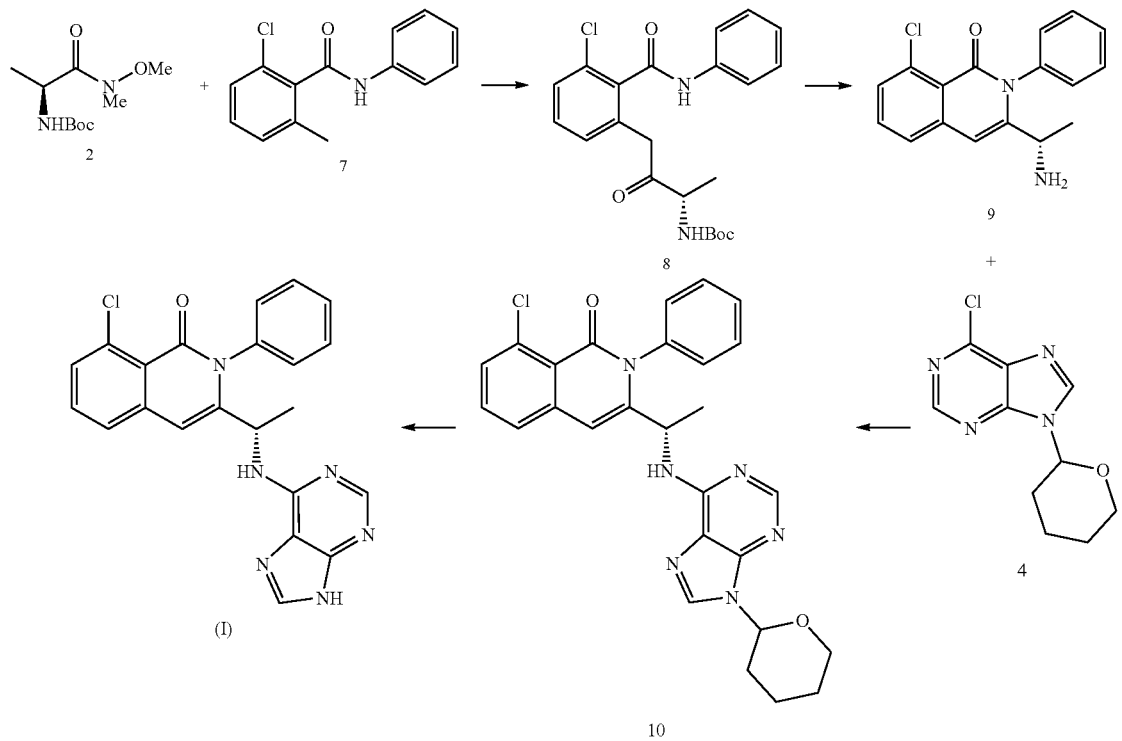

A mixture of Compound 7 (1 equiv.) and anhydrous THF (5 vol.) was prepared. Separately, a mixture of Compound 2 (1.3 equiv.) and anhydrous THF (5 vol.) was prepared. Both mixtures were stirred for about 15 min at about 20 to about 25° C. and then cooled to −25±15° C. n-Hexyl lithium (2.05 equiv.) was added to the Compound 7 mixture, maintaining the temperature at >5° C. i-PrMgCl (1.33 equiv.) was added to the Compound 2 mixture, maintaining the temperature at >5° C. The Compound 2 mixture was transferred to the Compound 7 mixture under anhydrous conditions at 0±5° C. The resulting mixture was warmed to 20±2° C. and held for about 1 h. Then, the reaction was cooled to −5±5° C., and 6 N HCl (3.5 equiv.) was added to quench the reaction, maintaining temperature at below about 25° C. The aqueous layer was drained, and the organic layer was distilled under reduced pressure until the volume was 2-3 volumes. IPA (3 vol.) was added and vacuum distillation was continued until the volume was 2-3 volumes. IPA (8 vol.) was added and the mixture temperature was adjusted to about 60° C. to about 75° C. Conc. HCl (1.5 vol.) was added and the mixture was subsequently held for 4 hours. The mixture was distilled under reduced pressure until the volume was 2.5-3.5 volumes. The mixture temperature was adjusted to 30±10° C. DI water (3 vol.) and DCM (7 vol.) were respectively added to the mixture. Then, NH₄OH was added to the mixture, adjusting the pH to about 7.5 to about 9. The temperature was adjusted to about 20 to about 25° C. The layers were separated and the aqueous layer was washed with DCM (0.3 vol.). The combined DCM layers were distilled until the volume was 2 volumes. i-PrOAc (3 vol.) was added and vacuum distillation was continued until the volume was 3 volumes. The temperature was adjusted to about 15 to about 30° C. Heptane (12 vol.) was charged to the organic layer, and the mixture was held for 30 min. The mixture was filtered and filter cake was washed with heptane (3 vol.). The cake was vacuum dried at about 45° C. afford Compound 9.

Then, MeOH (10 vol.) and Compound 9 (1 equiv.) were combined and stirred while the temperature was adjusted to 55±5° C. D-Tartaric acid (0.95 equiv.) was charged. The mixture was held at 55±5° C. for about 30 min and then cooled to about 20 to about 25° C. over about 3 h. The mixture was held for 30 min and then filtered. The filter cake was washed with MeOH (2.5 vol.) and then conditioned. Water (16 vol.) was added to the cake and the mixture was stirred at 25±5° C. NH₄OH was charged over 1 h adjusting the pH to about 8 to about 9. The mixture was then filtered and the resulting cake washed with water (4 vol.) and then heptanes (4 vol.). The cake was conditioned and then vacuum dried at 45-50° C. to afford Compound 9.

To a mixture of i-PrOH (4 vol.) and Compound 9 (1 equiv.) was added Compound 4 (1.8 equiv.), Et₃N (2.5 equiv.) and i-PrOH (4 vol.). The mixture was agitated and the temperature was adjusted to 82±5° C. The mixture was held for 24 h. Then the mixture was cooled to about 20 to about 25° C. over about 2 h. The mixture was filtered and the cake was washed with i-PrOH (2 vol.), DI water (25 vol.) and n-heptane (2 vol.) respectively. The cake was conditioned and then vacuum dried at 50±5° C. to afford Compound 10. To a mixture of EtOH (2.5 vol.) and Compound 10 (1 equiv.) was added EtOH (2.5 vol.) and DI water (2 vol.). The mixture was agitated at about 20 to about 25° C. Conc. HCl (3.5 equiv.) was added and the temperature was adjusted to 35±5° C. The mixture was held for about 1.5 h. The mixture was cooled to 25±5° C. and then polish filtered to a particulate free vessel. NH₄OH was added, adjusting the pH to about 8 to about 9. Crystal seeds of Form C of a compound of Formula (I) (0.3 wt %) were added to the mixture which was held for 30 minutes. DI water (13 vol.) was added over about 2 h. The mixture was held for 1 h and then filtered. The resulting cake was washed with DI water (4 vol.) and n-heptane (2 vol.) respectively. The cake was conditioned for about 24 h and then DCM (5 vol.) was added. This mixture was agitated for about 12 h at about 20 to about 25° C. The mixture was filtered and the cake washed with DCM (1 vol.). The cake was conditioned for about 6 h. The cake was then vacuum-dried at 50±5° C. To the cake was added DI water (10 vol.), and i-PrOH (0.8 vol.) and the mixture was agitated at 25±5° C. for about 6 h. An XRPD sample confirmed the compound of Formula (I) was Form C. The mixture was filtered and the cake was washed with DI water (5 vol.) followed by n-heptane (3 vol.). The cake was conditioned and then vacuum dried at 50±5° C. to afford a compound of Formula (I) as polymorph Form C.

Example 5

Synthesis of (S)-3-(1-(9H-purin-6-ylamino)ethyl)-8-chloro-2-phenylisoquinolin-1(2H)-one

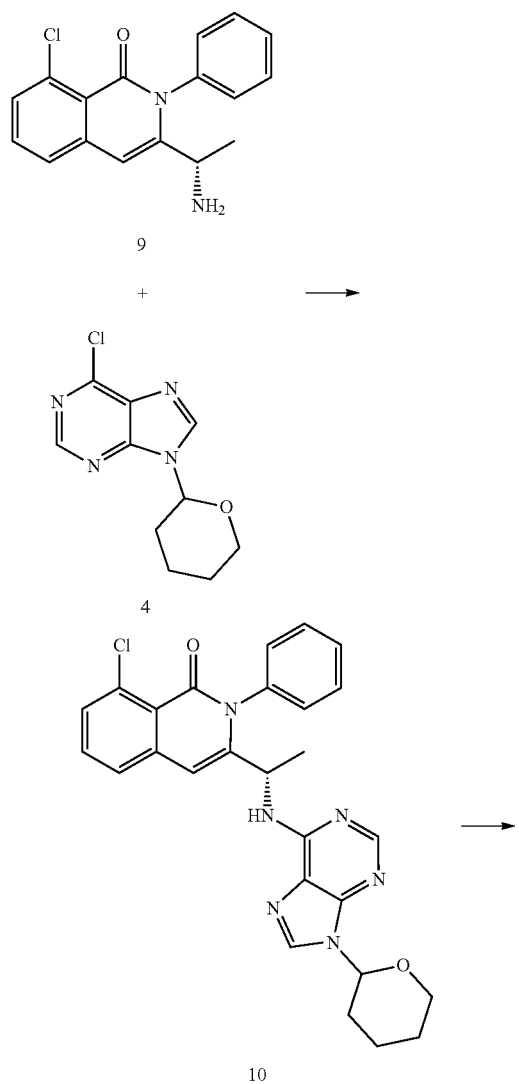

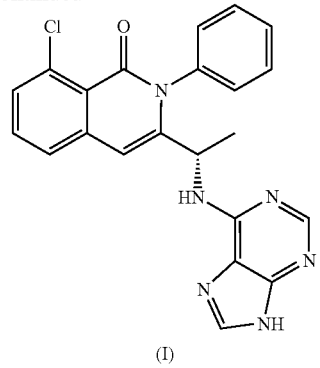

Example 5A

Compound 9 (2.39 kg) was treated with Compound 4 and triethylamine in isopropyl alcohol at 80° C. for 24 hours. The reaction was monitored by HPLC until completion, affording 8-chloro-2-phenyl-3-((1S)-1-(9-(tetrahydro-2H-pyran-2-yl)-9H-purin-6-ylamino)ethyl)isoquinolin-1(2H)-one (compound 10) as a tan solid in 94% yield with 98% (AUC) purity by HPLC analysis.

8-Chloro-2-phenyl-3-((1S)-1-(9-(tetrahydro-2H-pyran-2-yl)-9H-purin-6-ylamino)ethyl)-isoquinolin-1(2H)-one (compound 10) (3.63 kg) was treated with HCl in ethanol at 30° C. for 2.3 hours. The reaction was monitored by HPLC until completion, and afforded a compound of Formula (I) as a tan solid in 92% yield with >99% (AUC) purity and 90.9% (AUC) ee by HPLC analysis.

Example 5B 3-(1-Aminoethyl)-8-chloro-2-phenylisoquinolin-1(2H)-one (Compound 9) (0.72 mmol), 6-chloro-9-(tetrahydro-2H-pyran-2-yl)-9H-purine (Compound 4) (344 mg, 1.44 mmol) and DIPEA (279 mg, 2.16 mmol) were dissolved in n-BuOH (20 mL), and the resulting mixture was stirred at reflux for 16 h. The reaction mixture was concentrated in vacuo and purified by flash column chromatography on silica gel (eluting with 30% to 50% Hex/EA) to afford the product, 8-chloro-2-phenyl-3-((1S)-1-(9-(tetrahydro-2H-pyran-2-yl)-9H-purin-6-ylamino)ethyl)isoquinolin-1(2H)-one (Compound 10), as a white solid (60% yield).

8-Chloro-2-phenyl-3-((1S)-1-(9-(tetrahydro-2H-pyran-2-yl)-9H-purin-6-ylamino)ethyl)-isoquinolin-1(2H)-one (Compound 10) (0.42 mmol) was dissolved in HCl/EtOH (3 M, 5 mL), and the resulting mixture was stirred at room temperature for 1 h. The reaction mixture was quenched with saturated NaHCO₃ aqueous solution and the pH was adjusted to about 7-8. The mixture was extracted with CH₂Cl₂ (50 mL×3), dried over anhydrous Na₂SO₄, and filtered. The filtrate was concentrated in vacuo, and the residue was recrystallized from ethyl acetate and hexanes (1:1). The solid was collected by filtration and dried in vacuo to afford the product (S)-3-(1-(9H-purin-6-ylamino)ethyl)-8-chloro-2-phenylisoquinolin-1(2H)-one (Formula (I)) (90% yield) as a white solid as polymorph Form A.

Example 5C 3-(1-Aminoethyl)-8-chloro-2-phenylisoquinolin-1(2H)-one (Compound 9) and 6-chloro-9-(tetrahydro-2H-pyran-2-yl)-9H-purine (Compound 4) are combined in the presence of triethylamine and isopropyl alcohol. The reaction solution is heated at 82° C. for 24 hours to afford Compound 10. The intermediate compound 10 is treated with concentrated HCl and ethanol under aqueous conditions at 35° C. to remove the tetrahydropyranyl group to yield (S)-3-(1-(9H-purin-6-ylamino)ethyl)-8-chloro-2-phenylisoquinolin-1 (2H)-one. Isolation/purification under aqueous conditions affords polymorph Form C.

Example 6

Synthesis of (S)-3-(1-(9H-purin-6-ylamino)ethyl)-8-chloro-2-phenylisoquinolin-1(2H)-one

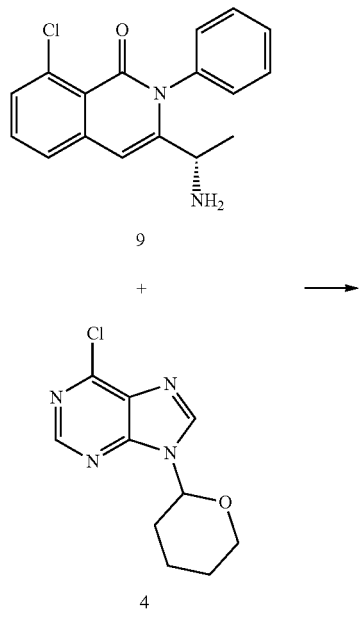

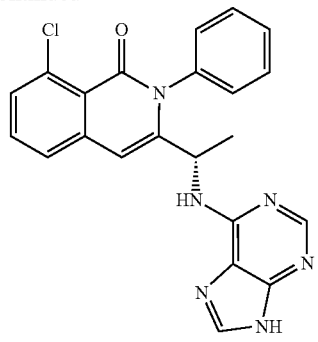

3-(1-Aminoethyl)-8-chloro-2-phenylisoquinolin-1(2H)-one (Compound 9) (150 g; 90% ee) and 6-chloro-9-(tetrahydro-2H-pyran-2-yl)-9H-purine (Compound 4) (216 g, 1.8 equiv) were charged to a round bottom flask followed by addition of IPA (1.2 L; 8 vol) and triethylamine (175 mL; 2.5 equiv). The resultant slurry was stirred at reflux for one day. Heptane (1.5 L; 10 vol) was added dropwise over two hours. The batch was then cooled to 0-5° C., held for one hour and filtered. The cake was washed with heptane (450 mL; 3 vol) and returned to the reactor. IPA (300 mL; 2 vol) and water (2.25 L; 15 vol) were added and the resultant slurry stirred at 20-25° C. for three and half hours then filtered. The cake was washed with water (1.5 L; 10 vol) and heptane (450 mL; 3 vol) and then vacuum dried at 48° C. for two and half days to give 227 g (90.1%) of the intermediate (Compound 10) as an off-white solid with >99% (AUC) purity and >94% ee (chiral HPLC). The ee was determined by converting a sample of the cake to the final product and analyzing it with chiral HPLC.

The intermediate (Compound 10) (200 g) was slurried in an ethanol (900 mL; 4.5 vol)/water (300 mL; 1.5 vol) mixture at 22° C. followed by addition of conc. HCl (300 mL; 1.5 vol) and holding for one and half hours at 25-35° C. Addition of HCl resulted in complete dissolution of all solids producing a dark brown solution. Ammonium hydroxide (260 mL) was added adjusting the pH to 8-9. Product seeds of polymorph Form C (0.5 g) (Form A seeds can also be used) were then added and the batch which was held for ten minutes followed by addition of water (3 L; 15 vol) over two hours resulting in crystallization of the product. The batch was held for 3.5 hours at 20-25° C. and then filtered. The cake was washed with water (1 L; 5 vol) followed by heptane (800 mL; 4 vol) and vacuum dried at 52° C. for 23 hours to give 155.5 g (93.5%) of product with 99.6% (AUC) purity and 93.8% ee (chiral HPLC).

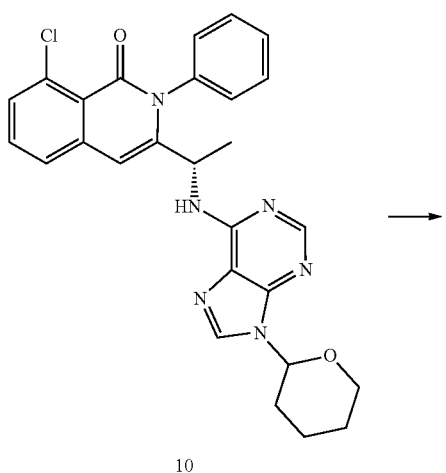

Example 7

Synthesis of (S)-3-(1-(9H-purin-6-ylamino)ethyl)-8-chloro-2-phenylisoquinolin-1(2H)-one

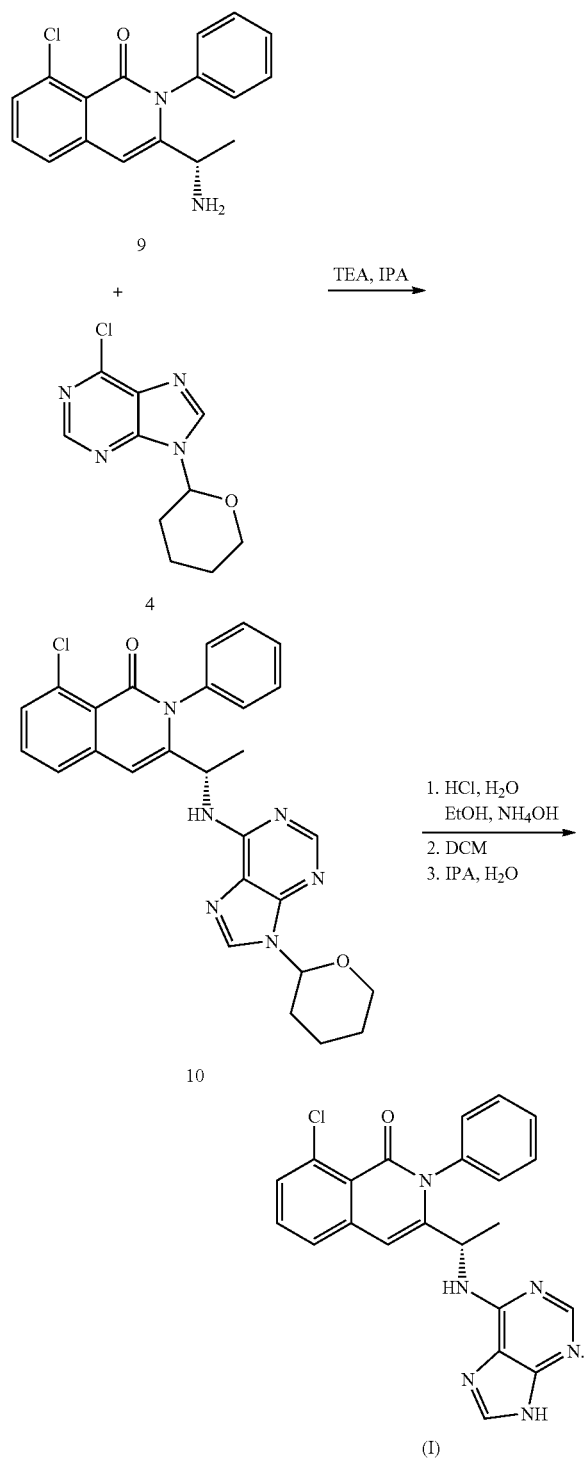

A mixture of isopropanol (20.20 kg, 8 vol.), Compound 9 (3.17 kg, 9.04 mol, 1 eq.), Compound 4 (4.61 kg, 16.27 mol, 1.8 eq.) and triethylamine (2.62 kg, 20.02 mol, 2.4 eq.) was prepared and heated to an internal temperature of 82±5° C. The mixture was stirred at that temperature for an additional about 24 h. The temperature was adjusted to 20±5° C. slowly over a period of about 2 h and the solids were isolated via vacuum filtration through a 24" polypropylene table top filter equipped with a Sharkskin paper. The filter cake was rinsed sequentially with IPA (5.15 kg, 3 vol.), purified water (80.80 kg, 25 vol.) and n-heptane (4.30 kg, 2 vol.). The cake was further dried for about 4 days in vacuo at 50±5° C. to afford Compound 10.

To a mixture of ethanol (17.7 kg, 5 vol.) and Compound 10 (4.45 kg, 8.88 mol. 1.0 eq.) was added purified water (8.94 kg, 2 vol.). To this mixture was slowly added concentrated HCl (3.10 kg, 3.5 eq.) while maintaining the temperature below about 35° C. The mixture was stirred at 30±5° C. for about 1.5 h and HPLC analysis indicated the presence the compound of Formula (I) in 99.8% (AUC) purity with respect to compound 10.

Then, the compound of Formula (I) mixture was cooled to 25±5° C. The pH of the mixture was adjusted to about 8 using pre filtered ammonium hydroxide (1.90 kg). After stirring for about 15 min, Form C crystal seeds (13.88 g) were added. After stirring for about 15 min, purified water (58.0 kg, 13 vol.) was charged over a period of about 2 h. After stirring the mixture for 15 h at 25±5° C., the solids were isolated via vacuum filtration through a 24" polypropylene table top filter equipped with a PTFE cloth over Sharkskin paper. The filter cake was rinsed with purified water (18.55 kg, 4 vol.) followed by pre-filtered n-heptane (6.10 kg, 2 vol.). After conditioning the filter cake for about 24 h, HPLC analysis of the filter cake indicated the presence the compound of Formula (I) in about 99.2% (AUC) purity.

To the filter cake was added dichloromethane (29.9 kg, 5 vol.) and the slurry was stirred at 25±5° C. for about 24 h. The solids were isolated via vacuum filtration through a 24" polypropylene table top filter equipped with a PTFE cloth over Sharkskin paper, and the filter cake was rinsed with DCM (6.10 kg, 1 vol.). After conditioning the filter cake for about 22 h, the filter cake was dried for about 2 days in vacuo at 50±5° C. to afford the compound of Formula (I) in 99.6% (AUC) purity. The compound of Formula (I) was consistent with a Form A reference by XRPD.

To this solid was added purified water (44.6 kg, 10 vol.) and pre filtered 2-propanol (3.0 kg, 0.8 vol.). After stirring for about 6 h, a sample of the solids in the slurry was analyzed by XRPD and was consistent with a Form C reference. The solids were isolated via vacuum filtration through a 24" polypropylene table top filter equipped with a PTFE cloth over Sharkskin paper, and the filter cake was rinsed with purified water (22.35 kg, 5 vol.) followed by pre filtered n-heptane (9.15 kg, 3 vol.). After conditioning the filter cake for about 18 h, the filter cake was dried in vacuo for about 5 days at 50±5° C.

This process afforded a compound of Formula (I) in about 99.6% (AUC) purity, and a chiral purity of greater than about 99% (AUC). An XRPD of the solid was consistent with a Form C reference standard. $^1$H NMR (DMSO-$d_6$) and IR of the product conformed with reference standard.

Example 8

Analytical Data of (S)-3-(1-(9H-purin-6-ylamino)ethyl)-8-chloro-2-phenylisoquinolin-1(2H)-one Provided herein are analytical data of various purified samples of (S)-3-(1-(9H-purin-6-ylamino)ethyl)-8-chloro-2-phenylisoquinolin-1(2H)-one, the compound of Formula (I). Confirmation of the structure of the compound of Formula (I) was obtained via single crystal X-ray diffraction, FT-IR, $^1$H-NMR and $^{13}$C-NMR spectra.

Figure 26:
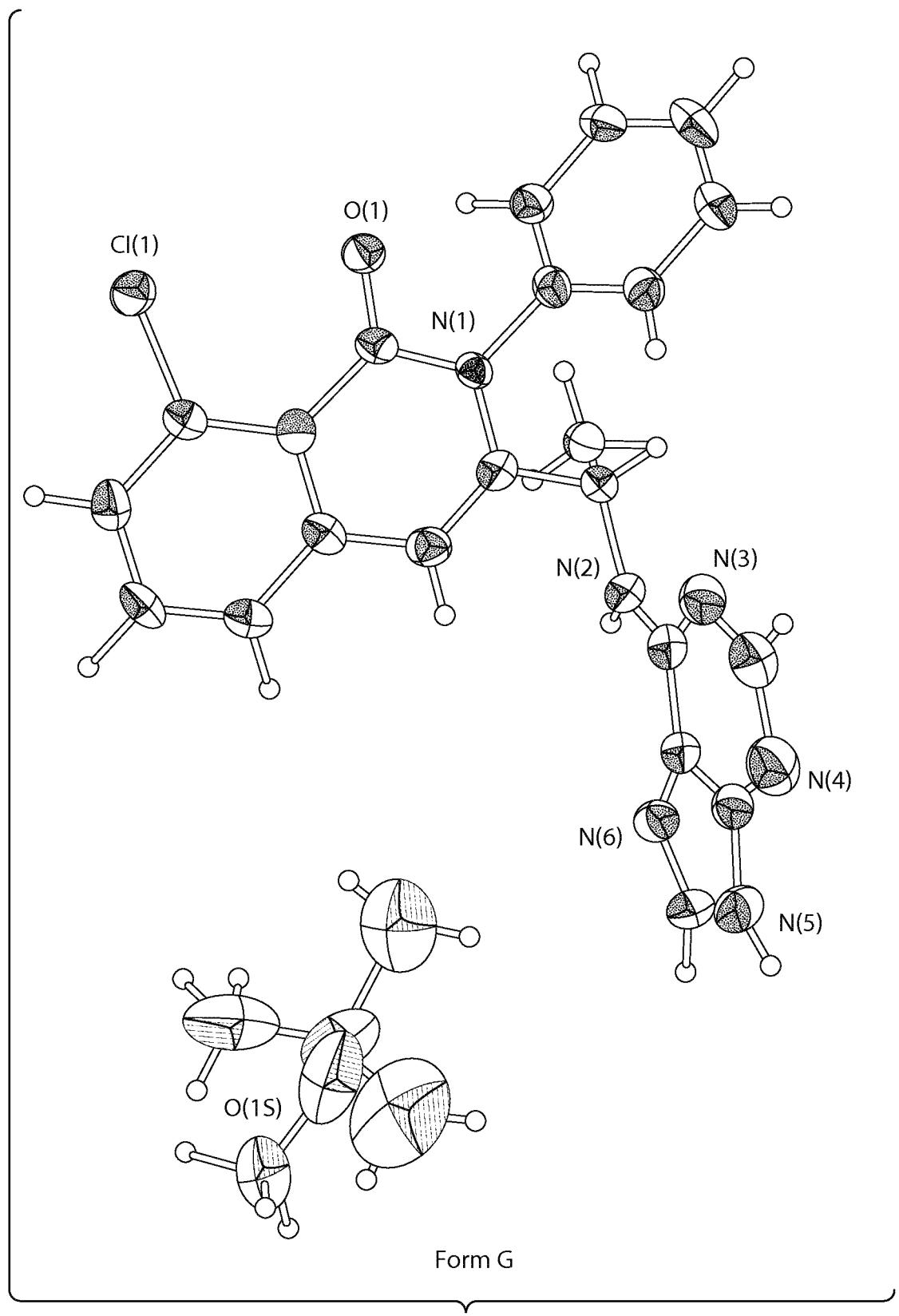
FIG. 26 shows a single crystal X-ray structure of Polymorph Form G MTBE (t-butyl methyl ether) solvate of a compound of Formula (I).

A single crystal structure of a tert-butyl methyl ether solvate of (S)-3-(1-(9H-purin-6-ylamino)ethyl)-8-chloro-2-phenylisoquinolin-1(2H)-one (e.g., polymorph Form G) was generated and single crystal X-ray data was collected. The structure is shown in FIG. 26, which further confirmed the absolute stereochemistry as the S-enantiomer.

Figure 27:
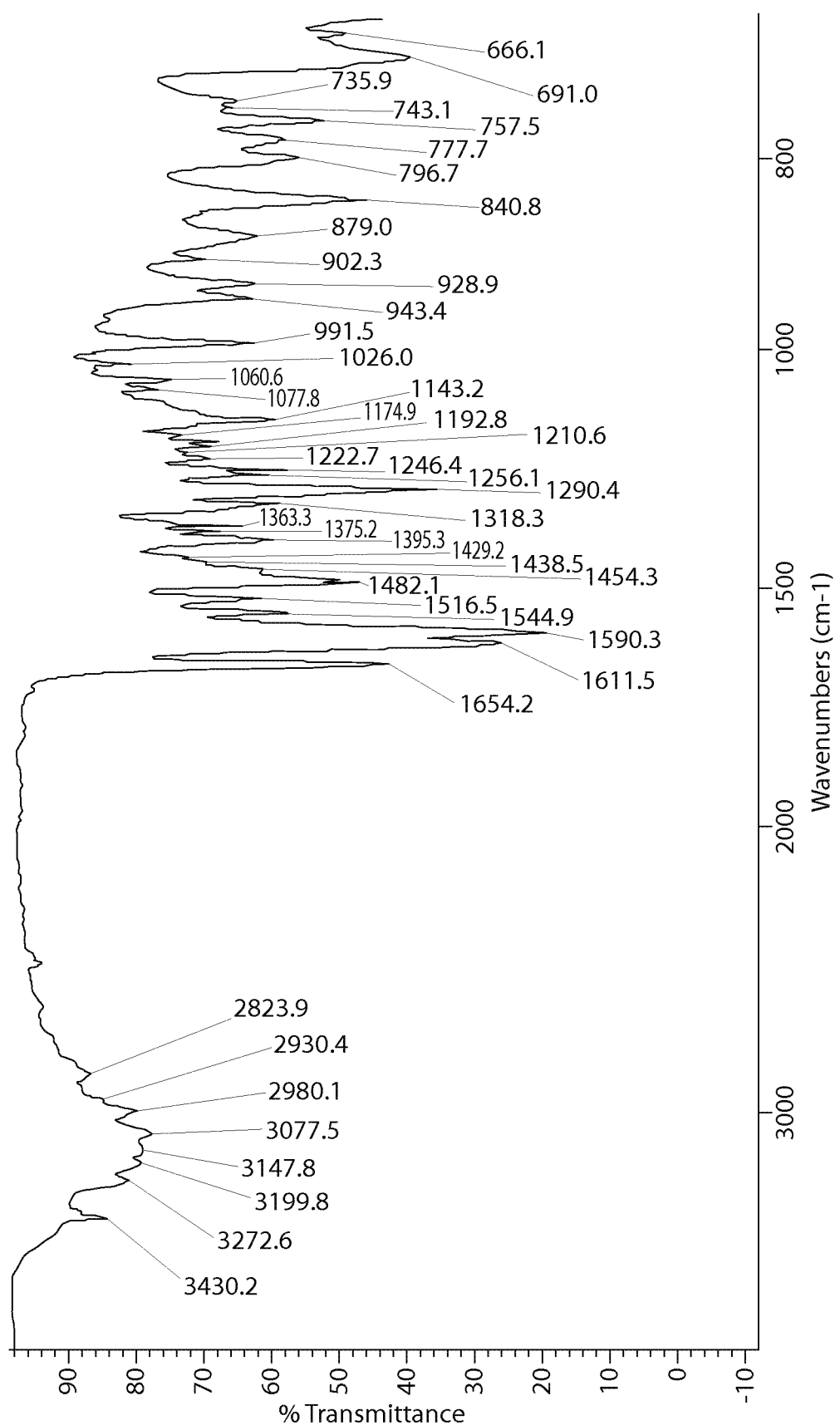
FIG. 27 shows an FT-IR spectra of Polymorph Form C.

FT-IR spectra of Form C of (S)-3-(1-(9H-purin-6-ylamino)ethyl)-8-chloro-2-phenylisoquinolin-1(2H)-one was obtained, and shown in FIG. 27.

Figure 28:
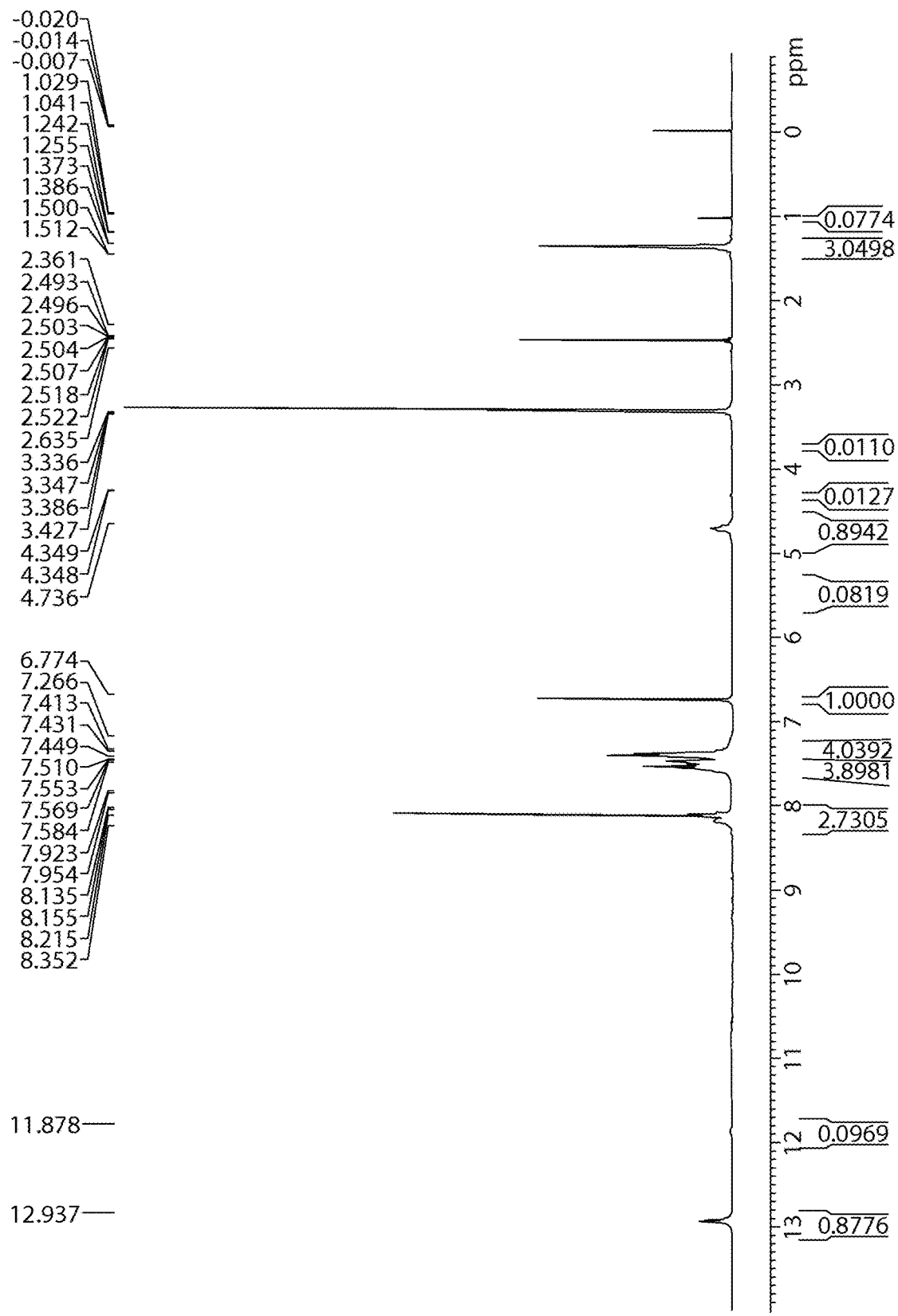
FIG. 28 shows a $^1$H-NMR spectra of Polymorph Form C.
Figure 29:
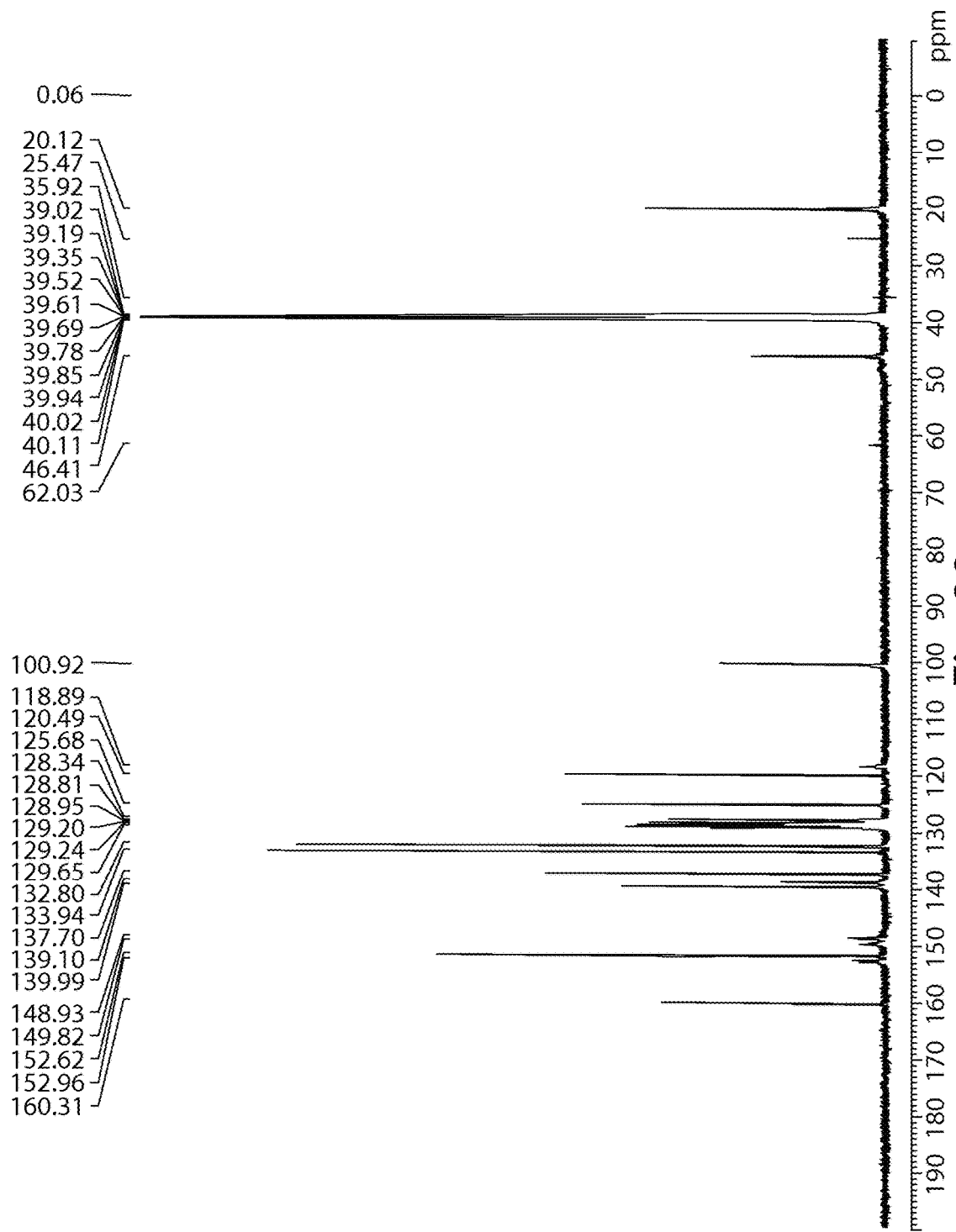
FIG. 29 shows a $^{13}$C-NMR spectra of Polymorph Form C.

$^1$H-NMR and $^{13}$C-NMR spectra of a sample of Form C of (S)-3-(1-(9H-purin-6-ylamino)ethyl)-8-chloro-2-phenylisoquinolin-1(2H)-one were obtained, and are provided in FIG. 28 and FIG. 29, respectively.

Example 9

General Methods for the Preparation of Polymorphs Form A, B, C, D, E, F, G, H, I, J of the Compound of Formula (I)

General Method A: Single Solvent Crystallization with Fast Cooling or Slow Cooling A sample of a compound of Formula (I) (e.g., Form A or Form C) is placed into a vial equipped with stir bar and dissolved with a minimal amount of solvent (such as about 0.2 mL to about 0.3 mL) at an elevated temperature. The resulting solution is polish filtered through a 0.45 μm syringe filter into a clean preheated vial. After hot filtration, the vial is placed in a refrigerator (e.g., about 4° C.) overnight in a fast cooling procedure, or cooled to ambient temperature at a rate of about 20° C./h and allowed to equilibrate without stirring at ambient temperature overnight in a slow cooling procedure. Optionally, a sample without solids can be scratched with an implement known in the art (e.g., a spatula) to initiate crystallization. The solution can be allowed to equilibrate for a period of time, such as approximately 8 hours. For a slow cooling sample, if scratching does not provide solids after about 8 hours, then a stir bar can be added and the sample then stirred overnight. A sample without precipitation can be evaporated to dryness under a gentle gas stream, such as argon, nitrogen, ambient air, etc. The precipitated solids can be recovered by vacuum filtration, centrifuge filtration, or decanted as appropriate to afford the Form as indicated below.

General Method B: Multi-Solvent Crystallization with Fast Cooling or Slow Cooling Multi-solvent (e.g., binary) solvent crystallizations can be performed. Primary solvents include, but are not limited to, ethanol, isopropyl alcohol, methanol, tetrahydrofuran, acetone, methyl ethyl ketone, dioxane, NMP, DME, and DMF. Anti-solvents include, but are not limited to, MTBE, DCM, toluene, heptane, and water.

A sample of a compound of Formula (I) (e.g., Form A or Form C) is placed into a vial equipped with stir bar and dissolved with a minimal amount of solvent (such as about 0.2 mL to about 0.3 mL) at an elevated temperature. The resulting solution is polish filtered through a 0.45 μm syringe filter into a clean preheated vial. After hot filtration, the anti-solvent is added until turbidity is observed. After hot filtration, the vial is placed in a refrigerator (e.g., about 4° C.) overnight in a fast cooling procedure, or cooled to ambient temperature at a rate of about 20° C./h and allowed to equilibrate without stirring at ambient temperature overnight in a slow cooling procedure. Optionally, a sample without solids can be scratched with an implement known in the art (e.g., a spatula) to initiate crystallization. The solution can be allowed to equilibrate for a period of time, such as approximately 8 hours. For a slow cooling sample, if scratching does not provide solids after about 8 hours, then a stir bar can be added and the sample then stirred overnight. A sample without precipitation can be evaporated to dryness under a gentle gas stream, such as argon, nitrogen, ambient air, etc. The precipitated solids can be recovered by vacuum filtration, centrifuge filtration, or decanted as appropriate to afford the Form as indicated below.

General Method C: Slurry Procedures to Afford Formula (I) Polymorph Forms

A mixture of one or more Forms (e.g., Form A or Form C) of the compound of Formula (I) are placed in a vial equipped with a stir bar. A minimal amount of solvent (e.g., a single solvent or a mixture/solution of two or more solvents) is added to the vial to form a heterogeneous slurry. Optionally, the vial can be sealed to prevent evaporation. The slurry is stirred for a period of time ranging from less than about an hour, to about 6 hours, to about 12 hours, to about 24 hours, to about 2 days, to about 4 days, to about 1 week, to about 1.5 weeks, to about 2 weeks or longer. Aliquots can be taken during the stirring period to assess the Form of the solids using, for example, XRPD analysis. Optionally, additional solvent(s) can be added during the stirring period. Optionally, seeds of a given polymorph Form of the compound of Formula (I) can be added. In some cases, the slurry is then stirred for a further period of time, ranging as recited above. The recovered solids can be recovered by vacuum filtration, centrifuge filtration, or decanted as appropriate to afford the Form as indicated below.

Example 10

Preparation of Polymorphs Form A, B, C, D, E, F, G, H, I, J of the Compound of Formula (I)

Form A

Single Solvent Crystallizations to Afford Formula (I) Form A

1. Fast Cooling Procedure From MeCN: Approximately 23 mg of Formula (I) Form A was placed into a 20-mL glass vial equipped with a stir bar. To the vial was added a minimal amount of acetonitrile (7.4 ml) to just dissolve the solids at 70° C. The resulting solution was polish filtered through a 0.45 μm syringe filter into a clean preheated vial. After hot filtration, the vial was placed in a refrigerator (4° C.) overnight. Once at 4° C., the contents of the vial were periodically scratched with a spatula to induce crystallization, and then allowed to equilibrate for approximately 8 hours. The crystals were collected by decanting off the liquid and dried under vacuum (30 inches Hg) at ambient temperature overnight. The dried solids were evaluated for crystallinity and form by XRPD which indicated the crystalline material was polymorph Form A.

2. Slow Cooling Procedure From MeCN: Approximately 24 mg of Formula (I) Form A was placed into a 20-mL glass vial equipped with a stir bar. To the vial was added a minimal amount of acetonitrile (8 ml) to just dissolve the solids at 70° C. The resulting solution was polish filtered through a 0.45 μm syringe filter into a clean preheated vial. After hot filtration, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form A.

3. Slow Cooling Procedure From n-Butanol: Approximately 23 mg of Formula (I) Form A was placed into a 2-dram glass vial equipped with a stir bar. To the vial was added a minimal amount of n-butanol (0.6 ml) to just dissolve the solids at 70° C. The resulting solution was polish filtered through a 0.45 μm syringe filter into a clean preheated vial. After hot filtration, the vials were cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. To further induce crystallization, a stir bar was added to the vial and the contents stirred overnight. The resulting crystals were collected by filtration and dried under vacuum (30 inches Hg) at ambient temperature overnight. The dried solids were evaluated for crystallinity and form by XRPD which indicated the crystalline material was polymorph Form A.

Binary Solvent Crystallizations to Afford Formula (I) Form A

1. Fast Cooling Procedure From Acetone/DCM: Approximately 23.5 mg of Formula (I) Form A was placed into a 2-dram glass vial equipped with a stir bar. To the vial was added a minimal amount of acetone (2.6 ml) to just dissolve the solids at 50° C. The resulting solution was polish filtered through a 0.45 μm syringe filter into a clean preheated vial. After hot filtration, DCM (5.0 ml) was added portion-wise. After the anti-solvent addition, the vials were placed in a refrigerator (4° C.) overnight. Once at 4° C., the contents of the vial were periodically scratched with a spatula to induce crystallization, and then allowed to equilibrate for approximately 8 hours. The crystals were collected by filtration and dried under vacuum (30 inches Hg) at ambient temperature overnight. The dried solids were evaluated for crystallinity and form by XRPD which indicated the crystalline material was polymorph Form A.

2. Fast Cooling Procedure From MEK/DCM: Approximately 23 mg of Formula (I) Form A was placed into a 2-dram glass vial equipped with a stir bar. To the vial was added a minimal amount of MEK (2.2 ml) to just dissolve the solids at 70° C. The resulting solution was polish filtered through a 0.45 μm syringe filter into a clean preheated vial. After hot filtration, DCM (5.0 ml) was added portion-wise. After the anti-solvent addition, the vial was placed in a refrigerator (4° C.) overnight. Once at 4° C., the contents of the vial were periodically scratched with a spatula to induce crystallization, and then allowed to equilibrate for approximately 8 hours. The crystals were collected by filtration and dried under vacuum (30 inches Hg) at ambient temperature overnight. The dried solids were evaluated for crystallinity and form by XRPD which indicated the crystalline material was polymorph Form A.

3. Fast Cooling Procedure From DMF/DCM: Approximately 24 mg of Formula (I) Form A was placed into a 2-dram glass vial equipped with a stir bar. To the vial was added a minimal amount of DCM (0.2 ml) to just dissolve the solids at 70° C. The resulting solution was polish filtered through a 0.45 μm syringe filter into a clean preheated vial. After hot filtration, DCM (7.0 ml) was added portion-wise. After the anti-solvent addition, the vial was placed in a refrigerator (4° C.) overnight. Once at 4° C., the contents of the vial were periodically scratched with a spatula to induce crystallization, and then allowed to equilibrate for approximately 8 hours. The crystals were collected by filtration and dried under vacuum (30 inches Hg) at ambient temperature overnight. The dried solids were evaluated for crystallinity and form by XRPD which indicated the crystalline material was polymorph Form A.

4. Fast Cooling Procedure From Dioxane/DCM: Approximately 24.4 mg of Formula (I) Form A was placed into a 2-dram glass vial equipped with a stir bar. To the vial was added a minimal amount of dioxane (0.8 ml) to just dissolve the solids at 70° C. The resulting solution was polish filtered through a 0.45 μm syringe filter into a clean preheated vial. After hot filtration, DCM (7.0 ml) was added portion-wise. After the anti-solvent addition, the vial was placed in a refrigerator (4° C.) overnight. Once at 4° C., the contents of the vial were periodically scratched with a spatula to induce crystallization, and then allowed to equilibrate for approximately 8 hours. The crystals were collected by filtration and dried under vacuum (30 inches Hg) at ambient temperature overnight. The dried solids were evaluated for crystallinity and form by XRPD which indicated the crystalline material was polymorph Form A.

5. Slow Cooling Procedure From Acetone/DCM: Approximately 22 mg of Formula (I) Form A was placed into a 2-dram glass vial equipped with a stir bar. To the vial was added a minimal amount of acetone (2.5 ml) to just dissolve the solids at 50° C. The resulting solution was polish filtered through a 0.45 μm syringe filter into a clean preheated vial. After hot filtration, DCM (5.0 ml) was added portion-wise. After the anti-solvent addition, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. To further induce crystallization, a stir bar was added to the vial and the contents stirred overnight. The resulting crystals were collected by filtration and dried under vacuum (30 inches Hg) at ambient temperature overnight. The dried solids were evaluated for crystallinity and form by XRPD which indicated the crystalline material was polymorph Form A.

6. Slow Cooling Procedure From MEK/DCM: Approximately 23.4 mg of Formula (I) Form A was placed into a 2-dram glass vial equipped with a stir bar. To the vial was added a minimal amount of MEK (2.2 ml) to just dissolve the solids at 70° C. The resulting solution was polish filtered through a 0.45 μm syringe filter into a clean preheated vial. After hot filtration, DCM (5.0 ml) was added portion-wise. After the anti-solvent addition, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. The resulting crystals were collected by filtration and dried under vacuum (30 inches Hg) at ambient temperature overnight. The dried solids were evaluated for crystallinity and form by XRPD which indicated the crystalline material was polymorph Form A.

7. Slow Cooling Procedure From Dioxane/DCM: Approximately 24 mg of Formula (I) Form A was placed into a 2-dram glass vial equipped with a stir bar. To the vial was added a minimal amount of dioxane (0.8 ml) to just dissolve the solids at 70° C. The resulting solution was polish filtered through a 0.45 μm syringe filter into a clean preheated vial. After hot filtration, DCM (7.0 ml) was added portion-wise. After the anti-solvent addition, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. To further induce crystallization, a stir bar was added to the vial and the contents stirred overnight. The resulting crystals were collected by filtration and dried under vacuum (30 inches Hg) at ambient temperature overnight. The dried solids were evaluated for crystallinity and form by XRPD which indicated the crystalline material was polymorph Form A.

8. Slow Cooling Procedure From DMF/DCM: Approximately 23.5 mg of Formula (I) Form A was placed into a 2-dram glass vial equipped with a stir bar. To the vial was added a minimal amount of DMF (0.2 ml) to just dissolve the solids at 70° C. The resulting solution was polish filtered through a 0.45 µm syringe filter into a clean preheated vial. After hot filtration, DCM (7.0 ml) was added portion-wise. After the anti-solvent addition, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. To further induce crystallization, a stir bar was added to the vial and the contents stirred overnight. To further induce crystallization, the contents of the vial were concentrated under a gentle stream of nitrogen to near dryness. The resulting crystals were collected by filtration and dried under vacuum (30 inches Hg) at ambient temperature overnight. The dried solids were evaluated for crystallinity and form by XRPD which indicated the crystalline material was polymorph Form A.

Slurry Procedure to Afford Formula (I) Form A

1. Procedure from CH$_2$Cl$_2$ and from IPA: Form C (1 g) was slurried in five volumes of dichloromethane. After holding for 15 hours, filtration, and drying, Form A was isolated in 82% yield. Scale-up was performed on a 20 g scale with a water-wet cake of Form C to yield Form A in 92% yield. Drying at 70° C. for six days indicated no degradation in chemical or chiral purity. Slurrying dry Form C in isopropyl alcohol using a similar method also yielded Form A.

2. Procedure for Competitive Slurry Experiment (using forms A, B and C): Competitive slurries were performed by charging approximately a 50/50 mixture of Forms A and C (11.2 mg of Form A and 11.7 mg Form C) to a 1-dram glass vial equipped with a glass stir bar. To the vial was added 600 µL of MeCN. The vial cap was wrapped with parafilm to prevent evaporation. The slurry was stirred for 1 day and an aliquot was taken. The contents of the vial were allowed to stir for an additional week and another aliquot was taken. Both aliquots were centrifuge filtered for five minutes at 8000 RPM. XRPD analysis was performed on the solids from each aliquot to show that the Formula (I) had converted to Form A at both time points. After the one week aliquot was taken, an additional 300 µL of acetonitrile was added to the remaining slurry and allowed to equilibrate for one day. The slurry was then seeded with approximately 3.2 mg of Form B and allowed to equilibrate for an additional three days. The solids were isolated by centrifuge filtration (5 minutes at 8000 RPM) and dried over night under vacuum. The dried solids were evaluated for crystallinity and form by XRPD which indicated the crystalline material was polymorph Form A.

3. Procedure for Competitive Slurry Experiment (using forms A, C, D, and E): Competitive slurries were performed by charging an approximately equal mixture of each form (7.8 mg of Form A, 7.7 mg Form C, 7.7 mg of Form D, and 8.2 mg of Form E) to a 1-dram glass vial equipped with a glass stir bar. To the vial was added 1 ml of 2-propanol. The vial cap was wrapped with parafilm to prevent evaporation. The slurry was mixed for 1 day and an aliquot was taken. The contents of the vial were allowed to stir for an additional week and another aliquot was taken. Both aliquots were centrifuge filtered for five minutes at 8000 RPM. XRPD analysis was performed on the solids from each aliquot to show that the Formula (I) had converted to Form A at both time points. After the one week aliquot was taken, the remaining solids were isolated by centrifuge filtration (5 minutes at 8000 RPM) and dried over night under vacuum. The dried solids were evaluated for crystallinity and form by XRPD which indicated the crystalline material was polymorph Form A.

Form B

To a pan for a thermogravimetric analysis (TGA) instrument was loaded 15-20 mg of Formula (I) Form A. Form C can also be used in this process. The crystalline sample was rapidly heated to 250° C. and held at that temperature inside the TGA instrument for 5 minutes. After the hold was complete, the sample was rapidly cooled to room temperature as fast as possible. The resulting sample was evaluated for crystallinity and form by XRPD which indicated the crystalline material was polymorph Form B.

Form C

Binary Solvent Crystallizations to Afford Formula (I) Form C

Using the General Method B of Example 9, the following experiments detailed in Tables 1 and 2 were performed to afford Formula (I) Form C. Table 1 experiments were conducted using the fast cooling procedure, while Table 2 experiments were conducted using the slow cooling procedure.

TABLE 1

Fast Cooling Procedure

| Formula (I) (mg) | Primary Solvent (mL) | Water Anti-solvent (mL) | Temp (° C.) | Precipitation/Isolation (scr = scratch) | Form |
|---|---|---|---|---|---|
| 24.3 | EtOH (0.9) | 3.00 | 70 | ppt/filter | C |
| 24.3 | IPA (0.6) | 2.00 | 70 | ppt/filter | C |
| 24.2 | THF (1.5) | 6.50 | 60 | ppt/filter | C |
| 23.4 | Acetone (2.5) | 5.00 | 50 | scr/ppt/filter | C |
| 23.5 | Dioxane (0.8) | 3.00 | 70 | ppt/filter | C |
| 24.2 | NMP (0.2) | 0.90 | 70 | ppt/filter | C |

TABLE 1-continued

Fast Cooling Procedure

| Formula (I) (mg) | Primary Solvent (mL) | Water Anti-solvent (mL) | Temp (° C.) | Precipitation/Isolation (scr = scratch) | Form |
|---|---|---|---|---|---|
| 24.2 | DME (2.5) | 5.00 | 70 | scr/ppt/filter | C |
| 23.7 | DMF (0.2) | 0.57 | 70 | ppt/filter | C |

TABLE 2

Slow Cooling Procedure

| Formula (I) (mg) | Primary Solvent (mL) | Water Anti-solvent (mL) | Temp (° C.) | Precipitation/Isolation (scr = scratch) | Form |
|---|---|---|---|---|---|
| 23.1 | EtOH (0.9) | 2.60 | 70 | ppt/filter | C |
| 23.4 | IPA (0.6) | 2.00 | 70 | ppt/filter | C |
| 23.7 | THF (1.5) | 6.00 | 60 | scr/filter | C |
| 23.7 | Acetone (2.5) | 5.00 | 50 | scr/filter | C |
| 24.5 | Dioxane (0.8) | 2.70 | 70 | ppt/filter | C |
| 23.1 | NMP (0.4) | 1.42 | 70 | ppt/filter | C |
| 23.4 | DME (2.5) | 5.00 | 70 | scr/filter | C |
| 25.3 | DMF (0.2) | 0.41 | 70 | ppt/filter | C |

Slurry Procedures to Afford Formula (I) Form C

1. Procedure for Competitive Slurry Experiment (using forms A, C, D, and E): Competitive slurries were performed by charging an approximately equal mixture of each form (7.9 mg of Form A, 7.8 mg Form C, 7.8 mg of Form D, and 8.1 mg of Form E) to a 1-dram glass vial equipped with a glass stir bar. To the vial was added 1 ml of water. The vial cap was wrapped with parafilm to prevent evaporation. The slurry was mixed for 1 day and an aliquot was taken. The contents of the vial were allowed to stir for an additional week and another aliquot was taken. Both aliquots were centrifuge filtered for five minutes at 8000 RPM. XRPD analysis was performed on the solids to show that the Formula (I) had converted to Form C at both timepoints. After the one week aliquot was taken, the remaining solids were isolated by centrifuge filtration (5 minutes at 8000 RPM) and dried overnight under vacuum. The dried solids were evaluated for crystallinity and form by XRPD which indicated the crystalline material was polymorph Form C.

2. Procedure for Competitive Slurry Experiment (using forms B and C): Approximately 4.9 mg of Form C was weighed into a 1 dram vial equipped with a magnetic stir bar. To this vial was added 0.3 mL of water to form a slurry which was allowed to equilibrate for approximately 24 hours at ambient temperature. An equal amount (approximately 5.4 mg) of Form B was added to the vial and the slurry was allowed to equilibrate for four days at ambient temperature. The resulting solids were isolated by centrifuge filtration (5 minutes at 8000 RPM) and dried over night under vacuum. The dried solids were evaluated for crystallinity and form by XRPD which indicated the crystalline material was polymorph Form C.

3. Procedure for Competitive Slurry Experiment (using forms A, B and C): Competitive slurries were performed by charging approximately a 50/50 mixture of Forms A and C (10.6 mg of Form A and 12 mg Form C) to a 1-dram glass vial equipped with a glass stir bar. To the vial was added 600 µL of a 50/50 v/v solution of water and ethanol. The vial cap was wrapped with parafilm to prevent evaporation. The slurry was mixed for 1 day and an aliquot was taken. The contents of the vial were allowed to stir for an additional week, and another aliquot was taken. Both aliquots were centrifuge filtered for five minutes at 8000 RPM. XRPD analysis was performed on the solids to show that all the Formula (I) had converted to Form C at both timepoints. After the one week aliquot was taken, an additional 300 µL of a 50/50 v/v solution of water and ethanol was added to the remaining slurry and allowed to equilibrate for one day. The slurries were then seeded with approximately 3.6 mg of Form B and allowed to equilibrate for an additional three days before isolation by centrifuge filtration (5 minutes at 8000 RPM). The solids were dried over night under vacuum at ambient temperature. The dried solids were evaluated for crystallinity and form by XRPD which indicated the crystalline material was polymorph Form C.

4. A 22 L round bottom flask was charged with Form A of (S)-3-(1-(9H-purin-6-ylamino)ethyl)-8-chloro-2-phenylisoquinolin-1(2H)-one (1.20 kg) in 1.2 L of isopropyl alcohol and 12 L of DI water, and stirred at 20±5° C. After stirring for 3 hours, the analysis of a sample by XRPD showed that the sample was Form C. The mixture was filtered through a Buchner funnel equipped with a shark skin filter paper, which was then rinsed with DI water (6 L) and heptanes (3.6 L). The cake was conditioned for 1 hour, and dried at 50° C. in a vacuum oven to constant weight to afford a compound of Formula (I) as Form C (1.18 kg) in 98% yield. Additional samples of Form C were prepared starting with Form A of (S)-3-(1-(9H-purin-6-ylamino)ethyl)-8-chloro-2-phenylisoquinolin-1(2H)-one using the following reaction condition variations to this procedure as shown in Table 3:

TABLE 3

| | Conditions | Purity (AUC) | Yield |
|---|---|---|---|
| 1 | Reslurry in EtOH (16 vol) at 70° C. | 99.34% | 40% |
| 2 | Recrystallize in EtOH/water (9/1 vol) from 65 to 21° C. | 99.63% | 42.6% |
| 3 | Recrystallize in EtOH/water (7/1 vol) from 65 to 21° C. | 99.64% | 52% |
| 4 | Recrystallize in EtOH/water (7/4 vol) from 82 to 21° C. | 99.54% | 77% |
| 5 | Recrystallize in EtOH/water (9/7 vol) from 82 to 21° C. | 99.40% | 77.4% |
| 6 | Recrystallize in EtOH/water (7/10 vol) from 82 to 21° C. | 99.07% | 90.4% |

Form D

Single Solvent Crystallizations to Afford Formula (I) Form D

1. Fast Cooling Procedure from Tetrahydrofuran (THF): Approximately 23 mg of Formula (I) Form A was placed into a 2-dram glass vial equipped with a stir bar. To the vial was added a minimal amount of THF (1.2 ml) to just dissolve the solids at 60° C. The resulting solution was polish filtered through a 0.45 μm syringe filter into a clean preheated vial. After hot filtration, the vials were placed in a refrigerator (4° C.) overnight. Once at 4° C., the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form D.

2. Fast Cooling Procedure from 2-Butanone (MEK): Approximately 23 mg of Formula (I) Form A was placed into a 2-dram glass vial equipped with a stir bar. To the vial was added a minimal amount of MEK (2.0 ml) to just dissolve the solids at 70° C. The resulting solution was polish filtered through a 0.45 μm syringe filter into a clean preheated vial. After hot filtration, the vials were placed in a refrigerator (4° C.) overnight. Once at 4° C., the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form D.

3. Fast Cooling Procedure from Dioxane: Approximately 25 mg of Form A was placed into a 2-dram glass vial equipped with a stir bar. To the vial was added a minimal amount of THF (1.5 ml) to just dissolve the solids at 70° C. The resulting solution was polish filtered through a 0.45 μm syringe filter into a clean preheated vial. After hot filtration, the vial was placed in a refrigerator (4° C.) overnight. Once at 4° C., the contents of the vial were periodically scratched with a spatula to induce crystallization, and then allowed to equilibrate for approximately 8 hours. To further induce crystallization, the contents of the vial were evaporated to near dryness under a gentle stream of nitrogen. The crystals were collected by decanting off any remaining liquids and dried under vacuum (30 inches Hg) at ambient temperature overnight. The dried solids were evaluated for crystallinity and form by XRPD which indicated the crystalline material was polymorph Form D.

4. Fast Cooling Procedure from N,N-dimethylformamide (DMF): Approximately 23.5 mg of Formula (I) Form A was placed into a 2-dram glass vial equipped with a stir bar. To the vial was added a minimal amount of DMF (0.3 ml) to just dissolve the solids at 70° C. The resulting solution was polish filtered through a 0.45 μm syringe filter into a clean preheated vial. After hot filtration, the vial was placed in a refrigerator (4° C.) overnight. Once at 4° C., the contents of the vial were periodically scratched with a spatula to induce crystallization, and then allowed to equilibrate for approximately 8 hours. To further induce crystallization, the contents of the vial were evaporated to near dryness under a gentle stream of nitrogen. The crystals were collected by decanting off any remaining liquids and dried under vacuum (30 inches Hg) at ambient temperature overnight. The dried solids were evaluated for crystallinity and form by XRPD which indicated the crystalline material was polymorph Form D.

5. Slow Cooling Procedure from Tetrahydrofuran (THF): Approximately 25 mg of Formula (I) Form A was placed into a 2-dram glass vial equipped with a stir bar. To the vial was added a minimal amount of THF (1.1 ml) to just dissolve the solids at 60° C. The resulting solution was polish filtered through a 0.45 μm syringe filter into a clean preheated vial. After hot filtration, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form D.

6. Slow Cooling Procedure from 2-Butanone (MEK): Approximately 24.5 mg of Formula (I) Form A was placed into a 2-dram glass vial equipped with a stir bar. To the vial was added a minimal amount of MEK (4 ml) to just dissolve the solids at 70° C. The resulting solution was polish filtered through a 0.45 μm syringe filter into a clean preheated vial. After hot filtration, the vials were cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form D.

7. Slow Cooling Procedure from Dioxane: Approximately 24 mg of Formula (I) Form A was placed into a 2-dram glass vial equipped with a stir bar. To the vial was added a minimal amount of dioxane (1.1 ml) to just dissolve the solids at 70° C. The resulting solution was polish filtered through a 0.45 μm syringe filter into a clean preheated vial. After hot filtration, the vial was cooled to ambient temperature at a rate of 20° C./h and allowed to equilibrate without stirring at ambient temperature overnight. After the equilibration hold at ambient temperature, the contents of the vial were periodically scratched with a spatula to induce crystallization, and then allowed to equilibrate for approximately 8 hours. The crystals were collected by decanting off the liquids and dried under vacuum (30 inches Hg) at ambient temperature overnight. The dried solids were evaluated for crystallinity and form by XRPD which indicated the crystalline material was polymorph Form D.

Binary Solvent Crystallizations to Afford Formula (I) Form D

Using the General Method B of Example 9, the following experiments detailed in Tables 4 and 5 were performed to afford Formula (I) Form C. Table 4 experiments were conducted using the fast cooling procedure, while Table 5 experiments were conducted using the slow cooling procedure.

TABLE 4

Fast Cooling Procedure

| Formula (I) (mg) | Primary Solvent (mL) | Anti-solvent (mL) | Temp (° C.) | Precipitation/Isolation (scr = scratch; evp = evaporation) | Form |
|---|---|---|---|---|---|
| 24.7 | THF (1.5) | MTBE (3.0) | 60 | filter | D |
| 22.5 | Dioxane (0.65) | MTBE (1.5) | 70 | filter | D |
| 24.2 | DMF (0.2) | MTBE (1.6) | 70 | scr/filter | D |
| 23.5 | THF (1.5) | DCM (6.0) | 60 | scr/evp/decant | D |
| 23.6 | IPA (0.6) | Toluene (6.5) | 70 | scr/evp/decant | D |
| 23.7 | THF (1.5) | Toluene (5.0) | 60 | scr/filter | D |
| 23.9 | DMF (0.2) | Toluene (3.0) | 70 | scr/filter | D |

TABLE 5

Slow Cooling Procedure

| Formula (I) (mg) | Primary Solvent (mL) | Anti-solvent (mL) | Temp (° C.) | Precipitation/Isolation (scr = scratch; evp = evaporation) | Form |
|---|---|---|---|---|---|
| 22.9 | MEK (2.2) | MTBE (2.0) | 70 | filter | D |
| 25.3 | DMF (0.2) | MTBE (1.4) | 70 | decant | D |
| 24.1 | THF (1.5) | DCM (6.0) | 60 | scr/stir/evp/decant | D |
| 23.3 | DME (2.6) | DCM (5.0) | 70 | scr/stir/evp/filter | D |
| 24.1 | IPA (0.7) | Toluene (6.0) | 70 | scr/stir/evp/decant | D |
| 24.4 | NNP (0.2) | Toluene (7.0) | 60 | filter | D |
| 24 | DME (2.5) | Toluene (5.0) | 70 | scr/stir/filter | D |

Slurry Procedures to Afford Formula (I) Form D

1. Approximately 122 mg of Formula (I), Form A, was weighed into 8 mL vial equipped with a magnetic stir bar. To the vial was added 3.0 mL of 2-butanone (MEK) to form a slurry. The contents of the vial were heated to 50° C., and held for approximately 1.5 hours. After the hold, the contents of the vial were slowly cooled at a rate of 20° C./h to room temperature. The mixture was then allowed to stir overnight. The product was isolated by vacuum filtration, and dried over night in vacuo. The dried solids were evaluated for crystallinity and form by XRPD which indicated the crystalline material was polymorph Form D.

2. Procedure for Competitive Slurry Experiment (using forms A, B and C): Competitive slurries were performed by charging approximately a 50/50 mixture of Forms A and C (10.3 mg of Form A and 11.7 mg Form C) to a 1-dram glass vial equipped with a glass stir bar. To the vial was added 600 µL of MEK. The vial cap was wrapped with parafilm to prevent evaporation. The slurry was mixed for 1 day and an aliquot was taken. The contents of the vial were allowed to stir for an additional week, and another aliquot was taken. Both aliquots were centrifuge filtered for five minutes at 8000 RPM. XRPD analysis was performed on the solids to show that the Formula (I) had converted to Form D at both timepoints. After the one week aliquot was taken, an additional 300 µL of MEK was added to the remaining slurry and allowed to equilibrate for one day. The slurries were then seeded with approximately 4.5 mg of Form B and allowed to equilibrate for an additional three days before isolation by centrifuge filtration (5 minutes at 8000 RPM). The solids were dried over night under vacuum at ambient temperature. The dried solids were evaluated for crystallinity and form by XRPD which indicated the crystalline material was polymorph Form D.

3. Procedure for Competitive Slurry Experiment (using forms B and D): Approximately 6 mg of Formula (I) Form D was weighed into a 1 dram vial equipped with magnetic stir bar. To this vial was added 0.3 mL of MEK to form a slurry and allowed to equilibrate for approximately 24 hours at ambient temperature. An equal amount (approximately 6 mg) of Form B was added to the vial and allowed to equilibrate for four days at ambient temperature. The resulting solids were isolated by centrifuge filtration (5 minutes at 8000 RPM) and dried over night under vacuum. The dried solids were evaluated for crystallinity and form by XRPD which indicated the crystalline material was polymorph Form D.

Forms A, C, and D

Slurry Procedures to Afford Formula (I) Forms a, C, and D

Using General Method C of Example 9, the following experiments detailed in Table 6 were performed to afford the polymorph Form of the compound of Formula (I) as indicated.

TABLE 6

| | Formula (I) (mg) | Initial Form | Solvent | Amount (mL) | Temp. (° C.) | Time | Observation/Isolation | Final Form |
|---|---|---|---|---|---|---|---|---|
| 1 | 15.4 | Form A | water | 0.75 | RT | 14 days | filter | C |
| 2 | 26.0 | Form A | EtOH | 0.75 | RT | 14 days | filter | A |
| 3 | 19.5 | Form A | MEK | 0.75 | RT | 14 days | filter | D |
| 4 | 15.9 | Form A | t-AmOH | 0.50 | RT | 14 days | filter, no solids obtained | n/a |

TABLE 6-continued

| | Formula (I) (mg) | Initial Form | Solvent | Amount (mL) | Temp. (° C.) | Time | Observation/ Isolation | Final Form |
|---|---|---|---|---|---|---|---|---|
| 5 | 19.5 | Form A | MeCN | 0.75 | RT | 14 days | filter | A |
| 6 | 17.6 | Form A | EtOAc | 0.75 | RT | 14 days | filter | Amorphous |
| 7 | 16.0 | Form C | water | 0.6 | RT | 14 days | filter | C |
| 8 | 15.6 | Form C | EtOH | 0.6 | RT | 14 days | filter, no solids obtained | n/a |
| 9 | 15.1 | Form C | MEK | 0.6 | RT | 14 days | filter | D |
| 10 | 17.4 | Form C | EtOAc | 0.6 | RT | 14 days | filter | Amorphous |
| 11 | 14.0 | Form C | MeCN | 0.6 | RT | 14 days | filter | A |
| 12 | 10.9 | Form D | water | 0.6 | RT | 14 days | filter | C |
| 13 | 3.5 + 3.7 | Form D | EtOH | 0.3 | RT | 14 days | filter, no solids obtained | n/a |
| 14 | 6.7 | Form D | MeCN | 0.3 | RT | 14 days | filter | A |
| 15 | 9.2 | Form E | water | 0.5 | RT | 17 days | filter | C |
| 16 | 10.5 | Form E | MEK | 0.5 | RT | 17 days | filter | D |
| 17 | 8 | Form E | MeCN | 0.5 | RT | 17 days | filter | A |

Form E

Single Solvent Crystallization to Afford Formula (I) Form E

Slow Cooling Procedure from Methanol: Approximately 23.5 mg of Formula (I) Form A was placed into a 2-dram glass vial equipped with a stir bar. To the vial was added a minimal amount of methanol (0.53 ml) to just dissolve the solids at 60° C. The resulting solution was polish filtered through a 0.45 µm syringe filter into a clean preheated vial. After hot filtration, the vials were cooled to ambient temperature at a rate of 20° C./h and allowed to equilibrate without stirring at ambient temperature overnight. After the equilibration hold at ambient temperature, the crystals were collected by decanting off the liquids and dried under vacuum (30 inches Hg) at ambient temperature overnight. The dried solids were evaluated for crystallinity and form by XRPD which indicated the crystalline material was polymorph Form E.

Binary Solvent Crystallizations to Afford Formula (I) Form E

1. Fast Cooling Procedure from Methanol/Water: Approximately 23.4 mg of Formula (I) Form A was placed into a 2-dram glass vial equipped with a stir bar. To the vial was added a minimal amount of methanol (0.6 ml) to just dissolve the solids at 60° C. The resulting solution was polish filtered through a 0.45 µm syringe filter into a clean preheated vial. After hot filtration, water (0.85 ml) was added portion-wise. After the anti-solvent addition, the vial was placed in a refrigerator (4° C.) overnight. The crystals were collected by filtration and dried under vacuum (30 inches Hg) at ambient temperature overnight. The dried solids were evaluated for crystallinity and form by XRPD which indicated the crystalline material was polymorph Form E.

2. Slow Cooling Procedure from Methanol/Water: Approximately 23 mg of Formula (I) Form A was placed into a 2-dram glass vial equipped with a stir bar. To the vial was added a minimal amount of methanol (0.6 ml) to just dissolve the solids at 60° C. The resulting solution was polish filtered through a 0.45 µm syringe filter into a clean preheated vial. After hot filtration, water (0.83 ml) was added portion-wise. After the anti-solvent addition, the vial was cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form E.

Slurry Procedures to Afford Formula (I) Form E

1. Approximately 127 mg of Formula (I), Form A, was weighed into an 8 mL vial equipped with a magnetic stir bar. To the vial was added 3.0 mL of methanol to form a slurry. The contents of the vial was heated to 50° C., and held for approximately 1.5 hours. After the hold, the contents of the vial were slowly cooled at a rate of 20° C./h to room temperature. The mixture was then allowed to stir over night. The product was isolated by vacuum filtration, and dried over night in vacuo. The dried solids were evaluated for crystallinity and form by XRPD which indicated the crystalline material was polymorph Form E.

2. Approximately 5.6 mg of Formula (I) Form E was weighed into a 1 dram vial equipped with a magnetic stir bar. To this vial was added 0.3 mL of methanol to form a slurry and the slurry was allowed to equilibrate for approximately 24 hours at ambient temperature. An equal amount (approximately 5.7 mg) of Form B was added to the vial and allowed to equilibrate for four days at ambient temperature. The resulting solids were isolated by centrifuge filtration (5 minutes at 8000 RPM) and dried over night under vacuum. The dried solids were evaluated for crystallinity and form by XRPD which indicated the crystalline material was polymorph Form E.

Form F

Binary Solvent Crystallizations to Afford Formula (I) Form F

1. Fast Cooling Procedure from NMP/MTBE: Approximately 23 mg of Formula (I) Form A was placed into a 2-dram glass vial equipped with a stir bar. To the vial was added a minimal amount of NMP (0.2 ml) to just dissolve the solids at 70° C. The resulting solution was polish filtered through a 0.45 µm syringe filter into a clean preheated vial. After hot filtration, MTBE (1.0 ml) was added portion-wise. After the anti-solvent addition, the vial was placed in a refrigerator (4° C.) overnight. The crystals were collected by filtration and dried under vacuum (30 inches Hg) at ambient temperature overnight. The dried solids were evaluated for crystallinity and form by XRPD which indicated the crystalline material was polymorph Form F.

2. Slow Cooling Procedure from NMP/MTBE: Approximately 23 mg of Formula (I) Form A was placed into a 2-dram glass vial equipped with a stir bar. To the vial was added a minimal amount of NMP (0.2 ml) to just dissolve the solids at 70° C. The resulting solution was polish filtered through a 0.45 μm syringe filter into a clean preheated vial. After hot filtration, MTBE (1.0 ml) was added portion-wise. After the anti-solvent addition, the vial was cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form F.

Form G

Binary Solvent Crystallizations to Afford Formula (I) Form G

1. Fast Cooling Procedure from ethanol/MTBE: Approximately 24.3 mg of Formula (I) Form A was placed into a 2-dram glass vial equipped with a stir bar. To the vial was added a minimal amount of ethanol (0.78 ml) to just dissolve the solids at 70° C. The resulting solution was polish filtered through a 0.45 μm syringe filter into a clean preheated vial. After hot filtration, MTBE (7.0 ml) was added portion-wise. After the anti-solvent addition, the vial was placed in a refrigerator (4° C.) overnight. Once at 4° C., the contents of the vial were periodically scratched with a spatula to induce crystallization, and then allowed to equilibrate for approximately 8 hours. The crystals were collected by decanting any liquids and dried under vacuum (30 inches Hg) at ambient temperature overnight. The dried solids were evaluated for crystallinity and form by XRPD which indicated the crystalline material was polymorph Form G.

2. Fast Cooling Procedure with IPA/MTBE: Approximately 23.7 mg of Formula (I) Form A was placed into a 2-dram glass vial equipped with a stir bar. To the vial was added a minimal amount of IPA (0.60 ml) to just dissolve the solids at 70° C. The resulting solution was polish filtered through a 0.45 m syringe filter into a clean preheated vial. After hot filtration, MTBE (6.0 ml) was added portion-wise. After the anti-solvent addition, the vial was placed in a refrigerator (4° C.) overnight. Once at 4° C., the contents of the vial were periodically scratched with a spatula to induce crystallization, and then allowed to equilibrate for approximately 8 hours. The crystals were collected by vacuum filtration and dried under vacuum (30 inches Hg) at ambient temperature overnight. The dried solids were evaluated for crystallinity and form by XRPD which indicated the crystalline material was polymorph Form G.

3. Fast Cooling Procedure with Methanol/MTBE: Approximately 24 mg of Formula (I) Form A was placed into a 2-dram glass vial equipped with a stir bar. To the vial was added a minimal amount of methanol (0.6 ml) to just dissolve the solids at 60° C. The resulting solution was polish filtered through a 0.45 μm syringe filter into a clean preheated vial. After hot filtration, MTBE (6.0 ml) was added portion-wise. After the anti-solvent addition, the vials were placed in a refrigerator (4° C.) overnight. Once at 4° C., the contents of the vial were periodically scratched with a spatula to induce crystallization, and then allowed to equilibrate for approximately 8 hours. The crystals were collected by decanting any liquids and dried under vacuum (30 inches Hg) at ambient temperature overnight. The dried solids were evaluated for crystallinity and form by XRPD which indicated the crystalline material was polymorph Form G.

Form H

Binary Solvent Crystallization to Afford Formula (I) Form H

Slow Cooling Procedure from Dioxane/MTBE: Approximately 23.2 mg of Formula (I) Form A was placed into a 2-dram glass vial equipped with a stir bar. To the vial was added a minimal amount of dioxane (0.6 ml) to just dissolve the solids at 70° C. The resulting solution was polish filtered through a 0.45 μm syringe filter into a clean preheated vial. After hot filtration, MTBE (1.0 ml) was added portion-wise. After the anti-solvent addition, the vial was cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form H.

Form I

Binary Solvent Crystallizations to Afford Formula (I) Form I

1. Slow Cooling Procedure from Acetone/Toluene: Approximately 23.3 mg of Formula (I) Form A was placed into a 2-dram glass vial equipped with a stir bar. To the vial was added a minimal amount of acetone (2.5 ml) to just dissolve the solids at 50° C. The resulting solution was polish filtered through a 0.45 μm syringe filter into a clean preheated vial. After hot filtration, toluene (5.0 ml) was added portion-wise. After the anti-solvent addition, the vial was cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form I.

2. Slow Cooling Procedure with MEK/Toluene: Approximately 24.1 mg of Formula (I) Form A was placed into a 2-dram glass vial equipped with a stir bar. To the vial was added a minimal amount of MEK (2.1 ml) to just dissolve the solids at 70° C. The resulting solution was polish filtered through a 0.45 μm syringe filter into a clean preheated vial. After hot filtration, toluene (6.0 ml) was added portion-wise. After the anti-solvent addition, the vial was cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form I.

3. Slow Cooling Procedure with Dioxane/Toluene: Approximately 24.5 mg of Formula (I) Form A was placed into a 2-dram glass vial equipped with a stir bar. To the vial was added a minimal amount of dioxane (0.8 ml) to just dissolve the solids at 70° C. The resulting solution was polish filtered through a 0.45 μm syringe filter into a clean preheated vial. After hot filtration, toluene (1.0 ml) was added portion-wise. After the anti-solvent addition, the vials were cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form I.

Form J

Binary Solvent Crystallizatios to Afford Formula (I) Form J

Slow Cooling Procedure with DMF/Toluene: Approximately 24.2 mg of Formula (I) Form A was placed into a 2-dram glass vial equipped with a stir bar. To the vial was added a minimal amount of DMF (0.2 ml) to just dissolve the solids at 70° C. The resulting solution was polish filtered through a 0.45 µm syringe filter into a clean preheated vial. After hot filtration, toluene (2.0 ml) was added portion-wise. After the anti-solvent addition, the vials were cooled to ambient temperature at a rate of 20° C./h and allowed to equilibrate without stirring at ambient temperature overnight. The resulting crystals were collected by filtration and dried under vacuum (30 inches Hg) at ambient temperature overnight. The dried solids were evaluated for crystallinity and form by XRPD which indicated the crystalline material was polymorph Form J.

Example 11

Preparation of Amorphous Compound of Formula (I)

To polymorph Form A of the compound of Formula (I) (2.0 g) was added 50 mL of t-butanol and 25 mL of water. The mixture was heated with stirring to 40° C. for 0.5 hours. After sonication for about 20 minutes, 25 mL of t-butanol was added. The mixture was then cooled to RT to give a homogeneous solution. After filtration, the resulting solution was lyophilized for 2 days and a fluffy solid resulted. The amorphous quality of the solid was confirmed by XRPD (see FIG. 11), DSC and TGA analyses.

Example 12

XRPD Studies

Using the XRPD instrument and parameters described above, the following XRPD peaks were observed for Formula (I) Polymorph Forms A, B, C, D. E, F, G, H, I, and J. The XRPD traces for these ten polymorph forms are given in FIGS. 1-10, respectively. In Table 7, peak position units are ° 2θ. In one embodiment, a given polymorph Form can be characterized as having at least one of the five XRPD peaks given in Set 1 in Table 7. In another embodiment, the given Form can be characterized as having at least one of the five XRPD peaks given in Set 1 in combination with at least one of the XRPD peaks given in Set 2 in Table 7. In some embodiments, one or more peak position values can be defined as being modified by the term "about" as described herein. In other embodiments, any given peak position is with ±0.2 2θ (e.g., 9.6±0.2 2θ).

TABLE 7

| Form | A | B | C | D | E | F | G | H | I | J |
|---|---|---|---|---|---|---|---|---|---|---|
| XRPD | 9.6 | 7.9 | 6.6 | 9.2 | 6.7 | 9.6 | 6.7 | 8.7 | 9.7 | 9.1 |
| Peaks | 12.2 | 13.4 | 10.4 | 11.4 | 9.3 | 14.0 | 9.5 | 9.2 | 11.4 | 16.4 |
| Set 1 | 15.6 | 14.0 | 12.5 | 17.4 | 12.7 | 17.3 | 10.6 | 14.1 | 14.2 | 17.3 |
| (°2θ) | 18.3 | 15.0 | 13.3 | 18.3 | 13.9 | 19.2 | 19.0 | 17.3 | 19.3 | 17.9 |
|  | 19.2 | 23.4 | 24.3 | 22.9 | 24.4 | 24.6 | 19.6 | 18.5 | 24.5 | 18.3 |
| XRPD | 9.1 | 9.5 | 8.8 | 9.8 | 12.4 | 12.4 | 13.4 | 7.1 | 9.2 | 9.4 |
| Peaks | 9.4 | 12.7 | 9.9 | 12.2 | 13.3 | 16.1 | 15.0 | 10.6 | 14.7 | 10.1 |
| Set 2 | 12.4 | 13.6 | 13.4 | 15.8 | 14.3 | 16.6 | 15.8 | 11.3 | 15.5 | 10.7 |
| (°2Th) | 14.8 | 14.2 | 15.5 | 16.2 | 15.5 | 17.1 | 17.8 | 11.6 | 16.7 | 14.0 |
|  | 16.3 | 15.7 | 16.9 | 16.8 | 17.4 | 20.8 | 20.7 | 16.2 | 17.3 | 14.3 |
|  | 17.7 | 19.0 | 19.8 | 18.9 | 18.5 | 21.5 | 21.2 | 18.3 | 18.4 | 15.5 |
|  | 21.1 | 22.3 | 21.3 | 19.9 | 22.0 | 22.0 | 22.8 | 18.8 | 21.4 | 16.9 |
|  | 21.9 | 24.2 | 23.6 | 20.0 | 23.9 | 24.3 | 23.8 | 20.3 | 22.9 | 19.9 |
|  | 24.0 | 24.8 | 25.3 | 24.9 | 24.1 | 25.2 | 24.3 | 21.7 | 29.1 | 24.0 |
|  | 26.9 | 26.9 | 27.9 | 29.3 | 26.4 | 25.4 | 25.6 | 24.7 | 34.1 | 24.7 |

Example 13

Differential Scanning Calorimetry (DSC) Studies

Using the DSC instrument and parameters described above, the following DSC peaks were observed for the compound of Formula (I) polymorph Forms A, B, C, D. E, F, G, H, I, and J. The DSC thermograms for these nine polymorph forms are given in FIGS. 12-24, respectively, and peak positions are given in Table 8. Further DSC data for Polymorph Forms A, B, C, D. E, F, G, H, I, and J is given in Table 9 below. Unless marked with a ^ that indicates an exothermic peak, all peaks are endothermic.

TABLE 8

| Form | FIG. | DSC peaks (° C.) |
|---|---|---|
| A | 12 | 239, 280 |
| A | 21 | 238, 280 |
| B | 13 | 281 |
| C | 14 | 208, 254^, 283 |
| C | 23 top | about 208, about 245^, 281 |
| C | 23 bottom | 206, 251^, 283 |
| D | 15 | 260, 283 |
| E | 16 | 131, 263, 267^, 282 |
| F | 17 | 181, 260, 266^, 282 |
| F | 24 | 181, 260, 266^, 282 |
| G | 18 | 162, 241^, 281 |
| H | 19 | 128, 258, 282 |
| I | 20 | 208, 263 |
| J | 21 | 121, 185, 259, 282 |

As observed in FIGS. 12-23, the DSC thermograms for Polymorph Forms A, B, C, D, E, F, G, H, and J each have a endothermic peak in the about 280° C. to about 282° C. range. This peak represents that upon heating, the given Form recrystallizes to Form B (see Example 10 where heating Form A or Form C to about 250° C. then cooling affords Form B) which then has its characteristic endothermic peak in the about 280° C. to about 282° C. range.

Example 14

Thermogravimetric Analysis (TGA) Studies

Using the TGA instrument and parameters described above, the following TGA peaks summarized in Table 9 were observed for Formula (I) Polymorph Forms C-J. The peaks correspond to when a weight loss (% wt) is observed at a given temperature as the sample is heated.

Example 15

Summary of Preparation and Analysis of Formula (I) Polymorph Forms A-J

Table 9 summarizes non-limiting exemplary preparation techniques for Formula (I) Polymorph Forms A-J and representative analytical data as described below and elsewhere.

TABLE 9

| Form | Polymorph details | General Conditions | Cooling profiles | Raman | DSC | TGA % wt loss (temp ° C.) | API:Solvent molar ratio |
|---|---|---|---|---|---|---|---|
| A | anhydrate | starting material, slurries in IPA, EtOH, and MeCN, crystallizations with DCM as anti-solvent | fast and slow cooling | Form A | 236, 280 | 0 | n/a |
| B | anhydrate | isothermal hold of Form A at 250° C. for 5 minutes | n/a | no spectrum | 281 | n/a | n/a |
| C | channel hydrate | slurries in water, or water as an anti-solvent | fast and slow cooling | Form C, generally | 204, 242^, 280 | 1.7% (80° C.), 0.2% (190° C.) | n/a |
| D | anhydrate | crystallizations in MEK, also seen during salt formations in MEK | fast and slow cooling | Form D, generally | 260, 283 | 0.2% (150° C.) | n/a |
| E | anhydrate | crystallizations in MeOH without anti-solvents | slow cooling only | Free Form E | 131, 263, 267^, 282 | 0.7% (80° C.), 1.3% (130° C.) | 1.0:0.06 API:MeOH |
| F | NMP Solvate | Crystallizations in NMP with MTBE as anti-solvent | fast and slow cooling | Free Form F | 181, 260, 266^, 282 | 15.8% (150° C.), 2.8% (180° C.) | 1.0:0.73 API:NMP |
| G | MTBE Solvate | Crystallizations in EtOH, IPA, and MeOH with MTBE as an anti-solvent | fast cooling only | Free Form G | 162, 241^, 281 | 18.5% (160° C.) | 1.0:0.87 API:MTBE |
| H | channel MTBE solvate | crystallization in dioxane with MTBE as anti-solvent only | slow cooling only | consistent with Form D | 128, 258, 281 | 7.5% (130° C.) | 1.0:0.34 API:MTBE |
| I | hemi-toluene solvate | crystallizations with toluene as anti-solvent | fast and slow cooling | consistent with Form D | 208, 263 | 10.5% (130° C.), 0.8% (200° C.) | 1.9:0.5 API:Toluene |
| J | hemi-toluene solvate | crystallization in DMF with toluene as anti-solvent | slow cooling only | consistent with Form D | 121, 185, 259, 282 | 10.8% (100° C.) | 1.0:0.5 API:Toluene |

Example 16

Stability Studies

Polymorphs Form A and Form C were subjected to stability studies where several samples of each given Form were packaged and subjected to the given temperature and humidity conditions as described in Table 10. At each timepoint, a sample for that study was opened and evaluated by HPLC for purity, Karl Fischer for moisture content, and XRPD for confirming the polymorph Form. In all studies detailed in Table 10 at each evaluation timepoint, no indication of instability of the polymorphic Form was observed.

TABLE 10

| Form | Packaging | Storage Conditions | Evaluation Timepoints |
|---|---|---|---|
| A | Double LDPE bags twist tied to close inside a fiberboard drum | 40° C. ± 2° C./ 75% RH ± 5% RH | 1, 2, 3, 6, and 12 months |

TABLE 10-continued

| Form | Packaging | Storage Conditions | Evaluation Timepoints |
|------|-----------|--------------------|-----------------------|
| C | Primary: Double LDPE bags twist tied to close Secondary: Polyethylene/foil bag twist tied to close Outer: HDPE drum | Study 1: 5° C. ± 3° C./ 60% RH ± 5% RH Study 2: 25° C. ± 2° C./ 60% RH ± 5% RH Study 3: 40° C. ± 2° C./ 75% RH ± 5% RH | For both Studies 1 and 2: 1, 3, 6, and 9 months For Study 3: 2 weeks, 1, month, 3 months, and 6 months |
| C | Primary: Double LDPE bags twist tied to close Secondary: Polyethylene/Mylar ® bag twist tied to close Outer: HDPE drum | Study 1: 5° C. ± 3° C./ 60% RH ± 5% RH Study 2: 25° C. ± 2° C./ 60% RH ± 5% RH Study 3: 40° C. ± 2° C./ 75% RH ± 5% RH | For all 3 Studies: 1, 3, and 6 months |
| C | Primary: Double LDPE bags twist tied to close Secondary: Polyethylene/foil bag twist tied to close Outer: HDPE drum | Study 1: 5° C. ± 3° C./ 60% RH ± 5% RH Study 2: 25° C. ± 2° C./ 60% RH ± 5% RH Study 3: 40° C. ± 2° C./ 75% RH ± 5% RH | For all 3 Studies: 1, 3, and 6 months |

Example 17

Dynamic Vapor Sorption Analysis

Figure 30:
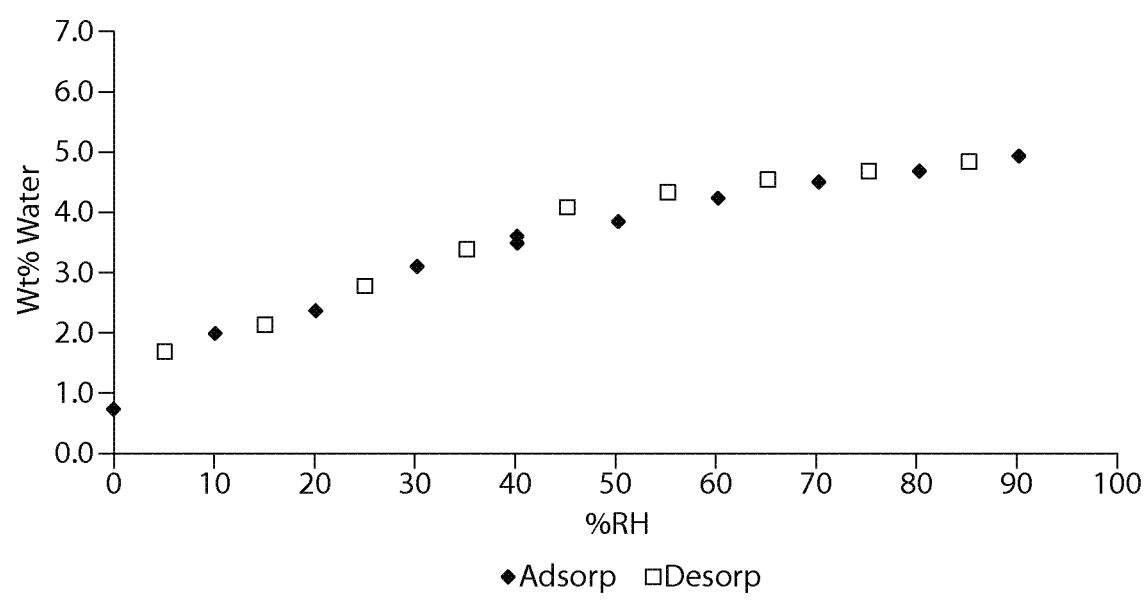
FIG. 30 shows a dynamic vapor sorption (DVS) analysis of Polymorph Form C.

Dynamic vapor sorption (DVS) analysis was performed on polymorph Forms A, B, C, D, and E using the DVS instrument and parameters as described above. Form A was observed to be slightly hygroscopic and showed 0.7 wt % moisture uptake at 60% RH and 2.6 wt % moisture uptake at 90% RH. Hysteresis indicative of hemi-hydrate formation was observed. Form B was observed to be slightly hygroscopic and showed 1.0 wt % moisture uptake at 60% RH and 1.7 wt % moisture uptake at 90% RH. Form C was observed to be moderately hygroscopic, showing 4.2% moisture uptake at 60% RH and 4.9% moisture uptake at 90% RH (see FIG. 30). Form D was observed to be slightly hygroscopic and showed 0.4 wt % moisture uptake at 60% RH and 1.7 wt % moisture uptake at 90% RH. Form E was observed to be slightly hygroscopic and showed 1.9 wt % moisture uptake at 60% RH and 2.2 wt % moisture uptake at 90% RH. Both Forms A and C were held in humidity chambers at 9% RH and 95% RH and showed no changes in Form after 1 week.

Example 18

Thermal Stability

Forms A, B, C, D, and E were held at 60° C. for 10 days followed by analysis by XRPD. In each case, 8 mL vials were charged with approximately 20 mg of material, with the exception of Form B for which 10 mg of material was charged. Samples equilibrated in an oven for 10 days. No polymorph Form changes were observed by XRPD. All Forms were observed to be stable.

Example 19

Grinding Stability

Forms A, C, D, and E were subjected to grinding experiments performed using a mortar and pestle by hand. Samples were lightly grounded for 2 minutes then analyzed by XRPD. Material was then returned to the mortar and pestle and grounded for an additional 3 minutes, for a total of 5 minutes of grinding, and reanalyzed by XRPD. Form A was observed to remain consistent after both 2 and 5 minutes of grinding. Form C was observed to remain consistent after both 2 and 5 minutes of grinding.

Example 20

Summary of Examples 17-19

Table 11 summarizes non-limiting representative analytical data for Formula (I) Polymorph Forms A-E as described below and elsewhere.

TABLE 11

| Form | NMR | DVS | Thermal stability (60° C.) | Grinding (mortar & pestle) | Solubility (mg/mL) |
|------|-----|-----|---------------------------|----------------------------|--------------------|
| A | consistent | 0.7% @ 60% RH 2.6% @ 90% RH | stable after 1 week | remained Form A after 5 min. | 0.030 ($H_2O$) 21.800 (SGF) |
| B | consistent | 1.0% @ 60% RH 1.7% @ 90% RH | stable after 1 week | n/a | n/a |
| C | consistent; 1.9% water by KF | 4.2% @ 60% RH 4.9% @ 90% RH | stable after 1 week | remained Form C after 5 min, v. low intensity | 0.001 ($H_2O$) 9.133 (SGF) |
| D | consistent | 0.4% @ 60% RH 1.7% @ 90% RH | stable after 1 week | amorphous after 2 min. | n/a |
| E | 0.5 wt % MeOH | 1.9% @ 60% RH 2.2% @ 90% RH | stable after 1 week | amorphous after 5 min. | n/a |

Example 21

Salt Screen

Figure 25:
FIG. 25 shows a panel of salts tested for formation of crystalline solids in various solvents.

Salts of a compound of Formula (I) were formed with L-tartaric acid, p-toluenesulfonic acid, D-glucaronic acid, ethane-1,2-disulfonic acid (EDSA), 2-naphthalenesulfonic acid (NSA), hydrochloric acid (HCl) (mono and bis), hydrobromic acid (HBr), citric acid, naphthalene-1,5-disulfonic acid (NDSA), DL-mandelic acid, fumaric acid, sulfuric acid, maleic acid, methanesulfonic acid (MSA), benzenesulfonic acid (BSA), ethanesulfonic acid (ESA), L-malic acid, phosphoric acid, and aminoethanesulfonic acid (taurine). Various salts and the free base were tested against various solvents for formation of crystalline solids, as shown in FIG. 25. Tables 12 and 13 summarize representative data for exemplary salts of a compound of Formula (I). A compound of Formula (I) was observed to form semi-crystalline to crystalline mono-salts with ethane-1,2-disulfonic acid (EDSA), 2-naphthalenesulfonic acid (NSA), hydrochloric acid (HCl), hydrobromic acid (HBr), citric acid, and amorphous monosalt with naphthalene-1,5-disulfonic acid (NDSA) and an amorphous bis-salt with HCl from various solvents.

TABLE 12

| Counter ion | Solvent | Form by XRPD | API:CI (ratio by NMR or IC) | DSC (° C.) | TGA (wt loss %) |
|---|---|---|---|---|---|
| Free Form A | n/a | Free Form A | consistent | 236, 242, 280 | 0 |
| EDSA | acetone | semi-cryst | 1.0:1.1 | 63, 210, 260, 284 | 1.1, 1.1 |
|  | MEK | semi-cryst | 1.0:1.1 | 57, 209, 259, 283 | 1.0 |
| NSA | acetone | crystalline | 1.0:1.1 | 252 | 0 |
|  | acetone | crystalline | 1.0:1.06 | n/a | n/a |
| HCl | MEK | crystalline | 1.0:1.2 | 163, 177, 213 | 5.7, 10.0 |
|  |  |  | (MEK solvate) |  |  |
| Bis HCL | IPA/IPAc | amorphous | 1.0:1.8 | 182, 215 | 0.5, 12.8, 6.0 |
| NDSA | MEK | amorphous | 1.0:0.92 | 96, 216, 273 | 6.1 |

TABLE 13

| Counter ion | Solubility in water (mg/mL) (pH) | Moisture Sorption (wt % water) | Comments |
|---|---|---|---|
| Free Form A | 0.03 (3.29) | 60% RH: 0.7 90% RH: 2.6 | high melt B form |
| EDSA | 9.4 (1.43) | 60% RH: 7.5 90% RH: 28.1 | Forms sticky/oily material in water |
| NSA | 0.05 (3.01) | 60% RH: 0.3 90% RH: 0.7 | n/a |
| HCl | n/a | n/a | MEK solvate |
| Bis HCL | 11.8 (1.80) | 60% RH: 9.9 90% RH: 12.3 | n/a |
| NDSA | 0.3 (1.68) | n/a | n/a | n/a—not analyzed
CI—Counter-ion
IC—Ion Chromatography

Example 22

Formulations and Dosage Forms

Example 22A: Capsule Formulations for Formula (I) Form C Polymorph

Capsules containing a compound of Formula (I) Form C polymorph (API) were prepared according to the following procedures. The capsules included a hard gelatin capsule filled with a formulated dry blend powder fill of Formula (I) Form C polymorph and one or more excipients. In some examples, the capsule components included Formula (I) Form C polymorph (about 1% to about 30% w/w); a filler/glidant such as silicified microcrystalline cellulose (about 70% to about 99% w/w); a disintegrant such as crospovidone (0% to about 7% w/w); and a lubricant such as magnesium stearate (0% to about 2% w/w).

Other excipients that can be used in exemplary capsule formulations include, but are not limited to, fillers such as lactose, mannitol, starch, sorbitol, sucrose, dicalcium phosphate, and microcrystalline cellulose; disintegrants such as croscarmellose sodium and sodium starch glycolate; glidants such as colloidal silicon dioxide, silicon dioxide, magnesium silicate, and talc; lubricants such as sodium stearyl fumarate and stearic acid; and surfactants such as sodium lauryl sulphate, sodium dodecyl sulphate, Tween® 80, and Lutrol®. The choice and the percentage of the filler/glidant can be based on the flowability of the blend. The choice and the percentage of the disintegrant can be based on the release profile of the capsule in 0.1N Hydrochloric acid with no surfactants.

For a given formulation, part of the filler/glidant and the disintegrant were each separately passed through a #30 mesh screen. The Formula (I) Form C polymorph and part of the filler/glidant were combined and passed through a #30 mesh screen. The lubricant was passed through a #40 mesh screen. Each component, except for the lubricant, was weighed and separately transferred into a Patterson Kelley's V-blender and blended for about 5 to about 15 minutes after each addition. Then, the mixture was milled through a Quadro® Comil® using a 0.039R mesh screen at about 40 rpm speed. Finally, the lubricant was added and the mixture was blended for about 5 minutes. The mixture was then used to fill the appropriate capsules using an IN-CAP encapsulation machine.

A non-limiting example of formulation and capsule preparation is given in Table 14. A low strength formulation was prepared for the 1 mg/5 mg capsules, and a high strength formulation was prepared for the 25 mg/100 mg strengths. The 1 mg and 25 mg strengths were in size 2, opaque white, hard gelatin capsules while the 5 mg strength was in size 2, opaque Swedish orange, hard gelatin capsules and the 100 mg strength was in size 0, opaque white, hard gelatin capsules.

TABLE 14

Capsule Formulations

| Components (% w/w) | 1 mg and 5 mg capsules | 25 mg and 100 mg capsules | Category |
|---|---|---|---|
| Formula (I) Form C polymorph | 2.3 | 25.0 | API |
| Silicified Microcrystalline Cellulose (SMCC), NF | 91.7 | 68.5 | Filler/Glidant |
| Crospovidone, EP, USP/NF, JP | 5.0 | 5.0 | Disintegrant |
| Magnesium Stearate, NF, BP, JP | 1.0 | 1.5 | Lubricant |
| Hard Gelatin Capsule | 2 White (1 mg) 2 Swedish orange (5 mg) | 2 White (25 mg) 0 White (100 mg) | Encapsulation |

Example 22B: Large-scale Capsule Formulations for Formula (I) Form C Polymorph

The formulations were evaluated for their manufacturability, scalability to automated encapsulation equipment, content uniformity, dissolution, and stability. To evaluate the above mentioned factors, large scale batches were manufactured for all strengths. For the 1/5 mg blend, approximately 2 kg of API formulation was manufactured as indicated in Example 22A, allowing production of about 9000 capsules of each strength. For the 25/100 mg blend, approximately 2.5 kg of API formulation was manufactured as indicated in Example 22A, allowing production of about 6000 capsules of each strength. Tables 15 and 16 below summarize the results of several assays of these formulations.

TABLE 15

1/5 mg Formulation Characteristics

| Assay | 1 mg Capsules | 5 mg Capsules |
|---|---|---|
| Blend uniformity before co-milling | 2.4% w/w, 5% RSD | |
| Blend uniformity after co-milling | 2.2% w/w, 4% RSD | |
| Blend uniformity after lubrication | 2.3% w/w, 4% RSD | |
| Bulk and Tapped Density (g/cc) | 0.58 | 0.68 |
| Moisture Content (% w/w) | 4.71 | 4.55 |
| Assay of Capsules (% LC) | 102.0 | 98.0 |
| Purity (% a/a) | 99.67 | 99.72 |
| Content Uniformity (% LC) | 104.8 | 97.7 |
| AV, and Range | 6.8, 102.4-106.6 | 6, 93.2-99.4 |
| Dissolution (% LC) | 15 min-88 | 15 min-83 |
| | 30 min-92 | 30 min-91 |
| | 45 min-96 | 45 min-94 |
| | 60 min-98 | 60 min-95 |
| | Inf.-103 | Inf.-99 |

TABLE 16

25/100 mg Formulation Characteristics

| Assay | 25 mg Capsules | 100 mg Capsules |
|---|---|---|
| Blend uniformity before lubrication | 26.5% w/w, 2.2% RSD | |
| Blend uniformity after lubrication | 24.7% w/w, 0.4% RSD | |
| Bulk and Tapped Density (g/cc) | 0.40 | 0.61 |
| Moisture Content (% w/w) | 4.36 | 4.28 |
| Assay of Capsules (% LC) | 100.2 | 97.9 |
| Purity (% a/a) | 99.6 | 99.6 |
| Content Uniformity (% LC) | 100.5 | 98.2 |
| AV, and Range | 11, 94.7-107.7 | 7, 94.0-102.7 |
| Dissolution (% LC) | 15 min-79 | 15 min-86 |
| | 30 min-83 | 30 min-87 |
| | 45 min-84 | 45 min-90 |
| | 60 min-86 | 60 min-91 |
| | Inf.-102 | Inf.-102 |

The stability of the capsules in a container closure was evaluated at long-term and accelerated conditions. Container closure conditions used were (i) 60-cc high density polyethylene (HDPE), wide mouth, round, white bottle; and (ii) child resistant 33-mm white plastic cap with a heat induction foil inner seal liner. The containers containing the capsules were subjected to the following conditions: (1) −20° C.±5° C.; (2) 5° C.±3° C.; (3) 25° C.±2° C., 60% RH±5% RH; (4) 40° C.±2° C., 75% RH±5% RH; (5) 25° C.±2° C., 60% RH±5% RH, open bottle; (6) 40° C.±2° C., 75% RH±5% RH, open bottle; and (7) 30° C.±2° C., 65% RH±5% RH. Samples of the capsule formulations were analyzed at certain time intervals. The API remained stable at 25° C.±2° C., 60% RH±5% RH and 40° C.±2° C., 45% RH±5% RH for at least 6 months. The API remained stable for at least 6 month at −20° C.±5° C., 5° C.±3° C. when stored in induction-sealed HDPE bottles. The API was stable for at least 6 months at 25° C.±2° C., 60% RH±5% RH and 40° C.±2° C., 75% RH±5% RH in open HDPE bottles.

Manufacturing, packaging, labeling, storage, and testing of the capsules were performed in accordance with current Good Manufacturing Practices (cGMP). The capsules were packaged in High Density Polyethylene (HDPE) bottles. Other suitable packaging vessels include, but are not limited to, glass bottles, low density polyethylene bottles/drums, fiber drums, HDPE drums, and blister packaging which can include materials like aluminum foil, Aclar®, and/or PVC/PVdC/PE films.

Karl Fischer analysis of the API in the capsules indicated a water content of between about 4% w/w and about 5% w/w (e.g., about 4.2%, about 4.3%, about 4.5%, about 4.7%, about 4.9%, about 5.0%)

Figure 31:
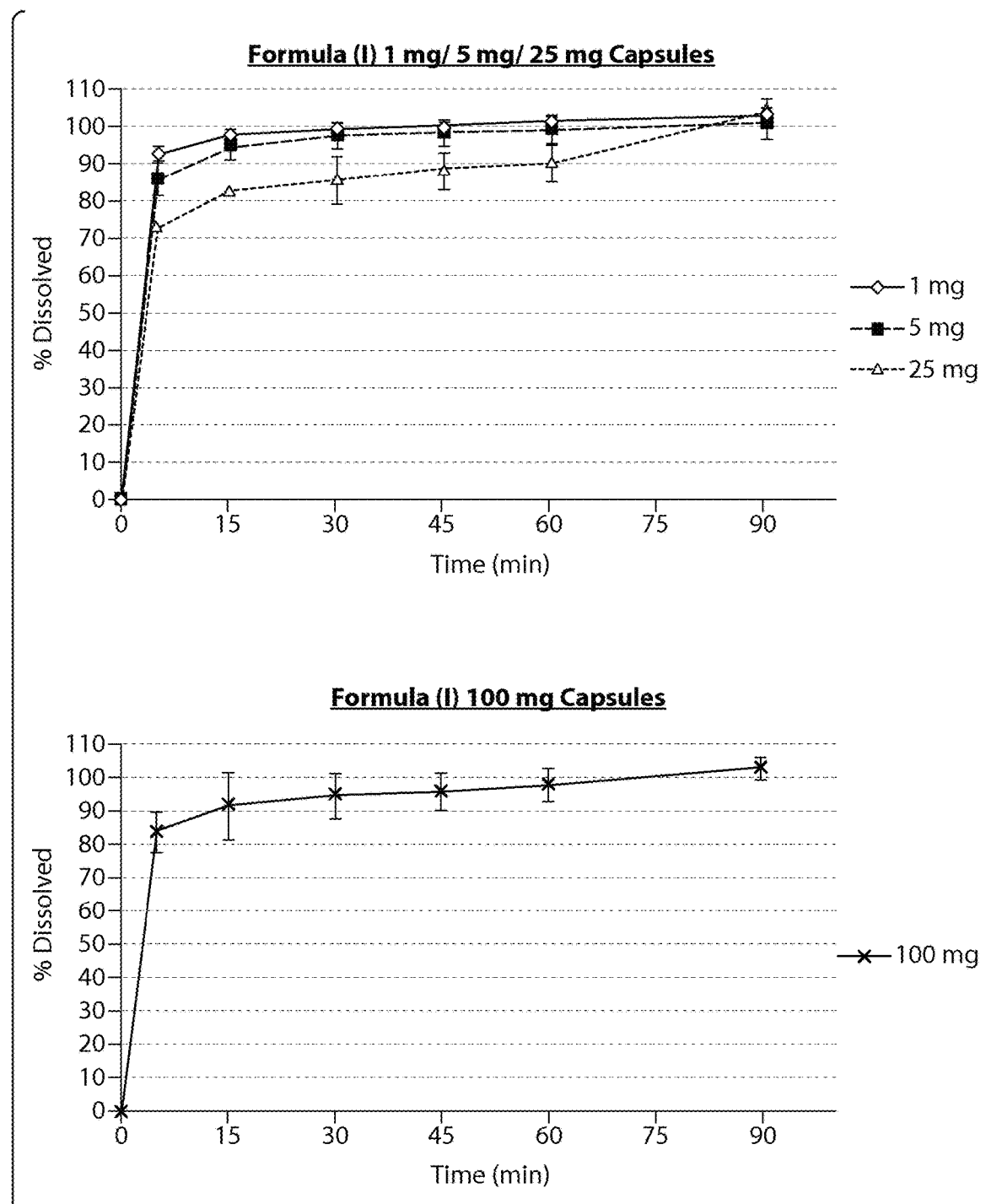
FIG. 31 shows representative dissolution profiles of capsules containing Polymorph Form C.

A representative capsule dissolution profile for the 1, 5, 25, and 100 mg capsules is shown in FIG. 31. The dissolution of the capsules was consistent with that of an immediate-release solid oral dosage form. At 60 min, greater than about 90% of API had been dissolved. The dissolution conditions were USP Apparatus II (Paddle), 0.1 N HCl at 37° C., 500 mL (for 1, 5, 25 mg) or 900 mL (for 100 mg), 50 RPM paddle speed.

Example 23

Biological Activity Assessment

A PI3-Kinase HTRF® assay kit (cat No. 33-016) purchased from Millipore Corporation was used to screen compounds disclosed herein. This assay used specific, high affinity binding of the GRP1 pleckstrin homology (PH) domain to PIP3, the product of a Class 1A or 1B PI3 Kinase acting on its physiological substrate PIP2. During the detection phase of the assay, a complex was generated between the GST-tagged PH domain and biotinylated short chain PIP3. The biotinylated PIP3 and the GST-tagged PH domain recruited fluorophores (Streptavidin-Allophycocyanin and Europium-labeled anti-GST respectively) to form the fluorescence resonance energy transfer (FRET) architecture, generating a stable time-resolved FRET signal. The FRET complex was disrupted in a competitive manner by non-biotinylated PIP3, a product formed in the PI3 Kinase assay.

PI3 Kinase α, β, γ and δ activity was assayed using the PI3 Kinase HTRF® assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K) and PI3Kδ (catalogue No. 14-604-K) were obtained from Millipore Corporation. Purified recombinant PI3K enzyme was used to catalyze the phosphorylation of phosphatidylinositol 4,5-bisphosphate (PIP2 at 10 μM) to phosphatidylinositol 3,4,5-trisphosphate (PIP3) in the presence of 10 μM ATP. The assay was carried out in 384-well format and detected using a Perkin Elmer EnVision Xcite Multilabel Reader. Emission ratios were converted into percent inhibitions and imported into GraphPad Prism® software. The concentration necessary to achieve inhibition of enzyme activity by 50% ($IC_{50}$) was calculated using concentrations ranging from 20 μM to 0.1 nM (12-point curve). $IC_{50}$ values were determined using a nonlinear regression model available in GraphPad Prism® 5.

Example 24

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 μM stock solution to an aliquot of PBS (in duplicate) to give a final assay volume of 400 μL, containing 5 μM test compound and 1% DMSO (for half-life determination a total sample volume of 700 μL is prepared). Reactions are incubated, with shaking, for 24 hours at 37° C.; for half-life determination samples are incubated for 0, 2, 4, 6, and 24 hours. Reactions are stopped by adding immediately 100 μL of the incubation mixture to 100 μL of acetonitrile and vortexing for 5 minutes. The samples are then stored at −20° C. until analysis by HPLC-MS/MS. Optionally, a control compound or a reference compound such as chlorambucil (5 μM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, Cl2, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 25

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). $IC_{50}$ values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration of 10 or 100 μM and allowed to proceed for 5 minutes at room temperature. For TLC analysis, reactions are then terminated by the addition of 105 μl 1N HCl followed by 160 μl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol: 1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, $IC_{50}$ determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including, but not limited to, PI 3-Kinase α, β, δ, and γ. An exemplary system is PI 3-Kinase (human) HTRF® Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 μl per well. In the first step, each well receives 2 μl of test compound in 20% dimethylsulphoxide resulting in a 2% DMSO final concentration. Next, approximately 14.5 μl of a kinase/PIP2 mixture (diluted in 1× reaction buffer) is added per well for a final concentration of 0.25-0.3 g/ml kinase and 10 μM PIP2. The plate is sealed and incubated for 15 minutes at room temperature. To start the reaction, 3.5 μl of ATP (diluted in 1× reaction buffer) is added per well for a final concentration of 10 μM ATP. The plate is sealed and incubated for 1 hour at room temperature. The reaction is stopped by adding 5 μl of Stop Solution per well and then 5 μl of Detection Mix is added per well. The plate is sealed, incubated for 1 hour at room temperature, and then read on an appropriate plate reader. Data is analyzed and $IC_{50}$s are generated using GraphPad Prism® 5.

Example 26

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using AlamarBlue® reduction. Balb/c splenic B cells are purified over a Ficoll-Paque™ PLUS gradient followed by magnetic cell separation using a MACS B cell Isolation Kit (Miletenyi). Cells are plated in 90 µl at 50,000 cells/well in B Cell Media (RPMI+10% FBS+Penn/Strep+50 µM bME+5 mM HEPES). A compound disclosed herein is diluted in B Cell Media and added in a 10 µl volume. Plates are incubated for 72 hours at 37° C. and 5% $CO_2$. A volume of 15 µL of AlamarBlue® reagent is added to each well and plates are incubated for 5 hours at 37° C. and 5% $CO_2$. AlamarBlue® fluoresce is read at 560Ex/590Em, and $IC_{50}$ or $EC_{50}$ values are calculated using GraphPad Prism® 5.

Example 27

Tumor Cell Line Proliferation Assay

The ability of one or more subject compounds to inhibit tumor cell line proliferation can be determined according to standard procedures known in the art. For instance, an in vitro cellular proliferation assay can be performed to measure the metabolic activity of live cells. The assay is performed in a 96 well microtiter plate using AlamarBlue® reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 µl at 5,000 cells/well in Tumor Cell Media. A compound disclosed herein is diluted in Tumor Cell Media and added in a 10 µl volume. Plates are incubated for 72 hours at 37° C. and 5% $CO_2$. A volume of 10 µL of AlamarBlue® reagent is added to each well and plates are incubated for 3 hours at 37° C. and 5% $CO_2$. AlamarBlue® fluoresce is read at 560Ex/590Em, and $IC_{50}$ values are calculated using GraphPad Prism® 5.

Example 28

Antitumor Activity In Vivo

The compounds described herein can be evaluated in a panel of human and murine tumor models.
Paclitaxel-Refractory Tumor Models
 1. Clinically-Derived Ovarian Carcinoma Model.
 This tumor model is established from a tumor biopsy of an ovarian cancer patient. Tumor biopsy is taken from the patient. The compounds described herein are administered to nude mice bearing staged tumors using an every 2 days×5 schedule.
 2. A2780Tax Human Ovarian Carcinoma Xenograft Mutated Tubulin).
 A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.
 3. HCT116/VM46 Human Colon Carcinoma Xenograft Multi-Drug Resistant).
 HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days×5 schedule.
 4. M5076 Murine Sarcoma Model
 M5076 is a mouse fibrosarcoma that is inherently refractory to paclitaxel in vivo. The compounds described herein can be administered to mice bearing staged tumors on an every 2 days×5 schedule.
 One or more compounds as disclosed herein can be used in combination other therapeutic agents in vivo in the multidrug resistant human colon carcinoma xenografts HCT/VM46 or any other model known in the art including those described herein.

Example 29

Microsome Stability Assay

The stability of one or more subject compounds is determined according to standard procedures known in the art. For example, stability of one or more subject compounds is established by an in vitro assay. For example, an in vitro microsome stability assay is established that measures stability of one or more subject compounds when reacting with mouse, rat or human microsomes from liver. The microsome reaction with compounds is performed in 1.5 mL Eppendorftube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of dd$H_2O$. Negative control (without NADPH) tube contains 75 µL of 20.0 mg/ml mouse, rat or human liver microsome; 0.4 µL of 0.2 M phosphate buffer, and 525 µL of dd$H_2O$. The reaction is started by adding 1.0 L of 10.0 mM tested compound. The reaction tubes are incubated at 37° C. 100 µL sample is collected into new Eppendorf tube containing 300 µL cold methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 30

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

In one embodiment, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, Cl2, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 31

Kinase Signaling in Blood

PI3K/Akt/mTor signaling is measured in blood cells using the phosflow method (*Methods Enzymol.* (2007) 434:131-54). This method is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. Inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g., 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g., with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells is then analyzed by flow cytometry.

Example 32

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+ H4435, Stem Cell Tehcnologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 33

In Vivo Effect of Kinase Inhibitors on Leukemic Cells

Female recipient mice are lethally irradiated from a γ source in two doses about 4 hr apart, with approximately 5 Gy each. About 1 hr after the second radiation dose, mice are injected i.v. with about $1\times10^6$ leukemic cells (e.g., Ph+ human or murine cells, or p190 transduced bone marrow cells). These cells are administered together with a radio-protective dose of about $5\times10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents can reduce leukemic blood cell counts as compared to treatment with known chemotherapeutic agents (e.g., Gleevec®) alone under the conditions tested.

Example 34

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to demonstrate that the kinase inhibitors disclosed herein can suppress or delay the onset of lupus symptoms in lupus disease model mice.

Example 35

Murine Bone Marrow Transplant Assay

Female recipient mice are lethally irraiated from a γ ray source. About 1 hr after the radiation dose, mice are injected with about 1×106 leukemic cells from early passage p190 transduced cultures (e.g., as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g., imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to demonstrate that effective therapeutic doses of the compounds disclosed herein can be used for inhibiting the proliferation of leukemic cells.

Example 36

Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds disclosed herein that inhibit angiogenesis and are thus expected to be useful in treating ocular disorders related to aberrant angiogenesis and/or vascular permeability.

Example 37

Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as Elvax® (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including, but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results can indicate one or more compounds disclosed herein inhibit angiogenesis and thus can be useful in treating ocular disorders related to aberrant angiogenesis and/or vascular permeability.

Example 38

Microtiter-plate Angiogenesis Assay

The assay plate is prepared by placing a collagen plug in the bottom of each well with 5-10 cell spheroids per collagen plug each spheroid containing 400-500 cells. Each collagen plug is covered with 1100 µl of storage medium per well and stored for future use (1-3 days at 37° C., 5% $CO_2$). The plate is sealed with sealing. Test compounds are dissolved in 200 µl assay medium with at least one well including a VEGF positive control and at least one well without VEGF or test compound as a negative control. The assay plate is removed from the incubator and storage medium is carefully pipeted away. Assay medium containing the test compounds are pipeted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 ml of 10% paraformaldehyde in Hanks BSS per well, and storing at 4° C. The results are expected to identify compounds that inhibit angiogenesis in various cell types tested, including cells of ocular origin.

Example 39

Combination Use of PI3K-δ Inhibitors and Agents that Inhibit IgE Production or Activity The compounds as disclosed herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy) phenylacetamide)benzoic acid, rapamycin, rapamycin analogs (i.e., rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3K-δ can be efficacious in treatment of autoimmune and inflammatory disorders (AIID), for example, rheumatoid arthritis. If any of the compounds causes an undesired level of IgE production, one can choose to administer it in combination with an agent that inhibits IgE production or IgE activity. Additionally, the administration of PI3K-δ or PI3K-δ/γ inhibitors as disclosed herein in combination with inhibitors of mTOR can also exhibit synergy through enhanced inhibition of the PI3K pathway. Various in vivo and in vitro models can be used to establish the effect of such combination treatment on AIID including, but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3K-δ inhibitors as disclosed herein with and without mTOR inhibitors such as rapamycin, rapalogs, or mTORC1/ C2 inhibitors. The results are expected to show that in the presence of mTOR inhibitors (e.g., rapamycin) alone, there is little to no substantial effect on IgG and IgE response. However, in the presence of PI3K-δ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3K-δ inhibitors alone.

(b) TNP Assay

Mice are immunized with TNP-Ficoll or TNP-KHL and treated with: vehicle, a PI3K-δ inhibitor, an mTOR inhibitor, for example rapamycin, or a PI3K-δ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3K-δ inhibitor and mTOR inhibitor exhibit a reduction in antigen specific IgG3 response as compared to the mice treated with vehicle alone. Additionally, the mice treated with both PI3K-δ inhibitor and mTOR inhibitor exhibit a decrease in IgE response as compared to the mice treated with PI3K-δ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3K-δ inhibitor, or PI3K-δ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

The combination treatment using a compound as disclosed herein and rapamycin can provide greater efficacy than treatment with PI3K-δ inhibitor alone.

Example 40

Delayed Type Hypersensitivity Model

DTH was induced by sensitizing 60 BALB/c male mice on day 0 and day 1 with a solution of 0.05% 2,4 dinitrofluorobenzene (DNFB) in a 4:1 acetone/olive oil mixture. Mice were gently restrained while 20 µL of solution was applied to the hind foot pads of each mouse. The hind foot pads of the mice were used as they represent an anatomical site that can be easily isolated and immobilized without anesthesia. On day 5, mice were administered a single dose of vehicle, a compound disclosed herein at 10, 3, 1, or 0.3 mg/kg, or dexamethasone at a dose of 5 mg/kg by oral gavage. Thirty minutes later mice were anaesthetized, and a solution of 0.25% DNFB in a 4:1 acetone/olive oil solution was applied to the left inner and outer ear surface. This application resulted in the induction of swelling to the left ear and under these conditions, all animals responded to this treatment with ear swelling. A vehicle control solution of 4:1 acetone/olive oil was applied to the right inner and outer ear. Twenty four hours later, mice were anaesthetized, and measurements of the left and right ear were taken using a digital micrometer. The difference between the two ears was recorded as the amount of swelling induced by the challenge of DNFB. Drug treatment groups were compared to vehicle control to generate the percent reduction in ear swelling. Dexamethasone is routinely used as a positive control as it has broad anti-inflammatory activity.

Example 41

Peptidoglycan-Polysaccharide Rat Arthritic Model (a) Systemic Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 µg/g of bodyweight) suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 ug/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (I.V.) injection of PG-PS (concentration 250 uL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds will be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

Example 42

Pharmacokinetic Data for Single and Repeat Dosing

A randomized, double-blind, placebo-controlled, single and repeat dose study was conducted to evaluate the pharmacokinetics (PK) of a compound of Formula (I) Form C polymorph when orally administered to healthy adult male and female subjects. Subjects received a single oral dose of a compound of Formula (I) Form C polymorph under fasting conditions at a dose of 1 mg, 2 mg, 5 mg, 10 mg, 20 mg, and 30 mg. Blood samples were collected for plasma analysis pre-dose, and at 0.5, 1, 1.5, 2, 3, 4, 6, 9, 12, 16, and 24 hours. Doses of 1 mg, 2 mg, 5 mg, 10 mg, 20 mg, and 30 mg gave a $C_{max}$ value range of greater than 10 ng/mL to less than 1,500 ng/mL, an $AUC_{0-24}$ value range of greater than 100 ng*h/mL to less than 4,000 ng*h/mL, and a half-life value range of greater than 3 hours to less than 10 hours, in a dose dependent manner.

Repeat oral dose administration of a compound of Formula (I) Form C polymorph was administered once per day (QD) in the morning on Days 1 and 14 and twice daily (BID) on Days 2 through 13. Administration of the compound occurred after an overnight fast on Days 1 and 14. Blood samples were collected for plasma analysis on Day 14 following 1, 2, 5 and 10 mg repeat dosing. Blood samples were collected on Day 14 prior to dosing and at 0.5, 1, 1.5, 2, 3, 4, 6, 9, 12, 16 and 24 hours after administration to determine plasma concentrations of the compound of Formula (I) Form C polymorph. Doses of 1 mg, 2 mg, 5 mg, and 10 mg gave a $C_{max}$ value range of greater than 10 ng/mL to less than 1,000 ng/mL in a dose dependent manner. In addition doses of 1 mg, 2 mg, 5 mg, and 10 mg gave an $AUC_{tau,ss}$ value range of greater than 100 ng*h/mL to less than 2,500 ng*h/mL, in a dose dependent manner. For the BID regimens, the AUC over a 24 hour interval was obtained by multiplying $AUC_{tau,ss}$ by 2.

While various embodiments of the present disclosure have been shown and described herein, it will be apparent to those skilled in the art that such embodiments are provided by way of example only. Numerous variations, changes, and substitutions will now occur to those skilled in the art without departing from the present disclosure. It should be understood that various alternatives to the embodiments of the disclosure described herein can be employed in view of the present disclosure.

What is claimed is:

1. A method of treating a PI3K mediated disorder in a subject having the disorder, comprising administering to the subject a therapeutically effective amount of a solid form comprising a compound of Formula (I):

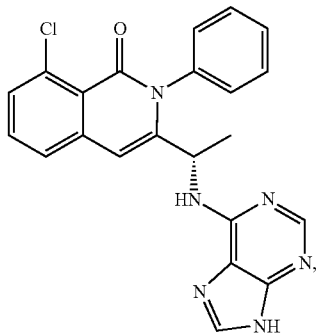

Formula (I)

having the following characteristic X-ray Powder Diffraction (XRPD) peaks: 2θ=11.4° (±0.2°), 17.4° (±0.2°), and 22.9° (±0.2°), wherein the disorder is a hematological cancer, asthma, rheumatoid arthritis, or lupus.

2. The method of claim 1, wherein the disorder is asthma, rheumatoid arthritis, or lupus.

3. The method of claim 1, wherein the disorder is a hematological cancer.

4. The method of claim 3, wherein the cancer is leukemia or lymphoma.

5. The method of claim 3, wherein the cancer is acute myelogenous leukemia (AML), acute lymphocytic leukemia, hairy cell leukemia, chronic myelogenous leukemia (CIVIL), multiple myeloma myelodysplastic syndrome (MDS), or human lymphotropic virus-type 1 (HTLV-1) leukemia.

6. The method of claim 3, wherein the cancer is B-cell immunoblastic lymphoma, small non-cleaved cell lymphoma, adult T-cell lymphoma, mantle cell lymphoma (MCL), Hodgkin disease, AIDS-related lymphoma, peripheral T-cell lymphoma, cutaneous T-cell lymphoma, multiple myeloma, follicular lymphoma, or Waldenström Macroglobulinemia.

7. The method of claim 3, wherein the cancer is chronic lymphocytic leukemia (CLL).

8. The method of claim 3, wherein the cancer is non-Hodgkin lymphoma.

9. The method of claim 8, wherein the non-Hodgkin lymphoma is indolent non-Hodgkin lymphoma (iNHL).

10. The method of claim 3, wherein the cancer is peripheral T-cell lymphoma.

11. The method of claim 3, wherein the cancer is cutaneous T-cell lymphoma.

12. The method of claim 3, wherein the cancer is mantle cell lymphoma (MCL).

13. The method of claim 3, wherein the cancer is diffuse large B-cell lymphoma.

14. The method of claim 3, wherein the cancer is follicular lymphoma.

15. The method of claim 3, wherein the cancer is Waldenström Macroglobulinemia.

16. The method of claim 3, wherein the cancer is post-transplantational lymphoproliferative disorder (PLD).

17. The method of claim 1, further comprising administering one or more second therapeutic agents to the subject.

18. The method of claim 17, wherein the second therapeutic agent is a therapeutic antibody.

19. The method of claim 18, wherein the therapeutic antibody is an anti-CD20 antibody.

20. The method of claim 18, wherein the therapeutic antibody is selected from cetuximab, panitumumab, trastuzumab, rituximab, tositumomab, alemtuzumab, bevacizumab, and gemtuzumab.

21. The method of claim 18, wherein the therapeutic antibody is rituximab.

22. The method of claim 17, wherein the second therapeutic agent is everolimus.

23. The method of claim 17, wherein the second therapeutic agent is a nitrogen mustard.

24. The method of claim 23, wherein the nitrogen mustard is bendamustine.

25. The method of claim 17, wherein the second therapeutic agents are rituximab and bendamustine.

26. The method of claim 17, wherein the second therapeutic agent is chlorambucil, chlornaphazine, estramustine, ifosfamide, mechlorethamine, mechlorethamine oxide hydrochloride, melphalan, novembichin, phenesterine, prednimustine, trofosfamide, uracil mustard, fludarabine, or cyclophosphamide.

27. The method of claim 17, wherein the second therapeutic agent is fludarabine, cyclophosphamide, or rituximab, or a combination thereof.

28. The method of claim 17, wherein the second therapeutic agent is bortezomib.

29. The method of claim 17, wherein the second therapeutic agent is gemcitabine.

30. The method of claim 17, wherein the second therapeutic agent is a corticosteroid.

31. The method of claim 17, wherein the second therapeutic agent is dexamethasone.

* * * * *